United States Patent
Shao et al.

(10) Patent No.: US 11,279,697 B2
(45) Date of Patent: Mar. 22, 2022

(54) AROMATIC DERIVATIVE, PREPARATION METHOD FOR SAME, AND MEDICAL APPLICATIONS THEREOF

(71) Applicant: BIOARDIS LLC, San Diego, CA (US)

(72) Inventors: Ning Shao, Beijing (CN); Ding Wang, Beijing (CN); Hongbin Yuan, Shanghai (CN); Frank Kayser, San Francisco, CA (US)

(73) Assignee: BIOARDIS LLC, San Diego, CA (US)

( * ) Notice: Subject to any disclaimer, the term of this patent is extended or adjusted under 35 U.S.C. 154(b) by 7 days.

(21) Appl. No.: 16/644,919

(22) PCT Filed: Sep. 4, 2018

(86) PCT No.: PCT/CN2018/104007
§ 371 (c)(1),
(2) Date: Mar. 5, 2020

(87) PCT Pub. No.: WO2019/047826
PCT Pub. Date: Mar. 14, 2019

(65) Prior Publication Data
US 2020/0262827 A1    Aug. 20, 2020

(30) Foreign Application Priority Data

Sep. 5, 2017   (CN) .......................... 201710791233.1

(51) Int. Cl.
| | |
|---|---|
| *C07D 413/10* | (2006.01) |
| *A61P 35/04* | (2006.01) |
| *C07D 231/12* | (2006.01) |
| *C07D 231/38* | (2006.01) |
| *C07D 231/54* | (2006.01) |
| *C07D 403/04* | (2006.01) |
| *C07D 403/10* | (2006.01) |
| *C07D 471/04* | (2006.01) |

(52) U.S. Cl.
CPC ............ *C07D 413/10* (2013.01); *A61P 35/04* (2018.01); *C07D 231/12* (2013.01); *C07D 231/38* (2013.01); *C07D 231/54* (2013.01); *C07D 403/04* (2013.01); *C07D 403/10* (2013.01); *C07D 471/04* (2013.01)

(58) Field of Classification Search
CPC .. C07D 413/10; C07D 231/12; C07D 231/38; C07D 231/54; C07D 403/04; C07D 403/10; C07D 471/04; A61P 35/04; A61K 31/415; A61K 31/416
See application file for complete search history.

(56) References Cited

U.S. PATENT DOCUMENTS

| | | | |
|---|---|---|---|
| 2016/0136168 A1 | 5/2016 | Sootome | |
| 2017/0114000 A1 | 4/2017 | Knauf | |

FOREIGN PATENT DOCUMENTS

| | | |
|---|---|---|
| CN | 104540809 A | 4/2015 |
| CN | 105658642 A | 6/2016 |
| EP | 3029864 A1 | 6/2016 |
| WO | WO2012174476 A2 | 12/2012 |
| WO | WO2012174476 A3 | 2/2013 |
| WO | WO2014011900 A2 | 1/2014 |
| WO | WO2014011900 A3 | 2/2014 |
| WO | WO2015008844 A1 | 1/2015 |
| WO | WO2015057938 A1 | 4/2015 |
| WO | WO2015057963 A1 | 4/2015 |
| WO | WO2015059668 A1 | 4/2015 |
| WO | WO2015061572 A1 | 4/2015 |
| WO | WO2015197519 A1 | 12/2015 |
| WO | WO2016064960 A1 | 4/2016 |
| WO | WO2016134294 A1 | 8/2016 |

(Continued)

OTHER PUBLICATIONS

Acute Leukemia, Merck Manual (Online Edition) 6 pages, pp. 1-6 (2013).*

(Continued)

*Primary Examiner* — Deepak R Rao
(74) *Attorney, Agent, or Firm* — Morrison & Foerster LLP

(57) ABSTRACT

An aromatic derivative as represented by formula (I), a pharmaceutically acceptable salt thereof or a pharmaceutical composition comprising same, a preparation method therefor, and uses of the aromatic derivative and the pharmaceutically acceptable salt thereof or the pharmaceutical composition comprising same in preparing a therapeutic agent, specifically an FGFR4 tyrosine kinase inhibitor, and in preparing a medicament for treating and/or preventing neoplastic and inflammatory diseases. The substituents of formula (I) are same as defined in the description.

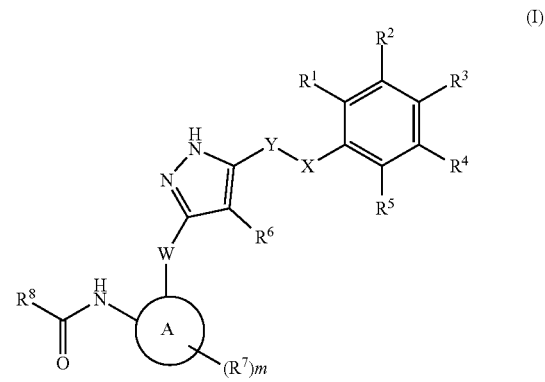

22 Claims, No Drawings

(56) References Cited

FOREIGN PATENT DOCUMENTS

| WO | WO2016134314 A1 | 8/2016 |
| WO | WO2016134320 A1 | 8/2016 |
| WO | 2016164703 A1 | 10/2016 |
| WO | WO2020082651 A1 | 4/2020 |
| WO | WO2020082816 A1 | 4/2020 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Bundgaard, Design of Prodrugs, p. 1, 1985.*
Banker et al., Prodrugs, Modern Pharmaceutics, Third Edition, Revised and Expanded, pp. 451 and 596 (1996).*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Tomassi et al., Indazole-based covalent inhibitors to target drug-resistant epidermal growth factor receptor, Journal of Medicinal Chemistry, 60 (6), pp. 2361-2372 (2017).*
Berge, S.M. et al. (Jan. 1977). "Pharmaceutical Salts," J. Pharm. Sci. 66(1):11-19.
Brown, A.P. et al. (2005). "Cartilage Dysplasia and Tissue Mineralization in the Rat Following Administration of a FGF Receptor Tyrosine Kinase Inhibitor," Toxicol. Pathol. 33:449-455.
Cao, L. et al. (2010, e-pub. Jul. 27, 2010). "Genome-Wide Identification of PAX3-FKHR Binding Sites in Rhabdomyosarcoma Reveals Candidate Target Genes Important for Development and Cancer," Cancer Res. 70 (16):6497-6508.
Ding, L. et al. (Oct. 23, 2008). "Somatic Mutations Affect key Pathways in Lung Adenocarcinoma," Nature 455 (7216):1069-1075, 17 pages.
Ho, H.K. et al. (2008, e-pub. Oct. 12, 2008). "Fibroblast Growth Factor Receptor 4 Regulates Proliferation, Anti-Apoptosis and Alpha-Fetoprotein Secretion During Hepatocellular Carcinoma Progression and Represents a Potential Target for Therapeutic Intervention," Journal of Hepatology 50:118-127.
Roidl, A. et al. (2010, e-pub. Nov. 30, 2009). "The FGFR4 Y367C Mutant is a Dominant Oncogene in MDA-MB453 Breast Cancer Cells," Oncogene 29(10): 1543-1552.
Sawey, E.T. et al. (Mar. 15, 2011). "Identification of a Therapeutic Strategy Targeting Amplified FGF19 in Liver Dancer by Oncogenomic Screening," Cancer Cell 19:347-358.
Taylor, J.G. et al. (Nov. 2009). "Identification of FGFR4-Activation Mutations in Human Rhabdomyosarcomas That Promote Metastasis in Xenotransplanted Models," J Clin Invest 119(11):3395-3407.
Vergnes, L. et al. (Jun. 4, 2013). "Dietl Functions in the FGF15/19 Enterophepatic Signaling Axis to Modulated Bile Acid and Lipid Levels," Cell Metabolism 17(6):916-928, 26 pages.
Nu, X. et al. (Feb. 19, 2010). "FGF19-lnduce Hepatocyte Proliferation is Mediated Through FGFR4 Activation," J Biol Chem 285(8):5165-5170.
Zaid, T.M. et al. (2013, e-pub. Jan. 23, 2013). "Identification of FGFR4 as a Potential Therapeutic Target for Advanced-Stage, High-Grade Serous Ovarian Cancer," Clin Cancer Res. 19(4):809-820.
Fairhurst, R.A. et al. (Jun. 8, 2017). "Approaches to Selective Fibroblast Growth Factor Receptor 4 Inhibition Through Targeting the ATP-Pocket Middle-Hinge Region," Med. Chem. Comm. 8(8):1604-1613.

* cited by examiner

AROMATIC DERIVATIVE, PREPARATION METHOD FOR SAME, AND MEDICAL APPLICATIONS THEREOF

CROSS REFERENCE TO RELATED APPLICATIONS

This application is a national stage application under 35 U.S.C. § 371 of International Application No. PCT/CN2018/104007, filed internationally on Sep. 4, 2018, which claims priority benefit to Chinese Application No. 201710791233.1, filed Sep. 5, 2017, the contents of which are incorporated herein by reference in their entirety.

FIELD OF THE INVENTION

The present invention relates to a novel aromatic derivative or a pharmaceutically acceptable salt, tautomer, racemate, enantiomer, diastereoisomer, prodrug, hydrate or solvate thereof, and a mixture thereof, or a pharmaceutical composition containing the same, and a preparation method thereof. The present invention further relates to a method of using the aromatic ether derivative to treat and/or prevent FGFR4 tyrosine kinase-mediated diseases, and use of the aromatic ether derivative in the preparation of FGFR4 tyrosine kinase inhibitors and drugs.

BACKGROUND

Fibroblast growth factor (FGF) is a polypeptide secreted by the pituitary gland and the hypothalamus. FGF plays important roles in promotion of fibroblast mitosis, mesoblastema growth, stimulation of angiopoiesis, wound healing, and limb regeneration. The FGF receptor (FGFR) signaling system plays a critical role in the normal developmental and physiological processes. FGFR has 4 subtypes, i.e., FGFR1 to FGFR4, which have highly conservative amino acid sequences. FGFR1 to FGFR4 have different binding forces towards different growth factors, and their tissue distributions are different from each other. A complete FGFR receptor protein comprises an extracellular part, a hydrophobic single-chain cell membrane part, and an intracellular tyrosine kinase part. When the extracellular part of the FGFR interacts with the FGF growth factor, downstream chain signaling (Ras-MAPK, AKT-PI3K, phospholipase C) is initiated, eventually influencing and regulating cell growth, division, and differentiation (Eswarakumar, *Cytokine & Growth Factor Reviews*, 2005).

Abnormal stimulation of this signaling pathway (including over-expression of the FGF growth factor, over-expression of the FGFR receptor, and gene mutation of the FGFR receptor) leads to tumor growth and tolerance to treatment. It has been found from DNA sequencing thousands of tumor samples that the FGFR pathway often mutates. FGFR4 is a protein encoded by the FGFR-4 gene. The FGFR4 gene has 18 exons. The FGF-FGFR signal disorder is related to tumorigenesis and tumor evolution. It has been found that the FGFR4-FGF19 signal axis is closely related to hepatocellular cancer (HCC) in mice. FGFR4 expression is significantly increased with several types of cancer, such as liver cancer. Also, FGFR4 is needed for liver cancer to develop. The offspring of FGF19 transgenic mice may develop liver cancer, whereas the offspring of FGFR4 knock-out mice will not develop liver cancer. After FGF19 is neutralized by the FGF19 specific antibody, tumor growth is inhibited. In addition, FGFR4 over-expression also occurs in other types of tumor, including breast cancer, colorectal cancer, pancreatic cancer, prostate cancer, lung cancer, and thyroid cancer. FGFR4 mutation occurs in rhabdomyosarcoma. Small molecule targeted inhibition of FGFR4 can be used in cancer treatment. When mice are treated with FGFR-1 inhibitors, it is found that side effects such as calcium phosphate deposition occur in soft tissues (Brown, A P et al., *Toxicol. Pathol.*, 2005, p. 449-455). This indicates that rather than extensive inhibition of FGFR1 to FGFR4 receptors, selective inhibition of the FGFR4 receptor would avoid such side effects.

Although a series of patent applications for FGFR4 inhibitors including WO2014011900, WO2015061572, WO20150197519, WO2015008844, WO2015057938, WO2015059668, WO2012174476, WO2015057963, WO2016064960, WO2016134294, WO2016134314 and WO2016134320 and the like have been disclosed thus far, the development of novel compounds having better efficacy is still needed. Through unremitting efforts, a compound having the structure as shown in the general formula (I) is designed in the present invention, and it is found that compounds with such structure demonstrate excellent results and properties.

SUMMARY

The present invention relates to the following technical solutions:

In one aspect, the present invention provides a compound as shown in the general formula (I) or a pharmaceutically acceptable salt, tautomer, racemate, enantiomer, diastereoisomer, prodrug, hydrate or solvate thereof, and a mixture thereof:

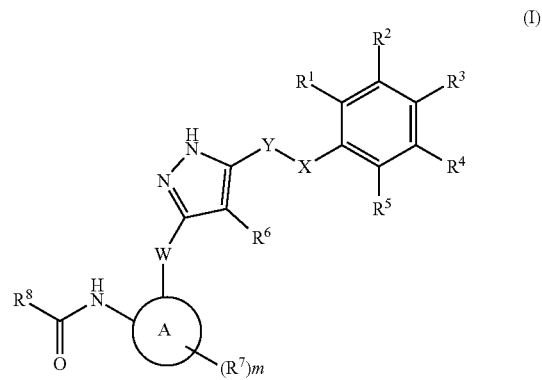

(I)

wherein
ring A is not present or is selected from the group consisting of 6-14 membered arylene, 5-10 membered heteroarylene, $C_3$-$C_8$ cycloalkylene and 3-10 membered heterocyclylene;
$R^1$, $R^2$, $R^3$, $R^4$ and $R^5$ are each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^3$;
$R^6$ is each independently selected from the group consisting of H and —$CH_2CH_2$—, and when $R^6$ is —$CH_2CH_2$—, the other end thereof is connected to X, and optionally one methylene group of —$CH_2CH_2$— is replaced with —O— or —NH—;

$R^7$ is each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$ or —$NR^aR^b$, wherein $R^a$ and $R^b$ are each independently selected from the group consisting of H and $C_1$-$C_6$ alkyl optionally substituted by —$NR^cR^d$; and $R^c$ and $R^d$ are each independently selected from the group consisting of H and $C_1$-$C_6$ alkyl;

$R^8$ is selected from the group consisting of optionally substituted $C_2$-$C_6$ alkenyl and $C_2$-$C_6$ alkynyl;

$R^{11}$, $R^{12}$ and $R^{13}$ are each independently selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl;

X is selected from the group consisting of —O—, —NH— and —$CH_2$—; and Y is selected from the group consisting of —O—, —NH— and —$CH_2$—; provided that at least one of X and Y is $CH_2$;

W is selected from the group consisting of a chemical bond, —NH— and —$CH_2$—;

m is 0, 1, 2, 3 or 4; and p is 1 or 2.

In another aspect, the present invention provides a pharmaceutical composition, containing the compound of the present invention or a pharmaceutically acceptable salt, tautomer, racemate, enantiomer, diastereoisomer, prodrug, hydrate or solvate thereof, and a mixture thereof, and a pharmaceutically acceptable excipient. In particular embodiments, the compound of the present invention is provided in the pharmaceutical composition in an effective amount. In particular embodiments, the compound of the present invention is provided in a therapeutically effective amount. In particular embodiments, the compound of the present invention is provided in a prophylactically effective amount. In another embodiment, the pharmaceutical composition of the present invention further contains other therapeutic agents.

In another aspect, the present invention provides a kit, comprising: a first container containing the compound of the present invention or a pharmaceutically acceptable salt, tautomer, racemate, enantiomer, diastereoisomer, prodrug, hydrate or solvate thereof, and a mixture thereof; and optionally, a second container containing other therapeutic agents; and optionally, a third container containing a pharmaceutically acceptable excipient for diluting or suspending the compound and/or other therapeutic agents.

In another aspect, the present invention further provides the compound of the present invention or a pharmaceutically acceptable salt, tautomer, racemate, enantiomer, diastereoisomer, prodrug, hydrate or solvate thereof, and a mixture thereof, or use of the pharmaceutical composition of the present invention in the preparation of FGFR4 tyrosine kinase inhibitors.

In another aspect, the present invention further provides the compound of the present invention or a pharmaceutically acceptable salt, tautomer, racemate, enantiomer, diastereoisomer, prodrug, hydrate or solvate thereof, and a mixture thereof, or use of the pharmaceutical composition of the present invention in the preparation of a drug for treating and/or preventing FGFR4 tyrosine kinase-mediated diseases.

In another aspect, the present invention further provides the compound of the present invention or a pharmaceutically acceptable salt, tautomer, racemate, enantiomer, diastereoisomer, prodrug, hydrate or solvate thereof, and a mixture thereof, or the pharmaceutical composition of the present invention, for use in the treatment and/or prevention of FGFR4 tyrosine kinase-mediated diseases.

In another aspect, the present invention further provides a method for treating and/or preventing FGFR4 tyrosine kinase-mediated diseases in a subject, comprising administering to the subject the compound of the present invention or a pharmaceutically acceptable salt, tautomer, racemate, enantiomer, diastereoisomer, prodrug, hydrate or solvate thereof and a mixture thereof, or the pharmaceutical composition of the present invention.

In the particular embodiments of the above aspects, the disease is tumor, e.g., gastric cancer, thyroid cancer, prostate cancer, breast cancer, sarcoma (e.g., rhabdomyosarcoma), skin cancer (e.g., melanoma), liver cancer (e.g., hepatocellular cancer and cholangiocarcinoma), pancreatic cancer (e.g., intraepithelial neoplasia of pancreas and ductal adenocarcinoma of pancreas), lung cancer (e.g., non-small-cell lung cancer and pulmonary adenocarcinoma), kidney cancer (e.g., renal cell carcinom), colorectal cancer and ovarian cancer.

DETAILED DESCRIPTION

Definition

The terms used in the present invention have the meanings well known to those of skill in the art. When a definition is given in the present invention, the definition in the present invention is employed preferentially.

When a range of values is listed, it is established to include each value and subranges within the range. For example, "$C_1$-$C_6$ alkyl" includes $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$ alkyl.

"$C_1$-$C_6$ alkyl" refers to a linear or branched saturated hydrocarbon group with 1 to 6 carbon atoms, and is also known as "lower alkyl." In some embodiments, $C_1$-$C_4$ alkyl is particularly preferred. Examples of alkenyl include, but are not limited to, methyl, ethyl, n-propyl, i-propyl, n-butyl, i-butyl, t-butyl, s-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, and various branched isomers thereof. Alkyl may be optionally substituted or unsubstituted.

"$C_2$-$C_6$ alkenyl" refers to a linear or branched hydrocarbon group having 2 to 6 carbon atoms and one or more carbon-carbon double bonds (e.g., 1, 2 or 3 carbon-carbon double bonds). The one or more carbon-carbon double bonds may be inside (e.g., in 2-butenyl) or at the end (e.g., in 1-butenyl). In some embodiments, $C_2$-$C_4$ alkenyl is particularly preferred. Examples of alkenyl include, but are not limited to, vinyl, 1-propenyl, 2-propenyl, 1-butenyl, 2-butenyl, butadienyl, pentenyl, pentadienyl, hexenyl, and various branched isomers thereof. Alkenyl may be optionally substituted or unsubstituted.

"$C_2$-$C_6$ alkynyl" refers to a linear or branched hydrocarbon group having 2 to 6 carbon atoms, one or more carbon-carbon triple bonds (e.g., 1, 2 or 3 carbon-carbon triple bonds), and optionally one or more carbon-carbon double bonds (e.g., 1, 2 or 3 carbon-carbon double bonds). In some embodiments, $C_2$-$C_4$ alkynyl is particularly preferred. In some embodiments, alkynyl does not contain any double bond. The one or more carbon-carbon triple bonds may be inside (e.g., in 2-butynyl) or at the end (e.g., in 1-butynyl). Examples of alkynyl include, but are not limited to, ethynyl, 1-propynyl, 2-propynyl, 1-butynyl, 2-butynyl, pentynyl, hexynyl, and various branched isomers thereof. Alkynyl may be optionally substituted or unsubstituted.

"$C_1$-$C_6$ heteroalkyl" refers to alkyl defined herein, which further contains one or more (e.g., 1, 2, 3 or 4) heteroatoms in the parent chain (e.g., oxygen, sulfur, nitrogen, boron, silicon, phosphorus), wherein the one or more heteroatoms are between adjacent carbon atoms in the parent carbon chain, and/or the one or more heteroatoms are between a carbon atom and the parent molecule, i.e., between the connection points. Heteroalkyl may be optionally substituted or unsubstituted. In some embodiments, as particular examples, $C_1$-$C_6$ heteroalkyl includes $C_1$-$C_6$ alkoxy, $C_1$-$C_6$ alkylthio, $C_1$-$C_6$ alkylamino, etc., which are defined in detail as follows.

"$C_1$-$C_6$ alkoxy" refers to the group —OR, wherein R is a substituted or unsubstituted $C_1$-$C_6$ alkyl. In some embodiments, $C_1$-$C_4$ alkoxy is particularly preferred. Particularly, the alkoxy group includes, but is not limited to, methoxy, ethoxy, n-propoxy, i-propoxy, n-butoxy, t-butoxy, s-butoxy, n-pentoxy, n-hexoxy and 1,2-dimethylbutoxy, and various branched isomers thereof. Alkoxy may be optionally substituted or unsubstituted.

"$C_1$-$C_6$ alkylthiol" refers to the group —SR, wherein R is optionally substituted $C_1$-$C_6$ alkyl. In some embodiments, $C_1$-$C_4$ alkylthiol is particularly preferred. Particularly, the $C_1$-$C_6$ alkylthiol group includes, but is not limited to, methylthio, ethylthio, n-propylthio, i-propylthio, n-butylthio, t-butylthio, s-butylthio, n-pentylthio, n-hexylthio and 1,2-dimethylbutylthio, and various branched isomers thereof, etc. Alkylthiol may be optionally substituted or unsubstituted.

"$C_1$-$C_6$ alkylamino" refers to the group —NHR or —$NR_2$, wherein R is optionally substituted $C_1$-$C_6$ alkyl. In some embodiments, $C_1$-$C_4$ alkylamino is particularly preferred. Particularly, the $C_1$-$C_6$ alkylamino group includes, but is not limited to, methylamino, ethylamino, n-propylamino, i-propylamino, n-butylamino, t-butylamino, dimethylamino, methylethylamino and diethylamino, and various branched isomers thereof, etc. Alkylamino may be optionally substituted or unsubstituted.

"Halogen" refers to fluorine (F), chlorine (Cl), bromine (Br) and iodine (I).

"Cyano" refers to —CN.

"$C_1$-$C_6$ haloalkyl" and "$C_1$-$C_6$ haloalkoxy" refer to the above "$C_1$-$C_6$ alkyl" and "$C_1$-$C_6$ alkoxy," replaced by one or more halogen groups. In some embodiments, $C_1$-$C_4$ haloalkyl is particularly preferred, and $C_1$-$C_2$ haloalkyl is more preferred. In some embodiments, $C_1$-$C_4$ haloalkoxy is particularly preferred, and $C_1$-$C_2$ haloalkoxy is more preferred. Exemplarily, the haloalkyl includes, but is not limited to, —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, etc. Exemplarily, the haloalkoxy includes, but is not limited to, —$OCH_2F$, —$OCHF_2$, —$OCF_3$, etc. Haloalkyl and haloalkoxy may be optionally substituted or unsubstituted.

"$C_3$-$C_8$ cycloalkyl" refers to a non-aromatic cyclohydrocarbon group with 3 to 8 ring carbon atoms and 0 heteroatom. In some embodiments, $C_3$-$C_6$ cycloalkyl is particularly preferred, and $C_5$-$C_6$ cycloalkyl is more preferred. Cycloalkyl further includes a ring system in which the above cycloalkyl group is fused, bridged or spiro-joined to one or more cycloalkyl, heterocyclyl, aryl or heteroaryl, wherein the connection points are on the cycloalkyl ring, and in such a case, the number of carbon continues to represent the number of carbon in the cycloalkyl system. Exemplarily, the cycloalkyl includes, but is not limited to, cyclopropyl, cyclopropenyl, cyclobutyl, cyclobutenyl, cyclopentyl, cyclopentenyl, cyclohexyl, cyclohexenyl, cyclohexadienyl, cycloheptyl, cycloheptenyl, cycloheptadienyl, cycloheptatrienyl, cyclooctyl, cyclooctenyl, bicyclo[2.2.1]heptyl, bicyclo[2.2.2]octyl, and various branched isomers thereof, etc. Cycloalkyl may be optionally substituted or unsubstituted.

"3-10 membered heterocyclyl" refers to a group of a 3-10 membered non-aromatic ring system with ring carbon atoms and 1 to 4 ring heteroatoms, wherein each heteroatom is independently selected from the group consisting of nitrogen, oxygen, sulfur, boron, phosphorus and silicon. In heterocyclyl containing one or more nitrogen atoms, the connection point may be a carbon or nitrogen atom as long as the valence permits. In some embodiments, 3-8 membered heterocyclyl is preferred, which is a 3-8 membered non-aromatic ring system with ring carbon atoms and 1 to 3 ring heteroatoms. In some embodiments, 4-7 membered heterocyclyl is particularly preferred, which is a 4-7 membered non-aromatic ring system with ring carbon atoms and 1 to 3 ring heteroatoms; and 5-6 membered heterocyclyl is more preferred, which is a 5-6 membered non-aromatic ring system with ring carbon atoms and 1 to 3 ring heteroatoms. Exemplary 3 membered heterocyclyl comprising one heteroatom includes, but is not limited to, azacyclopropyl, oxacyclopropyl and thiacyclopropyl. Exemplary 4 membered heterocyclyl comprising one heteroatom includes, but is not limited to, azacyclobutyl, oxacyclobutyl and thiacyclobutyl. Exemplary 5 membered heterocyclyl comprising one heteroatom includes, but is not limited to, tetrahydrofuryl, dihydrofuryl, tetrahydrothienyl, dihydrothienyl, pyrrolidinyl, dihydropyrrolyl and pyrrolyl-2,5-dione. Exemplary 5 membered heterocyclyl comprising two heteroatoms includes, but is not limited to, dioxacyclopentyl, oxathiacyclopentyl, dithiacyclopentyl and oxazolidin-2-one. Exemplary 5 membered heterocyclyl comprising three heteroatoms includes, but is not limited to, triazolinyl, oxadiazolinyl and thiadiazolinyl. Exemplary 6 membered heterocyclyl comprising one heteroatom includes, but is not limited to, piperidyl, dihydropyranyl, tetrahydropyranyl, dihydropyridinyl and thiacyclohexyl. Exemplary 6 membered heterocyclyl comprising two heteroatoms includes, but is not limited to, piperazinyl, morpholinyl, dithiacyclohexyl, and dioxanyl. Exemplary 6 membered heterocyclyl comprising three heteroatoms includes, but is not limited to, hexahydrotriazinyl. Exemplary 7 membered heterocyclyl comprising one heteroatom includes, but is not limited to, azacycloheptyl, oxacycloheptyl and thiacycloheptyl. Exemplary 8 membered heterocyclyl comprising one heteroatom includes, but is not limited to, azacyclooctyl, oxacyclooctyl and thiacyclooctyl. Exemplary 6 membered aromatic ring-fused 5 membered heterocyclyl (herein also referred to as 5,6-bicycloheterocyclyl) includes, but is not limited to, indolinyl, i-indolinyl, dihydrobenzofuryl, dihydrobenzothienyl, and benzoxazolinonyl, etc. Exemplary 6 membered aromatic ring-fused 6 membered heterocyclyl (herein also referred to as 6,6-bicycloheterocyclyl) includes, but is not limited to, tetrahydroquinolyl, and tetrahydroisoquinolyl, etc. Heterocyclyl includes heterocyclyl of spiral rings, fused rings and bridged rings.

"Spiroheterocyclyl" refers to 5-20 membered polycyclic heterocyclyl with one atom (referred to as a spiro atom) shared between monocyclic rings, wherein one or more of the ring atoms are heteroatoms selected from the group consisting of nitrogen, oxygen or $S(O)_m$ (wherein m is an integer of 0 to 2), and the remaining ring atoms are carbon.

They may contain one or more double bonds, but none of the rings has aromaticity. They are preferably 6 to 14 membered, and more preferably 7 to 10 membered. According to the number of spiro atoms shared between rings, spiro alkyl is classified into mono-spiro heterocyclyl, double-spiro heterocyclyl or multi-spiro heterocyclyl, and preferably mono-spiro cycloalkyl and double-spiro cycloalkyl. They are more preferably 4 membered/4 membered, 4 membered/5 membered, 4 membered/6 membered, 5 membered/5 membered, or 5 membered/6 membered mono-spiro alkyl. Non limiting examples of spiro alkyl include:

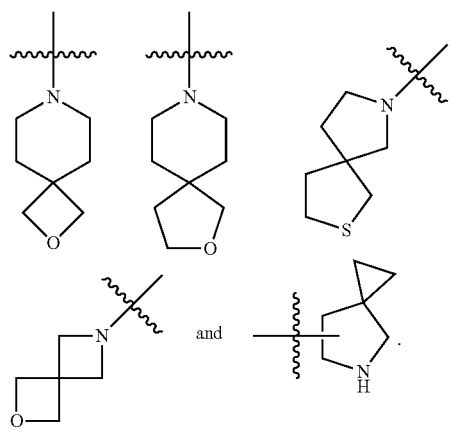

"Fused heterocyclyl" refers to 5 to 20 membered polycyclic heterocyclyl where each ring in the system shares a pair of adjacent atoms with other rings in the system, one or more rings may contain one or more double bonds, but none of the rings has aromaticity, where one or more ring atoms are selected from the group consisting of heteroatoms of nitrogen, oxygen and $S(O)_m$ (where m is an integer of 0 to 2), and the remaining ring atoms are carbon. They are preferably 6 to 14 membered, and more preferably 7 to 10 membered. According to the number of constituent rings, they can be classified into bicyclic, tricyclic, tetracyclic or polycyclic fused heterocyclyl, and they are preferably bicyclic or tricyclic, and more preferably 5 membered/5 membered, or 5 membered/6 membered bicyclic fused heterocyclyl. Non-limiting examples of fused heterocyclyl include:

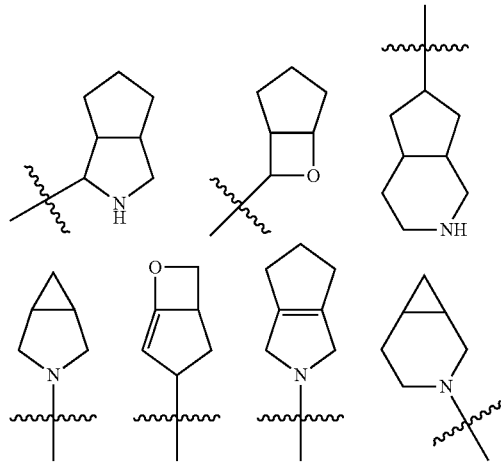

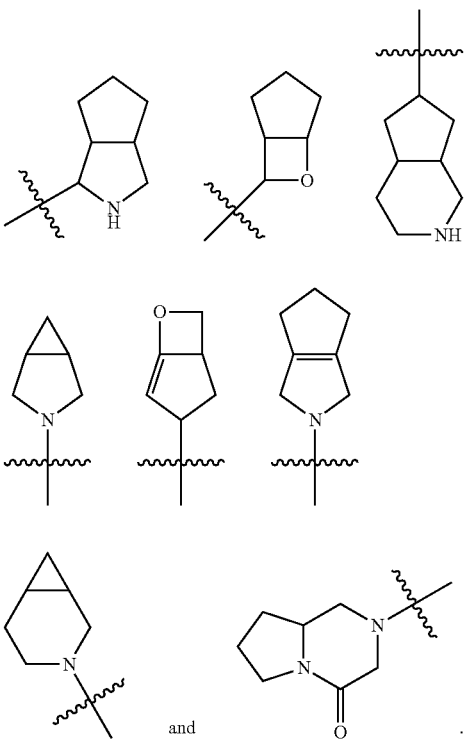

The heterocyclyl ring may be fused to an aryl, heteroaryl or cycloalkyl ring, in which the ring connected with the parent structure is heterocyclyl, and non-limiting examples include:

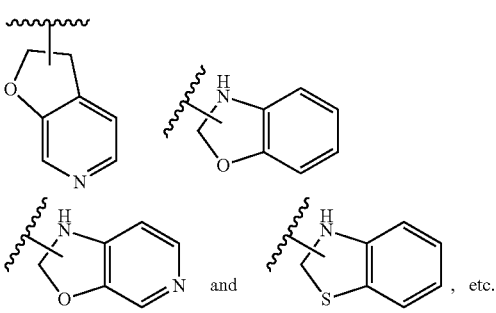

Heterocyclyl may be optionally substituted or unsubstituted.

"6-14 membered aryl" refers to a group of monocyclic or polycyclic (e.g., bicyclic or tricyclic) 4n+2 aromatic ring system (e.g., with 6, 10 or 14 pi electrons shared in a circular arrangement) with 6 to 14 ring carbon atoms and 0 heteroatom. In some embodiments, aryl has 6 ring carbon atoms ("6 membered aryl;" e.g., phenyl). In some embodiments, aryl has 10 ring carbon atoms ("10 membered aryl;" e.g., naphthyl, for example, 1-naphthyl and 2-naphthyl). In some embodiments, aryl has 14 ring carbon atoms ("14 membered aryl;" e.g., anthryl). In some embodiments, 6-10 membered aryl is particularly preferred, and 6 membered aryl is more preferred. The aryl may be fused to a heteroaryl, heterocyclyl or cycloalkyl ring, in which the ring connected with the parent structure is the aryl ring, and non-limiting examples include:

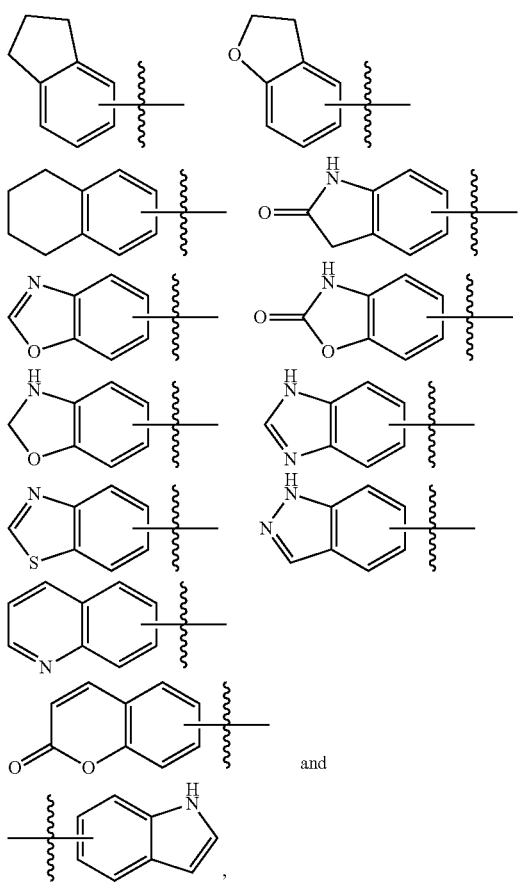

aryl may be substituted or unsubstituted.

"5-10 membered heteroaryl" refers to a group of 5-10 membered monocyclic or bicyclic 4n+2 aromatic ring system (e.g., with 6 or 10 pi electrons shared in a circular arrangement) with ring carbon atoms and 1 to 4 ring heteroatoms, wherein each heteroatom is independently selected from the group consisting of nitrogen, oxygen and sulfur. In heteroaryl containing one or more nitrogen atoms, the connection point may be a carbon or nitrogen atom as long as the valence permits. In some embodiments, 5-6 membered heteroaryl is particularly preferred, which is a 5-6 membered monocyclic 4n+2 aromatic ring system with ring carbon atoms and 1 to 4 ring heteroatoms. Exemplary 5 membered heteroaryl containing one heteroatom includes, but is not limited to, pyrrolyl, furyl and thienyl. Exemplary 5 membered heteroaryl containing two heteroatoms includes, but is not limited to, imidazolyl, pyrazolyl, oxazolyl, i-oxazolyl, thiazolyl and i-thiazolyl. Exemplary 5 membered heteroaryl containing three heteroatoms includes, but is not limited to, triazolyl, oxadiazolyl and thiadiazolyl. Exemplary 5 membered heteroaryl containing four heteroatoms includes, but is not limited to, tetrazolyl. Exemplary 6 membered heteroaryl containing one heteroatom includes, but is not limited to, pyridinyl. Exemplary 6 membered heteroaryl containing two heteroatoms includes, but is not limited to, pyridazinyl, pyrimidinyl and pyrazinyl. Exemplary 6 membered heteroaryl containing three or four heteroatoms respectively includes, but is not limited to, triazinyl and tetrazinyl. Exemplary 7 membered heteroaryl containing one heteroatom includes, but is not limited to, azacycloheptatrienyl, oxacycloheptatrienyl and thiacycloheptatrienyl. Exemplary 5,6-bicyclic heteroaryl includes, but is not limited to, indolyl, i-indolyl, indazolyl, benzotriazolyl, benzothienyl, i-benzothienyl, benzofuryl, benzoisofuryl, benzmidazolyl, benzoxazolyl, benzoisooxazolyl, benzoxadiazolyl, benzothiazolyl, benzoisothiazolyl, benzothiadiazolyl, indolazinyl and purinyl. Exemplary 6,6-bicyclic heteroaryl includes, but is not limited to, naphthyridinyl, pteridyl, quinolyl, i-quinolyl, cinnolinyl, quinoxalyl, phthalazinyl and quinazolinyl. The heteroaryl ring may be fused to an aryl, heterocyclyl or cycloalkyl ring, in which the ring connected with the parent structure is the heteroaryl ring, and non-limiting examples include:

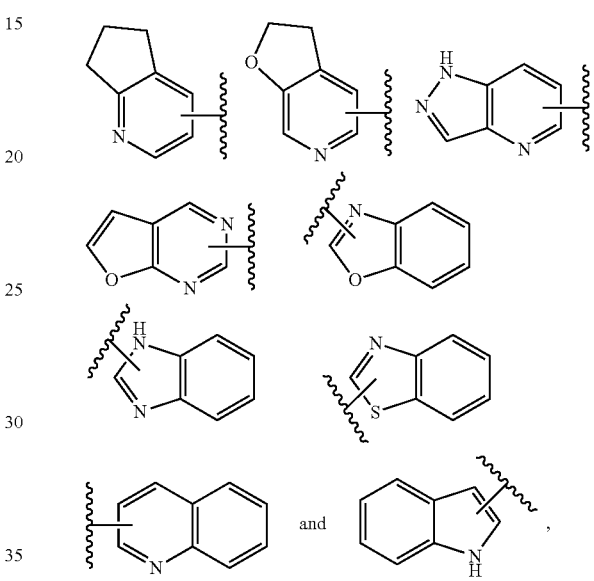

heteroaryl may be optionally substituted or unsubstituted.

"Alkylene," "alkenylene," "alkynylene," "arylene," "heteroarylene," "cycloalkylene" and "heterocyclylene" used herein respectively refer to bivalent radicals of the above alkyl, alkenyl, alkynyl, aryl, heteroaryl, cycloalkyl and heterocyclyl. The group may be optionally substituted or unsubstituted.

"$C_1$-$C_6$ alkylene" refers to divalent alkylene formed by removing one hydrogen from $C_1$-$C_6$ alkyl, and may be substituted or unsubstituted alkylene. In some embodiments, $C_1$-$C_4$ alkylene is particularly preferred. Unsubstituted alkylene includes, but is not limited to, methylene (—CH$_2$—), ethylidene (—CH$_2$CH$_2$—), propylidene (—CH$_2$CH$_2$CH$_2$—), butylidene (—CH$_2$CH$_2$CH$_2$CH$_2$—), pentylidene (—CH$_2$CH$_2$CH$_2$CH$_2$CH$_2$—), hexylidene (—CH$_2$CH$_2$CH$_2$CH$_2$CH$_2$CH$_2$—), etc. Exemplary substituted alkylene, e.g., the alkylene substituted by one or more alkyl (methyl), includes, but is not limited to, substituted methylene (—CH(CH$_3$)— and —C(CH$_3$)$_2$—), substituted ethylidene (—CH(CH$_3$)CH$_2$—, —CH$_2$CH(CH$_3$)—, —C(CH$_3$)$_2$CH$_2$—, and —CH$_2$C(CH$_3$)$_2$—), substituted propylidene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, and —CH$_2$CH$_2$C(CH$_3$)$_2$—), etc.

"$C_2$-$C_6$ alkenylene" refers to divalent alkenyl formed by removing one hydrogen from $C_2$-$C_6$ alkenyl, and may be substituted or unsubstituted alkenylene. In some embodiments, $C_2$-$C_4$ alkenylene is particularly preferred. Exemplary unsubstituted alkenylene includes, but is not limited to, ethylene (—CH=CH—) and propenylidene (e.g., —CH=CHCH$_2$— and —CH$_2$—CH=CH—). Exemplary substituted alkenylene, e.g., alkenylene substituted by one or more alkyl (methyl), includes, but is not limited to, substituted ethylene (—C(CH$_3$)=CH—, and —CH=C(CH$_3$)—), substituted propenylidene (—C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, and —CH$_2$—CH=C(CH$_3$)—), etc.

"C$_2$-C$_6$ alkynylene" refers to divalent alkynylene formed by removing one hydrogen from C$_2$-C$_6$ alkynyl, and may be substituted or unsubstituted alkynylene. In some embodiments, C$_2$-C$_4$ alkynylene is particularly preferred. Exemplarily, the alkynylene includes, but is not limited to, ethynylene (—C≡C—) and substituted or unsubstituted propynylene (—C≡CCH$_2$—), etc.

"6-14 membered arylene," "5-10 membered heteroarylene," "C$_3$-C$_8$ cycloalkylene" and "3-10 membered heterocyclylene" respectively refer to divalent groups formed by removing one hydrogen from the above 6-14 membered aryl, 5-10 membered heteroaryl, C$_3$-C$_8$ cycloalkyl and 3-10 membered heterocycloalkyl.

All groups herein are optionally substituted. "Optional" or "optionally" means that an event or situation described subsequently may occur, but does not necessarily occur, which includes both the occurrence and non-occurrence of the event or situation. For example, "heterocyclyl optionally substituted by alkyl" means that alkyl may, but does not necessarily exist, including cases where heterocyclyl is substituted by alkyl and not substituted by alkyl.

"Substituted" refers that one or more hydrogen atoms, preferably at most 5 and more preferably 1 to 3 hydrogen atoms, in a group are substituted independently by a corresponding number of substituents. It goes without saying that, substituents are only in their possible chemical positions, and those of skill in the art can determine (experimentally or theoretically) possible or impossible substitutions without a lot of efforts. For example, amino or hydroxy groups having free hydrogen may be unstable when combined with carbon atoms having unsaturated (e.g. olefinic) bonds.

Exemplary substituents on the carbon atom include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^a$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{aa}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, cycloalkyl, heterocyclyl, aryl and heteroaryl, wherein, each alkyl, alkenyl, alkynyl, cycloalkyl, heterocyclyl, aryl and heteroaryl are independently substituted by 0, 1, 2, 3, 4, or 5 R$^{dd}$ groups;

or two gem-hydrogens on a carbon atom are substituted by a group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$ or =NOR$^{cc}$;

R$^{aa}$ is each independently selected from the group consisting of alkyl, haloalkyl, alkenyl, alkynyl, cycloalkyl, heterocyclyl, aryl and heteroaryl, or two R$^{aa}$ groups are binded to form a heterocyclyl or heteroaryl ring, wherein each alkyl, alkenyl, alkynyl, cycloalkyl, heterocyclyl, aryl and heteroaryl are independently substituted by 0, 1, 2, 3, 4, or 5 R$^{dd}$ groups;

R$^{bb}$ is each independently selected from the group consisting of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, cycloalkyl, heterocyclyl, aryl and heteroaryl, or two R$^{bb}$ groups are binded to form a heterocyclyl or heteroaryl ring, wherein each alkyl, alkenyl, alkynyl, cycloalkyl, heterocyclyl, aryl and heteroaryl are independently substituted by 0, 1, 2, 3, 4, or 5 R$^{dd}$ groups;

R$^{cc}$ is each independently selected from the group consisting of hydrogen, alkyl, haloalkyl, alkenyl, alkynyl, cycloalkyl, heterocyclyl, aryl and heteroaryl, or two R$^{cc}$ groups are binded to form a heterocyclyl or heteroaryl ring, wherein each alkyl, alkenyl, alkynyl, cycloalkyl, heterocyclyl, aryl and heteroaryl are independently substituted by 0, 1, 2, 3, 4, or 5 R$^{dd}$ groups;

R$^{dd}$ is each selected from the group consisting of halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, cycloalkyl, heterocyclyl, aryl and heteroaryl, wherein each alkyl, alkenyl, alkynyl, cycloalkyl, heterocyclyl, aryl and heteroaryl are independently substituted by 0, 1, 2, 3, 4, or 5 R$^{gg}$ groups, or two gem-R$^{dd}$ substituents may be binded to form =O or =S;

R$^{ee}$ is each independently selected from the group consisting of alkyl, haloalkyl, alkenyl, alkynyl, cycloalkyl, aryl, heterocyclyl and heteroaryl, wherein each alkyl, alkenyl, alkynyl, cycloalkyl, heterocyclyl, aryl and heteroaryl are independently substituted by 0, 1, 2, 3, 4, or 5 R$^{gg}$ groups;

R$^{ff}$ is each independently selected from the group consisting of hydrogen, alkyl, haloalkyl, alkenyl, alkynyl, cycloalkyl, heterocyclyl, aryl and heteroaryl, or two R$^{ff}$ groups are binded to form a heterocyclyl or heteroaryl ring, wherein each alkyl, alkenyl, alkynyl, cycloalkyl, heterocyclyl, aryl and heteroaryl are independently substituted by 0, 1, 2, 3, 4, or 5 R$^{gg}$ groups; and R$^{gg}$ is each independently halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$haloalkyl, alkenyl, C$_2$-C$_6$ alkynyl, C$_3$-C$_7$ cycloalkyl, C$_6$-C$_{10}$ aryl, C$_3$-C$_7$ heterocyclylene, C$_5$-C$_{10}$ heteroaryl; or two gem-R$^{gg}$ substituents may be binded to form =O or =S; wherein, X$^-$ is a counter ion.

Exemplary substituents on the nitrogen atom include, but are not limited to, halogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, cycloalkyl, heterocyclyl, aryl and heteroaryl, or two R$^{11}$ groups connected to the nitrogen atom are binded to form a heterocyclyl or heteroaryl ring, wherein each alkyl, alkenyl, alkynyl, cycloalkyl, heterocyclyl, aryl and heteroaryl are independently substituted by 0, 1, 2, 3, 4, or 5 R$^{dd}$ group, and wherein R$^{aa}$, R$^{bb}$, R$^{cc}$ and R$^{dd}$ are as stated above.

The term "pharmaceutically acceptable salts" refers to those salts that are suitable for contacting tissues of human and lower animals without excessive toxicity, irritation, allergy and the like, and are proportionate to a reasonable benefit/risk ratio, within the scope of reliable medical judgment. Pharmaceutically acceptable salts are well known in the art. For example, pharmaceutically acceptable salts described in detail in Berge et al., *J. Pharmaceutical Sciences* (1977) 66: 1-19. Pharmaceutically acceptable salts of the compound of the present invention include salts derived from suitable inorganic and organic acids and inorganic and organic bases. Examples of pharmaceutically acceptable nontoxic acid addition salts are those formed with inorganic acids, such as hydrochloric acid, hydrobromic acid, phosphoric acid, sulfuric acid and perchloric acid, or with organic acids, such as acetic acid, oxalic acid, maleic acid, tartaric acid, citric acid, succinic acid or malonic acid. Salts formed by conventional methods in the art, such as the ion exchange method, are also included. Other pharmaceutically acceptable salts include: adipate, alginate, ascorbate, aspartate, benzene sulfonate, benzoate, bisulfate, borate, butyrate, camphorate, camphorsulfonate, citrate, cyclopentyl propionate, diglucosate, dodecyl sulfate, ethanesulfonate, formate, fumarate, gluconate, glycerophosphate, gluconate, hemisulfate, heptanate, hexanoate, hydroiodate, 2-hydroxyethanesulfonate, lactoate, lactate, laurate, lauryl sulfate, malate, malonate, methanesulfonate, 2-naphthalenesulfonate, niacin, nitrate, oleate, oxalate, palmitate, dihydroxynaphthalenate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like. Pharmaceutically acceptable salts derived from suitable bases include alkali metals, alkaline earth metals, ammonium and N$^+$ (C$_{1-4}$ alkyl)$_4$ salts. Representative alkali metal or alkaline earth metal salts include sodium, lithium, potassium, calcium, magnesium salts, and the like. If appropriate, other pharmaceutically acceptable salts include nontoxic ammonium salts, quaternary ammonium salts and amine cations formed with counter ions such as halogen ions, hydroxyl radicals, carboxylate radicals, sulfate radical, phosphate radicals, nitrate radicals, lower alkylsulfonate radicals and arylsulfonate radicals.

"Subjects" administered include, but are not limited to, human (i.e., men or women of any age group, e.g., pediatric subjects (e.g., infants, children, and adolescents) or adult subjects (e.g., young adults, middle-aged adults or older adults) and/or non-human animals, for example, mammals, such as primates (e.g., cynomolgus monkeys, and rhesus monkeys), cattle, pigs, horses, sheep, goats, rodents, cats and/or dogs. In some embodiments, the subject is a human. In some embodiments, the subject is a non-human animal.

"Disease," "disturbance" and "disorder" herein are used interchangeably.

Unless otherwise specified, the term "treatment" as used herein includes the effect occurring in a subject suffering from a specific disease, disturbance or disorder, of reducing the severity of the disease, disturbance or disorder, or delaying or slowing the development of the disease, disturbance or disorder ("therapeutic treatment"), and it also includes the effect occurring before the subject begins to suffer from a specific disease, disturbance, or disorder ("prophylactic treatment").

Generally, the "effective amount" of a compound refers to the amount sufficient to cause the target biological reaction. As understood by those of ordinary skill in the art, the effective amount of the compound of the present invention can be changed according to, for example, biological objectives, pharmacokinetics of the compound, the disease to be treated, the dosage mode, and age, health and symptoms of the subjects. The effective amount includes the therapeutically effective amount and the prophylactically effective amount.

Unless otherwise stated, the "therapeutically effective amount" of the compound used herein is an amount sufficient to provide therapeutic benefits in the process of treating a disease, disturbance or disorder, or an amount to delay or minimize one or more symptoms associated with the disease, disturbance or disorder. The therapeutically effective amount of the compound refers to the amount of the therapeutic agent when used alone or in combination with other therapies, and provides therapeutic benefits in the process of treating the disease, disturbance or disorder. The term "therapeutically effective amount" may include the amount needed to improve the treatment overall, the amount needed to reduce or avoid symptoms or causes of the disease or disorder, or the amount needed to enhance the therapeutic effect of other therapeutic agents.

Unless otherwise stated, the "prophylactically effective amount" of the compound used herein is an amount sufficient to prevent a disease, disturbance or disorder, or an amount sufficient to prevent one or more symptoms associated with the disease, disturbance or disorder, or an amount to prevent the recurrence of the disease, disturbance or disorder. The prophylactically effective amount of the compound refers to the amount of the therapeutic agent when used alone or in combination with other agents, and provides prophylactical benefits in the process of preventing the disease, disturbance or disorder. The term "prophylactically effective amount" may include the amount needed to improve the overall prevention, or the amount needed to enhance the prophylactical effect of other prophylactical agents.

"Combination" and related terms refer to simultaneous or sequential dosage of the compound of the present invention and other therapeutic agents. For example, the compound of the present invention may be administered simultaneously or sequentially with other therapeutic agents in separate unit dosage forms, or simultaneously with other therapeutic agents in a single unit dosage form.

The "prodrug" refers to a compound that is converted into an active form with a medical effect in the body by hydrolysis, for example, in the blood. Pharmaceutically acceptable prodrugs are described in T. Higuchi and V. Stella, *Prodrugs as Novel Delivery Systems*, A.C.S. Symposium Series, Vol. 14; Edward B. Roche, ed., *Bioreversible Carriers in Drug Design*, American Pharmaceutical Association and Pergamon Press (1987); and D. Fleisher, S. Ramon and H. Barbra, "Improved Oral Drug Delivery: Solubility Limitations Overcome by the Use of Prodrugs," *Advanced Drug Delivery Reviews* (1996) 19(2): 115-130, each of which is incorporated herein as a reference.

The prodrug is any covalently bonded carrier, and releases the compound of the present invention in vivo when this prodrug is given to a patient. Prodrugs are usually prepared by modifying functional groups, and this modification makes the prodrugs split in vivo to produce parent compounds. A prodrug includes, for example, the compound of the present invention in which hydroxy, amino or mercapto is bonded to any group, and when the prodrug is given to a patient, it can split to form hydroxy, amino or mercapto. Therefore, representative examples of prodrugs include, but are not limited to, covalent derivatives of the compound according to the present invention formed with acetic acid, formic acid or benzoic acid through the hydroxy, amino or mercapto functional groups therein. In addition, in the case of carboxylic acid (—COOH), esters, such as methyl ester and ethyl ester, can be used. The ester itself can be active, and/or hydrolyzable at the condition within the human body. Suitable pharmaceutically acceptable in vivo hydrolyzable esters include those that are easy to decompose in the human body and release the parent acid or salts thereof.

It shall be understood by those of skill in the art that, many organic compounds can form composites with a solvent in which they react, precipitate, or crystallize therefrom. These composites are referred to as "solvates." When the solvent is water, the composites are referred to as "hydrates." The present invention encompasses all solvates of the compound according to the present invention.

The compound of the present invention may include one or more asymmetric centers, and thus may have multiple stereoisomer forms, e.g., enantiomer, diastereomer, and racemate forms. For example, the compound of the present invention may be a separate enantiomer, diastereomer, or geometric isomer (e.g., cis and trans-isomers), or may be in the form of a mixture of stereoisomers, including racemic mixtures and mixtures rich in one or more stereoisomers. Isomers may be separated from mixtures by methods known to those of skill in the art, including: chiral high-pressure liquid chromatography (HPLC) and the formation and crystallization of chiral salts; or preferred isomers may be prepared by asymmetric synthesis.

In addition, the compound of the present invention can also exist as a "tautomer." "Tautomers" refer to isomers produced by the phenomenon of equilibrium and mutual conversion between two functional groups due to the structure of the organic compound.

Compound

In one embodiment, the present invention provides a compound as shown in the general formula (I) or a pharmaceutically acceptable salt, tautomer, racemate, enantiomer, diastereoisomer, prodrug, hydrate or solvate thereof, and a mixture thereof:

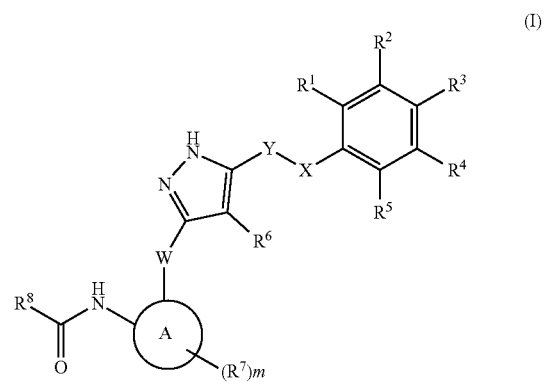

(I)

wherein
ring A is not present or is selected from the group consisting of 6-14 membered arylene, 5-10 membered heteroarylene, $C_3$-$C_8$ cycloalkylene and 3-10 membered heterocyclylene;
$R^1$, $R^2$, $R^3$, $R^4$ and $R^5$ are each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^{13}$;
$R^6$ is each independently selected from the group consisting of H and —$CH_2CH_2$—, and when $R^6$ is —$CH_2CH_2$—, the other end thereof is connected to X, and optionally one methylene group of —$CH_2CH_2$— is replaced with —O— or —NH—;
$R^7$ is each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$ or —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl (e.g., 6 membered heterocyclyl), which is optionally substituted by $C_1$-$C_6$ alkyl or $C_1$-$C_6$ haloalkyl;
$R^8$ is selected from the group consisting of optionally substituted $C_2$-$C_6$ alkenyl and $C_2$-$C_6$ alkynyl; $R^{11}$, $R^{12}$ and $R^{13}$ are each independently selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl;
X is selected from the group consisting of —O—, —NH— and —$CH_2$—; and Y is selected from the group consisting of —O—, —NH— and —$CH_2$—; provided that at least one of X and Y is $CH_2$;
W is selected from the group consisting of a chemical bond, —NH— and —$CH_2$—;
m is 0, 1, 2, 3 or 4; and
p is 1 or 2.

In particular embodiments, $R^1$, $R^2$, $R^3$, $R^4$ and $R^5$ are each independently selected from the group consisting of H, halogen, $C_1$-$C_6$ alkyl, $C_1$-$C_6$ haloalkyl, $C_1$-$C_6$ alkoxy and $C_1$-$C_6$ haloalkoxy.

In particular embodiments, $R^1$ and $R^5$ are each independently halogen, and preferably Cl or F.

In particular embodiments, $R^2$ and $R^4$ are each independently $C_1$-$C_6$ alkoxy, and preferably methoxy.

In particular embodiments, $R^3$ is H.

In particular embodiments, $R^6$ is H.

In particular embodiments, $R^7$ is each independently selected from the group consisting of H, $C_1$-$C_6$ alkyl, $C_1$-$C_6$ haloalkyl or —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl, or $R^a$ and $R^b$ together with the N atom connected thereto form 3-10 membered heterocyclyl (e.g., 6 membered heterocyclyl), which is optionally substituted by $C_1$-$C_6$ alkyl or $C_1$-$C_6$ haloalkyl; and preferably $R^7$ is selected from the group consisting of H, $C_1$-$C_6$ alkyl and —$NR^aR^b$, and preferably methyl or —$N(CH_3)CH_2CH_2N(CH_3)_2$. In particular embodiments, $R^8$ is selected from the group consisting of $C_2$-$C_6$ alkenyl and $C_2$-$C_6$ alkynyl, and is preferably selected from the group consisting of vinyl and propynyl.

In particular embodiments, ring A is 6-14 membered arylene, and preferably 6 membered arylene.

In particular embodiments, ring A is 5-10 membered heteroarylene, preferably 5-6 membered heteroarylene, and preferably 5 membered heteroarylene.

In particular embodiments, ring A is $C_3$-$C_8$ cycloalkylene.

In particular embodiments, ring A is selected from the group consisting of bivalent radicals of phenyl, naphthyl, pyrrolyl, furyl, thienyl, imidazolyl, pyrazolyl, oxazolyl, isooxazolyl, thiazyl, isothiazolyl, triazolyl, oxadiazolyl, thiadiazolyl, tetrazolyl, pyridinyl, pyridazinyl, pyrimidinyl, pyrazinyl, triazinyl, tetrazinyl and cyclohexyl, and preferably ring A is selected from the group consisting of phenylene, pyrazolylene and cyclohexylene; In particular embodiments, W is a chemical bond.

In particular embodiments, m is 1.

In another embodiment, the present invention provides a compound as shown in the general formula (II) or a pharmaceutically acceptable salt, tautomer, racemate, enantiomer, diastereoisomer, prodrug, hydrate or solvate thereof, and a mixture thereof:

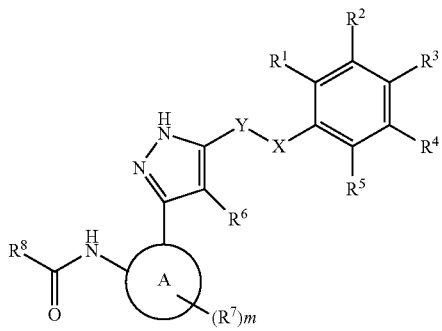

(II)

wherein
ring A is not present or is selected from the group consisting of 6-14 membered arylene, 5-10 membered heteroarylene, $C_3$-$C_8$ cycloalkylene and 3-10 membered heterocyclylene;
$R^1$, $R^2$, $R^3$, $R^4$ and $R^5$ are each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^5$;

$R^6$ is each independently selected from the group consisting of H and —$CH_2CH_2$—, and when $R^6$ is —$CH_2CH_2$—, the other end thereof is connected to X, and optionally one methylene of —$CH_2CH_2$— is replaced by —O— or —NH—;

$R^7$ is each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$ or —$NR^aR^b$, wherein
$R^a$ and $R^b$ are each independently selected from the group consisting of H and $C_1$-$C_6$ alkyl optionally substituted by —$NR^cR^d$; and $R^c$ and $R^d$ are each independently selected from the group consisting of H and $C_1$-$C_6$ alkyl;
$R^8$ is selected from the group consisting of optionally substituted $C_2$-$C_6$ alkenyl and $C_2$-$C_6$ alkynyl;
$R^{11}$, $R^{12}$ and $R^{13}$ are each independently selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl;
X is selected from the group consisting of —O—, —NH— and —$CH_2$—; and Y is selected from the group consisting of —O—, —NH— and —$CH_2$—; provided that at least one of X and Y is $CH_2$;
m is 0, 1, 2, 3 or 4; and
p is 1 or 2.

In particular embodiments, ring A is 6-14 membered arylene, and preferably 6 membered arylene.

In particular embodiments, ring A is 5-10 membered heteroarylene, preferably 5-6 membered heteroarylene, and preferably 5 membered heteroarylene.

In particular embodiments, ring A is $C_3$-$C_8$ cycloalkylene.

In particular embodiments, ring A is selected from the group consisting of bivalent radicals of phenyl, naphthyl, pyrrolyl, furyl, thienyl, imidazolyl, pyrazolyl, oxazolyl, isooxazolyl, thiazyl, isothiazolyl, triazolyl, oxadiazolyl, thiadiazolyl, tetrazolyl, pyridinyl, pyridazinyl, pyrimidinyl, pyrazinyl, triazinyl, tetrazinyl and cyclohexyl, and preferably ring A is selected from the group consisting of phenylene, pyrazolylene and cyclohexylene;

In particular embodiments, $R^1$, $R^2$, $R^3$, $R^4$ and $R^5$ are each independently selected from the group consisting of H, halogen, $C_1$-$C_6$ alkyl, $C_1$-$C_6$ haloalkyl, $C_1$-$C_6$ alkoxy and $C_1$-$C_6$ haloalkoxy.

In particular embodiments, $R^1$ and $R^5$ are each independently halogen, and preferably Cl or F.

In particular embodiments, $R^2$ and $R^4$ are each independently $C_1$-$C_6$ alkoxy, and preferably methoxy.

In particular embodiments, $R^3$ is H.

In particular embodiments, $R^6$ is each independently selected from the group consisting of H and —$CH_2CH_2$—, and when $R^6$ is —$CH_2CH_2$—, the other end thereof is connected to X. In particular embodiments, $R^6$ is H.

In particular embodiments, $R^6$ is selected from H.

In particular embodiments, $R^7$ is each independently selected from the group consisting of H, $C_1$-$C_6$ alkyl, $C_1$-$C_6$ haloalkyl and —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl, and $R^7$ is preferably selected from the group consisting of H, $C_1$-$C_6$ alkyl and —$NR^aR^b$, preferably methyl or —$N(CH_3)CH_2CH_2N(CH_3)_2$, and preferably H.

In particular embodiments, $R^8$ is selected from the group consisting of $C_2$-$C_6$ alkenyl and $C_2$-$C_6$ alkynyl, and is preferably selected from the group consisting of vinyl and propynyl.

In particular embodiments, X is selected from the group consisting of —O—, —NH— and —$CH_2$—; and Y is selected from the group consisting of —O—, —NH— and —CH$_2$—; provided that at least one of X and Y is CH$_2$;

In particular embodiments, X is —CH$_2$—; and Y is selected from the group consisting of —O—, —NH— and —CH$_2$—; and In particular embodiments, m is 1.

In another embodiment, the present invention provides a compound as shown in the general formula (III) or a pharmaceutically acceptable salt, tautomer, racemate, enantiomer, diastereoisomer, prodrug, hydrate or solvate thereof, and a mixture thereof:

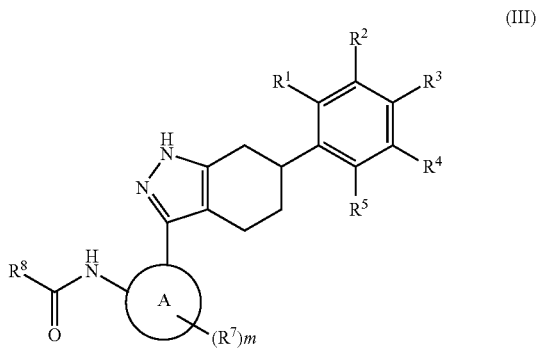

(III)

wherein
ring A is not present or is selected from the group consisting of 6-14 membered arylene, 5-10 membered heteroarylene, C$_3$-C$_8$ cycloalkylene and 3-10 membered heterocyclylene; R$^1$, R$^2$, R$^3$, R$^4$ and R$^5$ are each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR$^{13}$, —NR$^{11}$R$^{12}$, —C(O)R$^{13}$, —C(O)OR$^{13}$, —C(O)NR$^{11}$R$^{12}$, —NR$^{11}$C(O)R$^{13}$, —NR$^{11}$C(O)OR$^{13}$, —NR$^{11}$C(O)NR$^{11}$R$^{12}$, —OC(O)R$^{13}$, —OC(O)OR$^{13}$, —OC(O)NR$^{11}$R$^{12}$, —S(O)$_p$R$^{13}$, —S(O)$_p$OR$^{13}$, —S(O)$_p$NR$^{11}$R$^{12}$, —OS(O)$_p$R$^{13}$ and —NR$^{11}$S(O)$_p$R$^3$;
R$^7$ is each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR$^{13}$ or —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl; or R$^a$ and R$^b$ together with the N atom connected thereto form 3-10 membered heterocyclyl (e.g., 6 membered heterocyclyl), which is optionally substituted by C$_1$-C$_6$ alkyl or C$_1$-C$_6$ haloalkyl;
R$^8$ is selected from the group consisting of optionally substituted C$_2$-C$_6$ alkenyl and C$_2$-C$_6$ alkynyl;
R$^{11}$, R$^{12}$ and R$^{13}$ are each independently selected from the group consisting of H, C$_1$-C$_6$ alkyl, C$_1$-C$_6$ heteroalkyl, C$_3$-C$_8$ cycloalkyl, 3-10 membered heterocyclyl, 5-10 membered heteroaryl and 6-14 membered aryl;
m is 0, 1, 2, 3 or 4; and
p is 1 or 2.

In particular embodiments, ring A is 6-14 membered arylene, and preferably 6 membered arylene.

In particular embodiments, ring A is 5-10 membered heteroarylene, preferably 5-6 membered heteroarylene, and preferably 5 membered heteroarylene.

In particular embodiments, ring A is C$_3$-C$_8$ cycloalkylene.

In particular embodiments, ring A is selected from the group consisting of bivalent radicals of phenyl, naphthyl, pyrrolyl, furyl, thienyl, imidazolyl, pyrazolyl, oxazolyl, isooxazolyl, thiazyl, isothiazolyl, triazolyl, oxadiazolyl, thiadiazolyl, tetrazolyl, pyridinyl, pyridazinyl, pyrimidinyl, pyrazinyl, triazinyl, tetrazinyl and cyclohexyl, and preferably ring A is selected from the group consisting of phenylene, pyrazolylene and cyclohexylene;

In particular embodiments, R$^1$, R$^2$, R$^3$, R$^4$ and R$^5$ are each independently selected from the group consisting of H, halogen, C$_1$-C$_6$ alkyl, C$_1$-C$_6$ haloalkyl, C$_1$-C$_6$ alkoxy and C$_1$-C$_6$ haloalkoxy.

In particular embodiments, R$^1$ and R$^5$ are each independently selected from the group consisting of H and halogen, and preferably H, Cl or F.

In particular embodiments, R$^1$ and R$^5$ are each independently halogen, and preferably Cl or F.

In particular embodiments, R$^2$ and R$^4$ are each independently C$_1$-C$_6$ alkoxy, and preferably methoxy.

In particular embodiments, R$^3$ is H.

In particular embodiments, R$^7$ is each independently selected from the group consisting of H, halogen, C$_1$-C$_6$ alkyl, C$_1$-C$_6$ haloalkyl and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl; or R$^a$ and R$^b$ together with the N atom connected thereto form 3-10 membered heterocyclyl (e.g., 6 membered heterocyclyl), which is optionally substituted by C$_1$-C$_6$ alkyl or C$_1$-C$_6$ haloalkyl; and R$^7$ is preferably selected from the group consisting of H, halogen, methyl, —N(CH$_3$)CH$_2$CH$_2$N(CH$_3$)$_2$, —N(CH$_3$)$_2$, 4-alkyl-piperazinyl and morpholinyl, preferably H, halogen, methyl, —N(CH$_3$)CH$_2$CH$_2$N(CH$_3$)$_2$, —N(CH$_3$)$_2$ or 4-methyl-piperazinyl, preferably H, methyl, —N(CH$_3$)CH$_2$CHN(CH$_3$)$_2$ or 4-methyl-piperazinyl, preferably H or C$_1$-C$_6$ alkyl or —NR$^a$R$^b$, and preferably methyl or —N(CH$_3$)CH$_2$CH$_2$N(CH$_3$)$_2$.

In particular embodiments, R$^8$ is selected from the group consisting of C$_2$-C$_6$ alkenyl and C$_2$-C$_6$ alkynyl, preferably selected from the group consisting of vinyl and propynyl, and preferably vinyl.

In particular embodiments, m is 1.

In another embodiment, the present invention provides a compound as shown in the general formula (IV) or a pharmaceutically acceptable salt, tautomer, racemate, enantiomer, diastereoisomer, prodrug, hydrate or solvate thereof, and a mixture thereof:

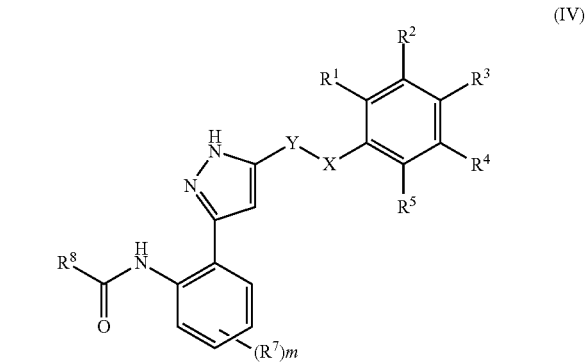

(IV)

wherein
R$^1$, R$^2$, R$^3$, R$^4$ and R$^5$ are each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR$^{13}$, —NR$^{11}$R$^{12}$, —C(O)R$^{13}$, —C(O)OR$^{13}$, —C(O)NR$^{11}$R$^{12}$, —NR$^{11}$C(O)R$^{13}$, —NR$^{11}$C(O)OR$^{13}$, —NR$^{11}$C(O)NR$^{11}$R$^{12}$, —OC(O)R$^{13}$, —OC(O)OR$^{13}$, —OC(O)NR$^{11}$R$^{12}$, —S(O)R$^{13}$, —S(O)$_p$OR$^{13}$, —S(O)$_p$NR$^{11}$R$^{12}$, —OS(O)$_p$R$^3$ and —NR$^{11}$S(O)$_p$R$^3$;

R[7] is each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR[13] and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl;

R[8] is selected from the group consisting of optionally substituted C$_2$-C$_6$ alkenyl and C$_2$-C$_6$ alkynyl;

R[11], R[12] and R[13] are each independently selected from the group consisting of H, C$_1$-C$_6$ alkyl, C$_1$-C$_6$ heteroalkyl, C$_3$-C$_8$ cycloalkyl, 3-10 membered heterocyclyl, 5-10 membered heteroaryl and 6-14 membered aryl;

X is selected from the group consisting of —O—, —NH— and —CH$_2$—; and Y is selected from the group consisting of —O—, —NH— and —CH$_2$—; provided that at least one of X and Y is CH$_2$;

m is 0, 1, 2, 3 or 4; and p is 1 or 2.

In particular embodiments, R[1], R[2], R[3], R[4] and R[5] are each independently selected from the group consisting of H, halogen, C$_1$-C$_6$ alkyl, C$_1$-C$_6$ haloalkyl, C$_1$-C$_6$ alkoxy and C$_1$-C$_6$ haloalkoxy.

In particular embodiments, R[1] and R[5] are each independently halogen, and preferably Cl or F.

In particular embodiments, R[2] and R[4] are each independently C$_1$-C$_6$ alkoxy, and preferably methoxy.

In particular embodiments, R[3] is H.

In particular embodiments, R[7] is each independently selected from the group consisting of H, C$_1$-C$_6$ alkyl, C$_1$-C$_6$ haloalkyl and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl, and R[7] is preferably selected from the group consisting of H, C$_1$-C$_6$ alkyl and —NR$^a$R$^b$, and preferably methyl or —N(CH$_3$)CH$_2$CH$_2$N(CH$_3$)$_2$.

In particular embodiments, R[8] is selected from the group consisting of C$_2$-C$_6$ alkenyl and C$_2$-C$_6$ alkynyl, and is preferably selected from the group consisting of vinyl and propynyl.

In particular embodiments, X is —NH—, and Y is —CH$_2$—.

In particular embodiments, X is —CH$_2$—, and Y is —NH—.

In particular embodiments, m is 1.

In another embodiment, the present invention provides a compound as shown in the general formula (V) or a pharmaceutically acceptable salt, tautomer, racemate, enantiomer, diastereoisomer, prodrug, hydrate or solvate thereof, and a mixture thereof:

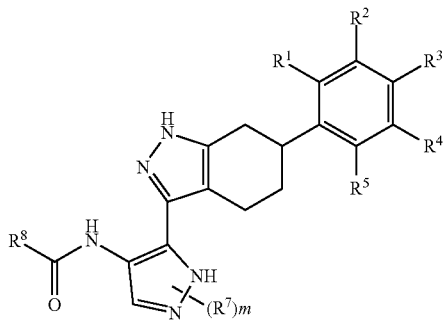

(V)

wherein

R[1], R[2], R[3], R[4] and R[5] are each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR[13], —NR[11]R[12], —C(O)R[13], —C(O)OR[13], —C(O)NR[11]R[12], —NR[11]C(O)R[13], —NR[11]C(O)OR[13], —NR[11]C(O)NR[11]R[12], —OC(O)R[13], —OC(O)OR[13], —OC(O)NR[11]R[12], —S(O)$_p$R[13], —S(O)$_p$OR[13], —S(O)$_p$NR[11]R[12], —OS(O)$_p$R[13] and —NR[11]S(O)$_p$R[13];

R[7] is each independently selected from the group consisting of H, halogen, cyano, NO$_2$, C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, —OR[13] and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl;

R[8] is selected from the group consisting of optionally substituted C$_2$-C$_6$ alkenyl and C$_2$-C$_6$ alkynyl;

R[11], R[12] and R[13] are each independently selected from the group consisting of H, C$_1$-C$_6$ alkyl, C$_1$-C$_6$ heteroalkyl, C$_3$-C$_8$ cycloalkyl, 3-10 membered heterocyclyl, 5-10 membered heteroaryl and 6-14 membered aryl;

m is 0, 1 or 2; and p is 1 or 2.

In particular embodiments, R[1], R[2], R[3], R[4] and R[5] are each independently selected from the group consisting of H, halogen, C$_1$-C$_6$ alkyl, C$_1$-C$_6$ haloalkyl, C$_1$-C$_6$ alkoxy and C$_1$-C$_6$ haloalkoxy.

In particular embodiments, R[1] and R[5] are each independently selected from the group consisting of H and halogen, and preferably H, Cl or F.

In particular embodiments, R[1] and R[5] are each independently halogen, and preferably Cl or F.

In particular embodiments, R[2] and R[4] are each independently C$_1$-C$_6$ alkoxy, and preferably methoxy.

In particular embodiments, R[3] is H.

In particular embodiments, R[7] is each independently selected from the group consisting of H, C$_1$-C$_6$ alkyl, C$_1$-C$_6$ haloalkyl and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl, and R[7] is preferably selected from the group consisting of H, C$_1$-C$_6$ alkyl and —NR$^a$R$^b$, preferably methyl or —N(CH$_3$)CH$_2$CH$_2$N(CH$_3$)$_2$, and preferably H or methyl.

In particular embodiments, R[8] is selected from the group consisting of C$_2$-C$_6$ alkenyl and C$_2$-C$_6$ alkynyl, preferably selected from the group consisting of vinyl and propynyl, and preferably vinyl.

In particular embodiments, m is 1.

In another embodiment, the present invention provides a compound as shown in the general formula (VI) or a pharmaceutically acceptable salt, tautomer, racemate, enantiomer, diastereoisomer, prodrug, hydrate or solvate thereof, and a mixture thereof, which is a compound as shown in the general formula (VI):

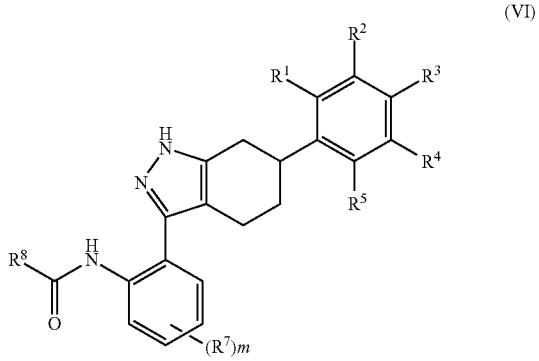

(VI)

wherein $R^1$, $R^2$, $R^3$, $R^4$ and $R^5$ are each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^3$;

$R^7$ is each independently selected from the group consisting of H, halogen, cyano, $NO_2$, C1-C6 alkyl, $C_1$-$C_6$ haloalkyl, C2-C6 alkenyl, C2-C6 alkynyl, C3-C8 cycloalkyl, —$OR^{13}$ or —$NR^aR^b$, wherein $R^a$ and $R^b$ are each independently selected from the group consisting of H and C1-C6 alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl (e.g., 6 membered heterocyclyl), which is optionally substituted by C1-C6 alkyl or $C_1$-$C_6$ haloalkyl;

$R^8$ is selected from the group consisting of optionally substituted $C_2$-$C_6$ alkenyl and $C_2$-$C_6$ alkynyl;

$R^{11}$, $R^{12}$ and $R^{13}$ are each independently selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl;

m is 0, 1, 2, 3 or 4; and p is 1 or 2.

In particular embodiments, $R^1$, $R^2$, $R^3$, $R^4$ and $R^5$ are each independently selected from the group consisting of H, halogen, $C_1$-$C_6$ alkyl, $C_1$-$C_6$ haloalkyl, $C_1$-$C_6$ alkoxy and $C_1$-$C_6$ haloalkoxy.

In particular embodiments, $R^1$ and $R^5$ are each independently selected from the group consisting of H and halogen, and preferably H, Cl or F.

In particular embodiments, $R^1$ and $R^5$ are each independently halogen, and preferably Cl or F.

In particular embodiments, $R^2$ and $R^4$ are each independently $C_1$-$C_6$ alkoxy, and preferably methoxy.

In particular embodiments, $R^3$ is H.

In particular embodiments, $R^7$ is each independently selected from the group consisting of H, $C_1$-$C_6$ alkyl, $C_1$-$C_6$ haloalkyl and —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl, or $R^a$ and $R^b$ together with the N atom connected thereto form 3-10 membered heterocyclyl (e.g., 6 membered heterocyclyl), which is optionally substituted by $C_1$-$C_6$ alkyl or $C_1$-$C_6$ haloalkyl; and $R^7$ is preferably selected from the group consisting of H, halogen, methyl, —$N(CH_3)CH_2CH_2N(CH_3)_2$, —$N(CH_3)_2$, 4-alkyl-piperazinyl and morpholinyl, preferably H, halogen, —$N(CH_3)CH_2CH_2N(CH_3)_2$, —$N(CH_3)_2$ or 4-methyl-piperazinyl, preferably H, —$N(CH_3)CH_2CH_2N(CH_3)_2$ or 4-methyl-piperazinyl, preferably H or $C_1$-$C_6$ alkyl or —$NR^aR^b$, and preferably methyl or —$N(CH_3)CH_2CH_2N(CH_3)_2$.

In particular embodiments, $R^8$ is selected from the group consisting of $C_2$-$C_6$ alkenyl and $C_2$-$C_6$ alkynyl, preferably selected from the group consisting of vinyl and propynyl, and preferably vinyl.

In particular embodiments, m is 1.

In another embodiment, the present invention provides a compound as shown in the general formula (VII) or a pharmaceutically acceptable salt, tautomer, racemate, enantiomer, diastereoisomer, prodrug, hydrate or solvate thereof, and a mixture thereof, which is a compound as shown in the general formula (VI):

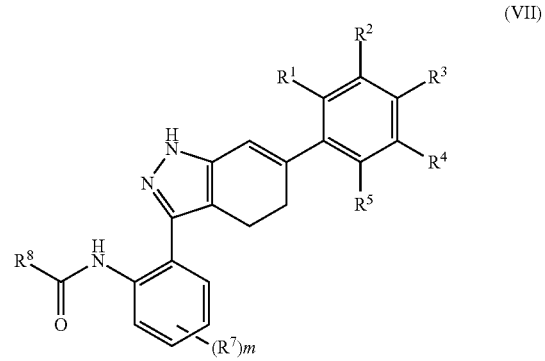

(VII)

wherein $R^1$ and $R^5$ are each independently halogen, and are preferably selected from the group consisting of Cl and F;

$R^2$ and $R^4$ are each independently $C_1$-$C_6$ alkoxy, and preferably —$OCH_3$;

$R^3$ is H;

$R^7$ is each independently selected from the group consisting of halogen, $C_1$-$C_6$ alkyl, $C_1$-$C_6$ haloalkyl or —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl (e.g., 6 membered heterocyclyl), which is optionally substituted by $C_1$-$C_6$ alkyl or $C_1$-$C_6$ haloalkyl; and preferably, $R^7$ is selected from the group consisting of halogen, methyl, —$N(CH_3)_2$, and morpholinyl; $R^8$ is optionally substituted $C_2$-$C_6$ alkenyl; and preferably, $R^8$ is vinyl;

m is 0, 1, 2, 3 or 4; preferably, m is 0, 1 or 2; and preferably, m is 1.

Typical compounds of the present invention include, but are not limited to:

| Compound number | Compound structure and name |
|---|---|
| 010 | 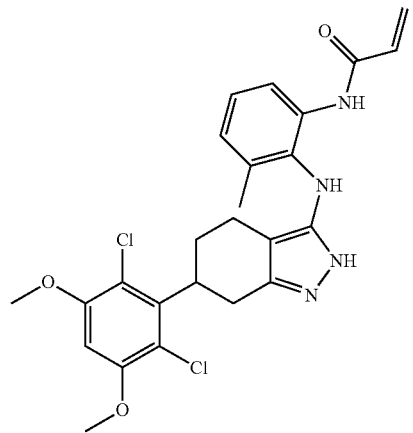 [SMILES: C=CC(=O)Nc1cccc(C)c1Nc1[nH]nc2c1CCC(c1c(Cl)c(OC)cc(OC)c1Cl)C2]<br>N-(2-((6-(2,6-dichloro-3,5-dimethoxyphenyl)-4,5,6,7-tetrahydro-1H-indazol-3-yl)amino)-3-methylphenyl)acrylamide |
| 015 | 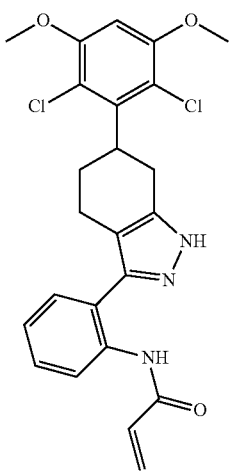<br>N-(2-(6-(2,6-dichloro-3,5-dimethoxyphenyl)-4,5,6,7-tetrahydro-1H-indazol-3-yl)phenyl)acrylamide |
| 027 | 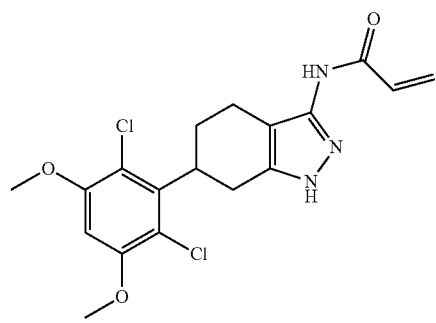 [SMILES: C=CC(=O)Nc1n[nH]c2c1CCC(c1c(Cl)c(OC)cc(OC)c1Cl)C2]<br>N-(6-(2,6-dichloro-3,5-dimethoxyphenyl)-4,5,6,7-tetrahydro-1H-indazol-3-yl)acrylamide |

-continued
| Compound number | Compound structure and name |
|---|---|
| 083 | 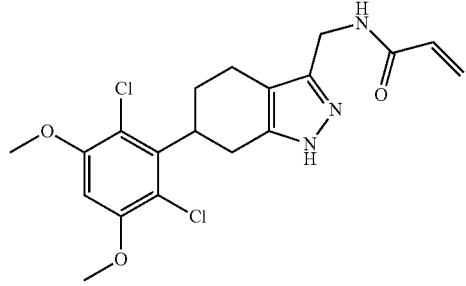 [SMILES: C=CC(=O)NCc1n[nH]c2c1CCC(c1c(Cl)c(OC)cc(OC)c1Cl)C2]<br>N-((6-(2,6-dichloro-3,5-dimethoxyphenyl)-4,5,6,7-tetrahydro-1H-indazol-3-yl)methyl)acrylamide |
| 091 | 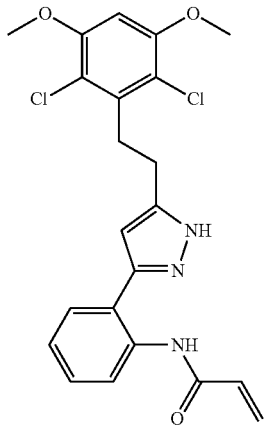 [SMILES: C=CC(=O)Nc1ccccc1-c1cc(CCc2c(Cl)c(OC)cc(OC)c2Cl)[nH]n1]<br>N-(2-(5-(2,6-dichloro-3,5-dimethoxyphenethyl)-1H-pyrazol-3-yl)phenyl)acrylamide |
| 093 | 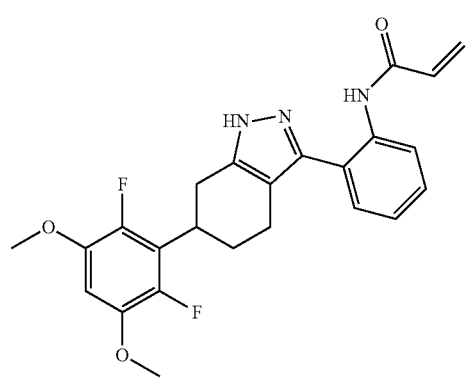 [SMILES: C=CC(=O)Nc1ccccc1-c1n[nH]c2c1CCC(c1c(F)c(OC)cc(OC)c1F)C2]<br>N-(2-(6-(2,6-difluoro-3,5-dimethoxyphenyl)-4,5,6,7-tetrahydro-1H-indazol-3-yl)phenyl)acrylamide |

-continued
| Compound number | Compound structure and name |
|---|---|
| 096 | 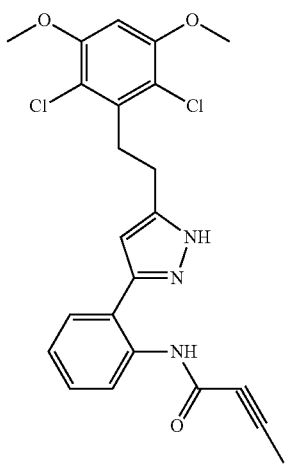 [SMILES: CC#CC(=O)Nc1ccccc1-c1cc(CCc2c(Cl)c(OC)cc(OC)c2Cl)[nH]n1]  N-(2-(5-(2,6-dichloro-3,5-dimethoxyphenethyl)-1H-pyrazol-3-yl)phenyl)but-2-ynoic amide |
| 098 | 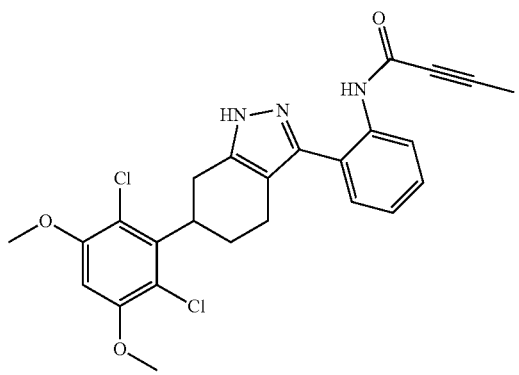 [SMILES: CC#CC(=O)Nc1ccccc1-c1n[nH]c2c1CCC(c1c(Cl)c(OC)cc(OC)c1Cl)C2]  N-(2-(6-(2,6-dichloro-3,5-dimethoxyphenyl)-4,5,6,7-tetrahydro-1H-indazol-3-yl)phenyl)but-2-ynoic amide |
| 100 | 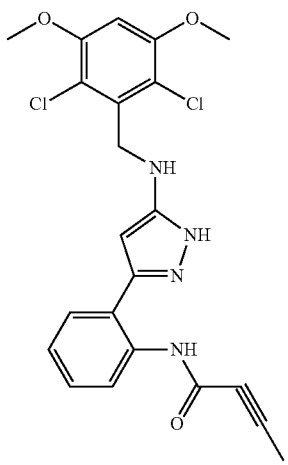 [SMILES: CC#CC(=O)Nc1ccccc1-c1cc(NCc2c(Cl)c(OC)cc(OC)c2Cl)[nH]n1]  N-(2-(5-(2,6-dichloro-3,5-dimethoxybenzylamino)-1H-pyrazol-3-yl)phenyl)but-2-ynoic amide |

| Compound number | Compound structure and name |
|---|---|
| 101 | 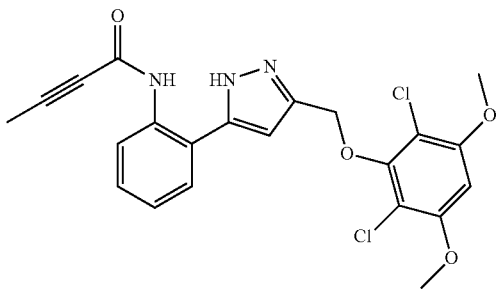 [SMILES: CC#CC(=O)Nc1ccccc1-c1cc(COc2c(Cl)c(OC)cc(OC)c2Cl)n[nH]1]<br>N-(2-(3-((2,6-dichloro-3,5-dimethoxyphenoxy)methyl)-1H-pyrazol-5-yl)phenyl)but-2-ynoic amide |
| 102 | 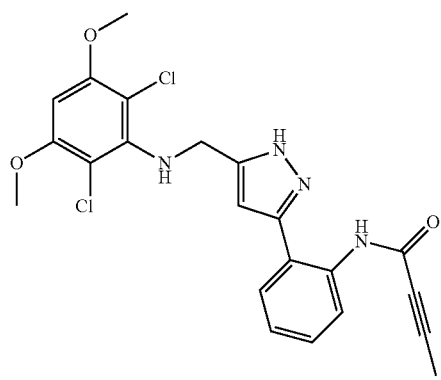 [SMILES: CC#CC(=O)Nc1ccccc1-c1cc(CNc2c(Cl)c(OC)cc(OC)c2Cl)[nH]n1]<br>N-(2-(5-(((2,6-dichloro-3,5-dimethoxyphenyl)amino)methyl)-1H-pyrazol-3-yl)phenyl)but-2-ynoic amide |
| 103 | 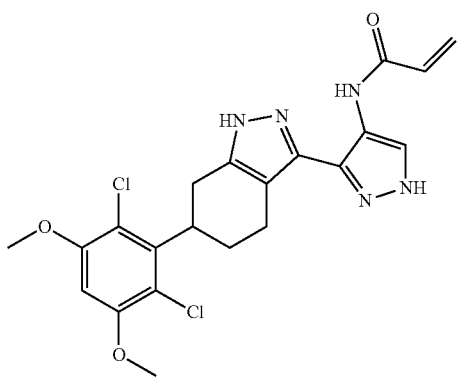 [SMILES: C=CC(=O)Nc1c[nH]nc1-c1n[nH]c2c1CCC(c1c(Cl)c(OC)cc(OC)c1Cl)C2]<br>N-(3-(6-(2,6-dichloro-3,5-dimethoxyphenyl)-4,5,6,7-tetrahydro-1H-indazol-3-yl)-1H-pyrazol-4-yl)acrylamide |

-continued
| Compound number | Compound structure and name |
|---|---|
| 107 | 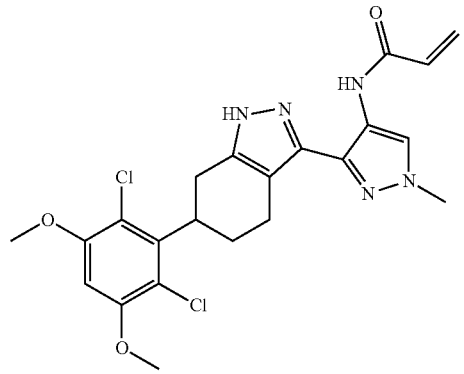 [SMILES: C=CC(=O)Nc1cn(C)nc1-c1n[nH]c2c1CCC(c1c(Cl)c(OC)cc(OC)c1Cl)C2]
N-(3-(6-(2,6-dichloro-3,5-dimethoxyphenyl)-4,5,6,7-tetrahydro-1H-indazol-3-yl)-1-methyl-1H-pyrazol-4-yl)acrylamide |
| 109 | 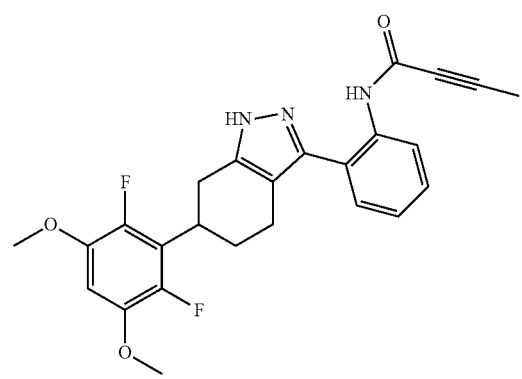 [SMILES: CC#CC(=O)Nc1ccccc1-c1n[nH]c2c1CCC(c1c(F)c(OC)cc(OC)c1F)C2]
N-(2-(6-(2,6-difluoro-3,5-dimethoxyphenyl)-4,5,6,7-tetrahydro-1H-indazol-3-yl)phenyl)but-2-ynoic amide |
| 111 | 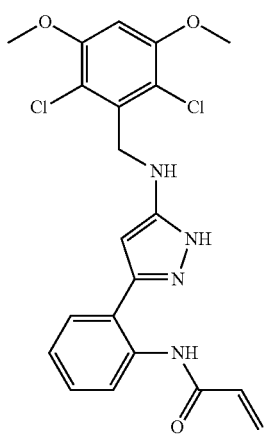 [SMILES: C=CC(=O)Nc1ccccc1-c1cc(NCc2c(Cl)c(OC)cc(OC)c2Cl)[nH]n1]
N-(2-(5-(2,6-dichloro-3,5-dimethoxybenzylamino)-1H-pyrazol-3-yl)phenyl)acrylamide |

-continued
| Compound number | Compound structure and name |
|---|---|
| 112 | 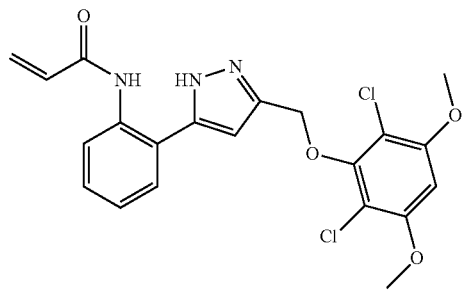 [SMILES: C=CC(=O)Nc1ccccc1-c1cc(COc2c(Cl)c(OC)cc(OC)c2Cl)n[nH]1]<br>N-(2-(3-((2,6-dichloro-3,5-dimethoxyphenoxy)methyl)-1H-pyrazol-5-yl)phenyl)acrylamide |
| 113 | 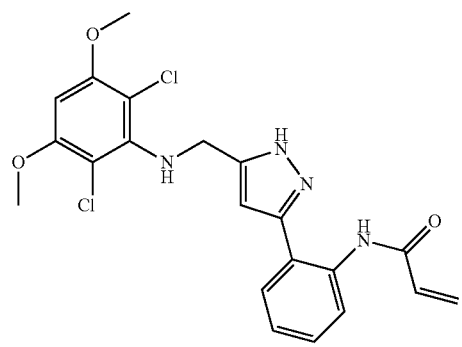 [SMILES: C=CC(=O)Nc1ccccc1-c1cc(CNc2c(Cl)c(OC)cc(OC)c2Cl)[nH]n1]<br>N-(2-(5-(((2,6-dichloro-3,5-dimethoxyphenyl)amino)methyl)-1H-pyrazol-3-yl)phenyl)acrylamide |
| 114 | 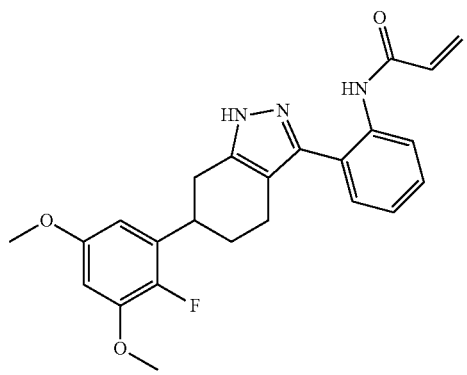 [SMILES: C=CC(=O)Nc1ccccc1-c1n[nH]c2c1CCC(c1cc(OC)cc(OC)c1F)C2]<br>N-(2-(6-(2-fluoro-3,5-dimethoxyphenyl)-4,5,6,7-tetrahydro-1H-indazol-3-yl)phenyl)acrylamide |

-continued
| Compound number | Compound structure and name |
|---|---|
| 117 | 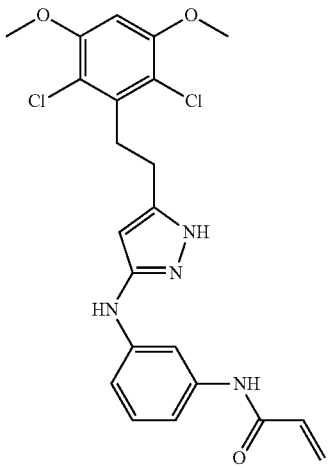 [SMILES: C=CC(=O)Nc1cccc(Nc2cc(CCc3c(Cl)c(OC)cc(OC)c3Cl)[nH]n2)c1]<br>N-(3-(5-(2,6-dichloro-3,5-dimethoxyphenethyl)-1H-pyrazol-3-ylamino)phenyl)acrylamide |
| 120 | 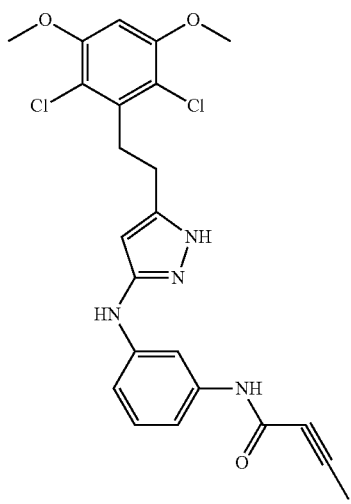 [SMILES: CC#CC(=O)Nc1cccc(Nc2cc(CCc3c(Cl)c(OC)cc(OC)c3Cl)[nH]n2)c1]<br>N-(3-(5-(2,6-dichloro-3,5-dimethoxyphenethyl)-1H-pyrazol-3-ylamino)phenyl)but-2-ynoic amide |
| 122 | 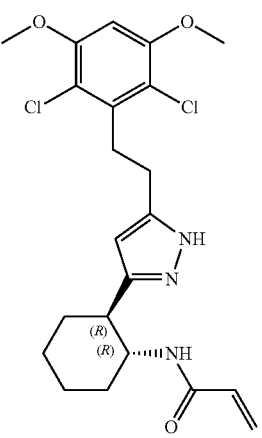<br>N-((1R,2R)-2-(5-(2,6-dichloro-3,5-dimethoxyphenethyl)-1H-pyrazol-3-yl)cyclohexyl)acrylamide |

| Compound number | Compound structure and name |
|---|---|
| 133 | 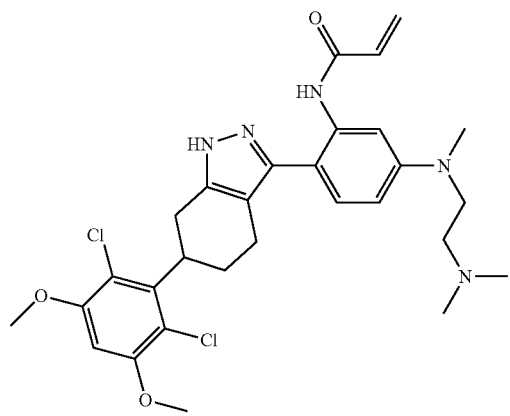<br>N-(2-(6-(2,6-dichloro-3,5-dimethoxyphenyl)-4,5,6,7-tetrahydro-1H-indazol-3-yl)-5-((2-(dimethylamino)ethyl)(methyl)amino)phenyl)acrylamide |
| 137 | 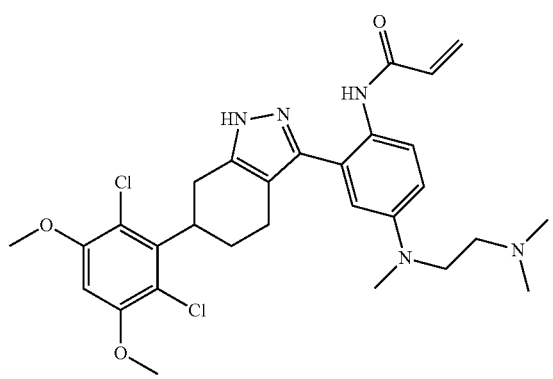<br>N-(2-(6-(2,6-dichloro-3,5-dimethoxyphenyl)-4,5,6,7-tetrahydro-1H-indazol-3-yl)-4-((2-(dimethylamino)ethyl)(methyl)amino)phenyl)acrylamide |
| 140 | 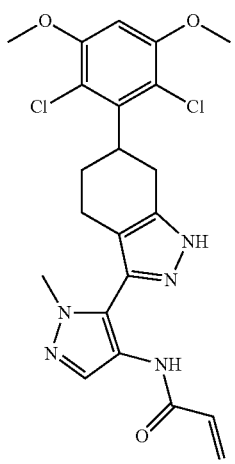<br>N-(5-(6-(2,6-dichloro-3,5-dimethoxyphenyl)-4,5,6,7-tetrahydro-1H-indazol-3-yl)-1-methyl-1H-pyrazol-4-yl)-2-carbonyl acetamide |

| Compound number | Compound structure and name |
|---|---|
| 015-P1 | 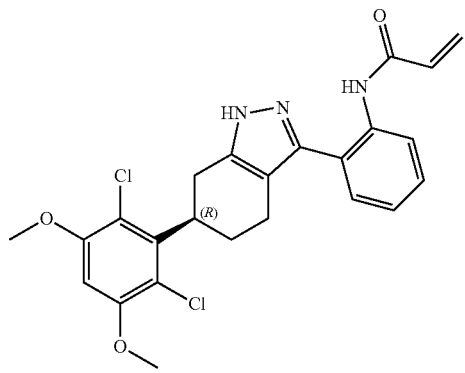<br>(R)-N-(2-(6-(2,6-dichloro-3,5-dimethoxyphenyl)-4,5,6,7-tetrahydro-1H-indazol-3-yl)phenyl)acrylamide |
| 015-P2 | 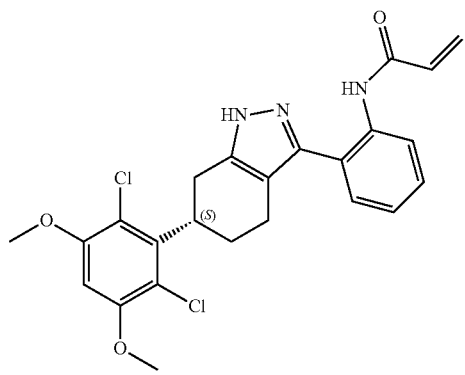<br>(S)-N-(2-(6-(2,6-dichloro-3,5-dimethoxyphenyl)-4,5,6,7-tetrahydro-1H-indazol-3-yl)phenyl)acrylamide |
| 095 | 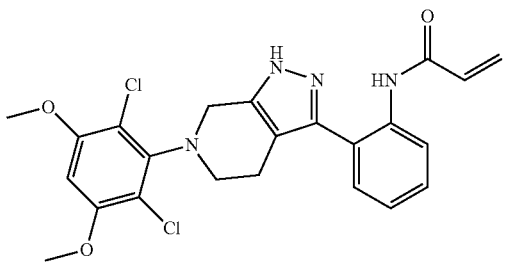 [SMILES: C=CC(=O)Nc1ccccc1-c1n[nH]c2c1CCN(c1c(Cl)c(OC)cc(OC)c1Cl)C2]<br>N-(2-(6-(2,6-dichloro-3,5-dimethoxyphenyl)-4,5,6,7-tetrahydro-1H-pyrazolo[3,4-c]pyridin-3-yl)phenyl)acrylamide |
| 281 | 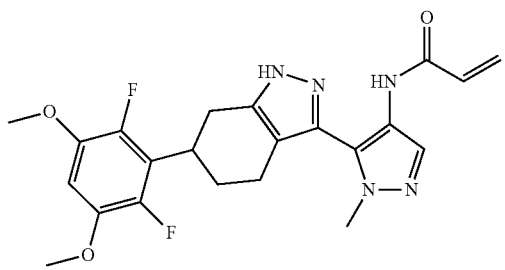 [SMILES: C=CC(=O)Nc1cnn(C)c1-c1n[nH]c2c1CCC(c1c(F)c(OC)cc(OC)c1F)C2]<br>N-(5-(6-(2,6-difluoro-3,5-dimethoxyphenyl)-4,5,6,7-tetrahydro-1H-indazol-3-yl)-1-methyl-1H-pyrazol-4-yl)acrylamide |

| Compound number | Compound structure and name |
|---|---|
| 283 | 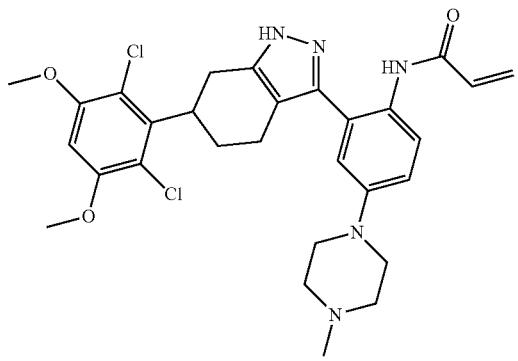 [SMILES: C=CC(=O)Nc1ccc(N2CCN(C)CC2)cc1-c1n[nH]c2c1CCC(c1c(Cl)c(OC)cc(OC)c1Cl)C2]<br>N-(2-(6-(2,6-dichloro-3,5-dimethoxyphenyl)-4,5,6,7-tetrahydro-1H-indazol-3-yl)-4-(4-methylpiperazin-1-yl)phenyl)acrylamide |
| 284 | 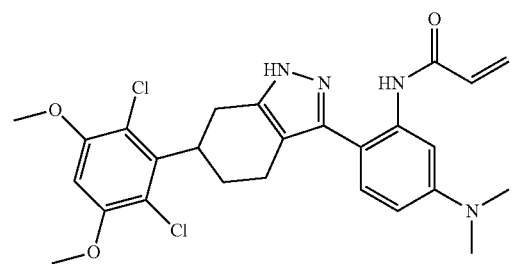 [SMILES: C=CC(=O)Nc1cc(N(C)C)ccc1-c1n[nH]c2c1CCC(c1c(Cl)c(OC)cc(OC)c1Cl)C2]<br>N-(2-(6-(2,6-dichloro-3,5-dimethoxyphenyl)-4,5,6,7-tetrahydro-1H-indazol-3-yl)-5-(dimethylamino)phenyl)acrylamide |
| 285 | 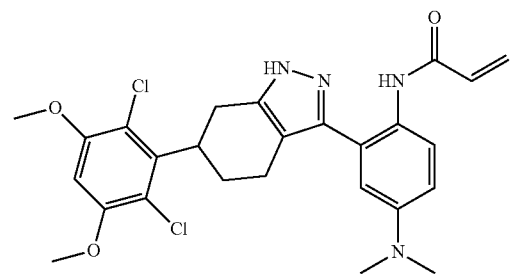 [SMILES: C=CC(=O)Nc1ccc(N(C)C)cc1-c1n[nH]c2c1CCC(c1c(Cl)c(OC)cc(OC)c1Cl)C2]<br>N-(2-(6-(2,6-dichloro-3,5-dimethoxyphenyl)-4,5,6,7-tetrahydro-1H-indazol-3-yl)-4-(dimethylamino)phenyl)acrylamide |
| 286 | 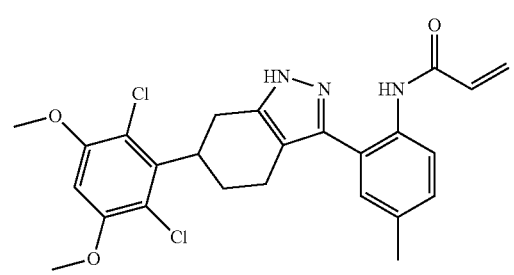 [SMILES: C=CC(=O)Nc1ccc(C)cc1-c1n[nH]c2c1CCC(c1c(Cl)c(OC)cc(OC)c1Cl)C2]<br>N-(2-(6-(2,6-dichloro-3,5-dimethoxyphenyl)-4,5,6,7-tetrahydro-1H-indazol-3-yl)-4-methylphenyl)acrylamide |

| Compound number | Compound structure and name |
|---|---|
| 287 | 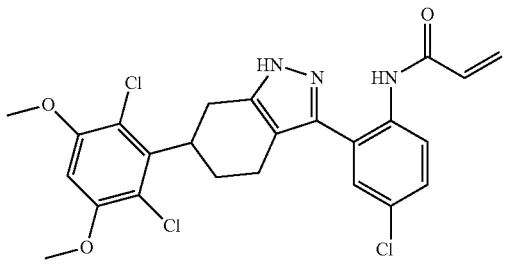 [SMILES: C=CC(=O)Nc1ccc(Cl)cc1-c1n[nH]c2c1CCC(c1c(Cl)c(OC)cc(OC)c1Cl)C2]
N-(4-chloro-2-(6-(2,6-dichloro-3,5-dimethoxyphenyl)-4,5,6,7-tetrahydro-1H-indazol-3-yl)phenyl)acrylamide |
| 288 | 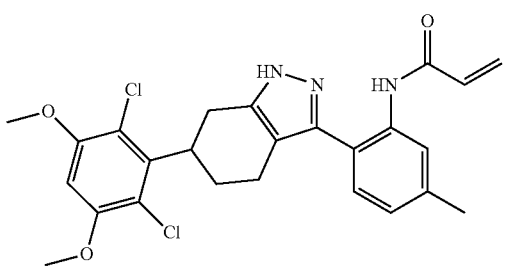 [SMILES: C=CC(=O)Nc1cc(C)ccc1-c1n[nH]c2c1CCC(c1c(Cl)c(OC)cc(OC)c1Cl)C2]
N-(2-(6-(2,6-dichloro-3,5-dimethoxyphenyl)-4,5,6,7-tetrahydro-1H-indazol-3-yl)-5-methylphenyl)acrylamide |
| 289 | 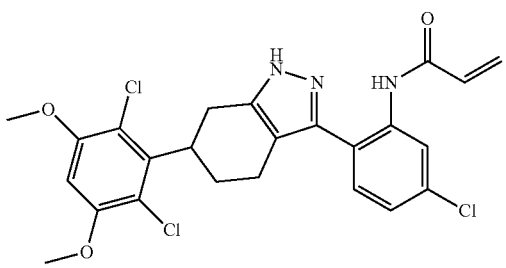 [SMILES: C=CC(=O)Nc1cc(Cl)ccc1-c1n[nH]c2c1CCC(c1c(Cl)c(OC)cc(OC)c1Cl)C2]
N-(5-chloro-2-(6-(2,6-dichloro-3,5-dimethoxyphenyl)-4,5,6,7-tetrahydro-1H-indazol-3-yl)phenyl)acrylamide |
| 291 | 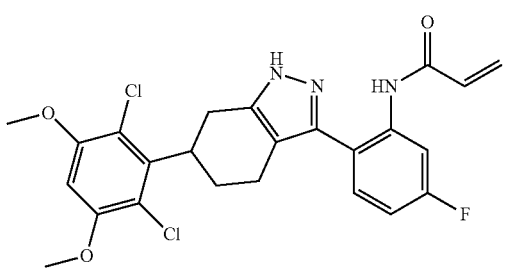 [SMILES: C=CC(=O)Nc1cc(F)ccc1-c1n[nH]c2c1CCC(c1c(Cl)c(OC)cc(OC)c1Cl)C2]
N-(2-(6-(2,6-dichloro-3,5-dimethoxyphenyl)-4,5,6,7-tetrahydro-1H-indazol-3-yl)-5-fluorophenyl)acrylamide |

| Compound number | Compound structure and name |
|---|---|
| 292 | 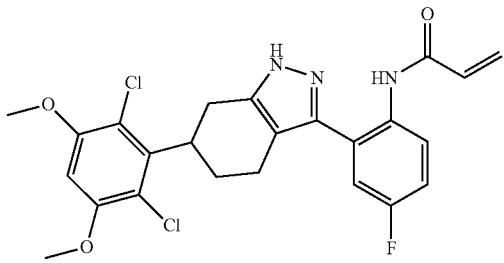 [SMILES: C=CC(=O)Nc1ccc(F)cc1-c1n[nH]c2c1CCC(c1c(Cl)c(OC)cc(OC)c1Cl)C2]
N-(2-(6-(2,6-dichloro-3,5-dimethoxyphenyl)-4,5,6,7-tetrahydro-1H-indazol-3-yl)-4-fluorophenyl)acrylamide |
| 293 | 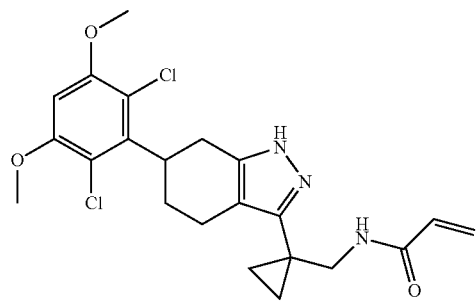 [SMILES: C=CC(=O)NCC1(c2n[nH]c3c2CCC(c2c(Cl)c(OC)cc(OC)c2Cl)C3)CC1]
N-((1-(6-(2,6-dichloro-3,5-dimethoxyphenyl)-4,5,6,7-tetrahydro-1H-indazol-3-yl)cyclopropyl)methyl)acrylamide |
| 295 | 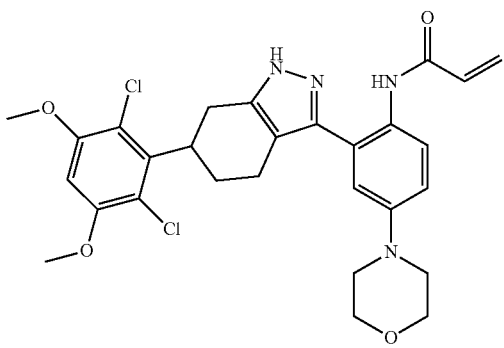 [SMILES: C=CC(=O)Nc1ccc(N2CCOCC2)cc1-c1n[nH]c2c1CCC(c1c(Cl)c(OC)cc(OC)c1Cl)C2]
N-(2-(6-(2,6-dichloro-3,5-dimethoxyphenyl)-4,5,6,7-tetrahydro-1H-indazol-3-yl)-4-morpholinophenyl)acrylamide |
| 296 | 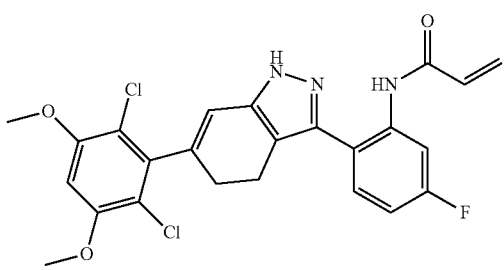 [SMILES: C=CC(=O)Nc1cc(F)ccc1-c1n[nH]c2c1CCC(c1c(Cl)c(OC)cc(OC)c1Cl)=C2]
N-(2-(6-(2,6-dichloro-3,5-dimethoxyphenyl)-4,5-dihydro-1H-indazol-3-yl)-5-fluorophenyl)acrylamide |

| Compound number | Compound structure and name |
|---|---|
| 297 | 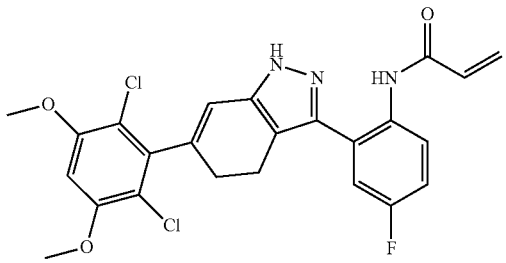 [SMILES: C=CC(=O)Nc1ccc(F)cc1-c1n[nH]c2c1CCC(c1c(Cl)c(OC)cc(OC)c1Cl)=C2]<br>N-(2-(6-(2,6-dichloro-3,5-dimethoxyphenyl)-4,5-dihydro-1H-indazol-3-yl)-4-fluorophenyl)acrylamide |
| 298 | 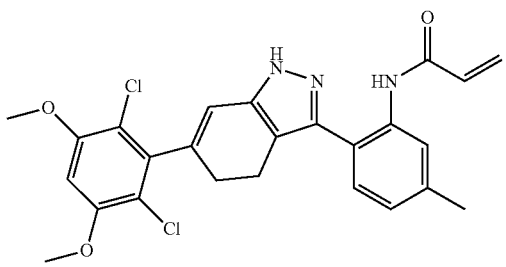 [SMILES: C=CC(=O)Nc1cc(C)ccc1-c1n[nH]c2c1CCC(c1c(Cl)c(OC)cc(OC)c1Cl)=C2]<br>N-(2-(6-(2,6-dichloro-3,5-dimethoxyphenyl)-4,5-dihydro-1H-indazol-3-yl)-5-methylphenyl)acrylamide |
| 299 | 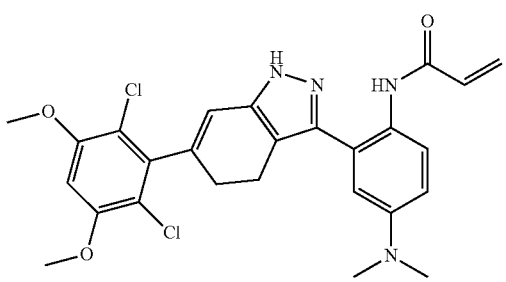 [SMILES: C=CC(=O)Nc1ccc(N(C)C)cc1-c1n[nH]c2c1CCC(c1c(Cl)c(OC)cc(OC)c1Cl)=C2]<br>N-(2-(6-(2,6-dichloro-3,5-dimethoxyphenyl)-4,5-dihydro-1H-indazol-3-yl)-4-(dimethylamino)phenyl)acrylamide |
| 300 | 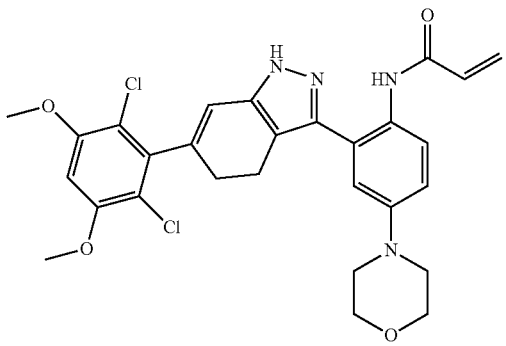 [SMILES: C=CC(=O)Nc1ccc(N2CCOCC2)cc1-c1n[nH]c2c1CCC(c1c(Cl)c(OC)cc(OC)c1Cl)=C2]<br>N-(2-(6-(2,6-dichloro-3,5-dimethoxyphenyl)-4,5-dihydro-1H-indazol-3-yl)-4-morpholinophenyl)acrylamide |

-continued
| Compound number | Compound structure and name |
|---|---|
| 301 | 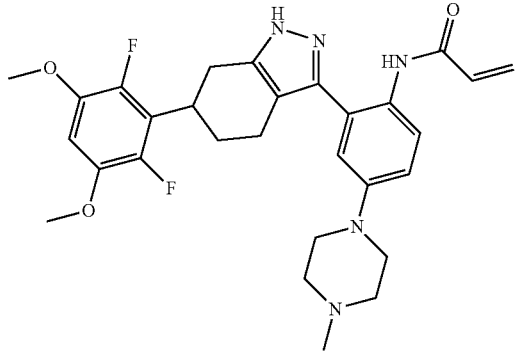 [SMILES: C=CC(=O)Nc1ccc(N2CCN(C)CC2)cc1-c1n[nH]c2c1CCC(c1c(F)c(OC)cc(OC)c1F)C2]<br>N-(2-(6-(2,6-difluoro-3,5-dimethoxyphenyl)-4,5,6,7-tetrahydro-1H-indazol-3-yl)-4-(4-methylpiperazin-1-yl)phenyl)acrylamide |
| 302 | 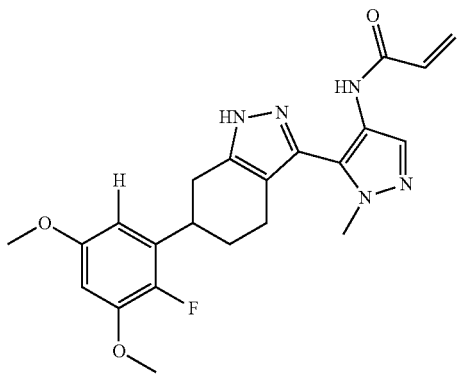 [SMILES: C=CC(=O)Nc1cnn(C)c1-c1n[nH]c2c1CCC(c1cc(OC)cc(OC)c1F)C2]<br>N-(5-(6-(2-fluoro-3,5-dimethoxyphenyl)-4,5,6,7-tetrahydro-1H-indazol-3-yl)-1-methyl-1H-pyrazol-4-yl)acrylamide |
| 303 | 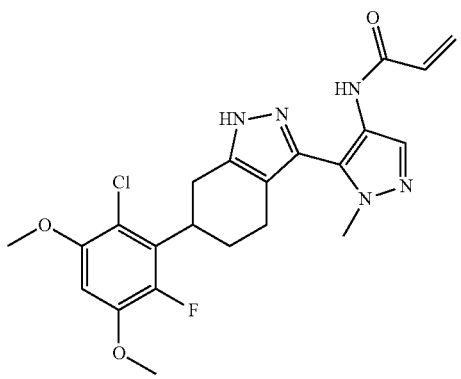 [SMILES: C=CC(=O)Nc1cnn(C)c1-c1n[nH]c2c1CCC(c1c(F)c(OC)cc(OC)c1Cl)C2]<br>N-(5-(6-(2-chloro-6-fluoro-3,5-dimethoxyphenyl)-4,5,6,7-tetrahydro-1H-indazol-3-yl)-1-methyl-1H-pyrazol-4-yl)acrylamide |

| Compound number | Compound structure and name |
|---|---|
| 304 | 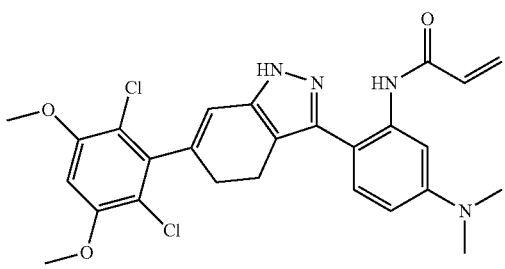
N-(2-(6-(2,6-dichloro-3,5-dimethoxyphenyl)-4,5-dihydro-1H-indazol-3-yl)-5-(dimethylamino)phenyl)acrylamide |
| 310 | 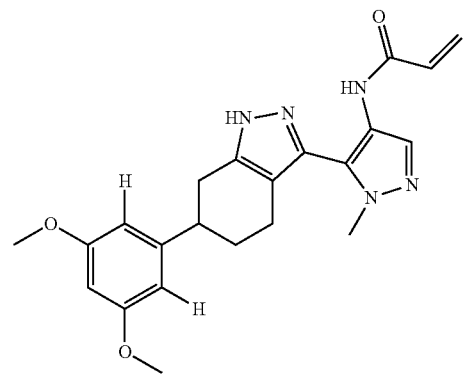 [SMILES: C=CC(=O)Nc1cnn(C)c1-c1n[nH]c2c1CCC(c1cc(OC)cc(OC)c1)C2]
N-(5-(6-(3,5-dimethoxyphenyl)-4,5,6,7-tetrahydro-1H-indazol-3-yl)-1-methyl-1H-pyrazol-4-yl)acrylamide |
| 311 | 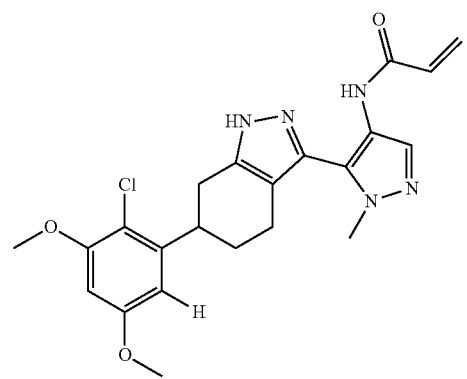
N-(5-(6-(2-chloro-3,5-dimethoxyphenyl)-4,5,6,7-tetrahydro-1H-indazol-3-yl)-1-methyl-1H-pyrazol-4-yl)acrylamide |

Group

In the general formulae (I), (II), (III), (IV), (V), (VI) and (VII) of the present invention, the groups $R^1$ to $R^8$, $R^{11}$ to $R^{13}$, X, Y, W, ring A and the like appearing in each general formula are defined as follows, if they exist in the general formulae. Similarly, the present invention also includes technical solutions obtained by combining their definitions with each other.

$R^1$

In the present invention, $R^1$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^{13}$, wherein $NR$, $R^{12}$, $R^{13}$ and p are as defined in the description. Preferably, $R^1$ is selected from the group consisting of H, F, Cl, methoxy and ethoxy. More preferably, $R^1$ is selected from the group consisting of H, F and Cl.

$R^2$

In the present invention, $R^2$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^3$, —$C(O)OR^3$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^3$, —$S(O)_pOR^{13}$, —$S(O)_pNR^{11}R^{12}$, —$OS(O)_pR^{13}$ and —$NR^{11}S(O)_pR^3$, wherein NR, $R^{12}$, $R^{13}$ and p are as defined in the description. Preferably, $R^2$ is selected from the group consisting of H, F, Cl, methoxy and ethoxy. More preferably, $R^2$ is selected from the group consisting of H, methoxy and ethoxy.

$R^3$

In the present invention, $R^3$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^3$, —$NR^{11}C(O)OR^3$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^{13}$, wherein NR, $R^{12}$, $R^{13}$ and p are as defined in the description. Preferably, $R^3$ is selected from the group consisting of H, F, Cl, methoxy and ethoxy. Preferably, $R^3$ is H.

$R^4$

In the present invention, $R^4$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^3$, —$NR^{11}C(O)OR^3$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^{13}$, wherein NR, $R^{12}$, $R^{13}$ and p are as defined in the description. Preferably, $R^4$ is selected from the group consisting of H, F, Cl, methoxy and ethoxy. Preferably, $R^4$ is selected from the group consisting of H, methoxy and ethoxy.

$R^5$

In the present invention, $R^5$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $OR^{13}$, —$NR^{11}R^{12}$, —$C(O)R^{13}$, —$C(O)OR^{13}$, —$C(O)NR^{11}R^{12}$, —$NR^{11}C(O)R^3$, —$NR^{11}C(O)OR^3$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^3$, wherein NR, $R^{12}$, $R^{13}$ and p are as defined in the description. Preferably, $R^5$ is selected from the group consisting of H, F, Cl, methoxy and ethoxy. Preferably, $R^8$ is selected from the group consisting of H, F, and Cl.

$R^6$

In the present invention, $R^6$ is selected from the group consisting of H and —$CH_2CH_2$—. When $R^6$ is —$CH_2CH_2$—, the other end thereof is connected to X, and optionally one methylene group of —$CH_2CH_2$— is replaced with —O— or —NH—

$R^7$

In the present invention, $R^7$ is selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^3$ and —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; and $R^{13}$ is as defined in the description. Preferably, $R^7$ is selected from the group consisting of H, $C_1$-$C_6$ alkyl and —$NR^aR^b$. Preferably, $R^7$ is methyl or —$N(CH_3)CH_2CH_2N(CH_3)_2$.

$R^8$

In the present invention, $R^8$ is selected from the group consisting of optionally substituted $C_2$-$C_6$ alkenyl and $C_2$-$C_6$ alkynyl, wherein the optional substituents are as defined in the description. Preferably, $R^7$ is vinyl, ethynyl or propynyl.

$R^{11}$

In the present invention, $R^{11}$ is selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl.

$R^{12}$

In the present invention, $R^{12}$ is selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl.

$R^{13}$

In the present invention, $R^3$ is selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl.

Ring A

In the present invention, ring A is selected from the group consisting of 6-14 membered aryl, 5-10 heteroaryl, $C_3$-$C_8$ cycloalkyl or 3-10 membered heterocyclylene; Preferably, ring A is 6-10 membered aryl or 5-6 membered heteroaryl. Preferably, ring A is 6 membered aryl or 5 membered heteroaryl. Preferably, ring A is selected from the group consisting of phenyl, naphthyl, pyrrolyl, furyl, thienyl, imidazolyl, pyrazolyl, oxazolyl, isooxazolyl, thiazyl, isothiazolyl, triazolyl, oxadiazolyl, thiadiazolyl, tetrazolyl, pyridinyl, pyridazinyl, pyrimidinyl, pyrazinyl, triazinyl, tetrazinyl and cyclohexyl, and preferably selected from the group consisting of phenyl, pyrazolyl and cyclohexyl.

X and Y

In the present invention, X is selected from the group consisting of —O—, —NH— and —$CH_2$—, and Y is selected from the group consisting of —O—, —NH— and —$CH_2$—; provided that at least one of X and Y is $CH_2$; Preferably, X is —O—, and Y is —$CH_2$—. Preferably, X is —NH—, and Y is —$CH_2$—. Preferably, X is —$CH_2$—, and Y is —$CH_2$—. Preferably, X is —O—, and Y is —$CH_2$—. Preferably, X is —NH—, and Y is —$CH_2$—. Moreover, when X is connected with $R^6$ to form a ring, X should not be —O—.

W

In the present invention, W is selected from the group consisting of a chemical bond, —NH— and —$CH_2$—.

Pharmaceutical Composition, Formulation, and Kit

In another aspect, the present invention provides a pharmaceutical composition, comprising the compound of the present invention (also referred to as "active component") and a pharmaceutically acceptable excipient. In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The pharmaceutically acceptable excipient for the invention refers to a nontoxic carrier, adjuvant or medium which will not damage the pharmacological activity of the compound formulated together. Pharmaceutically acceptable carriers, adjuvants or media useful for the composition of the present invention include, but are not limited to, ion exchangers, aluminium oxide, aluminum stearate, lecithin, serum protein (e.g., human serum albumin), buffer substances (e.g., phosphate), glycine, sorbic acid, potassium sorbate, partial glyceride mixtures of saturated vegetable fatty acids, water, salts or electrolyte (e.g., protamine sulfate), disodium hydrogen phosphate, potassium hydrogen phosphate, sodium chloride, zinc salts, silica gels, magnesium trisilicate, polyvinyl pyrrolidone, cellulose-based substances, polyethylene glycol, sodium carboxymethyl cellulose, polyacrylate, wax, polyethylene-polypropylene oxide-block polymer, polyethylene glycol and lanolin.

The present invention further includes a kit (e.g., a drug package). The kit provided may include the compound of the present invention, other therapeutic agents, and first and second containers (e.g., vials, ampoules, bottles, syringes, and/or dispersible packages or other suitable containers) containing the compound of the present invention and other therapeutic agents. In some embodiments, the kit provided may further optionally include a third container containing a pharmaceutical excipient for diluting or suspending the compound of the present invention and/or other therapeutic agents. In some embodiments, the compound of the present invention and other therapeutic agents provided in the first and second containers are combined to form a unit dose form.

Administration

The pharmaceutical composition provided by the present invention may be administered in many ways, including but not limited to, oral administration, parenteral administration, inhalation administration, topical administration, rectal administration, nasal administration, oral administration, vaginal administration, implant administration or other administration methods. For example, the parenteral administration used herein includes subcutaneous administration, intradermal administration, intravenous administration, intramuscular administration, intraarticular administration, intraarterial administration, intrasynovial administration, intrasternal administration, intrameninx administration, intrafocal administration, intracranial injection or infusion techniques.

Typically, an effective amount of the compound provided herein is given. According to relevant conditions, including the disorder treated, the selected route of administration, the compound actually given, the age, weight and response of the individual patient, the severity of the patient's symptoms and the like, the amount of the compound actually given can be determined by the doctor.

When used to prevent the disorder of the present invention, the compound provided herein is given to the subject at the risk of suffering from the disorder, typically based on the advice and under the supervision of the doctor, at a dose level as described above. Subjects at the risk of suffering from a specific disorder usually include those with a family history of the disorder, or those who are particularly sensitive to suffering from the disorder through genetic tests or screening.

The pharmaceutical composition provided herein may also be given for a long term ("long-term administration"). Long-term administration refers to giving a compound or its pharmaceutical composition over a long time, e.g., 3 months, 6 months, 1 year, 2 years, 3 years, 5 years, etc., or the administration may be continued indefinitely, e.g., for the rest of the subject's life. In some embodiments, long-term administration is intended to provide a constant level of the compound in the blood for a long time, e.g., within a treatment window.

Various methods of administration may be used to further deliver the pharmaceutical composition of the present invention. For example, in some embodiments, the pharmaceutical composition may be administered by injection, for example, in order to raise the concentration of the compound in the blood to an effective level. The injection dose depends on the target systemic level of the active component through the body, for example, intramuscular or subcutaneous injection dose makes the active component release slowly, while the injection directly delivered to the vein (e.g., through IV intravenous drip) can provide a faster deliver, making the concentration of the active component in the blood rapidly increase to the effective level. In other embodiments, the pharmaceutical composition may be given in the form of a continuous infusion, for example, by IV intravenous drip, thereby to provide a steady-state concentration of the active component in the subject's body. In addition, in other embodiments, the pharmaceutical composition at an injection dose may be given first, followed by continuous infusion.

The oral composition may be in the form of a bulk liquid solution or suspension or bulk powder. However, more generally, in order to facilitate the administration at a precise dose, the composition is provided in the form of unit doses. The term "the form of unit doses" refers to a physically discrete unit suitable as a unit dose for human patients and other mammals, each unit containing a predetermined number of active substances and appropriate pharmaceutical excipients suitable for producing therapeutic effects desired. Typical forms of unit doses include prepackaged, premeasured ampoules or syringes of liquid compositions, or pills, tablets, capsules and the like in the case of solid compositions. In this composition, the compound is usually a component in a small portion (about 0.1 to 5 about 50 wt %, or preferably about 1 to 40 wt %), and the remaining portion is various carriers or excipients and processing aids useful for forming the desired form of administration.

For oral doses, a representative protocol is 1 to 5, especially 2 to 4, and typically 3 oral doses per day. Using these dose administration modes, each dose provides about 0.01 to about 20 mg/kg the compound of the present invention, and preferred doses each provide about 0.1 to about 10 mg/kg, and particularly about 1 to about 5 mg/kg.

In order to provide a blood level similar to, or lower than, that when an injection dose is used, a transdermal dose is generally selected, in an amount of about 0.01 to about 20 wt %, preferably about 0.1 to about 20 wt %, preferably about 0.1 to about 10 wt %, and more preferably about 0.5 to about 15 wt %.

From about 1 to about 120 h, and especially 24 to 96 h, the injection dose level is in the range of about 0.1 mg/kg/h to at least 10 mg/kg/h. In order to obtain a sufficient level in a stable state, a preloaded injection of about 0.1 mg/kg to about 10 mg/kg or more may also be given. For human patients of 40 to 80 kg, the maximum total dose should not exceed about 2 g/day.

Liquid forms suitable for oral administration may include suitable aqueous or non-aqueous carriers, as well as buffering agents, suspending agents and dispensing agents, colorants, flavoring agents, and the like. The solid form may include, for example, any of the following components, or compounds with similar properties: binders, such as microcrystalline cellulose, tragacanth or gelatin; excipients, such as starch or lactose; disintegrating agents, such as alginic acid, Primogel or corn starch; lubricants, such as magnesium stearate; flow aids, such as colloidal silica; sweeteners, such as, sucrose or saccharine; or flavoring agents, such as mint, methyl salicylate, or orange flavoring agents.

Injectable compositions are typically based on sterile saline or phosphate buffered saline usable for injection, or other injectable excipients known in the art. As mentioned before, in this composition, the active compound is typically a component in a small portion, often about 0.05 to 10 wt %, and the remaining portion is the injectable excipient and the like.

The transdermal composition is typically formulated as a topical ointment or cream containing an active component. When formulated as an ointment, the active component is typically combined with paraffin or a water miscible ointment matrix. Alternatively, the active component may be formulated together with e.g., an oil-in-water cream matrix, into a cream. This transdermal formulation is well known in the art, and generally includes other components for enhancing stable skin penetration of active components or formulations. All such known transdermal formulations and components are included in the scope provided by the present invention.

The compound of the present invention may also be given through a percutaneous device. Therefore, percutaneous administration can be achieved through the use of reservoirs, or porous-membrane-type, or multiple-solid-matrix patches.

The above components of the composition for oral administration, injection or topical administration are only representative. Other materials, processing techniques and the like are illustrated in Part 8 of Remington's Pharmaceutical Sciences, 17th edition, 1985, Mack Publishing Company, Easton, Pa., which is incorporated herein by reference.

The compound of the present invention may also be given in a sustained release form, or from a sustained release administration system. Descriptions of representative sustained release materials may be found in Remington's Pharmaceutical Sciences.

The present invention also relates to pharmaceutically acceptable formulations of the compound of the present invention. In one embodiment, the formulation comprises water. In another embodiment, the formulation comprises a cyclodextrin derivative. The most common cyclodextrins are α-, β- and γ-cyclodextrins composed of 6, 7 and 8 α-1,4-linked glucose units, respectively. On the linked sugar part, they optionally include one or more substituents, including but not limited to, methylation, hydroxyalkylation, acylation and sulfoalkyl ether substitution. In some embodiments, the cyclodextrin is sulfoalkyl ether β-cyclodextrin, for example, sulfobutyl ether β-cyclodextrin, also known as Captisol. See, e.g., U.S. Pat. No. 5,376,645. In some embodiments, the formulation includes hexapropyl-β-cyclodextrin (e.g., 10-50% in water).

Combination

The compound of the present invention or the composition thereof may be administered in combination with other therapeutic agents, to treat the disease. Examples of known therapeutic agents include, but are not limited to, Adriamycin, dexamethasone, vincristine, cyclophosphamide, fluorouracil, topotecan, taxol, interferon, platin derivatives, taxane (e.g., paclitaxel), Vinca alkaloids (e.g., vinblastine), anthracycline (e.g., doxorubicin), epipodophyllotoxin (e.g., etoposide), cisplatin, mTOR inhibitors (e.g., rapamycin), methotrexate, actinomycin D, durastin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™. In other embodiments, the compound of the present invention is administered in combination with a biological agent such as Avastin or Vectibix.

In some embodiments, the compound of the present invention or the composition thereof may administered in combination with any one or more antiproliferatives or chemotherapeutic agents selected from the group consisting of abarelix, aldesleukin, alemtuzumab, alitretinoin, allopurinol, altretamine, amifostine, anastrozole, arsenic trioxide, asparaginase, azacitidine, BCG Live, bevacizumab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, actinomycin D, darbepetin alfa, donomicin, denileukin, dexrazoxane, docetaxel, doxorubicin, doxorubicin hydrochlorate, dromostanolone propionate, epirubicin, epoetin alfa, erlotinib, estramustine, etoposide phosphate, etoposide, exemestane, filgrastim, fluouridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon α-2a, interferon α-2b, irinotecan, lenalidomide, letrozole, leucovorin, leuprolide acetate, levamisole, lomustine, megestrol acetate, melphalan, mercaptourine, 6-MP, mesna, methotrexate, methoxsalen, mitomycin C, mitotane, mitoxantrone, nandrolone, nolarabine, nofetumomab, oprevekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargrammostim, sorafenib, streptozocin, sunitinib maleate, talc, tamoxifen, temozolomide, teniposide, VM-26, testolactone, thioguanine, 6-TG, thiotepa, topotecan, toremifene, tositumamab, trastuzumab, tretinoin, ATRA, uracil mustard, valrubicin, vinblastine, vincristine, vinorelbine, zoledronate or zoledronic acid.

Other examples of therapeutic agents with which the compound of the present invention can also be combined include, but are not limited to, therapeutic agents for Alzheimer's disease, such as donepezil hydrochloride and rivastigmine; therapeutic agents for Parkinson's disease, such as L-DOPA/carbidopa, entacapone, ropinrole, pramipexole, bromecycline, pergolide, trihexyphendyl and amantadine; therapeutic agents for multiple sclerosis (MS), such as 3 interferon, glatiramer acetate and mitoxantrone; therapeutic agents for asthma, such as albuterol and montelukast; therapeutic agents for schizophrenia, such as zyprexa, risperdal, seroquel and haloperidol; anti-inflammatory agents, such as corticosteroids, TNF blockers, IL-IRA, azathioprine, cyclophosphamide and sulfasalazine; immunomodulators and immunosuppressants, such as cyclosporin, tacrolimus, rapamycin, mycophenolate mofetil, interferon, corticosteroid, cyclophosphamide, azathioprine and sulfasalazine; neurotrophic factors, such as acetylcholinesterase inhibitors, MAO inhibitors, interferon, anticonvulsants, ion channel blockers, riluzole and agents against the Parkinson's disease; therapeutic agents for cardiovascular diseases, such as β blockers, ACE inhibitors, diuretics, nitrates, calcium channel blockers and statins; therapeutic agents for liver diseases, such as corticosteroids, cholesteramine interferons and antiviral agents; therapeutic agents for blood diseases, such as corticosteroids, anti-leukemia agents and growth factors; and therapeutic agents for immunologic deficiency disorders, such as gamma globulin.

Those other active agents may be administered separately from the composition containing the compound of the present invention, as a part of a multiple administration protocol. Alternatively, those active agents may be a part of a single dosage form, mixed in a single composition together with the compound of the present invention. If administered as a part of a multiple administration protocol, the two active agents may be provided at the same time, in sequence, or at intervals between each other for a period of time, usually at an interval of less than 5 h between each other.

Indications and Diseases

FGFR-4 regulates proliferation, survival, and alpha-fetoprotein secretion during the progression of hepatocellular cancer (HCC); and thus FGFR-4 inhibitors are promising potential therapeutic agents for this unmet medical need (Ho et al., *Journal of Hepatology*, 2009, 50: 118-27). HCC afflicts more than 550,000 people worldwide every year and has one of the worst one-year survival rates among any cancer type.

The involvement in the regulation of blood glucose, lipid and energy homeostasis, through FGF19 (a member of the fibroblast growth factor (FGF) family, which is composed of hormones), shows other evidences of the relationship between FGFR-4 and HCC. Increased hepatocyte proliferation and liver tumor formation have been observed in FGF19 transgenic mice. FGF19 activates FGFR-4 (the main receptor thereof in the liver), and FGFR-4 activation is believed to be the mechanism by which FGF19 can increase the proliferation of hepatocytes and induce the formation of hepatocellular cancer (Wu et al., J Biol chem (2010) 285 (8): 5165-5170). FGF19 has also been recognized as a driving gene in HCC (Sawey et al., Cancer Cell (2011) 19: 347-358). Therefore, it is considered that the compound disclosed herein, which is a potential and selective inhibitor of FGFR-4, can be used to treat HCC and other liver cancer.

The Y367C mutation of activated fibroblast growth factor receptor 4 (FGFR-4) has been identified by tumor genome screening in the human breast cancer cell line MDA-MB-453. Therefore, it has been suggested that FGFR-4 may be the driver of tumor growth in breast cancer (Roidl et al., Oncogene (2010) 29 (10): 1543-1552). Therefore, it is considered that the compound disclosed herein (which is a potent selective inhibitor of FGFR-4) can be used to treat FGFR-4-regulated breast cancer.

Molecular changes (e.g., translocation) in the upstream gene of FGFR-4 may lead to FGFR-4 activation/over-expression. For example, PAX3-FKHR translocation/gene-fusion will lead to FGFR-4 over-expression. Therefore, the FGFR-4 over-expression caused by the mechanism is associated with rhabdomyosarcoma (RMS) (Cao et al., *Cancer Res* (2010) 70 (16): 6497-6508). Mutations in FGFR-4 itself (e.g., kinase domain mutations) will lead to protein over-activation; and this mechanism has been associated with the RMS subgroup (Taylor et al., *J Clin Invest* (2009) 119: 3395-3407). Therefore, it is considered that the compound disclosed herein (which is a potent selective inhibitor of FGFR-4) can be used to treat FGFR-4-regulated RMS and other sarcoma.

Other diseases are associated with changes in FGFR-4 upstream genes or mutations in FGFR-4 itself. For example, mutations in the kinase domain of FGFR-4 lead to over-activation, which is associated with lung adenocarcinoma (Ding et al., Nature (2008) 455 (7216): 1069-1075). The amplification of FGFR-4 is associated with pathologies such as renal cell carcinoma (TCGA provisional data). In addition, silence of FGFR4 and inhibition of ligand-receptor binding significantly slow down the growth of ovarian tumors, indicating that FGFR4 inhibitors can be used to treat ovarian cancer (Zaid et al., *Clin. Cancer Res*. (2013) 809).

A pathogenic increase of the bile acid level is associated with changes in FGF19 levels (Vergnes et al., *Cell Metabolism* (2013) 17, 916-28). Therefore, a decrease of the FGF19 level may be beneficial in the promotion of the synthesis of bile acid and therefore in the treatment of hyperlipidemia.

Therefore, the compound of the present invention can be used to treat a variety of FGFR-related diseases, wherein the diseases include but are not limited to, gastric cancer, thyroid cancer, prostate cancer, breast cancer, sarcoma (e.g., rhabdomyosarcoma), skin cancer (e.g., melanoma), liver cancer (e.g., hepatocellular cancer and cholangiocarcinoma), pancreatic cancer (e.g., pancreatic intraepithelial neoplasia and pancreatic duct adenocarcinoma), lung cancer (e.g., non-small-cell lung cancer and lung adenocarcinoma), kidney cancer (e.g., renal cell carcinoma), colorectal cancer and ovarian cancer.

EMBODIMENTS

The compound stated in the general formula (I) of the present invention or the pharmaceutically acceptable salt thereof can be prepared by the exemplary method described in the following embodiments and the operation in relevant open literatures used by those of skill in the art, but these embodiments do not limit the scope of the present invention.

The structure of the compound is determined by nuclear magnetic resonance (NMR) or mass spectrometry (MS). In the determination by MR, a Bruker AVANCE-400 or Varian Oxford-300 nuclear magnetic instrument is used, the determination solvent is deuterated dimethyl sulfoxide (DMSO-d6), deuterated chloroform ($CDCl_3$) or deuterated methanol ($CD_3OD$), the internal standard is tetramethylsilane (TMS), and the chemical shift is given in a unit of $10^{-6}$ (ppm).

In the determination by MS, an Agilent SQD (ESI) mass spectrometer (manufacturer: Agilent, model: 6110) or a Shimadzu SQD (ESI) mass spectrometer (manufacturer: Shimadzu, model: 2020) is used.

In the determination by HPLC, Agilent 1200 DAD high pressure liquid chromatography (Sunfire C18, 150×4.6 mm, 5 μm, chromatographic column) and Waters 2695-2996 high pressure liquid chromatography (Gimini C18 150×4.6 mm, 5 μm chromatographic column) are used.

A Qingdao Marine GF254 silica gel plates is used as the silica gel plate for the thin-layer chromatography. The specification of the silica gel plate for the thin-layer chromatography (TLC) is 0.15 mm to 0.2 mm, and the specification of the silica gel plate for the thin-layer chromatography for separation and purification of products is 0.4 mm to 0.5 mm.

Qingdao Marine 200-300 mesh silica gel is generally used as the carrier in the column chromatography.

Known starting raw materials of the present invention may be synthesized by or according to the methods known in the art, or may be commercially available from companies such as ABCR GmbH&Co.KG, Acros Organics, Aldrich Chemical Company, and Accela ChemBio Inc., and Beijing Coupling Chemicals.

In the embodiments, the reactions are all carried out in an argon atmosphere or nitrogen atmosphere, unless specially described.

The argon atmosphere or nitrogen atmosphere refers that the reaction flask is connected to an argon or nitrogen balloon in a volume of about 1 L.

A hydrogen atmosphere refers that a reaction flask is connected to a hydrogen balloon in a volume about of 1 L.

A GCD-500G high-purity hydrogen generator and a BLT-2000 medium-pressure hydrogenation instrument from Beijing Jiawei Kechuang Technology Co., Ltd. are used for the pressurized hydrogenation reaction.

In the hydrogenation reaction, the reaction is usually vacuumized and filled with hydrogen gas, and this operation is repeated 3 times.

A microwave reactor of Model CEM Discover-SP is used in the microwave reaction.

In the embodiments, the reaction temperature is room temperature ranging from 20° C. to 30° C., unless specially noted.

In the embodiments, thin-layer chromatography (TLC) is employed to monitor the reaction progress, and the developer system used in the reaction includes A: a dichloromethane and methanol system; B: a petroleum ether and ethyl acetate system; and the ratio by volume of the solvents is adjusted according to different polarities of the compounds.

The eluent system for the column chromatography and the developer system for the thin-layer chromatography employed in the purification of compounds include A: a dichloromethane and methanol system; B: a petroleum ether and ethyl acetate system; and the ratio by volume of the solvents is adjusted according to different polarities of the compounds, or alternatively a small amount of an acidic or alkaline reagent (e.g., triethyl amine) may be added for adjustment.

Embodiment 10

N-(2-((6-(2,6-dichloro-3,5-dimethoxyphenyl)-4,5,6,7-tetrahydro-1H-indazol-3-yl)amino)-3-methylphenyl)acrylamide

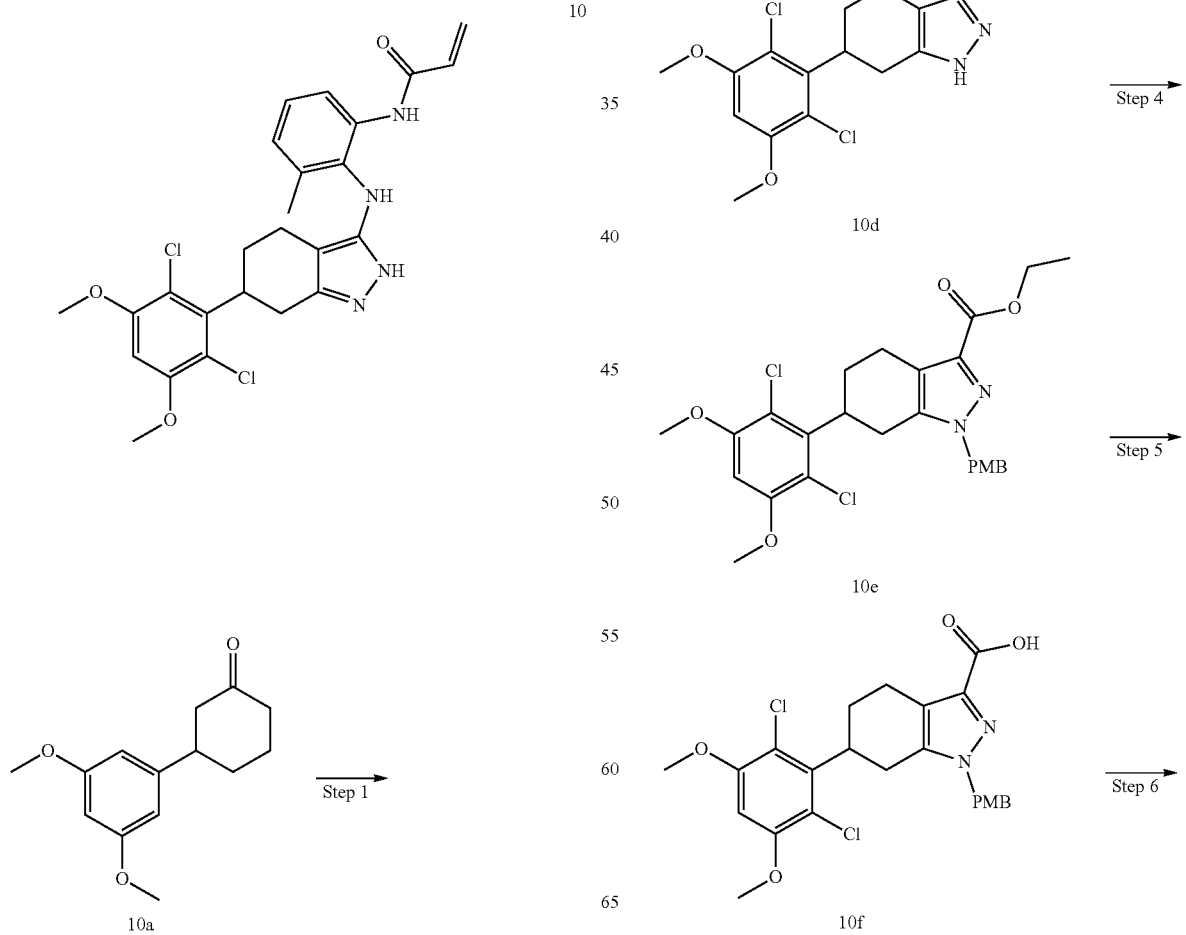

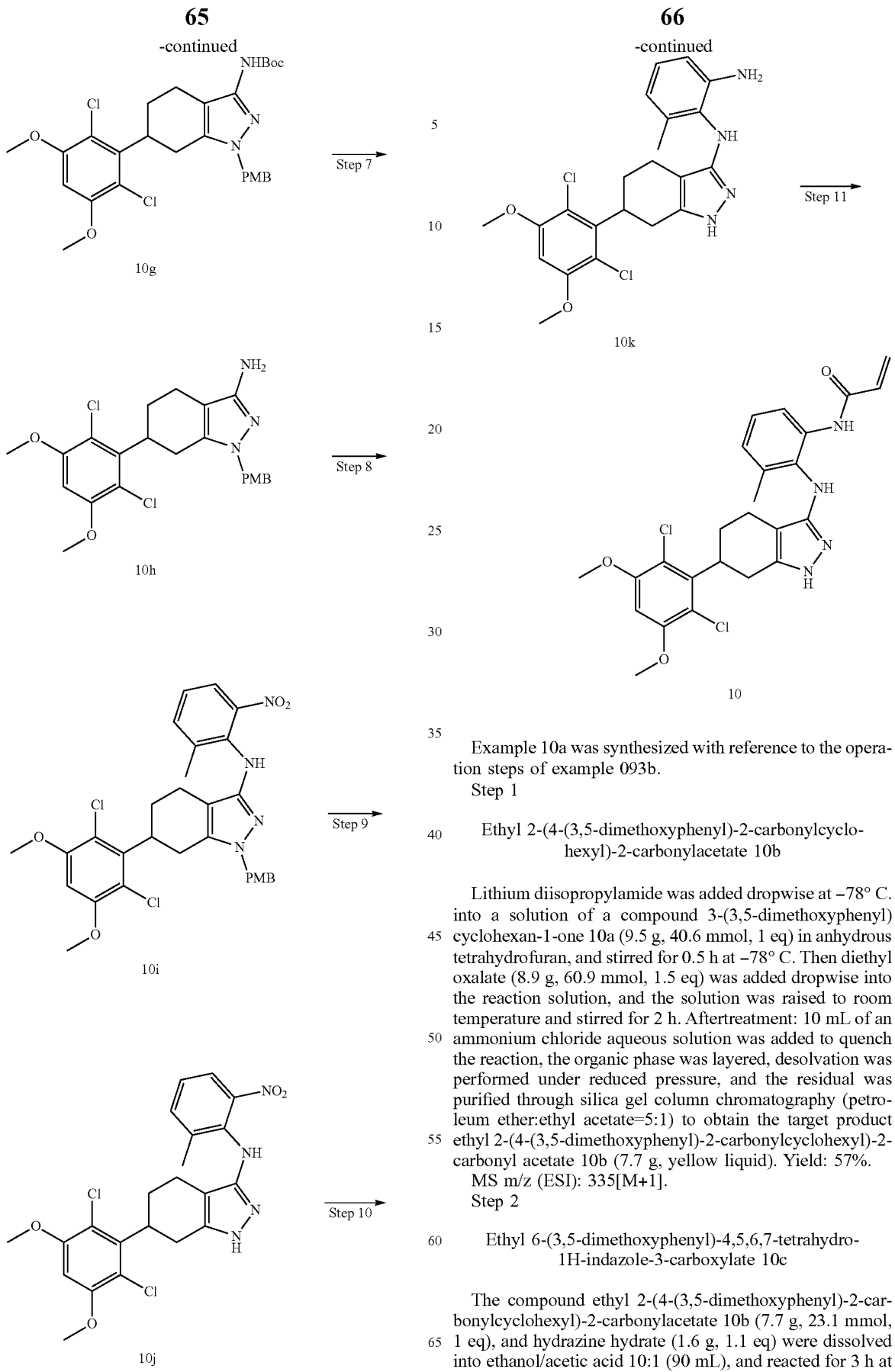

Example 10a was synthesized with reference to the operation steps of example 093b.

Step 1

Ethyl 2-(4-(3,5-dimethoxyphenyl)-2-carbonylcyclohexyl)-2-carbonylacetate 10b

Lithium diisopropylamide was added dropwise at −78° C. into a solution of a compound 3-(3,5-dimethoxyphenyl) cyclohexan-1-one 10a (9.5 g, 40.6 mmol, 1 eq) in anhydrous tetrahydrofuran, and stirred for 0.5 h at −78° C. Then diethyl oxalate (8.9 g, 60.9 mmol, 1.5 eq) was added dropwise into the reaction solution, and the solution was raised to room temperature and stirred for 2 h. Aftertreatment: 10 mL of an ammonium chloride aqueous solution was added to quench the reaction, the organic phase was layered, desolvation was performed under reduced pressure, and the residual was purified through silica gel column chromatography (petroleum ether:ethyl acetate=5:1) to obtain the target product ethyl 2-(4-(3,5-dimethoxyphenyl)-2-carbonylcyclohexyl)-2-carbonyl acetate 10b (7.7 g, yellow liquid). Yield: 57%.

MS m/z (ESI): 335[M+1].

Step 2

Ethyl 6-(3,5-dimethoxyphenyl)-4,5,6,7-tetrahydro-1H-indazole-3-carboxylate 10c

The compound ethyl 2-(4-(3,5-dimethoxyphenyl)-2-carbonylcyclohexyl)-2-carbonylacetate 10b (7.7 g, 23.1 mmol, 1 eq), and hydrazine hydrate (1.6 g, 1.1 eq) were dissolved into ethanol/acetic acid 10:1 (90 mL), and reacted for 3 h at 65° C. Aftertreatment: desolvation was performed under reduced pressure, the residual was purified through silica gel column chromatography (petroleum ether:ethyl acetate=2:1) to obtain the target product ethyl 6-(3,5-dimethoxyphenyl)-4,5,6,7-tetrahydro-1H-indazole-3-carboxylate 10c (3.5 g, yellow liquid). Yield: 46%.

MS m/z (ESI): 331[M+1].

Step 3

Ethyl 6-(2,6-dichloro-3,5-dimethoxyphenyl)-4,5,6,7-tetrahydro-1H-indazole-3-carboxylate 10d The compound ethyl 6-(3,5-dimethoxyphenyl)-4,5,6,7-tetrahydro-1H-indazole-3-carboxylate 10c (800 mg, 2.4 mmol, 1 eq) and potassium chloride (359 mg, 4.8 mmol, 2 eq) were dissolved into dioxane/water 3:1 (40 mL), and oxane (3.0 g, 4.8 mmol, 2 eq) was slowly added dropwise at a condition of 0° C. The mixture was further stirred for 3 h. Aftertreatment: 50 mL of a sodium bicarbonate aqueous solution was added for dilution, the mixture was extracted with ethyl acetate, the organic phase was subjected to desolvation under reduced pressure, the residual was purified through silica gel column chromatography (petroleum ether:ethyl acetate=2:1) to obtain the target product ethyl 6-(3,5-dimethoxyphenyl)-4,5,6,7-tetrahydro-1H-indazole-3-carboxylate 10d (700 mg, yellow liquid). Yield: 72%.

MS m/z (ESI): 399[M+1].

Step 4

Ethyl 6-(2,6-dichloro-3,5-dimethoxyphenyl)-1-(4-methoxybenzyl)-4,5,6,7-tetrahydro-1H-indazole-3-carboxylate 10e The compound ethyl 6-(2,6-dichloro-3,5-dimethoxyphenyl)-4,5,6,7-tetrahydro-1H-indazole-3-carboxylate 10d (2.5 g, 6.3 mmol, 1 eq) was dissolved into DMF (40 mL), sodium hydride (0.38 g, 9.5 mmol, 1.5 eq) was slowly added dropwise at a condition of 0° C. and stirred for 0.5 h. P-methoxybenzyl chloride (1.5 g, 9.5 mmol, 1.5 eq) was added therein, and the mixture was further stirred for 3 h. Aftertreatment: the reaction quenched with 50 mL of water added and extracted with ethyl acetate, and the organic phase was subjected to desolvation under reduced pressure, and the residual was purified through silica gel column chromatography (petroleum ether:ethyl acetate=3:1) to obtain the target product ethyl 6-(2,6-dichloro-3,5-methoxy-benzyl)-1-(4-methoxybenzyl)-4,5,6,7-tetrahydro-1H-indazole-3-carboxylate 10e (1.2 g, white solid).

MS m/z (ESI): 519[M+1].

Step 5

6-(2,6-dichloro-3,5-dimethoxyphenyl)-1-(4-methoxybenzyl)-4,5,6,7-tetrahydro-1H-indazole-3-carboxylate 10f The compound ethyl 6-(2,6-dichloro-3,5-dimethoxyphenyl)-1-(4-methoxybenzyl)-4,5,6,7-tetrahydro-1H-indazole-3-carboxylate 10e (2.0 g, 3.9 mmol, 1 eq) was dissolved in methanol/tetrahydrofuran/water=10:10:3 (23 mL), and sodium hydroxide (0.46 g, 11.6 mmol, 3 eq) was added dropwise at a condition of 0° C. The mixture was raised to 50° C. and stirred for 5 h. Aftertreatment: the organic phase was desolventized under reduced pressure, 50 mL of 1N dilute hydrochloric acid was added therein, the mixture was extracted with ethyl acetate, and the spin-dried residual was purified through silica gel column chromatography (petroleum ether:ethyl acetate=1:1) to obtain the target product 6-(2,6-dichloro-3,5-dimethoxyphenyl)-1-(4-methoxyben-zyl)-4,5,6,7-tetrahydro-1H-indazole-3-carboxylic acid 10f (1.1 g, white solid). Yield: 58%.

MS m/z (ESI): 491[M+1].

Step 6

T-butyl (6-(2,6-dichloro-3,5-dimethoxyphenyl)-1-(4-methoxybenzyl)-4,5,6,7-tetrahydro-1H-indazol-3-yl) carbamate 10g The compound 6-(2,6-dichloro-3,5-dimethoxyphenyl)-1-(4-methoxybenzyl)-4,5,6,7-tetrahydro-1H-indazole-3-carboxylic acid 10f (1.1 g, 2.2 mmol, 1 eq), diphenylphosphoryl azide (935 mg, 3.4 mmol, 1.5 eq), and triethyl amine (0.66 g, 6.6 mmol, 3 eq) were dissolved into t-butyl alcohol (20 mL), and reacted for 4 h under reflux under the protection of nitrogen gas. Aftertreatment: the organic phase was desolventized under reduced pressure, and the spin-dried residual was purified through silica gel column chromatography (petroleum ether:ethyl acetate=10:1) to obtain the target product t-butyl (6-(2,6-dichloro-3,5-dimethoxyphenyl)-1-(4-methoxybenzyl)-4,5,6,7-tetrahydro-1H-indazol-3-yl)carbamate 10g (0.6 g, white solid). Yield: 50/%.

MS m/z (ESI): 562[M+1].

Step 7

6-(2,6-dichloro-3,5-dimethoxyphenyl)-1-(4-methoxybenzyl)-4,5,6,7-tetrahydro-1H-indazole-3-amine 10h The compound t-butyl (6-(2,6-dichloro-3,5-dimethoxyphenyl)-1-(4-methoxybenzyl)-4,5,6,7-tetrahydro-1H-indazol-3-yl)carbamate 10g (600 mg, 1.1 mmol, 1 eq) was dissolved into anhydrous dichloromethane (15 mL), trifluoroacetic acid (3 mL) was added therein, and reaction was performed for 2 h at room temperature. Aftertreatment: the organic phase was desolventized under reduced pressure, a saturated sodium bicarbonate aqueous solution (50 mL) was added, and the mixture was extracted with ethyl acetate and spin-dried to obtain the target product 6-(2,6-dichloro-3,5-dimethoxyphenyl)-1-(4-methoxybenzyl)-4,5,6,7-tetrahydro-1H-indazole-3-amine 10h (0.3 g, white solid). Yield: 60%.

MS m/z (ESI): 342[M+1].

Step 8

6-(2,6-dichloro-3,5-dimethoxyphenyl)-1-(4-methoxybenzyl)-N-(2-methyl-6-nitrophenyl)-4,5,6,7-tetrahydro-1H-indazole-3-amine 10i The compound 6-(2,6-dichloro-3,5-dimethoxyphenyl)-1-(4-methoxybenzyl)-4,5,6,7-tetrahydro-1H-indazole-3-amine 10h (300 mg, 0.65 mmol, 1 eq), 2-bromo-1-methyl-3-nitrobenzene (280 mg, 1.30 mmol, 2 eq), tri(dibenzalacetone)dipalladium (119 mg, 0.13 mmol, 0.2 eq), 2-dicyclohexylphosphino-2,4,6-triisopropylbiphenyl (124 mg, 0.26 mmol, 0.4 eq), and caesium carbonate (424 mg, 1.32 mmol, 2 eq) were dissolved into DMF (10 mL), and heated for 4 h at 90° C. under the protection condition of nitrogen gas. Aftertreatment: the organic phase was desolventized under reduced pressure, an aqueous solution (20 mL) was added, the mixture was extracted with ethyl acetate, and the spin-dried residual was purified through silica gel column chromatography (petroleum ether:ethyl acetate=5:1) to obtain the target product 6-(2,6-dichloro-3,5-dimethoxyphenyl)-1-(4-methoxybenzyl)-N-(2-methyl-6-nitrophenyl)-4,5,6,7-tetrahydro-1H-indazole-3-amine 10i (0.13 g, yellow solid). Yield: 34%.

MS m/z (ESI): 597[M+1].

Step 9

6-(2,6-dichloro-3,5-dimethoxyphenyl)-N-(2-methyl-6-nitrophenyl)-4,5,6,7-tetrahydro-1H-indazole-3-amine 10j The compound 6-(2,6-dichloro-3,5-dimethoxyphenyl)-1-(4-methoxybenzyl)-N-(2-methyl-6-nitrophenyl)-4,5,6,7-tetrahydro-1H-indazole-3-amine 10i (130 mg, 0.22 mmol, 1 eq) was dissolved into anhydrous dichloromethane (30 mL), trifluoromethanesulfonic anhydride (0.5 mL) was added therein, and reaction was performed for 30 min at room temperature. Aftertreatment: a saturated sodium bicarbonate aqueous solution (20 mL) was added, and the mixture was extracted with dichloromethane and spin-dried to obtain the target product 6-(2,6-dichloro-3,5-dimethoxyphenyl)-N-(2-methyl-6-nitrophenyl)-4,5,6,7-tetrahydro-1H-indazole-3-amine 10j (90 mg, yellow solid). Yield: 86%.

MS m/z (ESI): 477[M+1].

Step 10

N1-(6-(2,6-dichloro-3,5-dimethoxyphenyl)-4,5,6,7-tetrahydro-1H-indazol-3-yl)-6-methylphenylene-1,2-diamine 10k The compound 6-(2,6-dichloro-3,5-dimethoxyphenyl)-N-(2-methyl-6-nitrophenyl)-4,5,6,7-tetrahydro-1H-indazole-3-amine 10j (90 mg, 0.19 mmol, 1 eq) was dissolved into ethanol (15 mL), zinc powder (123 mg, 1.9 mmol, 10 eq) and (218 mg, 1.9 mmol, 10 eq) were added therein, and reaction was performed for 3 h at 50° C. Aftertreatment: the mixture was spin-dried to remove the solvent, and diluted with ethyl acetate, washed with water, and spin-dried to obtain the target product N1-(6-(2,6-dichloro-3,5-dimethoxyphenyl)-4,5,6,7-tetrahydro-1H-indazol-3-yl)-6-methylphenylene-1,2-diamine 10k (60 mg, yellow solid). Yield: 70%.

MS m/z (ESI): 447[M+1].

Step 11

N-(2-((6-(2,6-dichloro-3,5-dimethoxyphenyl)-4,5,6,7-tetrahydro-1H-indazol-3-yl)amino)-3-methylphenyl)acrylamide 10

The compound N1-(6-(2,6-dichloro-3,5-dimethoxyphenyl)-4,5,6,7-tetrahydro-1H-indazol-3-yl)-6-methylphenylene-1,2-diamine 10k (40 mg, 0.09 mmol, 1 eq) and N,N-diisopropyl ethylamine (23 mg, 0.18 mmol, 1 eq) were dissolved into anhydrous dichloromethane (10 mL), and the mixture was cooled to −40° C. A solution of acryloyl chloride (8 mg, 0.09 mmol, 1 eq) in dichloromethane was slowly added therein, and reaction was performed for 0.5 h. The compound 2-(6-(2,6-dichloro-3,5-dimethoxyphenyl)-4,5,6,7-tetrahydro-1H-indazol-3-yl)aniline 15c (120 mg, 0.29 mmol, 1 eq) and N,N-diisopropyl ethylamine (75 mg, 0.58 mmol, 1 eq) were dissolved into anhydrous dichloromethane (10 mL), and the mixture was cooled to −40° C. A solution of acryloyl chloride (26 mg, 0.29 mmol, 1 eq) in dichloromethane was slowly added therein, and reaction was performed for 0.5 h. Aftertreatment: the mixture was spin-dried to remove the solvent, and subjected to preparative liquid phase separation and lyophilization to obtain the target product N-(2-((6-(2,6-dichloro-3,5-dimethoxyphenyl)-4,5,6,7-tetrahydro-1H-indazol-3-yl)amino)-3-methylphenyl)acrylamide 10 (5.8 mg, white solid). Yield: 14%.

MS m/z (ESI): 501 [M+1].

$^1$H NMR (400 MHz, DMSO) δ 11.77 (s, 1H), 9.67 (s, 1H), 7.58 (d, J=6.1 Hz, 1H), 7.12-6.97 (m, 2H), 6.88 (d, J=10.6 Hz, 1H), 6.46 (dd, J=17.0, 10.2 Hz, 1H), 6.21 (dd, J=17.0, 1.7 Hz, 1H), 5.73 (dd, J=10.2, 1.7 Hz, 1H), 3.90 (dd, J=18.3, 3.2 Hz, 7H), 3.32-3.20 (m, 2H), 2.57 (d, J=5.2 Hz, 1H), 2.34-2.24 (m, 1H), 2.16 (s, 3H), 1.70 (d, J=9.9 Hz, 1H).

Embodiment 15

N-(2-(6-(2,6-dichloro-3,5-dimethoxyphenyl)-4,5,6,7-tetrahydro-1H-indazol-3-yl)phenyl)acrylamide

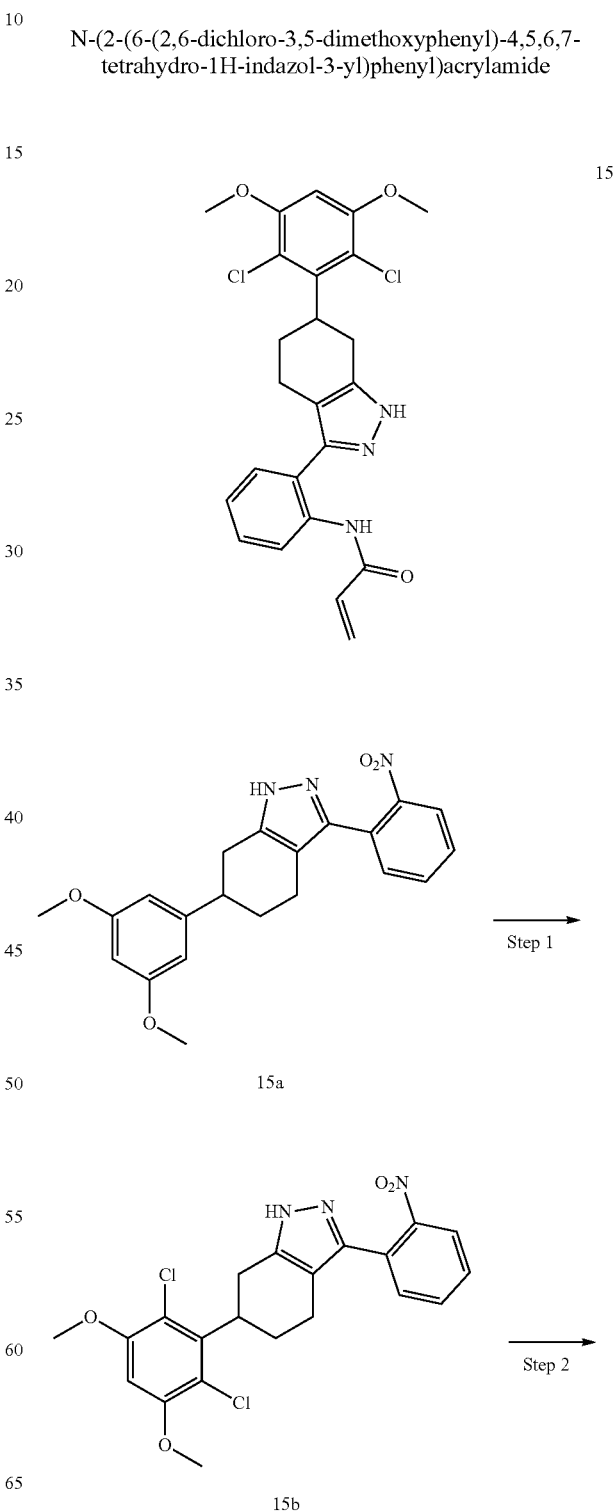

15a

15b

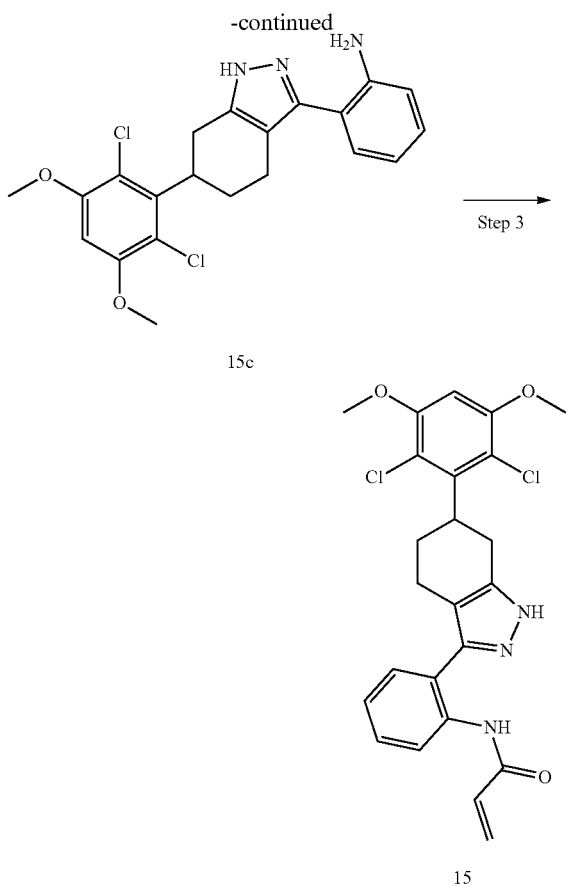

15c

Example 15a was synthesized with reference to the operation steps of example 093d.

Step 1

6-(2,6-dichloro-3,5-dimethoxyphenyl)-3-(2-nitrophenyl)-4,5,6,7-tetrahydro-1H-indazole 15b 6-(3,5-dimethoxyphenyl)-3-(2-nitrophenyl)-4,5,6,7-tetrahydro-1H-indazole 15a (250 mg, 0.66 mmol, 1 eq) was add to 5 ml of acetic acid, NCS (184 mg, 1.39 mmol, 2.1 eq) was added therein, and reaction was performed for 3 h at 50° C. Aftertreatment: desolvation was performed under reduced pressure, and the residual was passed through a silica gel chromatographic column with a petroleum ether/ethyl acetate (2:1) system to obtain a yellow solid product 6-(2, 6-dichloro-3,5-dimethoxyphenyl)-3-(2-nitrophenyl)-4,5,6, 7-tetrahydro-1H-indazole 15b (200 mg, yellow solid). Yield: 68%.

MS m/z (ESI): 448[M+1].

Step 2

2-(6-(2,6-dichloro-3,5-dimethoxyphenyl)-4,5,6,7-tetrahydro-1H-indazol-3-yl)aniline 15c The compound 6-(2,6-dichloro-3,5-dimethoxyphenyl)-3-(2-nitrophenyl)-4,5,6,7-tetrahydro-1H-indazole 15b (200 mg, 0.45 mmol, 1 eq) 15b (2.0 g, 3.9 mmol, 1 eq) was dissolved in ethanol (10 mL), zinc powder (290 mg, 4.5 mmol, 10 eq) and ammonium chloride (517 mg, 4.5 mmol, 10 eq) were added therein, and reaction was performed for 3 h at 50° C. Aftertreatment: the mixture was spin-dried to remove the solvent, and diluted with ethyl acetate and washed with water, and the organic phase was spin-dried to obtain the target product 2-(6-(2,6-dichloro-3,5-dimethoxyphenyl)-4,5,6,7-tetrahydro-1H-indazol-3-yl)aniline 15c (131 mg, yellow solid). Yield: 70%.

MS m/z (ESI): 418[M+1].

Step 3

N-(2-(6-(2,6-dichloro-3,5-dimethoxyphenyl)-4,5,6,7-tetrahydro-1H-indazol-3-yl)phenyl)acrylamide 15

The compound 2-(6-(2,6-dichloro-3,5-dimethoxyphenyl)-4,5,6,7-tetrahydro-1H-indazol-3-yl)aniline 15c (120 mg, 0.29 mmol, 1 eq) and N,N-diisopropyl ethylamine (75 mg, 0.58 mmol, 1 eq) were dissolved into anhydrous dichloromethane (10 mL), and the mixture was cooled to −40° C. A solution of acryloyl chloride (26 mg, 0.29 mmol, 1 eq) in dichloromethane was slowly added therein, and reaction was performed for 0.5 h. Aftertreatment: the mixture was spin-dried to remove the solvent, and subjected to preparative liquid phase separation and lyophilization to obtain the target product N-(2-(6-(2,6-dichloro-3,5-dimethoxyphenyl)-4,5,6,7-tetrahydro-1H-indazol-3-yl)phenyl)acrylamide 15 (5 mg, white solid). Yield: 4%.

MS m/z (ESI): 501[M+1].

$^1$H NMR (400 MHz, DMSO) δ 12.98 (s, 1H), 11.48 (s, 1H), 8.49 (d, J=6.9 Hz, 1H), 7.59 (d, J=7.0 Hz, 1H), 7.33 (t, J=7.6 Hz, 1H), 7.18 (t, J=7.1 Hz, 1H), 6.90 (s, 1H), 6.43-6.20 (m, 2H), 5.82 (d, J=9.2 Hz, 1H), 4.03 (s, 1H), 3.93 (d, J=3.6 Hz, 6H), 3.42 (d, J=12.8 Hz, 1H), 2.86-2.57 (m, 4H), 1.84 (d, J=11.6 Hz, 1H).

Embodiment 27

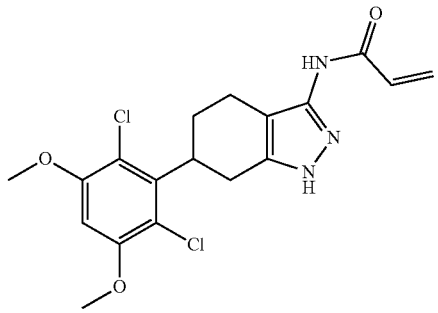

27

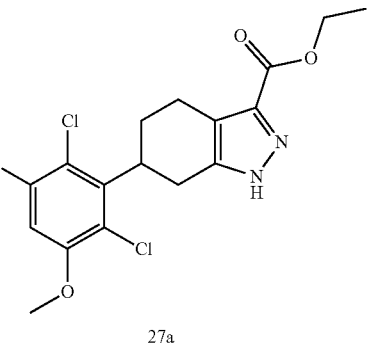

27a

-continued

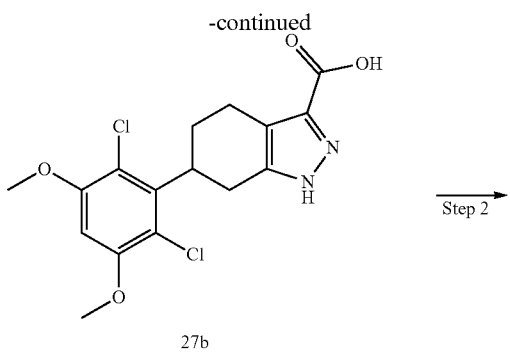

27b

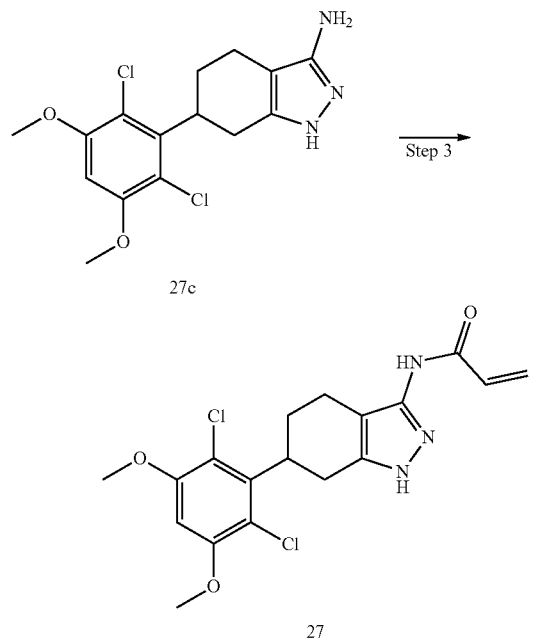

27c

27

Step 1

6-(2,6-dichloro-3,5-dimethoxyphenyl)-4,5,6,7-tetrahydro-1H-indazole-3-carboxylic acid 27b The compound ethyl 6-(2,6-dichloro-3,5-dimethoxyphenyl)-4,5,6,7-tetrahydro-1H-indazole-3-carboxylate 27a (700 mg, 1.76 mmol, 1 eq) was dissolved in methanol/tetrahydrofuran/water=5:5:2 (12 mL), and sodium hydroxide (0.21 g, 5.28 mmol, 3 eq) was added at a condition of 0° C. The mixture was raised to 50° C. and stirred for 5 h. Aftertreatment: the organic phase was desolventized under reduced pressure, 15 mL of 1N dilute hydrochloric acid added therein, and the solid was filtered and dried to obtain the target product 6-(2,6-dichloro-3,5-dimethoxyphenyl)-4,5,6,7-tetrahydro-1H-indazole-3-carboxylic acid 27b (0.52 g, white solid). Yield: 70%.

MS m/z (ESI): 371[M+1].

Step 2

6-(2,6-dichloro-3,5-dimethoxyphenyl)-4,5,6,7-tetrahydro-1H-indazole-3-amine 27c

The compound 6-(2,6-dichloro-3,5-dimethoxyphenyl)-4,5,6,7-tetrahydro-1H-indazole-3-carboxylic acid 27b (2.5 g, 6.8 mmol, 1 eq), diphenylphosphoryl azide (2.3 g, 8.1 mmol, 1.2 eq), triethyl amine (1.4 g, 13.6 mmol, 2 eq) were dissolved into acetonitrile (40 mL), and reacted for 4 h under reflux under the protection of nitrogen gas. Aftertreatment: the organic phase was desolventized under reduced pressure, and the spin-dried residual was purified through silica gel column chromatography (dichloromethane:methanol=10:1)) to obtain the target product 6-(2,6-dichloro-3,5-dimethoxyphenyl)-4,5,6,7-tetrahydro-1H-indazol-3-amine 27c (0.3 g, light yellow solid). Yield: 13%.

MS m/z (ESI): 342[M+1].

Step 3

N-(6-(2,6-dichloro-3,5-dimethoxyphenyl)-4,5,6,7-tetrahydro-1H-indazol-3-yl)acrylamide 27

The compound 6-(2,6-dichloro-3,5-dimethoxyphenyl)-4,5,6,7-tetrahydro-1H-indazole-3-amine 27c (10 mg, 0.03 mmol, 1 eq) was dissolved into 5 mL of dichloromethane, and N,N-diisopropyl ethylamine (8 mg, 0.06 mmol, 2 eq) was added therein. The mixture was cooled to −40° C., and a solution of acryloyl chloride (8 mg, 0.06 mmol, 1 eq) in dichloromethane was added dropwise and stirred for 30 min. Aftertreatment: desolvation was performed under reduced pressure, and the prepared liquid was subjected to phase separation, and freeze-dried to obtain the target product N-(6-(2,6-dichloro-3,5-dimethoxyphenyl)-4,5,6,7-tetrahydro-1H-indazol-3-yl)acrylamide 27 (3 mg, white solid). Yield: 25%.

MS m/z (ESI): 396 [M+1].

$^1$H NMR (400 MHz, MCOD) δ 8.53 (s, 1H), 7.42 (dd, J=17.3, 10.5 Hz, 1H), 6.78 (s, 1H), 6.60 (dd, J=17.3, 1.7 Hz, 1H), 6.01 (dd, J=10.5, 1.7 Hz, 1H), 4.12-4.00 (m, 1H), 3.95 (s, 6H), 3.44 (dd, J=16.6, 12.7 Hz, 1H), 2.74 (ddd, J=25.2, 12.6, 5.3 Hz, 1H), 2.65-2.55 (m, 2H), 2.37 (ddd, J=15.3, 12.4, 5.5 Hz, 1H), 1.86 (d, J=9.2 Hz, 1H).

Embodiment 083

N-((6-(2,6-dichloro-3,5-dimethoxyphenyl)-4,5,6,7-tetrahydro-1H-indazol-3-yl)methyl)acrylamide

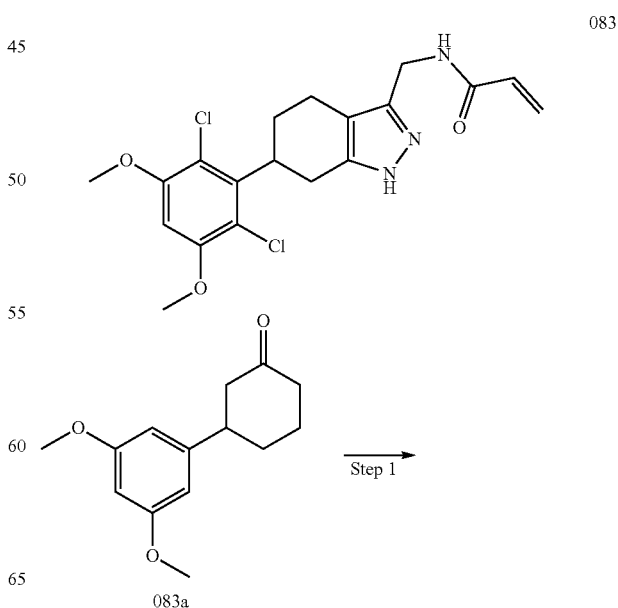

083a

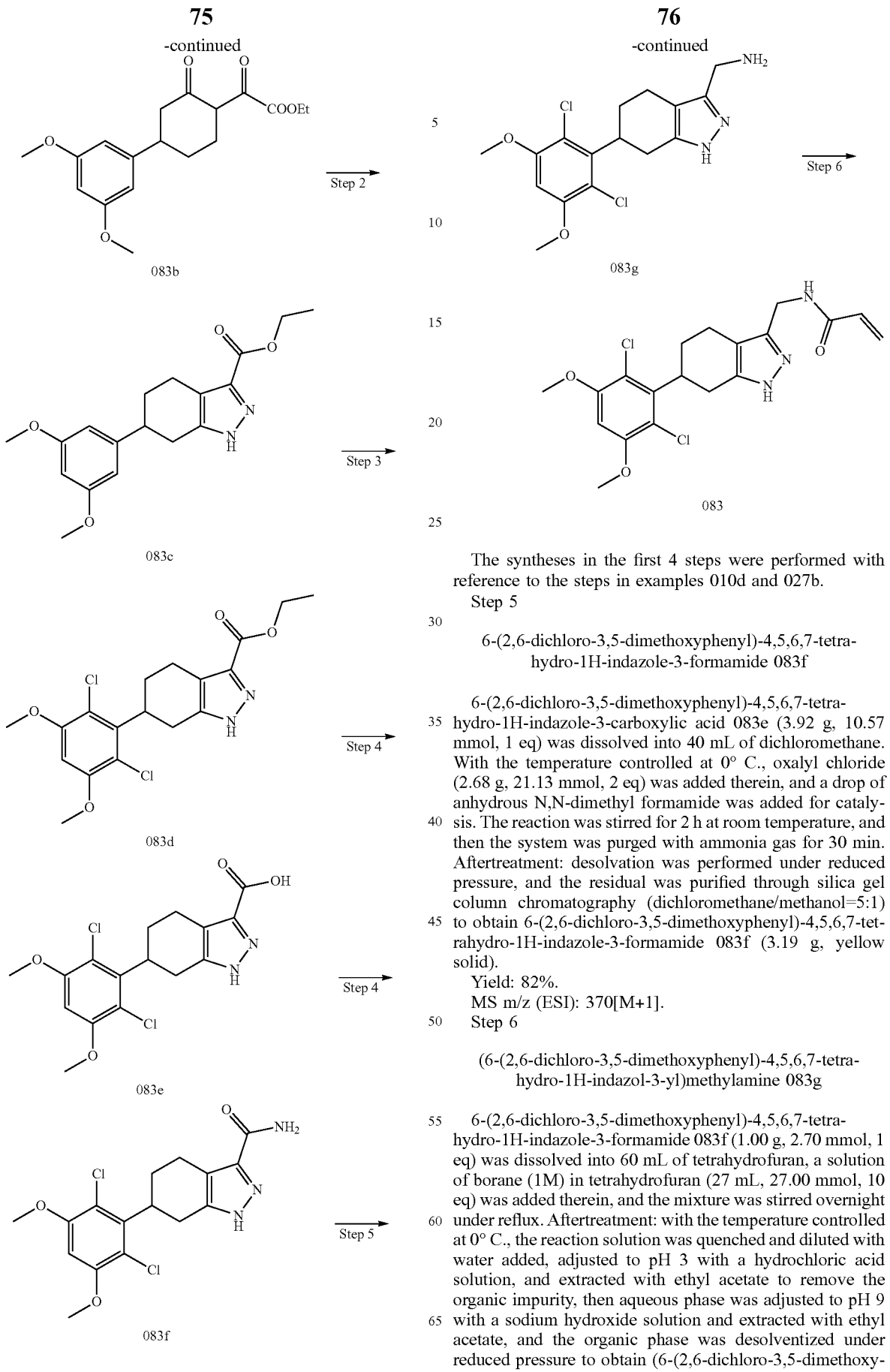

The syntheses in the first 4 steps were performed with reference to the steps in examples 010d and 027b.

Step 5

6-(2,6-dichloro-3,5-dimethoxyphenyl)-4,5,6,7-tetra-hydro-1H-indazole-3-formamide 083f 6-(2,6-dichloro-3,5-dimethoxyphenyl)-4,5,6,7-tetra-hydro-1H-indazole-3-carboxylic acid 083e (3.92 g, 10.57 mmol, 1 eq) was dissolved into 40 mL of dichloromethane. With the temperature controlled at 0° C., oxalyl chloride (2.68 g, 21.13 mmol, 2 eq) was added therein, and a drop of anhydrous N,N-dimethyl formamide was added for catalysis. The reaction was stirred for 2 h at room temperature, and then the system was purged with ammonia gas for 30 min. Aftertreatment: desolvation was performed under reduced pressure, and the residual was purified through silica gel column chromatography (dichloromethane/methanol=5:1) to obtain 6-(2,6-dichloro-3,5-dimethoxyphenyl)-4,5,6,7-tetrahydro-1H-indazole-3-formamide 083f (3.19 g, yellow solid).

Yield: 82%.

MS m/z (ESI): 370[M+1].

Step 6

(6-(2,6-dichloro-3,5-dimethoxyphenyl)-4,5,6,7-tetra-hydro-1H-indazol-3-yl)methylamine 083g 6-(2,6-dichloro-3,5-dimethoxyphenyl)-4,5,6,7-tetra-hydro-1H-indazole-3-formamide 083f (1.00 g, 2.70 mmol, 1 eq) was dissolved into 60 mL of tetrahydrofuran, a solution of borane (1M) in tetrahydrofuran (27 mL, 27.00 mmol, 10 eq) was added therein, and the mixture was stirred overnight under reflux. Aftertreatment: with the temperature controlled at 0° C., the reaction solution was quenched and diluted with water added, adjusted to pH 3 with a hydrochloric acid solution, and extracted with ethyl acetate to remove the organic impurity, then aqueous phase was adjusted to pH 9 with a sodium hydroxide solution and extracted with ethyl acetate, and the organic phase was desolventized under reduced pressure to obtain (6-(2,6-dichloro-3,5-dimethoxyphenyl)-4,5,6,7-tetrahydro-1H-indazol-3-yl)methylamine 083g (0.70 g, yellow solid). Yield: 73%.

MS m/z (ESI): 356[M+1].

Step 7

N-((6-(2,6-dichloro-3,5-dimethoxyphenyl)-4,5,6,7-tetrahydro-1H-indazol-3-yl)methyl)acrylamide The compound (6-(2,6-dichloro-3,5-dimethoxyphenyl)-4,5,6,7-tetrahydro-1H-indazol-3-yl)methylamine 083g (300 mg, 0.85 mmol, 1 eq) was dissolved into 15 mL of dichloromethane, and N,N-diisopropylethylamine (220 mg, 1.70 mmol, 2 eq) was added therein. The mixture was cooled to −40° C., and acryloyl chloride (76 mg, 0.85 mmol, 1 eq) was added therein dropwise and stirred for 30 min. Aftertreatment: the mixture was extracted with a water-ethyl acetate system, desolventized under reduced pressure, and the residual was separated and purified through high performance liquid chromatography to obtain N-((6-(2,6-dichloro-3,5-dimethoxyphenyl)-4,5,6,7-tetrahydro-1H-indazol-3-yl)methyl)acrylamide (15 mg, yellow solid). Yield: 4.3%.

MS m/z (ESI): 410 [M+1].

$^1$H NMR (400 MHz, DMSO) δ 8.47 (t, J=5.3 Hz, 1H), 6.88 (s, 1H), 6.28 (dd, J=17.1, 10.1 Hz, 1H), 6.13 (dd, J=17.1, 2.2 Hz, 1H), 5.61 (dd, J=10.1, 2.2 Hz, 1H), 4.32 (qd, J=15.1, 5.4 Hz, 2H), 3.90 (dd, J=15.8, 3.3 Hz, 7H), 3.39 (t, J=6.2 Hz, 1H), 2.75-2.53 (m, 3H), 2.40 (t, J=12.6 Hz, 1H), 1.77 (d, J=9.4 Hz, 1H), 1.31 (dd, J=14.9, 7.4 Hz, 1H).

Embodiment 91

N-(2-(5-(2,6-dichloro-3,5-dimethoxyphenethyl)-1H-pyrazol-3-yl)phenyl)acrylamide

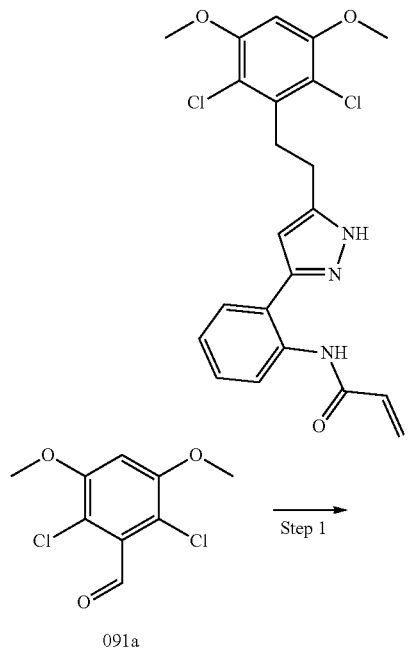

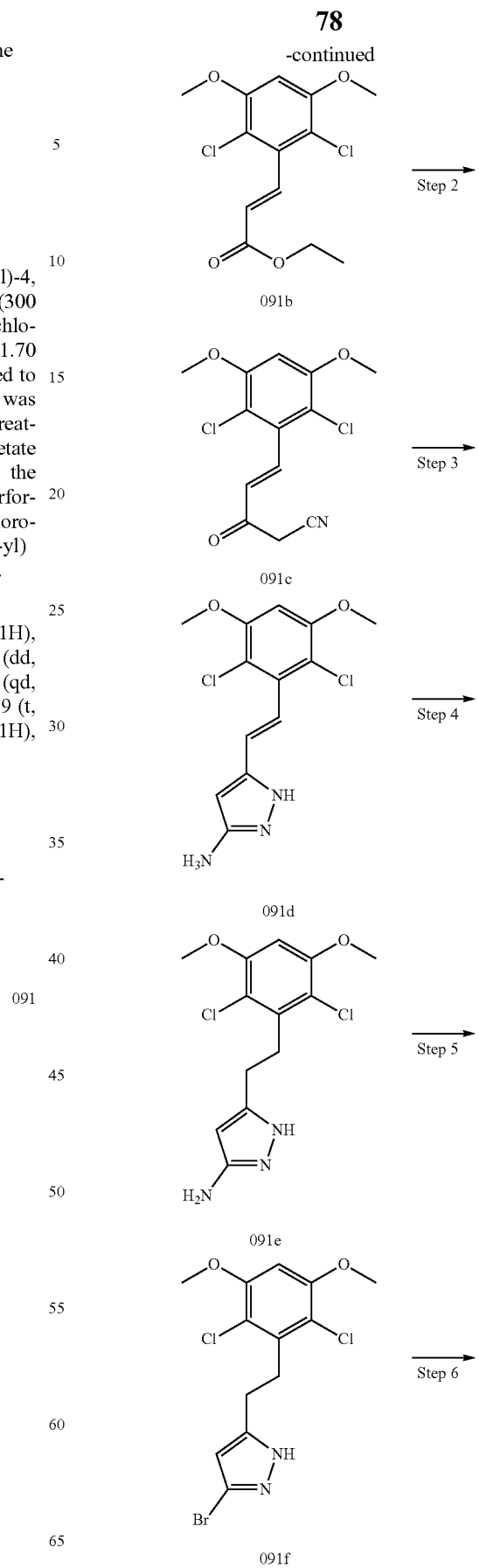

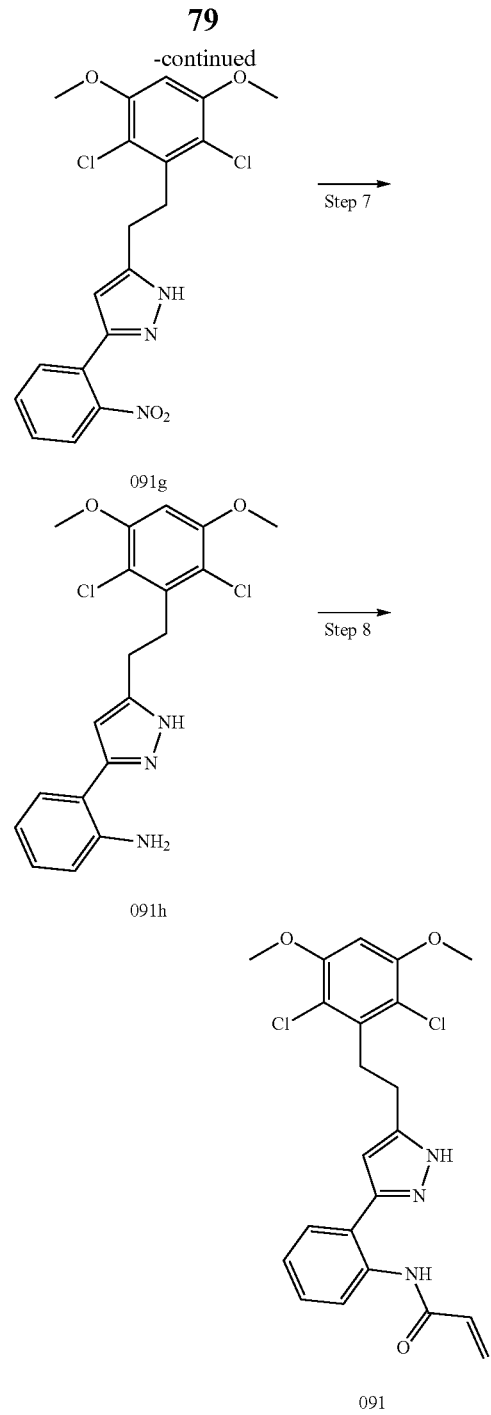

Step 1

Ethyl 3-(2,6-dichloro-3,5-dimethoxyphenyl)acrylate 091 b 2,6-Dichloro-3,5-dimethoxybenzaldehyde (1 g, 4.27 mmol), sodium hydride (60%) (512 mg, 8.54 mmol), and tetrahydrofuran (15 mL) were mixed and stirred at 0° C., and triethyl phosphonoacetate (1.43 g, 6.41 mmol) dissolved into tetrahydrofuran (3 mL) was slowly added dropwise into the reaction system. The system was warmed up to room temperature and further stirred for 2 h. Aftertreatment: a saturated ammonium chloride solution (20 mL) was added into this mixed solution, and the organic phase was desolventized under reduced pressure to obtain the target product ethyl 3-(2,6-dichloro-3,5-dimethoxyphenyl)acrylate 091b (1.1 g, white solid).

Yield: 84%.

MS m/z (ESI): 305[M+1].

Step 2

5-(2,6-dichloro-3,5-dimethoxyphenyl)-3-carbonyl-pent-4-enenitrile 091c

Under the protection of nitrogen gas, n-butyl lithium (3 mL, 7.2 mmol) was mixed at −78° C. into anhydrous tetrahydrofuran (20 mL). Acetonitrile (296 mg, 7.2 mmol) was slowly added dropwise into the reaction system, and reaction was performed for 1 h at −78° C. Ethyl 3-(2,6-dichloro-3,5-dimethoxyphenyl)acrylate (1.1 g, 3.6 mmol) dissolved in anhydrous tetrahydrofuran (5 mL) was slowly added dropwise to the reaction system, and the system was slowly warmed up to room temperature and stirred for 3 h. Aftertreatment: a saturated ammonia chloride aqueous solution (200 mL) was added into this mixture to quench the reaction, and the organic phase was desolventized under reduced pressure to obtain the target product 5-(2,6-dichloro-3,5-dimethoxyphenyl)-3-carbonylpent-4-enenitrile 091c (800 mg, white solid). Yield: 72%.

MS m/z (ESI): 300[M+1].

Step 3

5-(2,6-dichloro-3,5-dimethoxystyryl)-1H-pyrazole-3-amine 091d 5-(2,6-dichloro-3,5-dimethoxyphenyl)-3-carbonylpent-4-enenitrile (800 mg, 2.67 mmol), 80% hydrazine hydrate (2 mL), acetate (1 mL) and ethanol (10 mL) were mixed, warmed up to 60° C., and stirred for 3 h. Aftertreatment: the mixture was cooled to room temperature and desolventized under reduced pressure, and the residual was purified through silica gel column chromatography (petroleum ether: ethyl acetate=1:1) to obtain the target product 5-(2,6-dichloro-3,5-dimethoxystyryl)-1H-pyrazole-3-amine 091d (400 mg, white solid). Yield: 38%.

MS m/z (ESI): 314[M+1].

Step 4

5-(2,6-dichloro-3,5-dimethoxyphenethyl)-1H-pyrazole-3-amine 091e

Under the hydrogen atmosphere, 5-(2,6-dichloro-3,5-dimethoxystyryl)-1H-pyrazole-3-amine (400 mg, 1.27 mmol), a palladium carbon catalyst (100 mg), and methanol (10 mL) were mixed and stirred for 3 h at room temperature. Aftertreatment: the system was filtered and desolventized under reduced pressure to obtain the target product 5-(2,6-dichloro-3,5-dimethoxyphenethyl)-1H-pyrazole-3-amine 091e (380 mg, white solid). Yield: 95%.

MS m/z (ESI): 316[M+1].

Step 5

Bromo-5-(2,6-dichloro-3,5-dimethoxyphenethyl)-1H-pyrazole 091f 5-(2,6-dichloro-3,5-dimethoxyphenethyl)-1H-pyrazole-3-amine (5 g, 15.8 mmol) and hydrobromic acid (20 mL) were mixed and stirred for 1 h at room temperature. Sodium nitrite (1.2 g, 17.3 mmol) dissolved in water (5 mL) was slowly added dropwise at 0° C. to the reaction system and further stirred for 2 h. This mixed solution was added into a mixed solution of copper bromide (3.4 g, 23.4 mmol) and hydrobromic acid (50 mL), and stirred for 3 h at room temperature. Aftertreatment: this reaction solution was extracted with dichloromethane (200 mL×3) added therein, organic phases were combined and desolventized under reduced pressure, and the resulting residual was purified through silica gel column chromatography (petroleum ether: ethyl acetate=1:1) to obtain the target product 3-bromo-5-(2,6-dichloro-3,5-dimethoxyphenethyl)-1H-pyrazole 091f (1.8 g, white solid). Yield: 30%.

MS m/z (ESI): 378[M+1].

Step 6

5-(2,6-dichloro-3,5-dimethoxyphenethyl)-3-(2-nitro-phenyl)-1H-pyrazole 091g 3-bromo-5-(2,6-dichloro-3,5-dimethoxyphenethyl)-1H-pyrazole (500 mg, 1.32 mmol), o-nitrobenzene boronic acid (265 mg, 1.59 mmol), sodium hydroxide (158 mg, 3.96 mmol), a [1,1'-bis(diphenylphosphine)ferrocene]palladium chloride dichloromethane complex (430 mg, 0.528 mmol), glycol dimethyl ether (5 mL), and water (2.5 mL) were mixed, warmed up to 100° C. under the protection of nitrogen gas, and stirred for 6 h. Aftertreatment: glycol dimethyl ether was removed under reduced pressure, the residual was extracted with dichloromethane (50 mL) and water (50 mL), organic phases were combined and desolventized under reduced pressure, and the residual was purified through silica gel column chromatography (petroleum ether:ethyl acetate=1:1) to obtain 5-(2,6-dichloro-3,5-dimethoxyphenethyl)-3-(2-nitrophenyl)-1H-pyrazole 091g (300 mg, white solid). Yield: 53%.

MS m/z (ESI): 422[M+1].

Step 7

2-(5-(2,6-dichloro-3,5-dimethoxyphenethyl)-1H-pyrazol-3-yl) aniline 091h 5-(2,6-dichloro-3,5-dimethoxyphenethyl)-3-(2-nitrophenyl)-1H-pyrazole (300 mg, 0.71 mmol), zinc powder (463 mg, 7.1 mmol), ammonium chloride (376 mg, 7.1 mmol) and ethanol (5 mL) were mixed, warmed up to 50° C., and stirred for 2 h. Aftertreatment: the system was cooled to room temperature, filtered, and desolventized under reduced pressure to obtain the target product 2-(5-(2,6-dichloro-3,5-dimethoxyphenethyl)-1H-pyrazol-3-yl)aniline 091h (250 mg, white solid).

Yield: 85%.

MS m/z (ESI): 392[M+1].

Step 8

N-(2-(5-(2,6-dichloro-3,5-dimethoxyphenethyl)-1H-pyrazol-3-yl)phenyl)acrylamide 091

2-(5-(2,6-dichloro-3,5-dimethoxyphenethyl)-1H-pyrazol-3-yl)aniline (100 mg, 0.25 mmol), N,N-diisopropylethylamine (90 mg, 0.75 mmol) and dichloromethane (3 mL) were mixed. Acryloyl chloride (25 mg, 0.28 mmol) was slowly added therein while stirring at −40° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(2-(5-(2,6-dichloro-3,5-dimethoxyphenethyl)-1H-pyrazol-3-yl)phenyl)acrylamide 091 (15 mg, white solid). Yield: 13%.

MS m/z (ESI): 446[M+1].

¹H NMR (400 MHz, DMSO) δ 10.20 (s, 1H), 8.08 (s, 1H), 7.70 (ddd, J=12.8, 9.1, 4.7 Hz, 1H), 7.62 (d, J=8.0 Hz, 1H), 7.47 (d, J=7.7 Hz, 1H), 7.35 (t, J=7.8 Hz, 1H), 6.86 (s, 1H), 6.47 (dd, J=17.7, 9.3 Hz, 2H), 6.28 (dd, J=17.0, 1.5 Hz, 1H), 5.77 (m, 1H), 3.93 (s, 6H), 3.24 (m, 2H), 2.80 (m, 2H).

Example 093

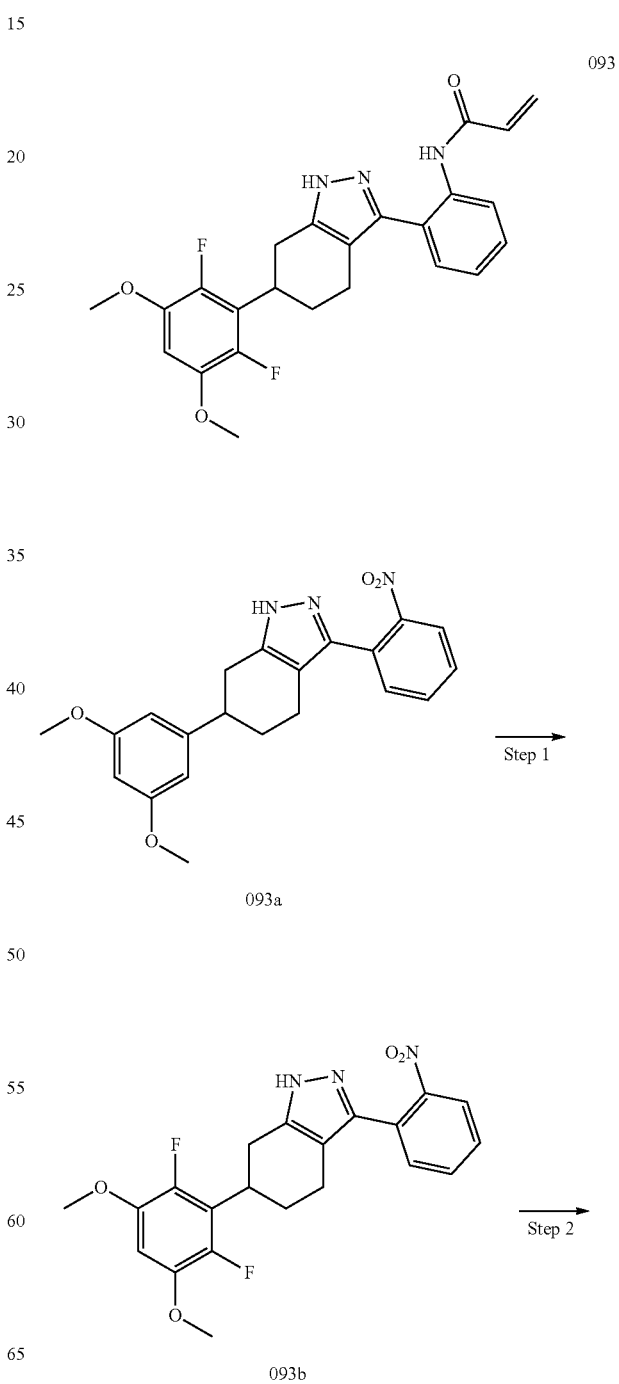

-continued

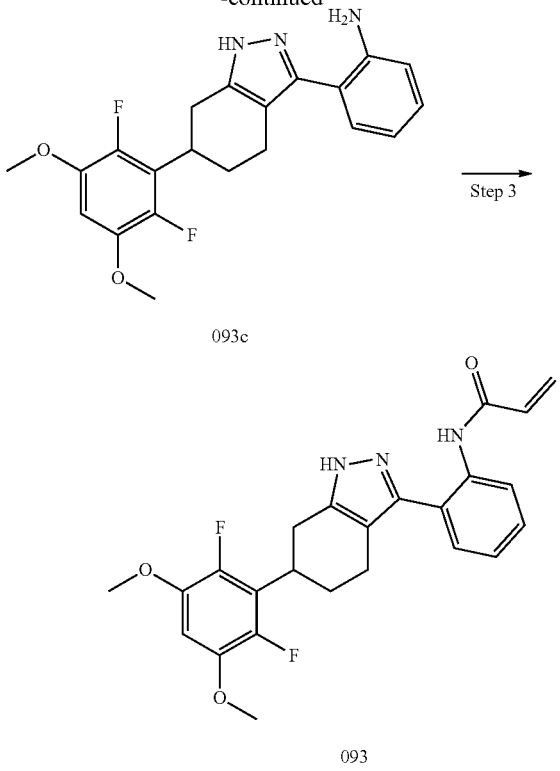

093c

093

Example 093a was synthesized with reference to example 098d.

Step 1

6-(2,6-difluoro-3,5-dimethoxyphenyl)-3-(2-nitrophenyl)-4,5,6,7-tetrahydro-1H-indazole 093b 6-(3,5-dimethoxyphenyl)-3-(2-nitrophenyl)-4,5,6,7-tetrahydro-1H-indazole 093d (2 g, 5 mmol) and acetonitrile (100 ml) were mixed, select F (3.5 g, 10 mmol) was added therein at 0° C., and the mixture was slowly warmed up to room temperature and stirred overnight. Aftertreatment: desolvation was performed, the residual was extracted with dichloromethane (100 mL) and water (100 mL) added therein, the organic phase was desolventized under reduced pressure, and the residual was purified through silica gel column chromatography (petroleum ether:ethyl acetate=5:4) to obtain 6-(2,6-difluoro-3,5-dimethoxyphenyl)-3-(2-nitrophenyl)-4,5,6,7-tetrahydro-1H-indazole 093b (640 mg, 1.5 mmol, yellow solid). Yield: 15%.

MS m/z (ESI): 416 [M+1].

Step 2

2-(6-(2,6-difluoro-3,5-dimethoxyphenyl)-4,5,6,7-tetrahydro-1H-indazol-3-yl)aniline 093c Zinc powder (135 mg, 3 mmol), ammonium chloride (260 mg, 5 mmol), water (1 mL) and ethanol (10 ml) were mixed into 6-(2,6-difluoro-3,5-dimethoxyphenyl)-3-(2-nitrophenyl)-4,5,6,7-tetrahydro-1H-indazole (200 mg, 0.5 mmol), warmed up to 50° C. and stirred for 2 h. Aftertreatment: the mixture was filtered, desolventized under reduced pressure, extracted with dichloromethane (10 mL) and water (10 mL) added therein, and the organic phase was desolventized under reduced pressure to obtain 2-(6-(2,6-difluoro-3,5-dimethoxyphenyl)-4,5,6,7-tetrahydro-1H-indazol-3-yl)aniline 093f (120 mg, 0.3 mmol, brown solid). Yield: 60%.

MS m/z (ESI): 386 [M+1].

Step 3

N-(2-(6-(2,6-difluoro-3,5-dimethoxyphenyl)-4,5,6,7-tetrahydro-1H-indazol-3-yl)phenyl)acrylamide 093

2-(6-(2,6-difluoro-3,5-dimethoxyphenyl)-4,5,6,7-tetrahydro-1H-indazol-3-yl)aniline (120 mg, 0.3 mmol), N,N-diisopropylethylamine (119 mg, 1 mmol) and dichloromethane (3 mL) were mixed, and acryloyl chloride (30 mg, 0.3 mmol) was slowly added therein while stirring at −40° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain N-(2-(6-(2,6-difluoro-3,5-dimethoxyphenyl)-4,5,6,7-tetrahydro-1H-indazol-3-yl)phenyl)acrylamide 093 (40 mg, 0.1 mmol, white solid). Yield: 60%.

MS m/z (ESI): 440 [M+1].

$^1$H NMR (400 MHz, DMSO) δ 12.98 (s, 1H), 11.51 (s, 1H), 8.47 (s, 1H), 7.57 (d, J=6.6 Hz, 1H), 7.33 (t, J=7.6 Hz, 1H), 7.18 (t, J=7.5 Hz, 1H), 6.94 (t, J=8.3 Hz, 1H), 6.42-6.21 (m, 2H), 5.81 (d, J=11.3 Hz, 1H), 3.97-3.80 (m, 7H), 3.41 (d, J=7.3 Hz, 1H), 2.94 (t, J=5.7 Hz, 5H), 2.11 (d, J=8.5 Hz, 1H).

P1 and P2 were obtained through chiral column resolution. Conditions for chiral resolution: device: SFC, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

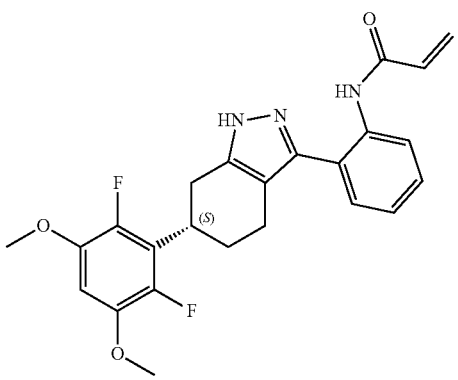

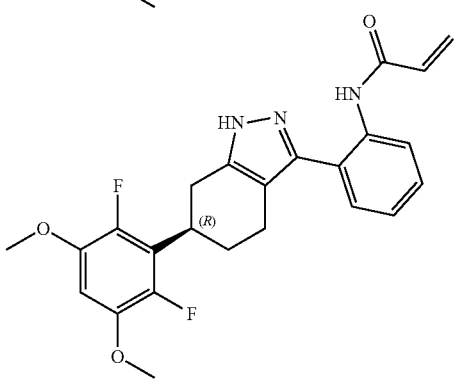

85
Embodiment 096

N-(2-(5-(2,6-dichloro-3,5-dimethoxyphenethyl)-1H-pyrazol-3-yl)phenyl)but-2-ynoic amide

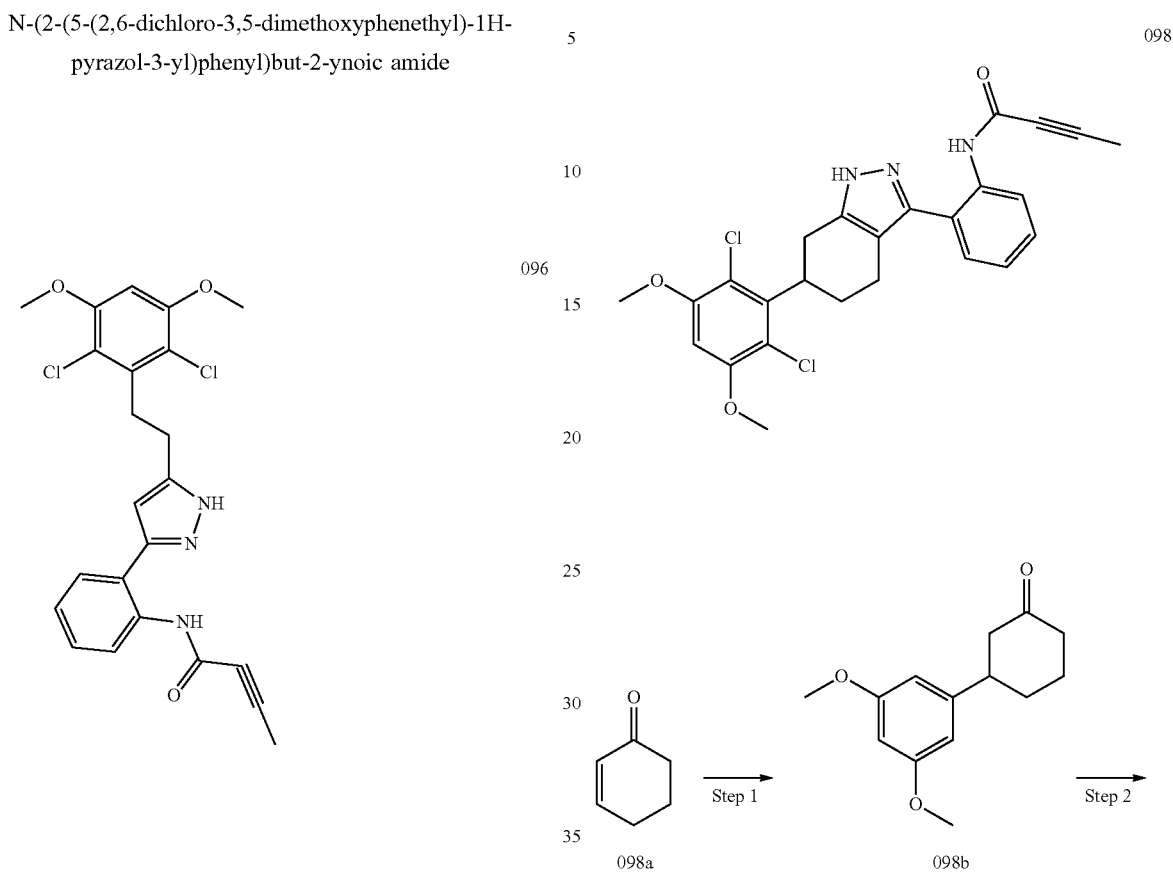

Embodiment 96 was synthesized with reference to the operation steps of embodiment 91, except that in Step 8, 2-(5-(2,6-dichloro-3,5-dimethoxyphenethyl)-1H-pyrazol-3-yl)aniline (100 mg, 0.25 mmol), 2-butynoic acid (23 mg, 0.28 mmol) and dichloromethane (5 mL) were mixed, and dicyclohexyl carbodiimide (57 mg, 0.28 mmol) and 4-dimethylaminopyridine (6 mg, 0.025 mmol) were slowly added dropwise while stirring at 0° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(2-(5-(2,6-dichloro-3,5-dimethoxybenzylamino)-1H-pyrazol-3-yl)phenyl)acrylamide 096 (10 mg, white solid). Yield: 8%.

MS m/z (ESI): 468[M+1].

$^1$H NMR (400 MHz, DMSO) δ 12.76 (s, 1H), 10.63 (s, 1H), 8.06 (s, 1H), 7.47 (t, J=8.3 Hz, 2H), 7.32 (s, 1H), 6.85 (s, 1H), 6.45 (s, 1H), 3.92 (s, 6H), 3.23 (m, 2H), 2.80 (s, 2H), 2.06 (s, 3H).

86
Example 098

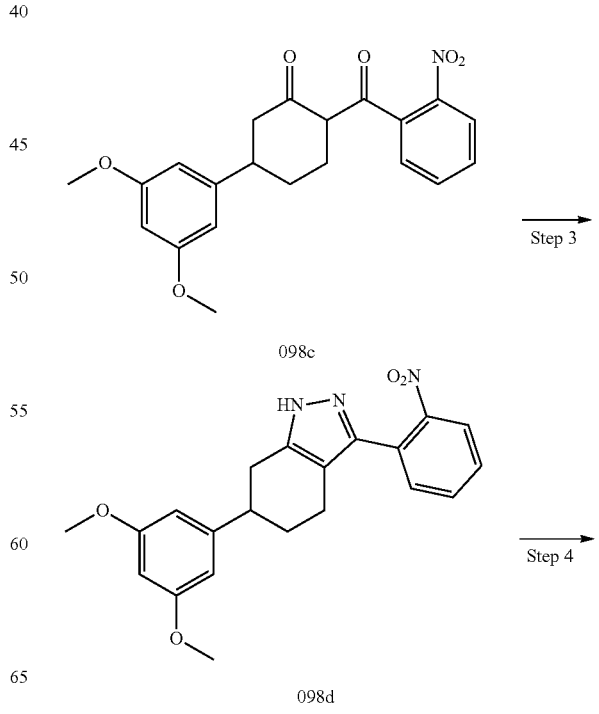

-continued

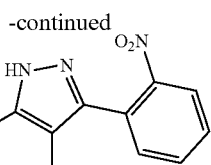

098e

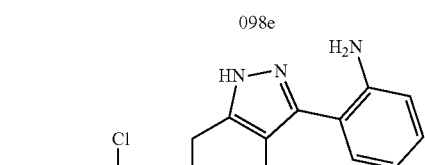

098f

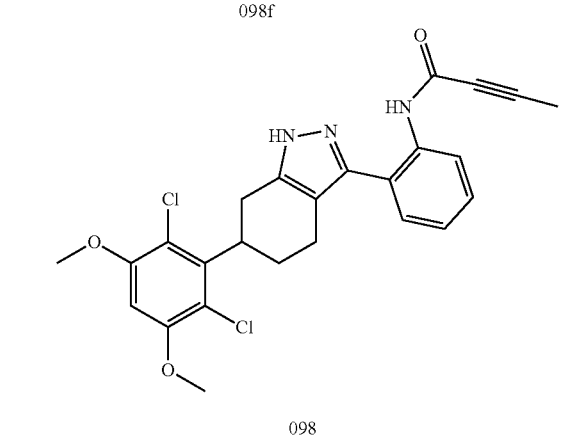

098

Step 1

3-(3,5-dimethoxyphenyl)cyclohexanone 098b

Cyclohexenone (4 g, 41 mmol), 2-5 dimethoxyphenylboronic acid (8.5 g, 47 mmol), caesium carbonate (13 g, 41 mmol), palladium acetate (1 g, 4 mmol), triphenylphosphine (2.2 g, 8 mmol), chloroform (0.5 mL) and toluene (100 mL) were mixed, warmed up to 85° C. under the protection of nitrogen gas, and stirred for 24 h. Aftertreatment: desolvation was performed under reduced pressure, and the residual was purified through silica gel column chromatography (petroleum ether:ethyl acetate=10:1) to obtain 3-(3,5-dimethoxyphenyl)cyclohexanone 098b (4.5 g, yellow liquid). Yield: 45%.

MS m/z (ESI): 235 [M+1].

Step 2

5-(3,5-dimethoxyphenyl)-2-(2-nitrobenzoyl)cyclohexanone 098c 3-(3,5-dimethoxyphenyl)cyclohexanone (4.2 g, 18 mmol) and tetrahydrofuran (100 ml) were mixed, and cooled to −78° C. under the protection of nitrogen gas. Lithium diisopropylamide (8.3 mL, 20 mmol) was slowly added therein dropwise, and the mixture was warmed up to −40° C. and stirred for 2 h. O-nitrobenzoyl chloride (3.5 g, 18 mmol) was slowly added therein, and the mixture was raised to room temperature and stirred for 3 h. Aftertreatment: the mixture was quenched with a saturated ammonium chloride aqueous solution, the organic phase was desolventized under reduced pressure, and the residual was purified through silica gel column chromatography (petroleum ether:ethyl acetate=3:1) to obtain 5-(3,5-dimethoxyphenyl)-2-(2-nitrobenzoyl)cyclohexanone 098c (3.6 g, yellow solid). Yield: 40%.

MS m/z (ESI): 384 [M+1].

Step 3

6-(3,5-dimethoxyphenyl)-3-(2-nitrophenyl)-4,5,6,7-tetrahydro-1H-indazole 098d 5-(3,5-dimethoxyphenyl)-2-(2-nitrobenzoyl)cyclohexanone (3.6 g, 10 mmol), hydrazine hydrate (5 mL), acetic acid (5 mL) and ethanol (50 mL) were mixed, warmed up to 65° C. and stirred for 3 h. Aftertreatment: desolvation was performed under reduced pressure, and the residual was purified through silica gel column chromatography (petroleum ether:ethyl acetate=3:1) to obtain 6-(3,5-dimethoxyphenyl)-3-(2-nitrophenyl)-4,5,6,7-tetrahydro-1H-indazole 098d (2 g, yellow solid). Yield: 65%.

MS m/z (ESI): 380 [M+1].

Step 4

6-(2,6-dichloro-3,5-dimethoxyphenyl)-3-(2-nitrophenyl)-4,5,6,7-tetrahydro-1H-indazole 098e 6-(3,5-dimethoxyphenyl)-3-(2-nitrophenyl)-4,5,6,7-tetrahydro-1H-indazole (2 g, 5 mmol), N-chlorosuccinimide (12 mmol) and acetic acid (100 mL) were mixed, warmed up 80° C. and reacted for 2 h. Aftertreatment: dichloromethane and water were added and layered, the organic phase was desolventized under reduced pressure, and the resultant was passed through a silica gel chromatographic column with a petroleum ether/ethyl acetate (1:1) system to obtain a yellow solid product 6-(2,6-dichloro-3,5-dimethoxyphenyl)-3-(2-nitrophenyl)-4,5,6,7-tetrahydro-1H-indazole 098e (2.2 g, 5 mmol, yellow solid). Yield: 90%.

MS m/z (ESI): 448 [M+1].

Step 5

2-(6-(2,6-dichloro-3,5-dimethoxyphenyl)-4,5,6,7-tetrahydro-1H-indazol-3-yl)aniline 098f 6-(2,6-dichloro-3,5-dimethoxyphenyl)-3-(2-nitrophenyl)-4,5,6,7-tetrahydro-1H-indazole 098e (400 mg, 1 mmol) was placed into 10 mL of DMF. Zinc powder (310 mg, 5 mmol, 5 eq), ammonium chloride (530 mg, 10 mmol, 10 eq) and 1 ml of water were added therein, and the system was reacted for 0.8 h at 50° C. Aftertreatment: desolvation was performed under reduced pressure, dichloromethane and the aqueous phase were layered, and the organic phase was spin-dried to obtain the a solid crude product 2-(6-(2,6-dichloro-3,5-dimethoxyphenyl)-4,5,6,7-tetrahydro-1H-indazol-3-yl)aniline 098f (230 mg, 0.5 mmol, white solid). Yield: 65%.

MS m/z (ESI): 418 [M+1].

Step 6

N-(2-(6-(2,6-dichloro-3,5-dimethoxyphenyl)-4,5,6,7-tetrahydro-1H-indazol-3-yl)phenyl)but-2-ynoic amide 098

2-(6-(2,6-dichloro-3,5-dimethoxyphenyl)-4,5,6,7-tetrahydro-1H-indazol-3-yl)aniline 098f (250 mg, 0.6 mmol) was placed into 20 mL of DCM. DIPEA (260 mg, 2 mmol, 3 eq) and HATU (300 mg, 0.8 mmol, 1.2 eq) were added therein, and then 2-butynoic acid (45 mg, 0.6 mmol, 1 eq) was slowly added. The mixture was raised from 0° C. to room temperature and reacted for 1 h. Aftertreatment: desolvation was performed under reduced pressure, dichloromethane and the aqueous phase were added and layered, the organic phase was rotary-evaporated to remove the solvent, and the preparative liquid phase separation afforded a white solid product N-(2-(6-(2,6-dichloro-3,5-dimethoxyphenyl)-4,5,6,7-tetrahydro-1H-indazol-3-yl)phenyl)but-2-ynoic amide 098 (80 mg, 0.16 mmol, white solid). Yield: 50%.

MS m/z (ESI): 484 [M+1].

$^1$H NMR (400 MHz, DMSO) δ 12.98 (s, 1H), 11.60 (s, 1H), 8.30 (s, 1H), 7.57 (s, 1H), 7.33 (s, 1H), 7.18 (s, 1H), 6.89 (s, 1H), 4.02 (s, 1H), 3.91 (m, 6H), 3.31 (m, 1H), 2.71 (m, 4H), 2.01 (m, 3H), 1.80 (s, 1H).

Embodiment 100

N-(2-(5-(2,6-dichloro-3,5-dimethoxybenzylamino)-1H-pyrazol-3-yl)phenyl)but-2-ynoic amide

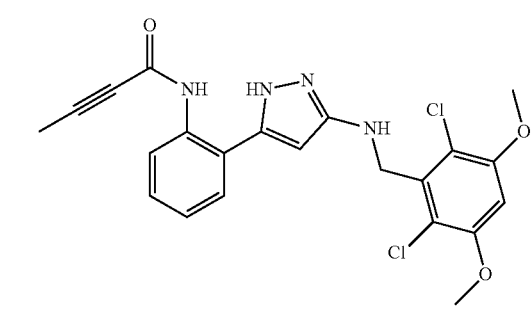

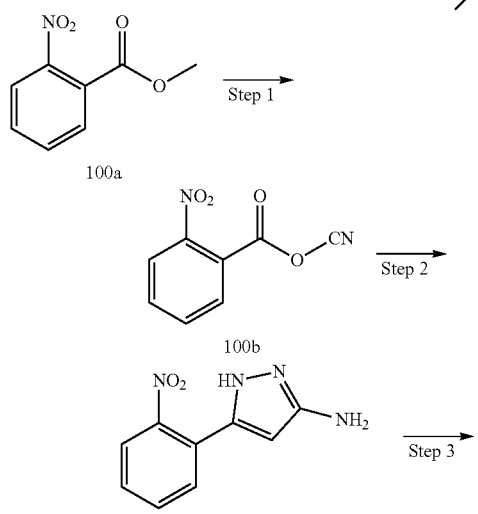

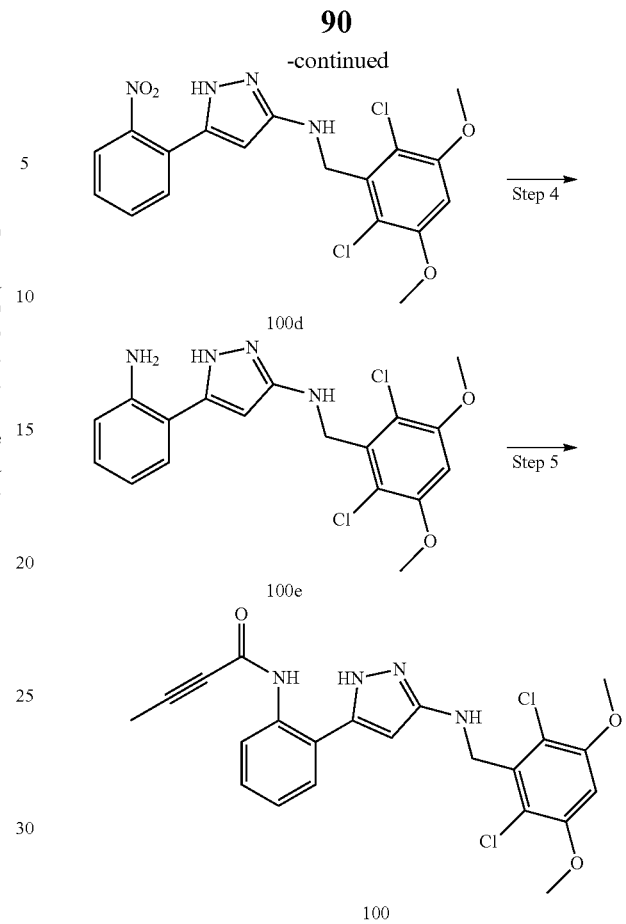

Step 1

3-(2-nitrophenyl)-3-carbonylpropionitrile 100b

Under the protection of nitrogen gas, n-butyl lithium (69 mL, 164 mmol) was mixed at −78° C. into anhydrous tetrahydrofuran (200 mL). Acetonitrile (6.7 g, 164 mmol) was slowly added dropwise to the reaction system, and the system was reacted for 1 h at −78° C. Methyl 2-nitrobenzoate (15 g, 82 mmol) dissolved in anhydrous tetrahydrofuran (100 mL) was slowly added dropwise to the reaction system, and the system was slowly warmed up to room temperature and stirred for 3 h. Aftertreatment: a saturated ammonia chloride aqueous solution (200 mL) was added into this mixture to quench the reaction, and the organic phase was desolventized under reduced pressure to obtain the target product 3-(2-nitrophenyl)-3-carbonylpropionitrile 100b (10 g, yellow solid).

Yield: 59%.

MS m/z (ESI): 191[M+1].

Step 2

5-(2-nitrophenyl)-1H-pyrazole-3-amine 100c 3-(2-nitrophenyl)-3-carbonylpropionitrile (10 g, 52 mmol), 80% hydrazine hydrate (3.15 g, 78 mmol), acetic acid (10 mL) and ethanol (100 mL) were mixed, warmed up to 60° C., and stirred for 3 h. Aftertreatment: the mixture was cooled to room temperature, desolventized under reduced pressure, and the residual was purified through silica gel column chromatography (petroleum ether:ethyl acetate=1:1)

to obtain the target product 5-(2-nitrophenyl)-1H-pyrazole-3-amine 100c (8 g, yellow solid). Yield: 79%.

MS m/z (ESI): 205[M+1].

Step 3

N-(2,6-dichloro-3,5-dimethoxybenzyl)-5-(2-nitrophenyl)-1H-pyrazole-3-amine 100d 5-(2-nitrophenyl)-1H-pyrazole-3-amine (1 g, 4.9 mmol), 2,6-dichloro-3,5-dimethoxybenzaldehyde (1.1 g, 4.9 mmol), acetic acid (2 mL) and methanol (10 mL) were mixed, and stirred for 3 h at room temperature. Sodium cyanoborohydride (455 mg, 7.35 mmol) was slowly added therein while stirring, and further stirred for 30 min. Aftertreatment: desolvation was performed under reduced pressure, and the residual was purified through silica gel column chromatography (petroleum ether:ethyl acetate=1:1) to obtain the target product N-(2,6-dichloro-3,5-dimethoxybenzyl)-5-(2-nitrophenyl)-1H-pyrazole-3-amine 100d (1.8 g, white solid). Yield: 87%.

MS m/z (ESI): 423[M+1].

Step 4

5-(2-aminophenyl)-N-(2,6-dichloro-3,5-dimethoxybenzyl)-1H-pyrazole-3-amine 100e

N-(2,6-dichloro-3,5-dimethoxybenzyl)-5-(2-nitrophenyl)-1H-pyrazole-3-amine (200 mg, 0.47 mmol), zinc powder (30 mg, 4.7 mmol), ammonium chloride (249 mg, 4.7 mmol) and ethanol (5 mL) were mixed, warmed up 50° C., and stirred for 2 h. Aftertreatment: the system was cooled to room temperature, filtered, and desolventized under reduced pressure to obtain the target product 5-(2-aminophenyl)-N-(2,6-dichloro-3,5-dimethoxybenzyl)-1H-pyrazole-3-amine 100e (150 mg, white solid). Yield: 80%.

MS m/z (ESI): 393 [M+1].

Step 5

N-(2-(5-(2,6-dichloro-3,5-dimethoxybenzylamino)-1H-pyrazol-3-yl)phenyl)but-2-ynoic amide 100

The compound 5-(2-aminophenyl)-N-(2,6-dichloro-3,5-dimethoxybenzyl)-1H-pyrazole-3-amine (150 mg, 0.38 mmol), 2-(7-oxidized benzotriazole)-N,N,N',N'-tetramethyluronium hexafluorophosphate (120 mg, 0.38 mmol), N,N-diisopropylethylamine (147 mg, 1.14 mmol) and dichloromethane (5 mL) were mixed. 2-butynoic acid (40 mg, 0.40 mmol) was slowly added therein while stirring at 0° C., and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(2-(5-(2,6-dichloro-3,5-dimethoxybenzylamino)-1H-pyrazol-3-yl)phenyl)but-2-ynoic amide 100 (15 mg, white solid). Yield: 9%.

MS m/z (ESI): 459[M+1].

$^1$H NMR (400 MHz, DMSO) δ 12.21 (d, J=41.7 Hz, 1H), 8.79 (m, 1H), 8.42 (s, 1H), 7.66 (m, 1H), 7.23 (dd, J=33.2, 25.1 Hz, 1H), 6.94 (s, 1H), 6.56 (s, 1H), 6.00 (d, J=35.9 Hz, 2H), 4.49 (d, J=5.5 Hz, 2H), 3.94 (s, 6H), 2.06 (s, 3H).

Embodiment 101

N-(2-(3-((2,6-dichloro-3,5-dimethoxyphenoxy)methyl)-1H-pyrazol-5-yl)phenyl)but-2-ynoic amide

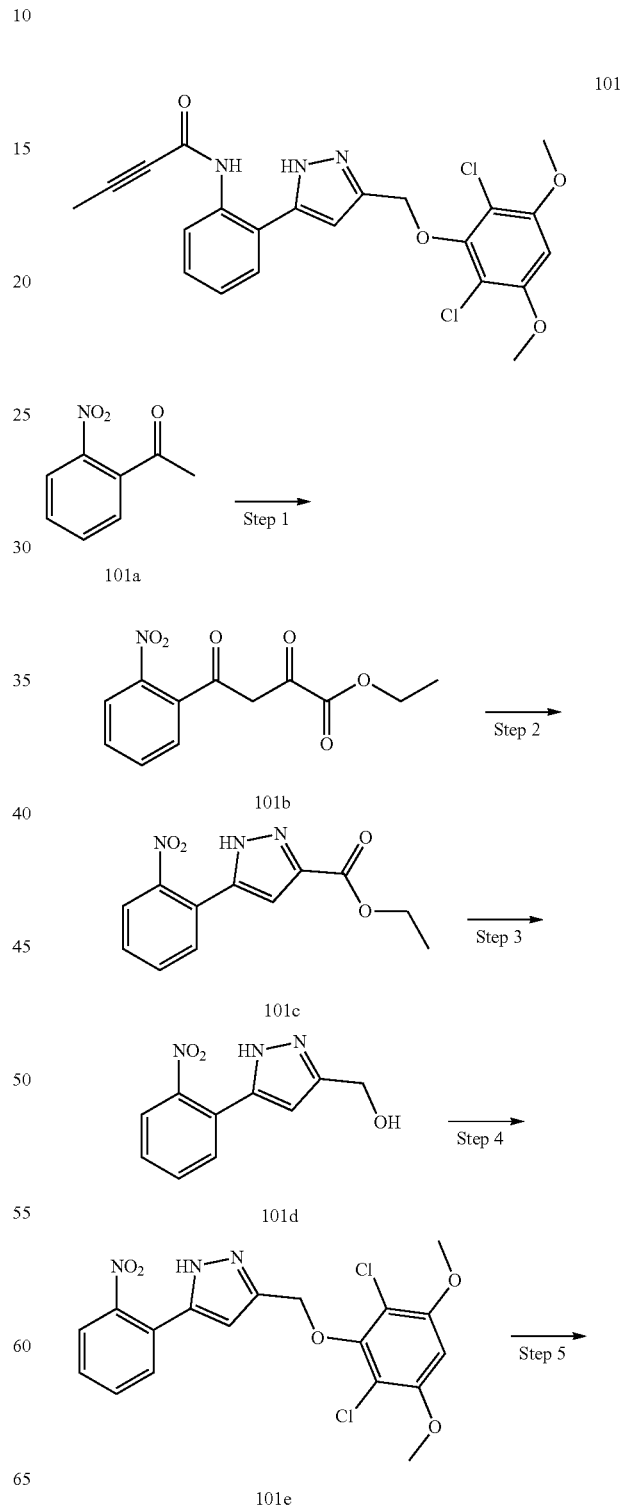

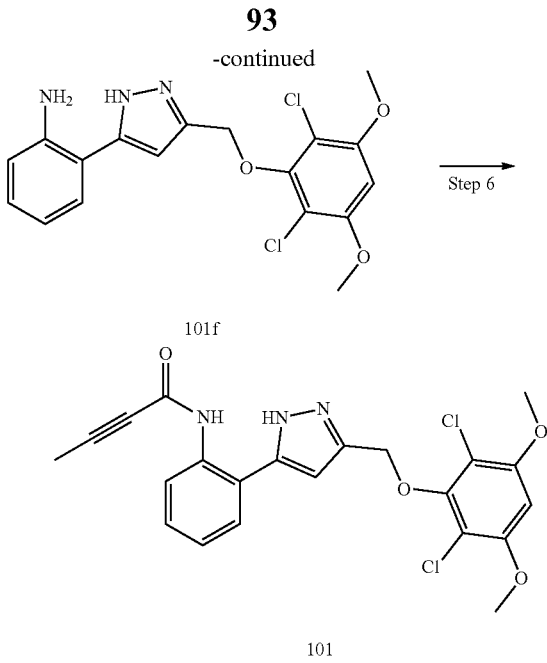

Step 1

Ethyl (2-nitrophenyl)-2,4-dicarbonylbutyrate

The compound 1-(2-nitrophenyl)ethan-1-one 101a (16.80 g, 101.82 mmol, 1 eq) and diethyl oxalate (29.73 g, 203.64 mmol, 2 eq) were dissolved in anhydrous tetrahydrofuran (85 mL). With the temperature controlled at 0° C. new-made sodium ethoxide (13.85 g, 203.64 mmol, 2 eq) was added in portions, and reaction was performed for 2 h at 0° C. Aftertreatment: the reaction was quenched with 50 mL of water added and extracted with ethyl acetate, and the organic phase was desolventized under reduced pressure to obtain the target product ethyl 4-(2-nitrophenyl)-2,4-dicarbonylbutyrate 101b (21.05 g, brown liquid). Yield: 78%.

MS m/z (ESI): 265[M+1].

Step 2

Ethyl (2-nitrophenyl)-1H-pyrazole-3-carboxylate

The compound ethyl 4-(2-nitrophenyl)-2,4-dicarbonyl butyrate 101b (21.05 g, 79.4 mmol, 1 eq) and hydrazine hydrate (7.94 g, 158.8 mmol, 2 eq) were dissolved in ethanol/acetic acid 10:1 (165 mL), and reacted for 2 h under reflux. Aftertreatment: desolvation was performed under reduced pressure, and the residual was purified through silica gel column chromatography (petroleum ether:ethyl acetate=5:1) to obtain the target product ethyl 5-(2-nitrophenyl)-1H-pyrazole-3-carboxylate 101c (16.7 g, yellow solid). Yield: 81%.

MS m/z (ESI): 261[M+1].

Step 3

(5-(2-nitrophenyl)-1H-pyrazol-3-yl)methanol

The compound ethyl 5-(2-nitrophenyl)-1H-pyrazole-3-carboxylate (7.48 g, 28.66 mmol, 1 eq) was dissolved in anhydrous tetrahydrofuran (120 mL). With the temperature controlled at 0° C., lithium aluminium tetrahydride (1.31 g, 34.39 mmol, 1.2 eq) was added in portions, and reaction was performed for 2 h at room temperature. Aftertreatment: with the temperature controlled at 0° C., 1.3 mL of water and 1.3 mL of a sodium hydroxide solution (15%) were added sequentially. After intensive stirring, the solid was filtered out, and the residual from desolvation of the filtrate under reduced pressure was purified through silica gel column chromatography (petroleum ether:ethyl acetate=1:1) to obtain the target product (5-(2-nitrophenyl)-1H-pyrazol-3-yl)methanol. 101d (4.52 g, yellow solid). Yield: 72%.

MS m/z (ESI): 219[M+1].

Step 4

3-((2,6-dichloro-3,5-dimethoxyphenoxy)methyl)-5-(2-nitrophenyl)-1H-pyrazole

The compound (5-(2-nitrophenyl)-1H-pyrazol-3-yl) methanol 101d (307 mg, 1.4 mmol, 1 eq), 1, 5-dichloro-2, 4-dimethoxyphenol 8b (312 mg, 1.4 mmol, 1 eq) and triphenylphosphine (440 mg, 1.68 mmol, 1.2 eq) were dissolved in 30 mL of anhydrous tetrahydrofuran, and cooled to 0° C. Diethyl azodiformate (292 mg, 1.68 mmol, 1.2 eq) was added therein dropwise, and the mixture was raised to room temperature and stirred for 2 h. 100 mL of saturated sodium chloride was added and layered. The aqueous phase was extracted with 100 mL of ethyl acetate. Organic phases were combined, dried and desolventized under reduced pressure. The residual was purified through silica gel column chromatography (petroleum ether/ethyl acetate=1:1) to obtain the target product 3-((2,6-dichloro-3,5-dimethoxyphenoxy)methyl)-5-(2-nitrophenyl)-1H-pyrazole 101e (550 mg, white solid). Yield: 93%.

MS m/z (ESI): 424[M+1].

Step 5

2-(3-((2,6-dichloro-3,5-dimethoxyphenoxy)methyl)-1H-pyrazol-5-yl)aniline

The compound 3-((2,6-dichloro-3,5-dimethoxyphenoxy)methyl)-5-(2-nitrophenyl)-1H-pyrazole 101e (515 mg, 1.21 mmol, 1 eq) was dissolved in ethanol (25 mL). Water (2.5 mL), zinc powder (395 mg, 6.07 mmol, 5 eq) and ammonium chloride (262 mg, 4.86 mmol, 4 eq) were added therein, and reaction was performed for 2 h at 50° C. Aftertreatment: the solid was filtered out, spin-dried to remove filtrate, diluted with ethyl acetate, washed with water, and spin-dried to obtain the target product 2-(3-((2, 6-dichloro-3,5-dimethoxyphenoxy)methyl)-1H-pyrazol-5-yl)aniline 101f (239 mg, yellow solid). Yield: 50%.

MS m/z (ESI): 394[M+1].

Step 6

N-(2-(3-((2,6-dichloro-3,5-dimethoxyphenoxy) methyl)-1H-pyrazol-5-yl)phenyl)but-2-ynoic amide The compound 2-(3-((2,6-dichloro-3,5-dimethoxyphenoxy)methyl)-1H-pyrazol-5-yl)aniline 101f (120 mg, 0.31 mmol, 1 eq), butynoic acid (26 mg, 0.31 mmol, 1 eq), and N,N-diisopropylethylamine (118 mg, 0.92 mmol, 3 eq) were dissolved in dichloromethane (20 mL). 2-(7-Oxidized benzotriazole)-N,N,N',N'-tetramethyluronium hexafluorophosphate (139 mg, 0.37 mmol, 1.2 eq) was added therein, and reaction was performed for 2 h at room temperature. Aftertreatment: the mixture was diluted with water added and then extracted with ethyl acetate, the organic phase was spin-dried, and preparative liquid phase separation and lyophilization afforded the target product N-(2-(3-((2,6-dichloro-3,5-dimethoxyphenoxy)methyl)-1H-pyrazol-5-yl) phenyl)but-2-ynoic amide 101(2.6 mg, light yellow solid). Yield: 1.9%.

MS m/z (ESI): 460[M+1].

$^1$H NMR (400 MHz, DMSO) δ 13.73 (s, 1H), 11.80 (s, 1H), 8.29 (s, 1H), 7.80 (d, J=7.9 Hz, 1H), 7.33 (t, J=7.8 Hz, 1H), 7.21 (d, J=7.5 Hz, 1H), 6.96 (s, 1H), 6.80 (s, 1H), 5.08 (s, 2H), 3.93 (s, 6H), 2.07 (s, 3H).

Embodiment 102

N-(2-(5-(((2,6-dichloro-3,5-dimethoxyphenyl)amino)methyl)-1H-pyrazol-3-yl)phenyl)but-2-ynoic amide

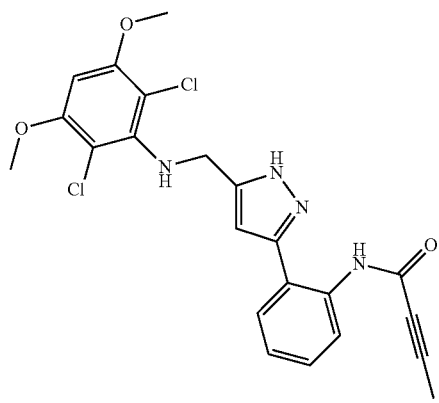

102

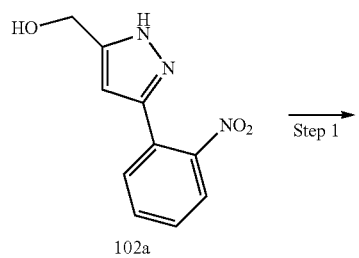

102a

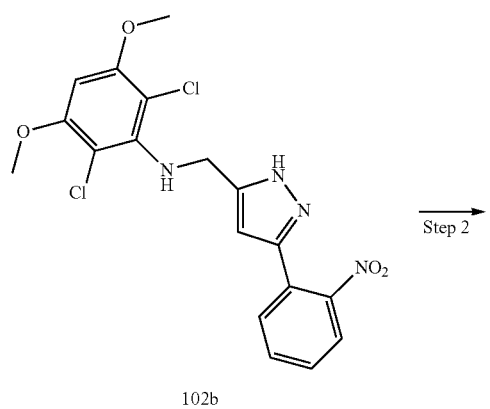

102b

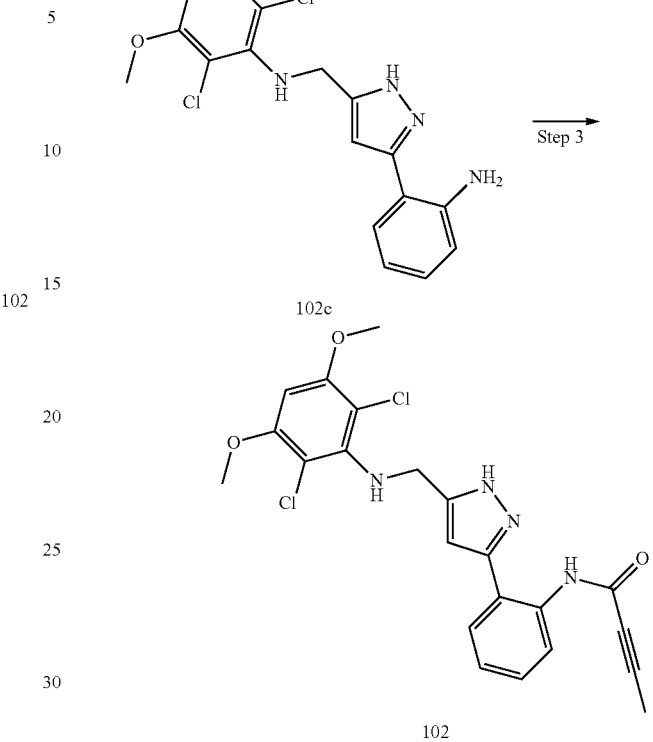

102a was synthesized referring to example 101d.

Step 1

2,6-dichloro-3,5-dimethoxy-N-((3-(2-nitrophenyl)-1H-pyrazol-5-yl)methyl)aniline 102b The compound (3-(2-nitrophenyl)-1H-pyrazol-5-yl)methanol 102a (100 mg, 0.46 mmol, 1 eq) and N,N-diisopropylethylamine (119 mg, 0.92 mmol, 2 eq) were added into anhydrous dichloromethane (15 mL). Under the protection of nitrogen gas, methylsulfonyl chloride (58 mg, 0.50 mmol, 1.1 eq) was added dropwise at 0° C., and the mixture was raised to room temperature and reacted for 30 min. Dichloromethane was spun out under reduced pressure, potassium carbonate (58 mg, 0.50 mmol, 1.1 eq), 2,6-dichloro-3,5-dimethoxyaniline (58 mg, 0.50 mmol, 1.1 eq) and 5 mL of DMF were added, and the mixture was heated to 80° C. and reacted for 2 h. Aftertreatment: the mixture was diluted with 15 mL of water added and extracted with ethyl acetate, the organic phase was desolventized under reduced pressure, and the residual was passed through a silica gel chromatographic column with a petroleum ether/ethyl acetate (1:2) system to obtain a yellow solid product 2,6-dichloro-3,5-dimethoxy-N-((3-(2-nitrophenyl)-1H-pyrazol-5-yl)methyl)aniline 102b (51 mg, yellow solid). Yield: 26%.

MS m/z (ESI): 423[M+1].

Step 2

N-((3-(2-aminophenyl)-1H-pyrazol-5-yl)methyl)-2,6-dichloro-3,5-dimethoxyaniline 102c The compound 2,6-dichloro-3,5-dimethoxy-N-((3-(2-nitrophenyl)-1H-pyrazol-5-yl)methyl)aniline 102b (520 mg, 1.2 mmol, 1 eq) was dissolved in ethanol (10 mL). Zinc powder (390 mg, 6.0 mmol, 5 eq) and ammonium chloride (690 mg, 6.0 mmol, 5 eq) were added therein, and reaction was performed for 3 h at 50° C. Aftertreatment: the mixture was spin-dried to remove the solvent, diluted with ethyl acetate and washed with water, the organic phase was spin-dried to obtain the target product N-((3-(2-aminophenyl)-1H-pyrazol-5-yl)methyl)-2,6-dichloro-3,5-dimethoxyaniline 102c (390 mg, yellow solid). Yield: 81%.

MS m/z (ESI): 393 [M+1].

Step 4

N-(2-(5-(((2,6-dichloro-3,5-dimethoxyphenyl)amino)methyl)-1H-pyrazol-3-yl)phenyl)but-2-ynoic amide 102

The compound N-((3-(2-aminophenyl)-1H-pyrazol-5-yl)methyl)-2,6-dichloro-3,5-dimethoxyaniline 102c (80 mg, 0.2 mmol, 1 eq), butynoic acid (19 mg, 0.2 mmol, 1 eq), N,N-diisopropylethylamine (52 mg, 0.4 mmol, 1 eq) were dissolved into DMF (6 mL). 2-(7-oxidized benzotriazole)-N,N,N',N'-tetramethyluronium hexafluorophosphate (114 mg, 0.3 mmol, 1.5 eq) was added therein, and reaction was performed for 3 h at room temperature. Aftertreatment: the mixture was diluted with water and extracted with ethyl acetate, the organic phase was spin-dried, and preparative liquid phase separation and lyophilization afforded the target product N-(2-(5-(((2,6-dichloro-3,5-dimethoxyphenyl)amino)methyl)-1H-pyrazol-3-yl)phenyl)but-2-ynoic amide 102 (2 mg, white solid). Yield: 7%.

MS m/z (ESI): 459[M+1].

$^1$H NMR (400 MHz, DMSO) δ 11.86 (s, 1H), 8.27 (dd, J=51.5, 7.8 Hz, 1H), 7.87-7.62 (m, 2H), 7.28 (dd, J=13.9, 8.2 Hz, 2H), 7.20-7.12 (m, 1H), 7.02 (s, 1H), 6.65 (s, 1H), 6.50 (s, 1H), 4.78-4.59 (m, 2H), 3.86 (s, 6H), 2.07 (d, J=6.5 Hz, 3H).

Example 103

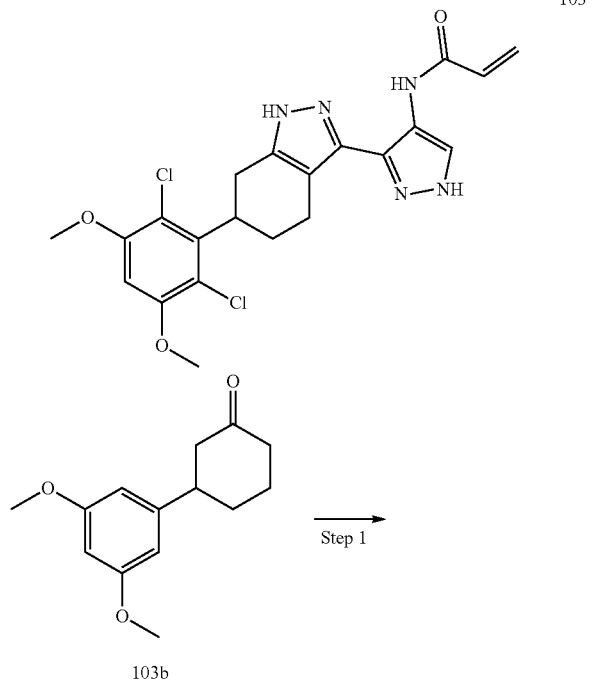

103

103b

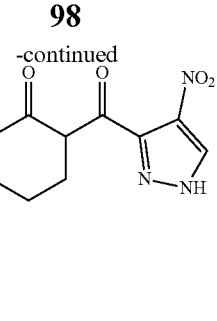

103c

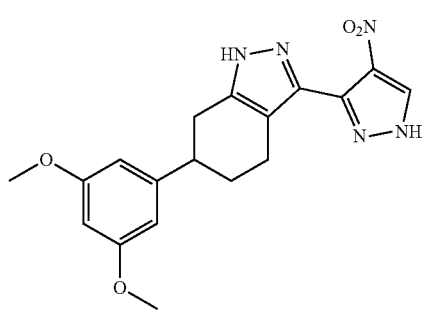

103d

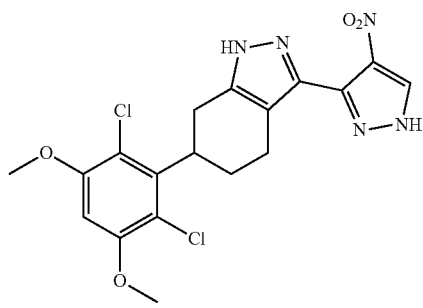

103e

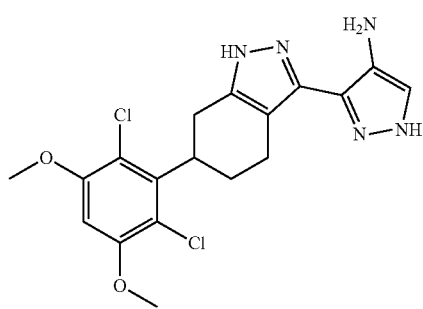

103f

-continued

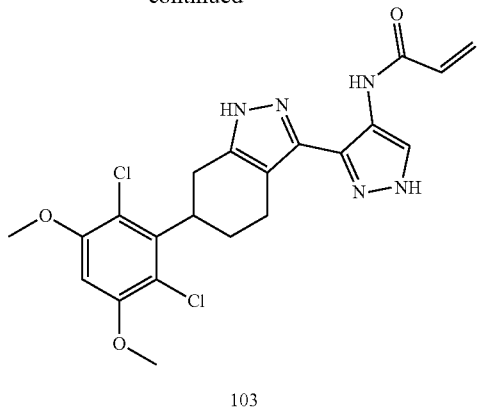

103

Step 1

3-(3,5-dimethoxyphenyl)cyclohexanone 103b was Synthesized with Reference to Example 098b MS m/z (ESI): 235 [M+1].

Step 2

5-(3,5-dimethoxyphenyl)-2-(4-nitro-1H-pyrazole-3-carbonyl)cyclohexanone 103c 3-(3,5-dimethoxyphenyl)cyclohexanone 103b (1.2 g, 5 mmol) was placed into 100 ml of tetrahydrofuran, and protected by nitrogen gas. LDA (6 mmol) was added at −78° C., and the mixture was warmed up to −40° C. and maintained for 2 h. 1-H-4-nitro-3-benzoylchloropyrazole (900 mg, 5 mmol) was added therein. The mixture was raised to room temperature and reacted for 3 h. Aftertreatment: the mixture was quenched with a saturated ammonium chloride aqueous solution, the organic phase was desolventized under reduced pressure, and the residual was purified through silica gel column chromatography (petroleum ether:ethyl acetate=3:1) to obtain 5-(3,5-dimethoxyphenyl)-2-(4-nitro-1H-pyrazole-3-carbonyl)cyclohexanone 103c (630 mg, 2 mmol, yellow solid). Yield: 40%.

MS m/z (ESI): 374 [M+1].

Step 3

6-(3,5-dimethoxyphenyl)-3-(4-nitro-1H-pyrazol-3-yl)-4,5,6,7-tetrahydro-1H-indazole 103d 5-(3,5-dimethoxyphenyl)-2-(4-nitro-1H-pyrazole-3-carbonyl)cyclohexanone 103c (630 mg, 1.7 mmol), hydrazine hydrate (5 mL), acetic acid (5 mL) and ethanol (50 mL) were mixed, warmed up to 65° C. and stirred for 3 h. Aftertreatment: desolvation was performed under reduced pressure, and the residual was purified through silica gel column chromatography (petroleum ether:ethyl acetate=3:1) to obtain a yellow solid product 6-(3,5-dimethoxyphenyl)-3-(4-nitro-1H-pyrazol-3-yl)-4,5,6,7-tetrahydro-1H-indazole 103d (580 mg, 1.2 mmol, yellow solid). Yield: 40%.

MS m/z (ESI): 370 [M+1].

Step 4

6-(2,6-dichloro-3,5-dimethoxyphenyl)-3-(4-nitro-1H-pyrazol-3-yl)-4,5,6,7-tetrahydro-1H-indazole 103e 6-(3,5-dimethoxyphenyl)-3-(4-nitro-1H-pyrazol-3-yl)-4,5,6,7-tetrahydro-1H-indazole 103d (295 mg, 0.8 mmol) and 20 ml of acetic acid were mixed. NCS (220 mg, 1.8 mmol) was added therein, and reaction was performed for 2 h at 80° C. Aftertreatment: dichloromethane and water were added and layered, the organic phase was desolventized under reduced pressure, and the resultant was passed through a silica gel chromatographic column with a petroleum ether/ethyl acetate (1:1) system to obtain a yellow solid product 6-(2,6-dichloro-3,5-dimethoxyphenyl)-3-(4-nitro-1H-pyrazol-3-yl)-4,5,6,7-tetrahydro-1H-indazole 103e (120 mg, 0.3 mmol, yellow solid).

Yield: 90%.

MS m/z (ESI): 438 [M+1].

Step 5

3-(6-(2,6-dichloro-3,5-dimethoxyphenyl)-4,5,6,7-tetrahydro-1H-indazol-3-yl)-1H-pyrazole-4-amine 103f 6-(2,6-dichloro-3,5-dimethoxyphenyl)-3-(4-nitro-1H-pyrazol-3-yl)-4,5,6,7-tetrahydro-1H-indazole 103e (120 mg, 0.3 mmol) and N,N-dimethyl formamide (10 mL) were mixed. Zinc powder (100 mg, 1.5 mmol), ammonium chloride (160 mg, 3 mmol), and 1 ml of water were added therein, and reaction was performed for 0.8 h at 50° C. Aftertreatment: desolvation was performed under reduced pressure, dichloromethane and the aqueous phase were added and layered, and the organic phase was desolventized under reduced pressure to obtain the a solid crude product 3-(6-(2,6-dichloro-3,5-dimethoxyphenyl)-4,5,6,7-tetrahydro-1H-indazol-3-yl)-1H-pyrazole-4-amine 103f (90 mg, 0.22 mmol, light yellow solid). Yield: 60%.

MS m/z (ESI): 408 [M+1].

Step 6

N-(3-(6-(2,6-dichloro-3,5-dimethoxyphenyl)-4,5,6,7-tetrahydro-1H-indazol-3-yl)-1H-pyrazol-4-yl)acrylamide 103

3-(6-(2,6-dichloro-3,5-dimethoxyphenyl)-4,5,6,7-tetrahydro-1H-indazol-3-yl)-1H-pyrazole-4-amine 103f (90 mg, 0.3 mmol) and dichloromethane (20 mL) were mixed, and diisopropyl ethylamine (129 mg, 1 mmol) was added therein. After the mixture was cooled to −40° C., acryloyl chloride (30 mg, 0.3 mmol) was slowly added therein, to carry out reaction for 1 h. Aftertreatment: dichloromethane and the aqueous phase were added and layered, the organic phase was desolventized under reduced pressure, and the preparative liquid phase separation afforded a white solid product N-(3-(6-(2,6-dichloro-3,5-dimethoxyphenyl)-4,5,6,7-tetrahydro-1H-indazol-3-yl)-1H-pyrazol-4-yl)acrylamide 103 (40 mg, 0.1 mmol, white solid). 30% Yield: 60%.

MS m/z (ESI): 462 [M+1].

$^1$H NMR (400 MHz, DMSO) δ 9.950 (s, 1H), 8.18 (s, 1H), 6.89 (s, 1H), 6.44 (m, 1H), 6.22 (d, J=16.9 Hz, 1H), 5.76 (d, J=10.4 Hz, 1H), 3.93 (s, 6H), 3.43 (m, 2H), 3.01 (d, J=12.7 Hz, 1H), 2.69 (m, 3H), 1.82 (d, J=8.6 Hz, 1H).

Example 107

N-(3-(6-(2,6-dichloro-3,5-dimethoxyphenyl)-4,5,6,7-tetrahydro-1H-indazol-3-yl)-1-methyl-1H-pyrazol-4-yl)acrylamide

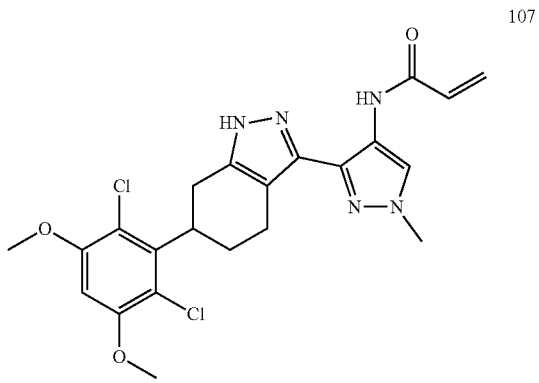 [SMILES: C=CC(=O)Nc1cn(C)nc1-c1n[nH]c2c1CCC(c1c(Cl)c(OC)cc(OC)c1Cl)C2]

107

Example 107 was synthesized with reference to example 103, except that in Step 2, 1-H-4-nitro-3-benzoylchloropyrazole was replaced with 1-methyl-4-nitro-3-benzoylchloropyrazole.

MS m/z (ESI): 476 [M+1].

$^1$H NMR (400 MHz, DMSO) δ 12.70 (s, 1H), 10.00 (s, 1H), 8.21 (s, 1H), 6.89 (s, 1H), 6.48-6.36 (m, 1H), 6.22 (d, J=16.6 Hz, 1H), 5.77 (d, J=10.7 Hz, 1H), 3.97 (d, J=7.9 Hz, 1H), 3.93 (s, 6H), 3.86 (s, 3H), 3.47-3.37 (m, 1H), 3.04 (s, 1H), 2.78-2.56 (m, 3H), 1.81 (s, 1H).

Example 109

N-(2-(6-(2,6-difluoro-3,5-dimethoxyphenyl)-4,5,6,7-tetrahydro-1H-indazol-3-yl)phenyl)but-2-ynoic amide

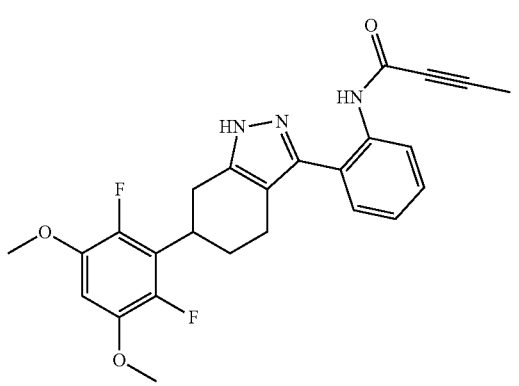

109

Example 109 was synthesized with reference to example 093, except that in Step 4, acryloyl chloride was replaced with 2-butynoic acid: 098f (200 mg, 0.5 mmol) and 20 mL of dichloromethane were mixed, N,N-diisopropylethylamine (190 mg, 1.5 mmol) and HATU (260 mg, 0.7 mmol) were added therein, then 2-butynoic acid (40 mg, 0.5 mmol) was slowly added therein, and the mixture was raised from 0° C. to room temperature and reacted for 1 h. Aftertreatment: dichloromethane and the aqueous phase were added and layered, the organic phase was desolventized under reduced pressure, and the preparative liquid phase separation afforded a white solid product N-(2-(6-(2,6-difluoro-3,5-dimethoxyphenyl)-4,5,6,7-tetrahydro-1H-indazol-3-yl)phenyl)but-2-ynoic amide 109 (60 mg, 0.13 mmol, white solid).

MS m/z (ESI): 452 [M+1].

$^1$H NMR (400 MHz, DMSO) δ 12.99 (s, 1H), 11.59 (s, 1H), 8.29 (s, 1H), 7.58 (s, 1H), 7.34 (s, 1H), 7.20 (s, 1H), 6.89 (s, 1H), 4.01 (s, 1H), 3.90 (m, 6H), 3.30 (m, 1H), 2.69 (m, 4H), 1.99 (m, 3H), 1.79 (s, 1H).

Embodiment 111

N-(2-(5-(2,6-dichloro-3,5-dimethoxybenzylamino)-1H-pyrazol-3-yl)phenyl)acrylamide

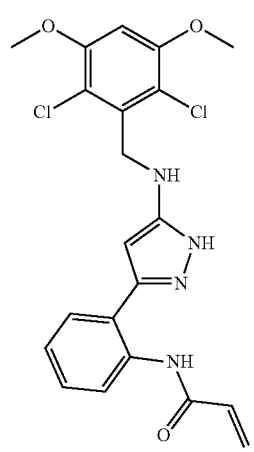

111

Embodiment 111 was synthesized with reference to the operation steps in embodiment 100, except that in Step 5, 5-(2-aminophenyl)-N-(2,6-dichloro-3,5-dimethoxybenzyl)-1H-pyrazole-3-amine (150 mg, 0.38 mmol), N,N-diisopropylethylamine (147 mg, 1.14 mmol) and dichloromethane (5 mL) were mixed, and acryloyl chloride (36 mg, 0.40 mmol) was slowly added dropwise while stirring at 0° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(2-(5-(2,6-dichloro-3,5-dimethoxybenzylamino)-1H-pyrazol-3-yl)phenyl)acrylamide 111 (10 mg, white solid). Yield: 6%.

MS m/z (ESI): 447[M+1].

$^1$H NMR (400 MHz, DMSO) δ 12.23 (s, 1H), 11.98 (s, 1H), 8.58 (s, 1H), 7.66 (d, J=7.6 Hz, 1H), 7.28 (t, J=7.7 Hz, 1H), 7.14 (t, J=7.3 Hz, 1H), 6.94 (s, 1H), 6.33 (d, J=8.0 Hz, 2H), 5.98 (s, 1H), 5.83 (m, 1H), 4.50 (d, J=5.6 Hz, 2H), 3.94 (s, 6H).

Embodiment 112

N-(2-(3-((2,6-dichloro-3,5-dimethoxyphenoxy)methyl)-1H-pyrazol-5-yl)phenyl)acrylamide

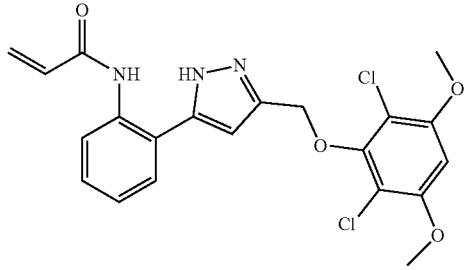

Example 112 was synthesized with reference to the steps in example 101, except that in Step 6, butynoic acid was replaced with acryloyl chloride, to prepare by synthesis N-(2-(3-((2,6-dichloro-3,5-dimethoxyphenoxy)methyl)-1H-pyrazol-5-yl)phenyl)acrylamide 112.

Step 6

N-(2-(3-((2,6-dichloro-3,5-dimethoxyphenoxy)methyl)-1H-pyrazol-5-yl)phenyl)acrylamide The compound 2-(3-((2,6-dichloro-3,5-dimethoxyphenoxy)methyl)-1H-pyrazol-5-yl)aniline 101f (100 mg, 0.25 mmol, 1 eq) was dissolved in 15 mL of dichloromethane, and N,N-diisopropylethylamine (98 mg, 0.76 mmol, 3 eq) was added therein. The mixture was cooled to −40° C., and acryloyl chloride (16 mg, 0.18 mmol, 0.7 eq) was added dropwise and stirred for 30 min. Aftertreatment: the mixture was extracted with a water-ethyl acetate system, and desolvation was performed under reduced pressure to obtain the target product N-(2-(3-((2,6-dichloro-3,5-dimethoxyphenoxy)methyl)-1H-pyrazol-5-yl)phenyl)acrylamide crude product, which could afford through preparation (1.5 mg, yellow solid). Yield: 1.3%.

MS m/z (ESI): 448 [M+1].

$^1$H NMR (400 MHz, DMSO) δ 13.57 (s, 1H), 11.76 (s, 1H), 8.53 (s, 1H), 7.82 (d, J=7.9 Hz, 1H), 7.33 (t, J=7.8 Hz, 1H), 7.17 (d, J=7.5 Hz, 1H), 6.96 (s, 1H), 6.79 (s, 1H), 6.32 (s, 2H), 5.86 (s, 1H), 5.10 (s, 2H), 3.89 (d, J=26.7 Hz, 6H).

Embodiment 113

N-(2-(5-(((2,6-dichloro-3,5-dimethoxyphenyl)amino)methyl)-1H-pyrazol-3-yl)phenyl)acrylamide

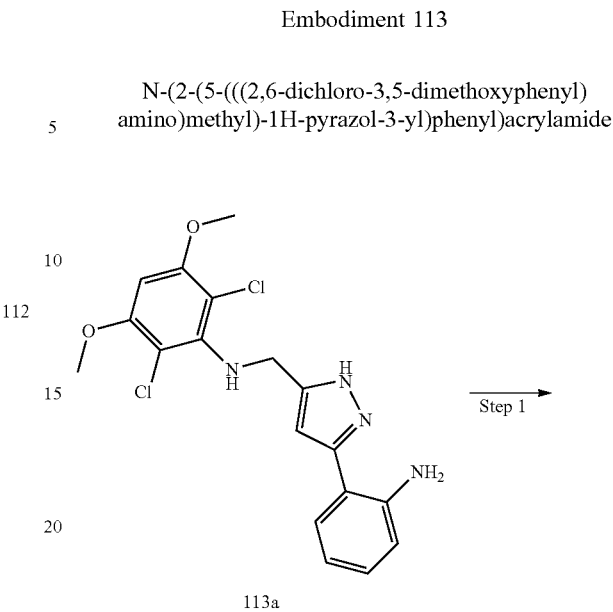

113a was synthesized referring to example 102.

The compound N-((3-(2-aminophenyl)-1H-pyrazol-5-yl)methyl)-2,6-dichloro-3,5-dimethoxyaniline 113a (100 mg, 0.26 25 mmol, 1 eq) was dissolved in dichloromethane (10 mL). N,N-diisopropylethylamine (67 mg, 0.52 mmol, 2 eq) was added therein, and the mixture was cooled to −40° C. A solution of acryloyl chloride (23 mg, 0.26 mmol, 1 eq) in dichloromethane was added dropwise and stirred for 30 min. Aftertreatment: the mixture was desolventized under reduced pressure, and subjected to preparative liquid phase separation and lyophilization to obtain the target product N-(2-(5-(((2,6-dichloro-3,5-dimethoxyphenyl)amino)methyl)-1H-pyrazol-3-yl)phenyl)acrylamide 113 (12 mg, white solid). Yield: 10%.

MS m/z (ESI): 447 [M+1].

$^1$H NMR (400 MHz, DMSO) δ 13.15 (s, 1H), 11.86 (s, 1H), 8.54 (d, J=7.3 Hz, 1H), 7.69 (d, J=7.5 Hz, 1H), 7.30 (t, J=7.5 Hz, 1H), 7.15 (d, J=7.0 Hz, 1H), 6.66 (s, 1H), 6.50 (s, 1H), 6.32 (d, J=9.6 Hz, 2H), 5.85 (d, J=7.1 Hz, 1H), 5.25 (s, 1H), 4.60 (d, J=6.9 Hz, 2H), 3.86 (s, 6H).

Example 114
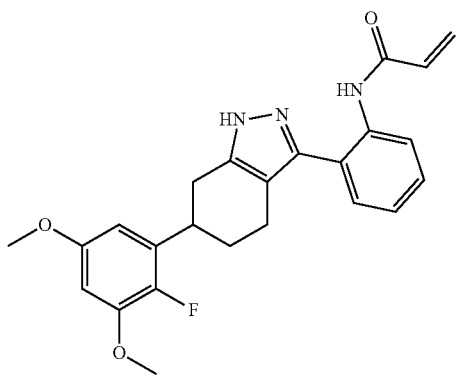
N-(2-(6-(2-fluoro-3,5-dimethoxyphenyl)-4,5,6,7-tetrahydro-1H-indazol-3-yl)phenyl)acrylamide 114 was Synthesized as in Example 093
MS m/z (ESI): 422 [M+1].
$^1$H NMR (400 MHz, DMSO) δ 12.98 (s, 1H), 11.59 (s, 1H), 8.48 (s, 1H), 7.58 (d, J=7.4 Hz, 1H), 7.33 (t, J=7.6 Hz, 1H), 7.19 (t, J=7.5 Hz, 1H), 6.63 (dd, J=6.9, 2.8 Hz, 1H), 6.55-6.45 (m, 1H), 6.38-6.19 (m, 2H), 5.82 (d, J=11.4 Hz, 1H), 3.79 (d, J=35.1 Hz, 6H), 3.28 (s, 1H), 2.96-2.74 (m, 4H), 1.97 (s, 2H).
Embodiment 117
N-(3-(5-(2,6-dichloro-3,5-dimethoxyphenethyl)-1H-pyrazol-3-ylamino)phenyl)acrylamide
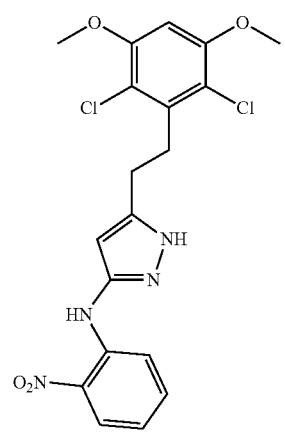
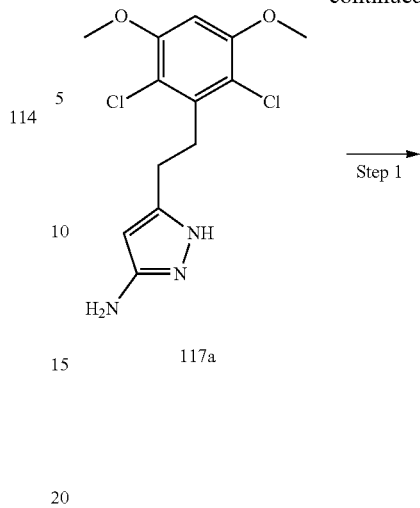
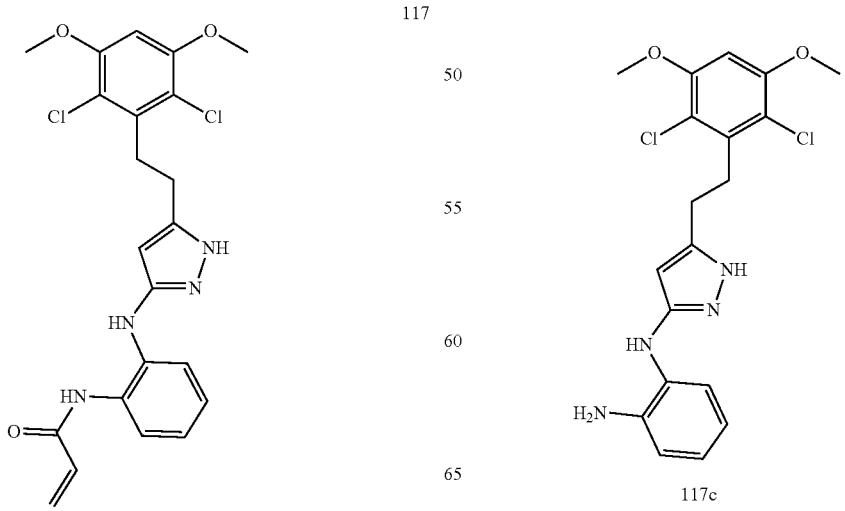

-continued

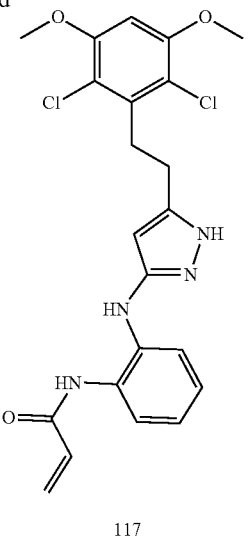

117

117a was synthesized with reference to embodiment 091e.

Step 1

3-(2,6-dichloro-3,5-dimethoxyphenethyl)-N-(2-nitrophenyl)-1H-pyrazole-5-amine 117b 5-(2,6-dichloro-3,5-dimethoxyphenethyl)-1H-pyrazole-3-amine (100 mg, 0.31 mmol), o-fluoronitrobenzene (53 mg, 0.37 mmol), and N,N-dimethyl formamide (3 mL) were mixed, and under the protection of nitrogen gas, the mixture was warmed up to 120° C. and stirred for 3 h.

Aftertreatment: desolvation was performed under reduced pressure, and the residual was purified through silica gel column chromatography (petroleum ether:ethyl acetate=1:1) to obtain 3-(2,6-dichloro-3,5-dimethoxyphenethyl)-N-(2-nitrophenyl)-1H-pyrazole-5-amine 117b (50 mg, yellow solid). Yield: 36%.

MS m/z (ESI): 436[M+1].

Step 2

N1-(3-(2,6-dichloro-3,5-dimethoxyphenethyl)-1H-pyrazol-5-yl)benzene-1,2-diamine 117c 3-(2,6-dichloro-3,5-dimethoxyphenethyl)-N-(2-nitrophenyl)-1H-pyrazole-5-amine (300 mg, 0.68 mmol), zinc powder (447 mg, 6.8 mmol), ammonium chloride (360 mg, 6.8 mmol) and ethanol (5 mL) were mixed, warmed up to 50° C. and stirred for 2 h. Aftertreatment: the system was cooled to room temperature, filtered, and desolventized under reduced pressure to obtain the target product N1-(3-(2,6-dichloro-3,5-dimethoxyphenethyl)-1H-pyrazol-5-yl)benzene-1,2-diamine 117c (240 mg, white solid). Yield: 86%.

MS m/z (ESI): 406[M+1].

Step 3

N-(2-(3-(2,6-dichloro-3,5-dimethoxyphenethyl)-1H-pyrazol-5-ylamino)phenyl)acrylamide N1-(3-(2,6-dichloro-3,5-dimethoxyphenethyl)-1H-pyrazol-5-yl)benzene-1,2-diamine (100 mg, 0.24 mmol), N,N-diisopropylethylamine (92 mg, 0.72 mmol) and dichloromethane (5 mL) were mixed, and acryloyl chloride (26 mg, 0.29 mmol) was slowly added dropwise while stirring at 0° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(2-(3-(2,6-dichloro-3,5-dimethoxyphenethyl)-1H-pyrazol-5-ylamino)phenyl)acrylamide (15 mg, white solid). Yield: 13%.

MS m/z (ESI): 460[M+1].

$^1$H NMR (400 MHz, DMSO) δ 11.93 (s, 1H), 9.63 (s, 1H), 7.58 (s, 1H), 7.37 (d, J=12.9 Hz, 2H), 7.07 (t, J=7.8 Hz, 1H), 6.85 (s, 1H), 6.79 (t, J=7.4 Hz, 1H), 6.51 (dd, J=16.8, 10.4 Hz, 1H), 6.25 (d, J=17.1 Hz, 1H), 5.74 (m, 2H), 3.92 (s, 6H), 3.18 (m, 2H), 2.73 (m, 2H).

Embodiment 120

N-(3-(5-(2,6-dichloro-3,5-dimethoxyphenethyl)-1H-pyrazol-3-ylamino)phenyl)but-2-ynoic amide

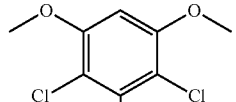
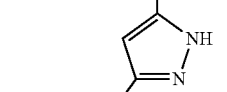
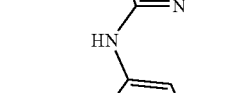
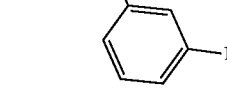

120

Embodiment 120 was synthesized with reference to the operation steps in embodiment 117, except that in Step 3, N1-(3-(2,6-dichloro-3,5-dimethoxyphenethyl)-1H-pyrazol-5-yl)benzene-1,2-diamine (100 mg, 0.24 mmol), 2-(7-oxidized benzotriazole)-N,N,N',N'-tetramethyluronium hexafluorophosphate (137 mg, 0.36 mmol), N,N-diisopropylethylamine (87 mg, 0.72 mmol) and dichloromethane (5 mL) were mixed, and 2-butynoic acid (29 mg, 1.2 mmol) was slowly added therein while stirring at 0° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-(3-(5-(2,6-dichloro-3,5-dimethoxyphenethyl)-1H-pyrazol-3-ylamino)phenyl)but-2-ynoic amide 120 (15 mg, white solid). Yield: 12%.

MS m/z (ESI): 472[M+1].

$^1$H NMR (400 MHz, DMSO) δ 11.91 (s, 1H), 9.95 (s, 1H), 7.59 (d, J=20.7 Hz, 1H), 7.35 (s, 1H), 7.28 (d, J=7.6 Hz, 1H), 7.08 (t, J=7.6 Hz, 1H), 6.84 (d, J=6.5 Hz, 1H), 6.77 (t, J=7.5 Hz, 1H), 5.72 (s, 1H), 3.92 (s, 6H), 3.18 (m, 2H), 2.73 (m, 2H), 2.05 (s, 3H).

Embodiment 122

N-((1R,2R)-2-(5-(2,6-dichloro-3,5-dimethoxybenzylamino)-1H-pyrazol-3-yl)cyclohexyl)acrylamide

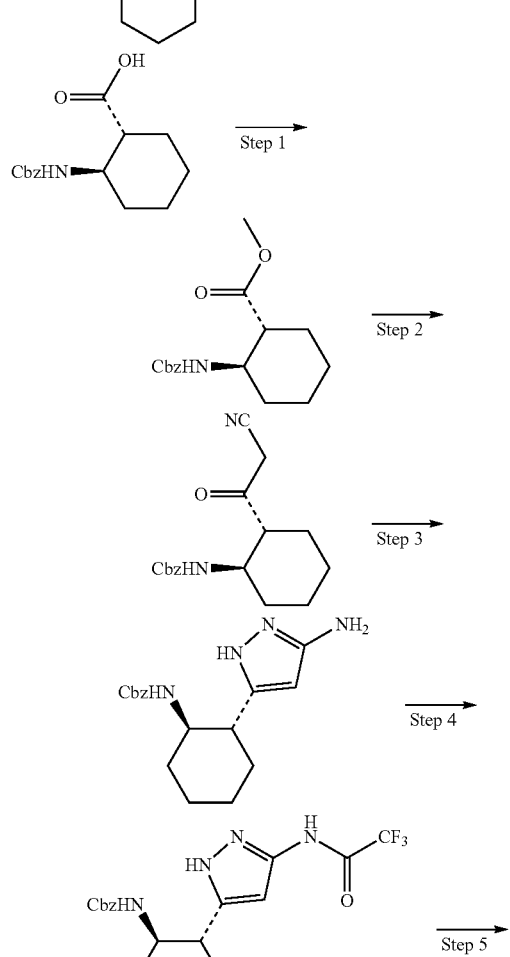

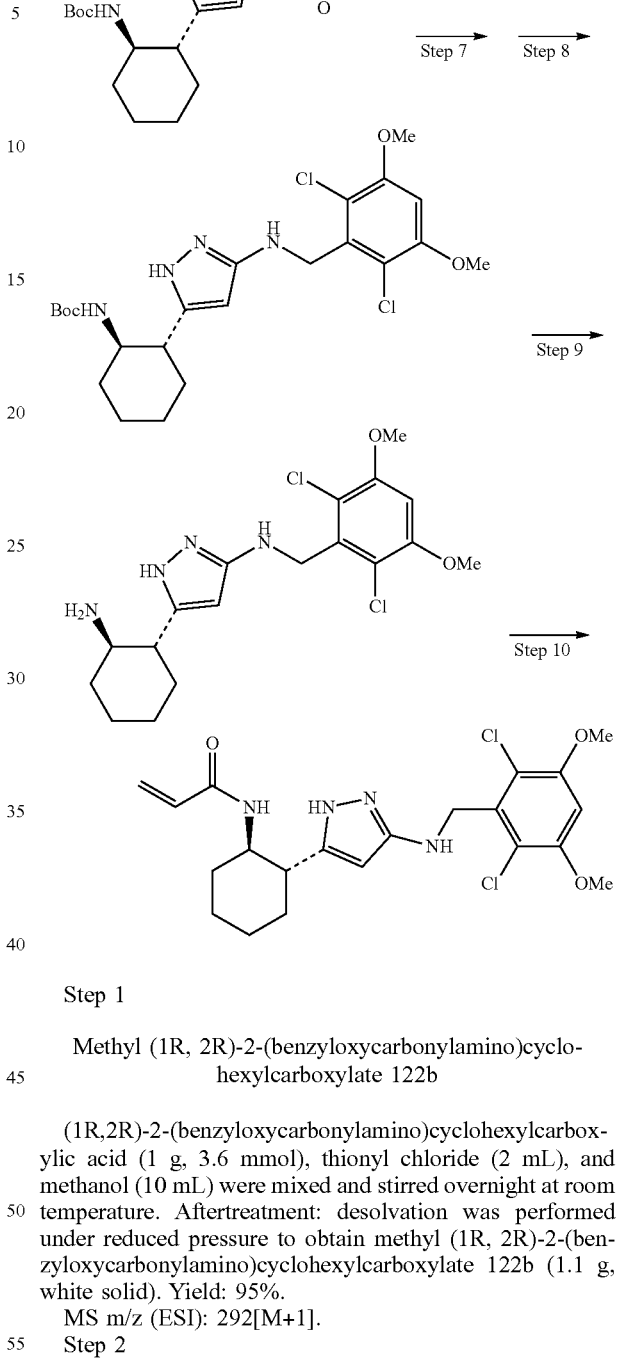

Step 1

Methyl (1R, 2R)-2-(benzyloxycarbonylamino)cyclohexylcarboxylate 122b (1R,2R)-2-(benzyloxycarbonylamino)cyclohexylcarboxylic acid (1 g, 3.6 mmol), thionyl chloride (2 mL), and methanol (10 mL) were mixed and stirred overnight at room temperature. Aftertreatment: desolvation was performed under reduced pressure to obtain methyl (1R, 2R)-2-(benzyloxycarbonylamino)cyclohexylcarboxylate 122b (1.1 g, white solid). Yield: 95%.

MS m/z (ESI): 292[M+1].

Step 2

Benzyl (1R,2R)-2-(2-cyanoacetyl)cyclohexylcarbamate 122c

Under the protection of nitrogen gas, n-butyl lithium (3.08 mL, 7.4 mmol) was mixed at −78° C. into anhydrous tetrahydrofuran (20 mL), acetonitrile (303 mg, 7.4 mmol) was slowly added dropwise into the reaction system, and reaction was performed for 1 h at −78° C. Methyl (1R,2R)-2-(benzyloxycarbonylamino)cyclohexylcarboxylate (1.1 g, 3.7 mmol) dissolved in anhydrous tetrahydrofuran (5 mL)

was slowly added dropwise to the reaction system, and the system was slowly warmed up to room temperature and stirred for 3 h. Aftertreatment: a saturated ammonia chloride aqueous solution (200 mL) was added to this mixture to quench the reaction, the organic phase was desolventized under reduced pressure, and the residual was purified through silica gel column chromatography (petroleum ether: ethyl acetate=1:1) to obtain the target product benzyl (1R, 2R)-2-(2-cyanoacetyl)cyclohexylcarbamate 122c (580 mg, white solid). Yield: 51%.

MS m/z (ESI): 301[M+1].

Step 3

Benzyl (1R,2R)-2-(3-amino-1H-pyrazol-5-yl)cyclohexylcarbamate 122d

Benzyl (1R,2R)-2-(2-cyanoacetyl)cyclohexylcarbamate (580 mg, 1.93 mmol), 80% hydrazine hydrate (2 mL), acetic acid (2 mL) and ethanol (20 mL) were mixed, warmed up to 60° C., and stirred for 3 h. Aftertreatment: the mixture was cooled to room temperature and desolventized under reduced pressure, and the residual was purified through silica gel column chromatography (petroleum ether:ethyl acetate=1:1) to obtain the target product benzyl (1R,2R)-2-(3-amino-1H-pyrazol-5-yl)cyclohexylcarbamate 122d (320 mg, yellow solid). Yield: 60%.

MS m/z (ESI): 315[M+1].

Step 4

Benzyl (1R,2R)-2-(3-(2,2,2-trifluoroacetamino)-1H-pyrazol-5-yl)cyclohexylcarbamate 122e Benzyl (1R,2R)-2-(3-amino-1H-pyrazol-5-yl)cyclohexylcarbamate (320 mg, 1.01 mmol), 4-dimethylaminopyridine (49 mg, 0.4 mmol), N,N-diisopropylethylamine (390 mg, 3.03 mmol) and dichloromethane (5 mL) were mixed, and trifluoroacetic anhydride (428 mg, 2.02 mmol) was slowly added therein while stirring at 0° C. The mixture was warmed up to room temperature and stirred for 3 h. Aftertreatment: 10 mL of water was added to this mixture, then the mixture was extracted with dichloromethane (10 mL×3), and organic phases were combined and then desolventized under reduced pressure to obtain the target product benzyl (1R, 2R)-2-(3-(2,2,2-trifluoroacetamino)-1H-pyrazol-5-yl) cyclohexylcarbamate 122e (300 mg, white solid). Yield: 69%.

MS m/z (ESI): 411[M+1].

Step 5

N-(5-((1R,2R)-2-Aminocyclohexyl)-1H-pyrazol-3-yl)-2,2,2-trifluoroacetamide 122f

Under a hydrogen atmosphere, benzyl (1R, 2R)-2-(3-(2, 2,2-trifluoroacetamino)-1H-pyrazol-5-yl)cyclohexylcarbamate (300 mg, 0.73 mmol), a palladium carbon catalyst (100 mg), and methanol (10 mL) were mixed, and stirred for 3 h at room temperature. Aftertreatment: the mixture was filtered and desolventized under reduced pressure to obtain the target product N-(5-((1R, 2R)-2-aminocyclohexyl)-1H-pyrazol-3-yl)-2,2,2-trifluoroacetamide 122f (110 mg, white solid). Yield: 95%.

MS m/z (ESI): 277[M+1].

Step 6 tert-Butyl ((1R,2R)-2-(3-(2,2,2-trifluoroacetamido)-1H-pyrazol-5-yl)cyclohexyl)carbamate 122g N-(5-((1R, 2R)-2-aminocyclohexyl)-1H-pyrazol-3-yl)-2, 2,2-trifluoroacetamide (110 mg, 0.39 mmol), N,N-trifluoroacetamide (150 mg, 1.17 mmol) and tetrahydrofuran (3 mL) were mixed, and di-t-butyl dicarbonate (102 mg, 20.47 mmol) was slowly added dropwise while stirring at room temperature and further stirred for 3 h. Aftertreatment: desolvation was performed under reduced pressure, and the residual was purified through silica gel column chromatography to obtain tert-butyl ((1R,2R)-2-(3-(2,2,2-trifluoroacetamido)-1H-pyrazol-5-yl)cyclohexyl)carbamate 122g (90 mg, white solid). Yield: 61%.

MS m/z (ESI): 377[M+1].

Step 7 tert-Butyl ((1 R,2R)-2-(3-amino-1H-pyrazol-5-yl) cyclohexyl)carbamate 122h tert-Butyl R,2R)-2-(3-(2,2,2-trifluoroacetamido)-1H-pyrazol-5-yl)cyclohexyl)carbamate (90 mg, 0.23 mmol), potassium hydroxide (26 mg, 0.46 mmol) and methanol (3 mL) were mixed, warmed up to 50° C. and stirred for 3 h. Aftertreatment: the mixture was filtered and desolventized under reduced pressure to obtain tert-butyl ((1R,2R)-2-(3-amino-1H-pyrazol-5-yl)cyclohexyl)carbamate 122h (60 mg, white solid). Yield: 89%.

MS m/z (ESI): 281[M+1].

Step 8 tert-Butyl R,2R)-2-(3-((2,6-dichloro-3,5-dimethoxybenzyl)amino)-1H-pyrazol-5-yl)cyclohexyl)carbamate 122i tert-Butyl ((1R,2R)-2-(3-amino-1H-pyrazol-5-yl)cyclohexyl)carbamate (100 mg, 0.35 mmol), 2, 6-dichloro-3, 5-dimethoxybenzaldehyde (99 mg, 0.42 mmol), acetic acid (0.5 mL) and methanol (3 mL) were mixed and stirred for 3 h at room temperature. Sodium cyanoborohydride (32 mg, 0.52 mmol) was slowly added therein while stirring, and further stirred for 30 min. Aftertreatment: desolvation was performed under reduced pressure, and the residual was purified through silica gel column chromatography (petroleum ether:ethyl acetate=1:1) to obtain tert-butyl ((1R,2R)-2-(3-((2,6-dichloro-3,5-dimethoxybenzyl)amino)-1H-pyrazol-5-yl)cyclohexyl)carbamate 122i (80 mg, white solid). Yield: 67%.

MS m/z (ESI): 499[M+1].

Step 9

5-((1R,2R)-2-Aminocyclohexyl)-N-(2,6-dichloro-3, 5-dimethoxybenzyl)-1H-pyrazole-3-amine 122j Benzyl (1R,2R)-2-(3-(2,6-dichloro-3,5-dimethoxybenzylamino)-1H-pyrazol-5-yl)cyclohexylcarbamate (150 mg, 0.30 mmol) and 4M dioxane hydrochloride (3 mL) were mixed and stirred for 3 h at room temperature. Aftertreatment: the mixture was desolventized under reduced pressure to obtain 5-((1R,2R)-2-aminocyclohexyl)-N-(2,6-dichloro-3,5-dimethoxybenzyl)-1H-pyrazole-3-amine 122j (100 mg, white solid). Yield: 84%.

MS m/z (ESI): 399[M+1].

Step 10

N-((1R, 2R)-2-(3-(2,6-dichloro-3,5-dimethoxybenzylamino)-1H-pyrazol-5-yl)cyclohexyl)acrylamide 122

5-((1R,2R)-2-aminocyclohexyl)-N-(2,6-dichloro-3,5-dimethoxybenzyl)-1H-pyrazole-3-amine (100 mg, 0.25 mmol), N,N-diisopropylethylamine (96 mg, 0.75 mmol) and dichloromethane (5 mL) were mixed, and acryloyl chloride (27 mg, 0.30 mmol) was slowly added dropwise while stirring at 0° C. and further stirred for 30 min. Aftertreatment: 10 mL of water was added to this mixture, then the mixture was extracted with dichloromethane (10 mL×3), organic phases were combined and then desolventized under reduced pressure, and the residual was subjected to preparative separation and purification through high performance liquid chromatography to obtain the target product N-((1R, 2R)-2-(3-(2,6-dichloro-3,5-dimethoxybenzylamino)-1H-pyrazol-5-yl)cyclohexyl)acrylamide 122 (15 mg, white solid). Yield: 13%.

MS m/z (ESI): 453[M+1].

$^1$H NMR (400 MHz, DMSO) δ 11.13 (s, 1H), 7.88 (d, J=8.6 Hz, 1H), 6.88 (s, 1H), 6.04 (m, 2H), 5.50 (dd, J=9.9, 2.4 Hz, 1H), 5.29 (s, 1H), 4.91 (s, 1H), 4.36 (d, J=5.8 Hz, 2H), 3.91 (s, 6H), 3.77 (m, 1H), 1.88 (d, J=10.2 Hz, 2H), 1.68 (d, J=11.6 Hz, 2H), 1.34 (m, 4H), 1.18 (s, 1H).

Embodiment 133

N-(2-(6-(2,6-dichloro-3,5-dimethoxyphenyl)-4,5,6,7-tetrahydro-1H-indazol-3-yl)-5-((2-(dimethylamino)ethyl)(methyl)amino)phenyl)acrylamide

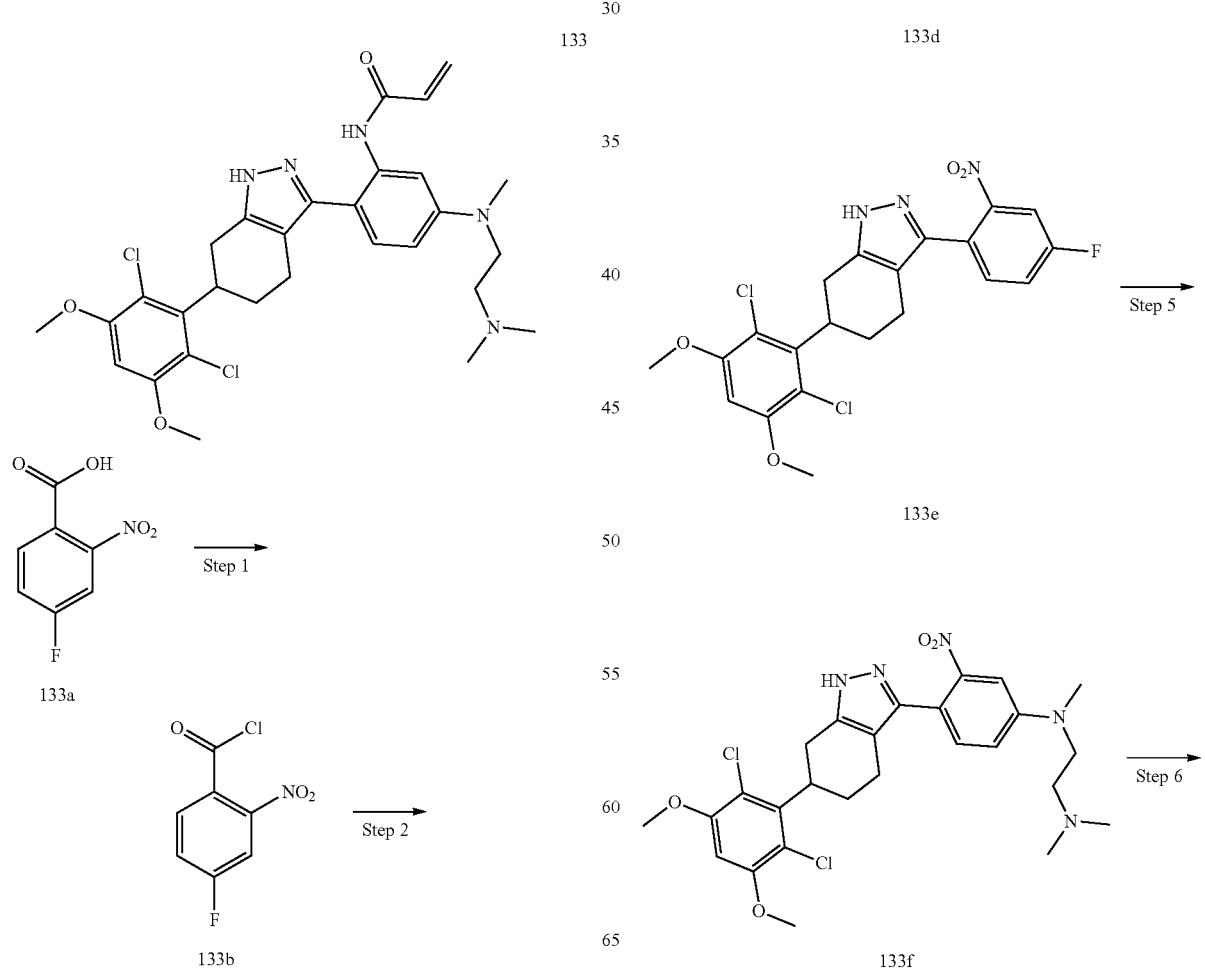

115

-continued

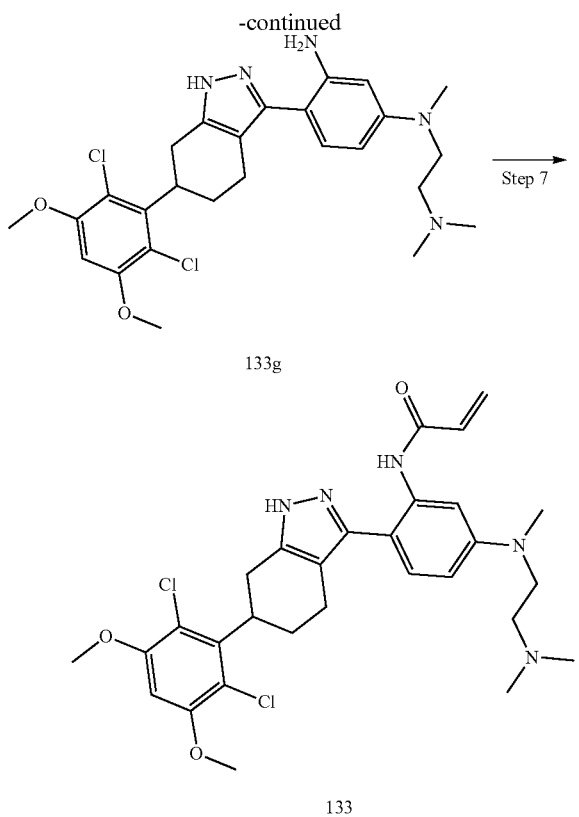

133g

133

Step 1

4-fluoro-2-nitrobenzoyl chloride 133b

The compound 4-fluoro-2-nitrobenzoic acid 133a (5 g, 27.0 mmol, 1 eq) was added into thionyl chloride (60 mL), and 1 mL of DMF was added therein dropwise for catalysis. The mixture was reacted for 3 h under reflux. Aftertreatment: the system was desolventized under reduced pressure and spin-dried to obtain the target product 4-fluoro-2-nitrobenzoyl chloride 133b (5.1 g, light yellow solid). Yield: 93%.

Step 2

5-(3,5-dimethoxyphenyl)-2-(4-fluoro-2-nitrobenzoyl)cyclohexan-1-one 133c

Lithium diisopropylamide (1.3 mL, 2.5 mmol, 1.1 eq) was slowly added dropwise at −78° C. to a solution of the compound 3-(3,5-dimethoxyphenyl)cyclohexan-1-one 10a (540 mg, 2.3 mmol, 1 eq) in anhydrous tetrahydrofuran (10 mL), and stirred for 2 h at −30° C. to −40° C. Then 4-fluoro-2-nitrobenzoyl chloride 133b (515 mg, 2.5 mmol, 1.1 eq) was added dropwise to the reaction solution, and the solution was raised to room temperature and stirred for 2 h. Aftertreatment: 10 mL of a ammonium chloride aqueous solution was added to quench the reaction, the organic phase was layered and desolventized under reduced pressure, and the residual was purified through silica gel column chromatography (petroleum ether:ethyl acetate=10:1) to obtain the target product ethyl 5-(3,5-dimethoxyphenyl)-2-(4-fluoro-2-nitrobenzoyl)cyclohexan-1-one 133c (470 mg, yellow liquid). Yield: 51%.

MS m/z (ESI): 402 [M+1].

116

Step 3

6-(3,5-dimethoxyphenyl)-3-(4-fluoro-2-nitrophenyl)-4,5,6,7-tetrahydro-1H-indazole 133d The compound 5-(3,5-dimethoxyphenyl)-2-(4-fluoro-2-nitrobenzoyl)cyclohexan-1-one 133c (460 mg, 1.15 mmol, 1 eq), and hydrazine hydrate (143 mg, 2.3 mmol, 2 eq) were dissolved into ethanol/acetic acid 10:1 (11 mL), and reacted for 3 h at 65° C. Aftertreatment: desolvation was performed under reduced pressure, and the residual was purified through silica gel column chromatography (petroleum ether:ethyl acetate=2:1) to obtain the target product 6-(3,5-dimethoxyphenyl)-3-(4-fluoro-2-nitrophenyl)-4,5,6,7-tetrahydro-1H-indazole 133d (240 mg, yellow solid). Yield: 53%.

MS m/z (ESI): 398 [M+1].

Step 4

6-(2,6-dichloro-3,5-dimethoxyphenyl)-3-(4-fluoro-2-nitrophenyl)-4,5,6,7-tetrahydro-1H-indazole 113e 6-(3,5-dimethoxyphenyl)-3-(4-fluoro-2-nitrophenyl)-4,5,6,7-tetrahydro-1H-indazole 133d (1 g, 2.5 mmol, 1 eq) was add to 5 ml of acetic acid, NCS (1 g, 7.5 mmol, 3 eq) was added therein, and reaction was performed for 3 h at 65° C. Aftertreatment: desolvation was performed under reduced pressure, and the residual was passed through a silica gel chromatographic column with a petroleum ether/ethyl acetate (2:1) system to obtain a yellow solid product 6-(2,6-dichloro-3,5-dimethoxyphenyl)-3-(4-fluoro-2-nitrophenyl)-4,5,6,7-tetrahydro-1H-indazole 113e (1 g, yellow solid). Yield: 86%.

MS m/z (ESI): 466 [M+1].

Step 5

N1-(4-(6-(2,6-dichloro-3,5-dimethoxyphenyl)-4,5,6,7-tetrahydro-1H-indazol-3-yl)-3-nitrophenyl)-N1,N2,N2-trimethylethane-1,2-diamine 113f 6-(2,6-dichloro-3,5-dimethoxyphenyl)-3-(4-fluoro-2-nitrophenyl)-4,5,6,7-tetrahydro-1H-indazole 113e (1.3 g, 2.8 mmol, 20 1 eq) was added to 10 ml of dimethyl sulfoxide. N1,N1,N2-trimethylethane-1,2-diamine (1.4 g, 14.0 mmol, 5 eq) was added therein, and reaction was performed for 3 h at 150° C. Aftertreatment: desolvation was performed under reduced pressure, and the residual was passed through a silica gel chromatographic column with a dichloromethane/methanol (8:1) system to obtain a yellow solid product N1-(4-(6-(2,6-dichloro-3,5-dimethoxyphenyl)-4,5,6,7-tetrahydro-1H-indazol-3-yl)-3-nitrophenyl)-N1,N2,N2-trimethylethane-1,2-diamine 113f (387 mg, yellow solid). Yield: 25%.

MS m/z (ESI): 548[M+1].

Step 6

4-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,3-diamine 113g The compound N1-(4-(6-(2,6-dichloro-3,5-dimethoxyphenyl)-4,5,6,7-tetrahydro-1H-indazol-3-yl)-3-nitrophenyl)-N1,N2,N2-trimethylethane-1,2-diamine 113f (380 mg, 0.69 mmol, 1 eq) was dissolved in ethanol (15 mL). Zinc powder (226 mg, 3.47 mmol, 5 eq) and ammonium chloride (184 mg, 3.47 mmol, 5 eq) were added therein, and reaction was performed for 3 h at 50° C. Aftertreatment: the mixture was spin-dried to remove the solvent, diluted with ethyl acetate and washed with water, and the organic phase was spin-dried to obtain the target product 4-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,3-diamine 113g (180 mg, yellow solid). Yield: 50%.

MS m/z (ESI): 518[M+1].

Step 7

N-(2-(6-(2,6-dichloro-3,5-dimethoxyphenyl)-4,5,6,7-tetrahydro-1H-indazol-3-yl)-5-((2-(dimethylamino)ethyl)(methyl)amino)phenyl)acrylamide 113

The compound 4-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,3-diamine 113g (180 mg, 0.35 mmol, 1 eq) was dissolved in 15 mL of dichloromethane. N,N-diisopropylethylamine (90 mg, 0.70 mmol, 2 eq) was added therein. The mixture was cooled to −40° C. A solution of acryloyl chloride (31 mg, 0.35 mmol, 1 eq) in dichloromethane was added dropwise and stirred for 30 min. Aftertreatment: the mixture was desolventized under reduced pressure, and subjected to preparative liquid phase separation and lyophilization to obtain the target product N-(2-(6-(2,6-dichloro-3,5-dimethoxyphenyl)-4,5,6,7-tetrahydro-1H-indazol-3-yl)-5-((2-(dimethylamino)ethyl)(methyl)amino)phenyl)acrylamide 113 (11 mg, white solid). Yield: 5.5%.

MS m/z (ESI): 572[M+1].

$^1$H NMR (400 MHz, DMSO) δ 12.84 (s, 1H), 10.87 (s, 1H), 8.16 (s, 1H), 6.89 (s, 1H), 6.80 (s, 1H), 6.71 (dd, J=9.1, 2.4 Hz, 1H), 6.32 (dd, J=16.9, 10.0 Hz, 1H), 6.18 (d, J=16.7 Hz, 1H), 5.72 (d, J=10.9 Hz, 1H), 4.08-3.98 (m, 1H), 3.93 (d, J=3.6 Hz, 6H), 3.57-3.35 (m, 4H), 2.93 (s, 3H), 2.70 (ddd, J=20.1, 14.1, 6.4 Hz, 4H), 2.28 (s, 6H), 1.80 (d, J=10.2 Hz, 1H).

P1 and P2 were obtained through chiral column resolution. Conditions for chiral resolution: device: SFC, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

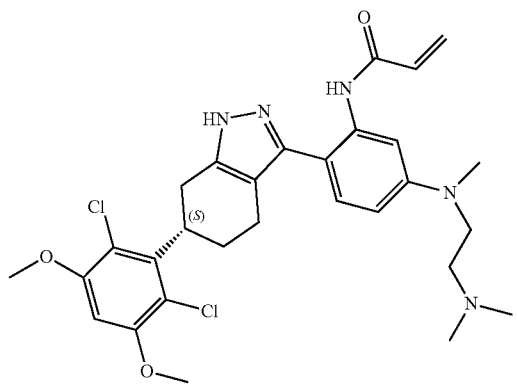

Example 137

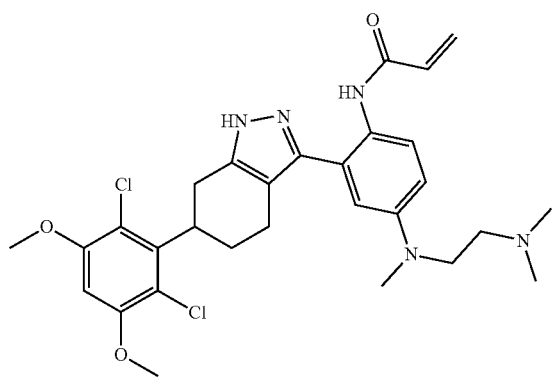

137

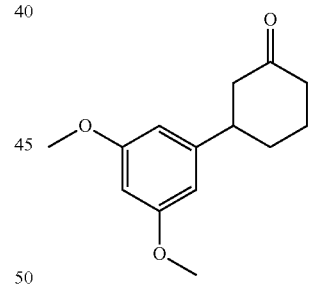

137b

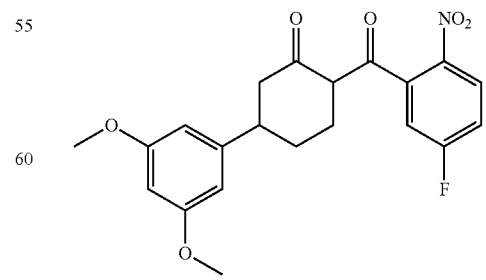

137c

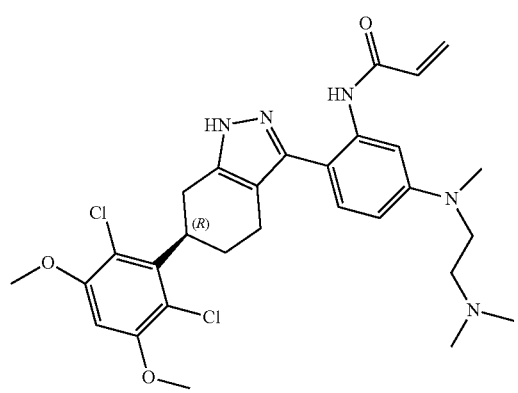

-continued

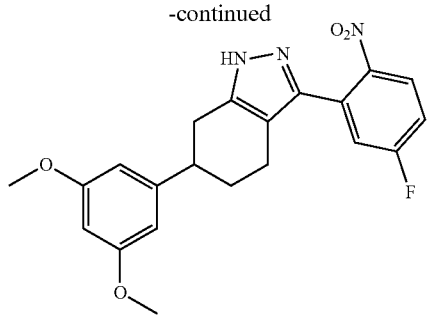

137d

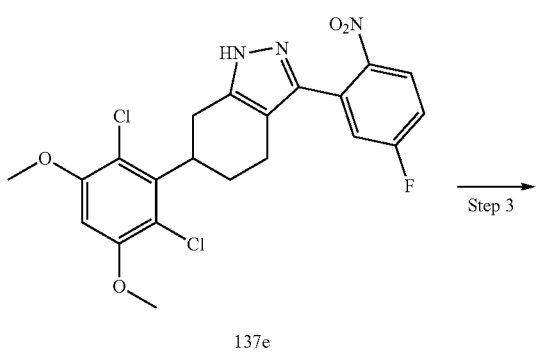

137e

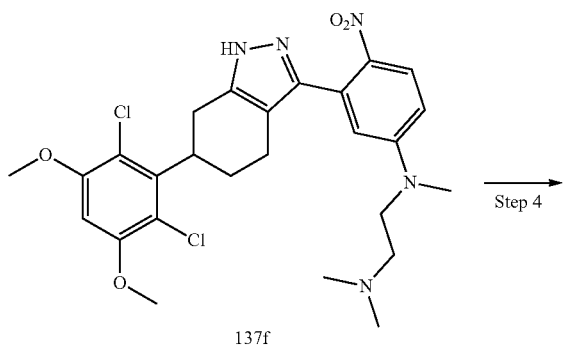

137f

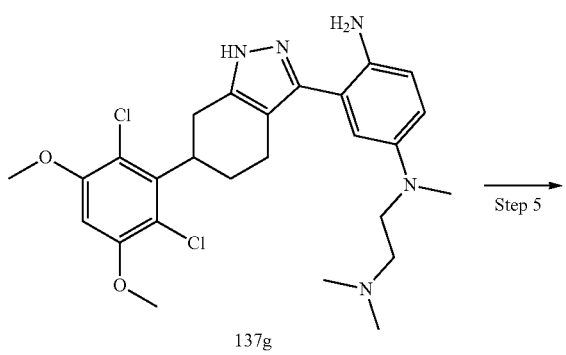

137g

-continued

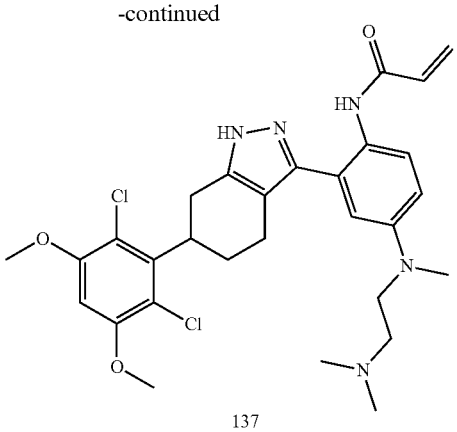

137

Step 1

3-(3,5-dimethoxyphenyl)cyclohexanone 137b was Synthesized with Reference to Example 098b Step 2

5-(3,5-dimethoxyphenyl)-2-(5-fluoro-2-nitrobenzoyl)cyclohexanone 103c 3-(3,5-dimethoxyphenyl)cyclohexanone 103b (4 g, 15 mmol) and 100 mL of tetrahydrofuran were mixed, and protected by nitrogen gas. Lithium diisopropylamide (9 mL, 18 mmol) was added at −78° C., and the mixture was warmed up to −40° C. and maintained for 2 h. 2-nitro-5-fluoro-benzoyl chloride (3.5 g, 15 mmol) was added therein. The mixture was raised to room temperature and reacted for 3 h. Aftertreatment: the mixture was quenched with a saturated ammonium chloride aqueous solution, dichloromethane and the aqueous phase were added and layered, the organic phase was desolventized under reduced pressure and then purified through a silica gel chromatographic column with petroleum ether/ethyl acetate (3:1) to obtain the product 5-(3,5-dimethoxyphenyl)-2-(5-fluoro-2-nitrobenzoyl)cyclohexanone 137c (5 g, 10 mmol, yellow solid). Yield: 40%.

MS m/z (ESI): 402 [M+1].

Step 3

6-(3,5-dimethoxyphenyl)-3-(5-fluoro-2-nitrophenyl)-4,5,6,7-tetrahydro-1H-indazole 137d 5-(3,5-dimethoxyphenyl)-2-(5-fluoro-2-nitrobenzoyl)cyclohexanone 137c (4 g, 10 mmol), hydrazine hydrate (2 g, 25 mmol) and 100 ml of acetic acid/ethanol (1:10) were mixed and stirred for 3 h at 65° C. Aftertreatment: dichloromethane and the aqueous phase were added and layered, the organic phase was desolventized under reduced pressure and passed through a silica gel chromatographic column with a petroleum ether/ethyl acetate (2:1) system to obtain a yellow solid product 137d (3.1 g, 7 mmol, yellow solid). Yield: 70%.

MS m/z (ESI): 398 [M+1].

Step 4

6-(2,6-dichloro-3,5-dimethoxyphenyl)-3-(5-fluoro-2-nitrophenyl)-4,5,6,7-tetrahydro-1H-indazole 137e 6-(3,5-dimethoxyphenyl)-3-(5-fluoro-2-nitrophenyl)-4,5,6,7-tetrahydro-1H-indazole 137d (1 g, 2.5 mmol) and 50 mL of acetic acid were mixed. N-chlorosuccinimide (1 g, 7.5 mmol) was added therein, and reaction was performed for 2 h at 80° C. Aftertreatment: dichloromethane and the aqueous phase were added and layered, the organic phase was desolventized under reduced pressure and then passed through a silica gel chromatographic column with a petroleum ether/ethyl acetate (1:1) system to obtain a yellow solid product 6-(2,6-dichloro-3,5-dimethoxyphenyl)-3-(5-fluoro-2-nitrophenyl)-4,5,6,7-tetrahydro-1H-indazole 137e (1.1 g, 2.3 mmol, yellow solid). Yield: 85%.

MS m/z (ESI): 466 [M+1].

Step 5

N1-(3-(6-(2,6-dichloro-3,5-dimethoxyphenyl)-4,5,6,7-tetrahydro-1H-indazol-3-yl)-4-nitrophenyl)-N1,N2,N2-trimethylethane-1,2-diamine 137f 6-(2,6-dichloro-3,5-dimethoxyphenyl)-3-(5-fluoro-2-nitrophenyl)-4,5,6,7-tetrahydro-1H-indazole 137e (1.1 g, 2.3 mmol), N—N'dimethyl-N-methylethylene diamine (1.2 g, 12 mmol) and 5 mL of dimethyl sulfoxide were mixed in a sealed tube, and reacted for 1 h at 110° C. Aftertreatment: desolvation was performed under reduced pressure to obtain a solid crude product N1-(3-(6-(2,6-dichloro-3,5-dimethoxyphenyl)-4,5,6,7-tetrahydro-1H-indazol-3-yl)-4-nitrophenyl)-N1,N2,N2-trimethylethane-1,2-diamine 137f (750 mg, 1.3 mmol, yellow solid).

Yield: 55%

MS m/z (ESI): 548 [M+1].

Step 6

3-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,4-diamine 137g N1-(3-(6-(2,6-dichloro-3,5-dimethoxyphenyl)-4,5,6,7-tetrahydro-1H-indazol-3-yl)-4-nitrophenyl)-N1,N2,N2-trimethylethane-1,2-diamine 137f (750 mg, 1.3 mmol) and 20 ml of ethanol were mixed. Zinc powder (500 mg, 8 mmol), ammonium chloride (700 mg, 13 mmol) and 3 ml of water were added therein, and reaction was performed for 2 h at 50° C. Aftertreatment: desolvation was performed under reduced pressure, dichloromethane and the aqueous phase were added and layered, and the organic phrase was passed through a neutral alumina chromatographic column with a dichloromethane/methanol (10:1) system to obtain a solid product 3-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,4-diamine 137g (400 mg, 0.77 mmol, white solid).

Yield: 60%.

MS m/z (ESI): 518[M+1].

Step 7

N-(2-(6-(2,6-dichloro-3,5-dimethoxyphenyl)-4,5,6,7-tetrahydro-1H-indazol-3-yl)-4-((2-(dimethylamino)ethyl)(methyl)amino)phenyl)acrylamide 137

3-(6-(2,6-dichloro-3,5-dimethoxyphenyl)-4,5,6,7-tetrahydro-1H-indazol-3-yl)-N1-(2-(dimethylamino)ethyl)-N1-methylbenzene-1,4-diamine 137 g (400 mg, 0.8 mmol) and 20 mL DCM were mixed, and N,N-diisopropylethylamine (300 mg, 2.4 mmol) was added therein. The mixture was cooled to −40° C., and then acryloyl chloride (40 mg, 0.5 mmol) was slowly added therein, to carry out reaction for 1 h. Aftertreatment: dichloromethane and the aqueous phase were added and layered, the organic phase was desolventized under reduced pressure, and subjected to preparative liquid phase separation to obtain a white solid product N-(2-(6-(2,6-dichloro-3,5-dimethoxyphenyl)-4,5,6,7-tetrahydro-1H-indazol-3-yl)-4-((2-(dimethylamino)ethyl)(methyl)amino)phenyl)acrylamide 137 (100 mg, 0.2 mmol, white solid).

Yield: 30/%.

MS m/z (ESI): 572 [M+1].

$^1$H NMR (400 MHz, DMSO) δ 12.84 (s, 1H), 10.87 (s, 1H), 8.16 (s, 1H), 6.89 (s, 1H), 6.80 (s, 1H), 6.71 (dd, J=9.1, 2.4 Hz, 1H), 6.32 (dd, J=16.9, 10.0 Hz, 1H), 6.18 (d, J=16.7 Hz, 1H), 5.72 (d, J=10.9 Hz, 1H), 4.08-3.98 (m, 1H), 3.93 (d, J=3.6 Hz, 6H), 3.57-3.35 (m, 4H), 2.93 (s, 3H), 2.70 (ddd, J=20.1, 14.1, 6.4 Hz, 4H), 2.28 (s, 6H), 1.80 (d, J=10.2 Hz, 1H).

P1 and P2 were obtained through chiral column resolution. Conditions for chiral resolution: SFC device, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

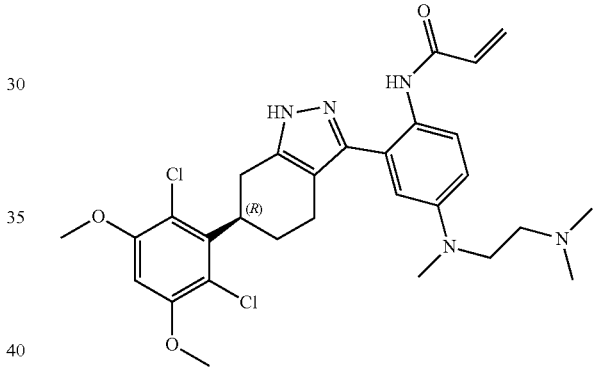

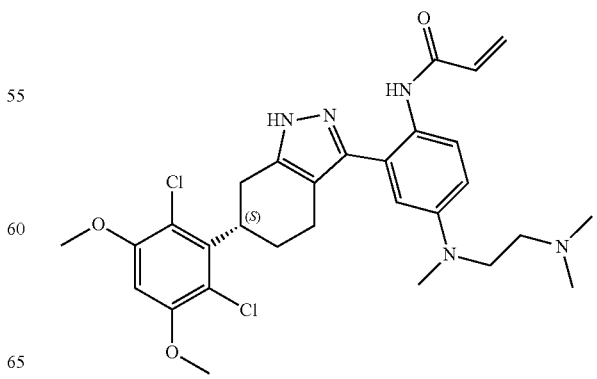

Embodiment 140

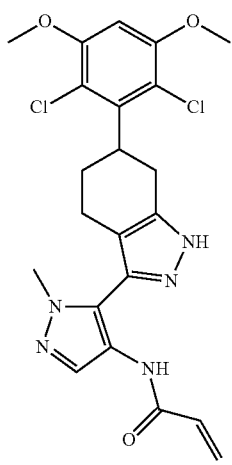

Embodiment 140 was synthesized with reference to the operation steps in embodiment 103, except that in Step 1, 1-H-4-nitro-3-benzoylchloropyrazole was replaced with 1-methyl-4-nitro-5-benzoylchloropyrazole.

MS m/z (ESI): 476 [M+1].

$^1$H NMR (400 MHz, DMSO) δ 12.91 (s, 1H), 9.47 (s, 1H), 7.85 (s, 1H), 6.89 (s, 1H), 6.52 (dd, J 17.2, 9.8 Hz, 1H), 6.19 (d, J=16.5 Hz, 1H), 5.70 (m, 1H), 3.93 (d, J=2.5 Hz, 6H), 3.77 (s, 3H), 2.73 (m, 2H), 2.34 (s, 1H), 1.74 (m, 2H), 1.24 (s, 2H).

P1 and P2 were obtained through chiral column resolution. Conditions for chiral resolution: device: SFC, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

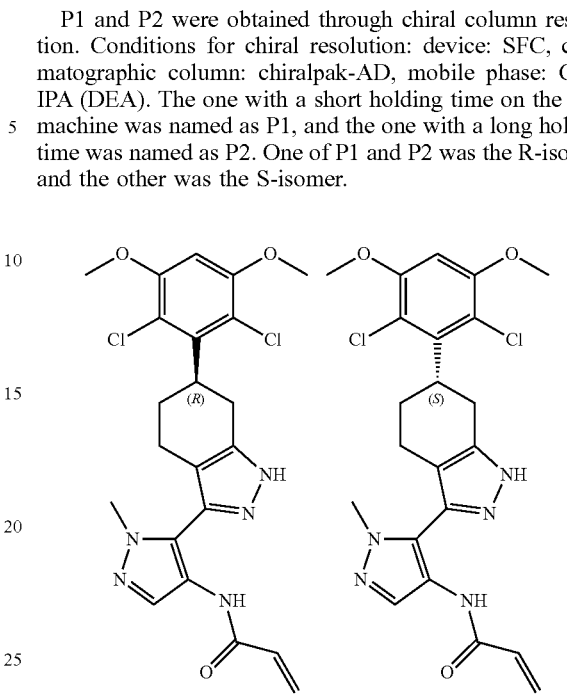

Embodiment 015-P1

(R)—N-(2-(6-(2,6-dichloro-3,5-dimethoxyphenyl)-4,5,6,7-tetrahydro-1H-indazol-3-yl)phenyl)acrylamide

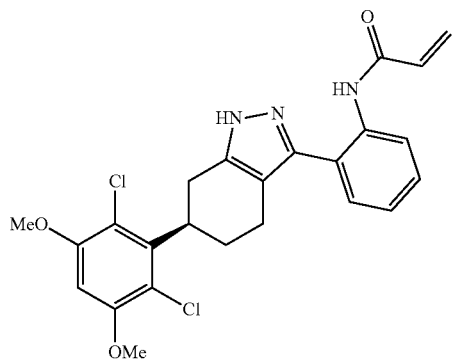

015P1

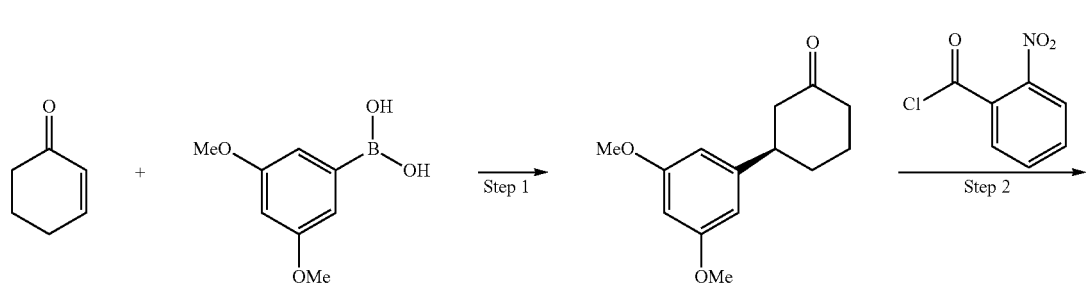

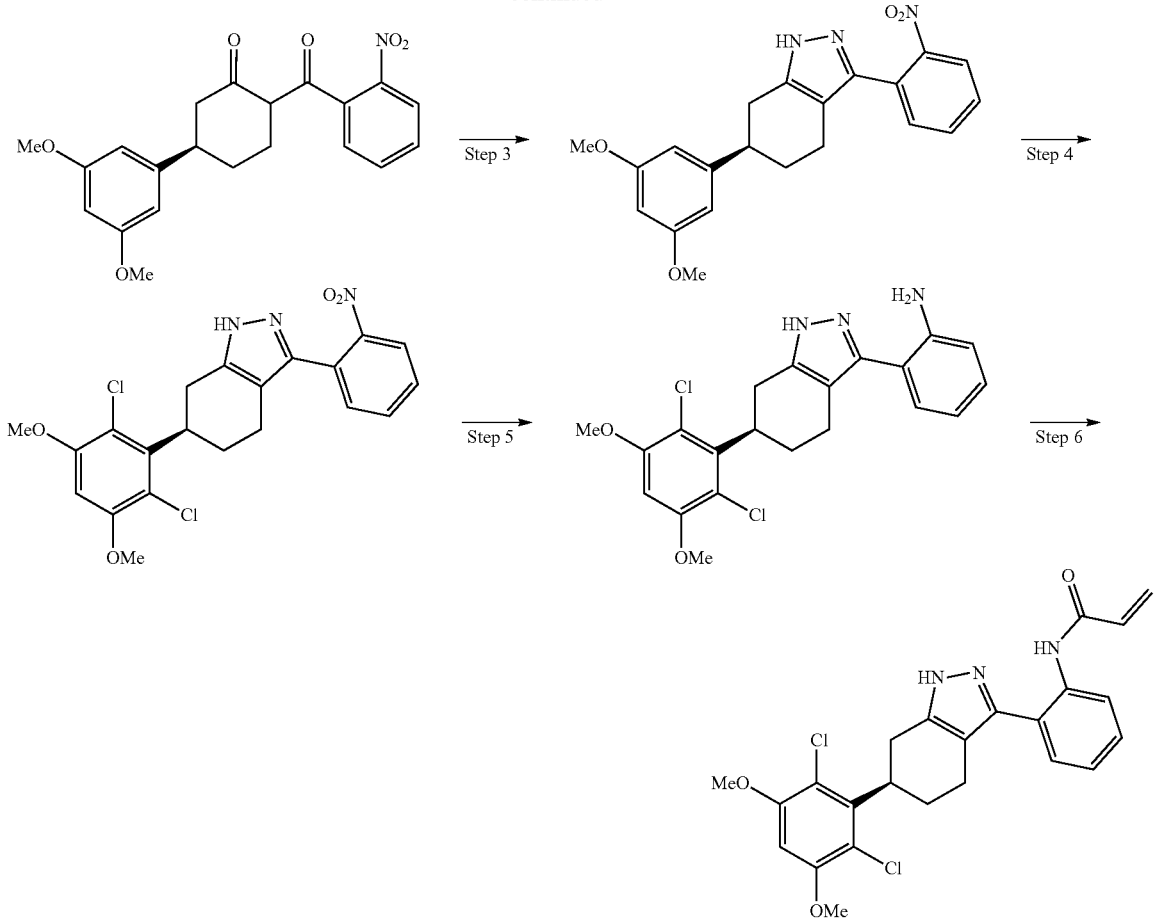

Step 1

(R)-3-(3,5-dimethoxyphenyl)cyclohexan-1-one

Under the protection of argon gas, 3,5-dimethoxyphenylboronic acid (22.7 g, 123 mmol), acetylacetonatobis(ethylene)rhodium (260 mg, 1 mmol), and (R)-BINAP (935 mg, 1.5 mmol) were added into a mixed solvent of 250 mL of dioxane and 25 mL of water, followed by the addition of 2-cyclohexen-1-one (4.8 g, 50 mmol). The above reaction solution was reacted for 6 h in a 105° C. oil bath. Aftertreatment: the mixture was cooled to room temperature, concentrated under reduced pressure to remove dioxane, then 150 mL of ethyl acetate was added, 150 ml of 1.2 M dilute hydrochloric acid was added to washed the organic phase, the aqueous phrase was discarded, the organic phase was then washed again with 150 mL of a 5% sodium hydroxide solution, the organic phase was separated out and concentrated dry, and the resulting oil was purified through neutral alumina column chromatography (petroleum ether: ethyl acetate=3:1) to obtain (R)-3-(3,5-dimethoxyphenyl)cyclohexan-1-one (4.2 g, 18 mmol, colorless oil). Yield: 36%.

MS m/z (ESI): 235 [M+1]$^+$ $^1$H NMR (400 MHz, CDCl$_3$): δ 6.39 (d, J=2.2 Hz, 2H), 6.36 (t, J=2.2 Hz, 1H), 3.81 (s, 6H), 3.01-2.90 (m, 1H), 2.64-2.36 (m, 4H), 2.19-2.07 (m, 2H), 1.92-1.70 (m, 2H).

Step 2

(R)-5-(3,5-dimethoxyphenyl)-2-(2-nitrobenzoyl)cyclohexanone (R)-3-(3,5-dimethoxyphenyl)cyclohexanone (4.0 g, 18 mmol) and tetrahydrofuran (100 ml) were mixed, and cooled to −78° C. under the protection of nitrogen gas. Lithium diisopropylamide (8.3 mL, 20 mmol) was slowly added therein dropwise, and the mixture was warmed up to −40° C. and stirred for 2h. O-nitrobenzoyl chloride (3.5 g, 18 mmol) was slowly added therein, and the mixture was raised to room temperature and stirred for 3 h. Aftertreatment: the mixture was quenched with a saturated ammonium chloride aqueous solution, and the organic phase was desolventized under reduced pressure to obtain (R)-5-(3,5-dimethoxyphenyl)-2-(2-nitrobenzoyl)cyclohexanone (8.7 g, light yellow oil), which was directly used in the next step without further purification.

MS m/z (ESI): 384 [M+1]$^+$

Step 3

(R)-6-(3,5-dimethoxyphenyl)-3-(2-nitrophenyl)-4,5,6,7-tetrahydro-1H-indazole

A (R)-5-(3,5-dimethoxyphenyl)-2-(2-nitrobenzoyl)cyclohexanone crude product (8.0 g), hydrazine hydrate (10 mL, 80%), acetic acid (10 mL) and ethanol (100 mL) were mixed, warmed up to 60° C., and stirred for 3 h. Aftertreatment: desolvation was performed under reduced pressure, and the residual was purified through silica gel column chromatography (petroleum ether:ethyl acetate=3:1) to obtain (R)-6-(3,5-dimethoxyphenyl)-3-(2-nitrophenyl)-4,5,6,7-tetrahydro-1H-indazole (3.2 g, yellow solid). Two-step yield: 50%.

MS m/z (ESI): 380 [M+1]

¹H NMR (400 MHz, CDCl₃): δ 7.80 (d, J=7.9 Hz, 1H), 7.62-7.57 (m, 2H), 7.46-7.38 (m, 1H), 6.43-6.36 (m, 3H), 3.83 (s, 6H), 3.02-2.92 (m, 1H), 2.87-2.82 (m, 1H), 2.66-2.60 (m, 1H), 2.56-2.53 (m, 2H), 2.13-2.04 (m, 1H), 1.94-1.78 (m, 1H).

Step 4

(R)-6-(2,6-dichloro-3,5-dimethoxyphenyl)-3-(2-nitrophenyl)-4,5,6,7-tetrahydro-1H-indazole (R)-6-(3,5-dimethoxyphenyl)-3-(2-nitrophenyl)-4,5,6,7-tetrahydro-1H-indazole (2.5 g, 6.5 mmol) was dissolved in 50 mL of acetonitrile. The mixture was cooled to −45° C., and then sulfonyl chloride (2.6 g, 20 mmol) was added dropwise. After the dropwise addition, reaction was performed for 3 h at −45° C., and 5 mL of methanol was added to quench the reaction. Aftertreatment: the mixture was naturally raised to room temperature and then concentrated to remove the solvent, 50 mL of water and 100 mL of ethyl acetate were added therein, the liquids were separated, the organic phase was desolventized under reduced pressure and passed through a silica gel chromatographic column with a petroleum ether/ethyl acetate (1:1) system to obtain (R)-6-(2,6-dichloro-3,5-dimethoxyphenyl)-3-(2-nitrophenyl)-4,5,6,7-tetrahydro-1H-indazole (2 g, 4.4 mmol, off-white solid). Yield: 86%.

MS m/z (ESI): 449 [M+1]⁺

¹H NMR (400 MHz, CDCl₃): δ 7.79-7.77 (m, 1H), 7.63-7.57 (m, 2H), 7.40-7.36 (m, 1H), 6.55 (s, 1H), 4.15-4.06 (m, 1H), 3.95 (s, 6H), 3.43-3.36 (m, 1H), 2.78-2.72 (m, 1H), 2.67-2.49 (m, 3H), 1.85-1.81 (m, 1H).

Step 5

(R)-2-(6-(2,6-dichloro-3,5-dimethoxyphenyl)-4,5,6,7-tetrahydro-1H-indazol-3-yl)aniline (R)-6-(2,6-dichloro-3,5-dimethoxyphenyl)-3-(2-nitrophenyl)-4,5,6,7-tetrahydro-1H-indazole (1.5 g, 3.3 mmol) was dissolved in 50 mL of ethyl acetate, palladium carbon (50 mg, 10%) was added therein, and the mixture was stirred for 10 h under a hydrogen atmosphere at room temperature. Aftertreatment: palladium carbon was removed by filtration, and the filtrate was concentrated to obtain a product (R)-2-(6-(2,6-dichloro-3,5-dimethoxyphenyl)-4,5,6,7-tetrahydro-1H-indazol-3-yl)aniline (1.5 g, white solid). Yield: 100%.

MS m/z (ESI): 419 [M+1]

¹H NMR (400 MHz, CDCl₃): δ 7.34-7.31 (m, 1H), 7.04-7.02 (m, 1H), 6.77-6.70 (m, 2H), 6.55 (s, 1H), 6.01 (s, 2H), 4.17-4.11 (m, 2H), 3.95 (s, 6H), 3.51-3.44 (m, 1H), 2.81-2.64 (m, 4H).

Step 6

(R)—N-(2-(6-(2,6-dichloro-3,5-dimethoxyphenyl)-4,5,6,7-tetrahydro-1H-indazol-3-yl)phenyl)acrylamide The compound (R)-2-(6-(2,6-dichloro-3,5-dimethoxyphenyl)-4,5,6,7-tetrahydro-1H-indazol-3-yl)aniline (120 mg, 0.29 mmol) and N,N-diisopropylethylamine (75 mg, 0.58 mmol) were dissolved in anhydrous dichloromethane (10 mL), and the mixture was cooled to −40° C. Acryloyl chloride (26 mg, 0.29 mmol) was slowly added therein, and reaction was performed for 0.5 h at −40° C. Aftertreatment: the reaction was quenched with 1 mL of methanol added, spin-dried to remove the solvent, and subjected to preparative liquid phase separation and lyophilization to obtain the target product (R)—N-(2-(6-(2,6-dichloro-3,5-dimethoxyphenyl)-4,5,6,7-tetrahydro-1H-indazol-3-yl)phenyl)acrylamide (85 mg, white solid). Yield: 62%.

MS m/z (ESI): 473 [M+1]⁺

¹HNMR (400 MHz, DMSO): δ 12.96 (s, 1H), 11.48 (s, 1H), 8.49 (d, J=7.9 Hz, 1H), 7.59 (d, J=7.3 Hz, 1H), 7.32 (t, J=7.7 Hz, 1H), 7.17 (t, J=7.3 Hz, 1H), 6.89 (s, 1H), 6.33-6.20 (m, 2H), 5.81 (d, J=10.8 Hz, 1H), 4.03 (br.s, 1H), 3.93 (d, J=3.7 Hz, 6H), 3.49-3.37 (m, 1H), 2.82-2.58 (m, 4H), 1.84 (d, J=11.2 Hz, 1H).

Purity of the alkaline high performance liquid phase: 99.59% (214 nm), 99.70% (254 nm).

ee: 96%

Embodiment 015-P2

(S)—N-(2-(6-(2,6-dichloro-3,5-dimethoxyphenyl)-4,5,6,7-tetrahydro-1H-indazol-3-yl)phenyl)acrylamide

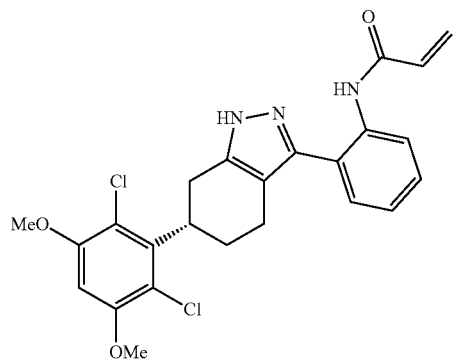

015P2

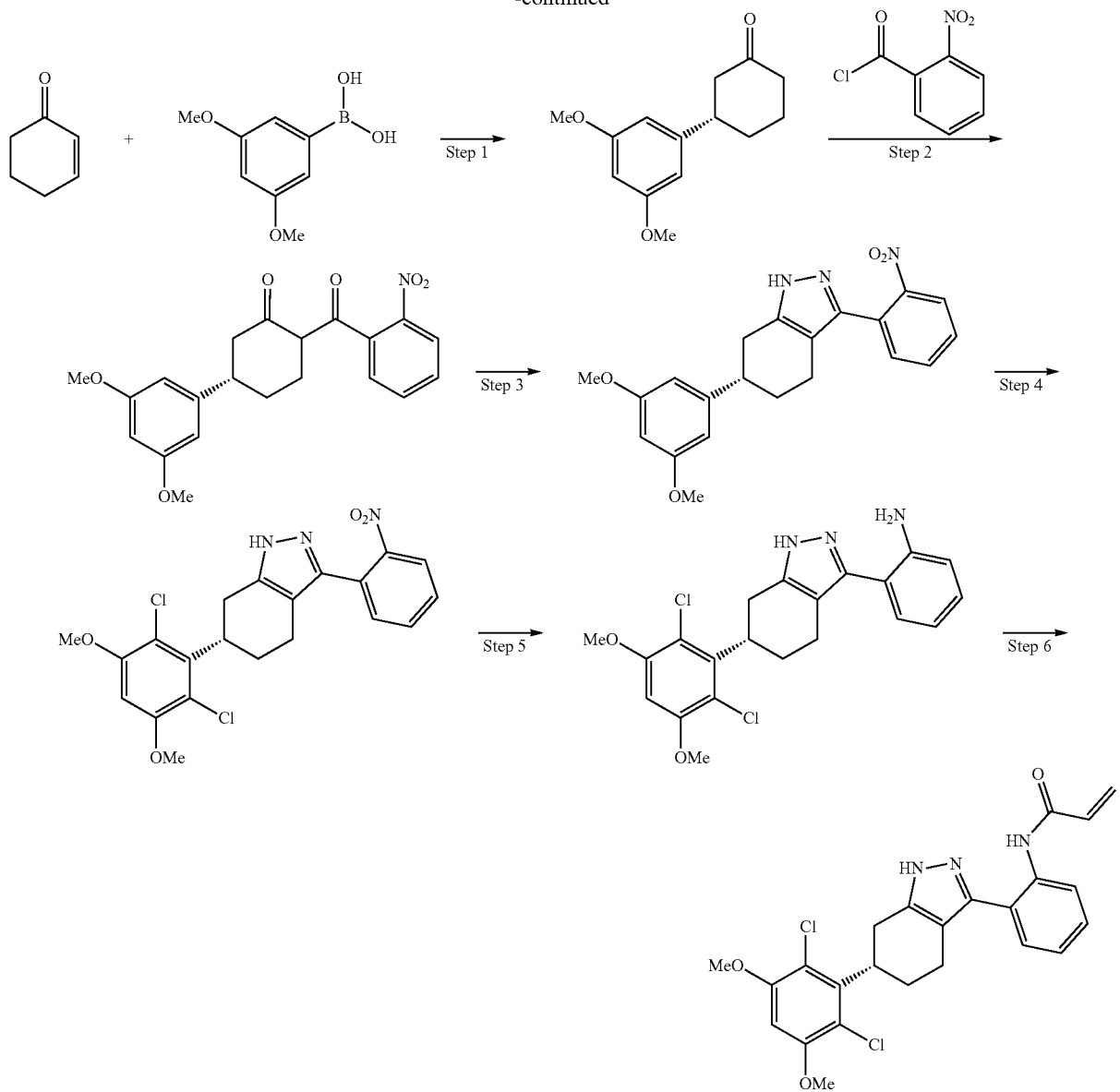

Step 1

(S)-3-(3,5-dimethoxyphenyl)cyclohexan-1-one

Under the protection of argon gas, 3,5-dimethoxyphenyl-boronic acid (22.7g, 123 mmol), aetylaetonatobis(ethylene) rhodium (260 g, 1 mmol), and (S)-BINAP (935 g, 1.5 mmol) were added into a mixed solvent of 250 mL of dioxane and 25 mL of water, followed by the addition of 2-cyclohexen-1-one (4.8 g, 50 mmol), and the above reaction solution was reacted for 6 h in a 105° C. oil bath. Aftertreatment: the mixture was cooled to room temperature, concentrated under reduced pressure to remove dioxane, then 150 mL of ethyl acetate was added, then 150 ml of 1.2 M dilute hydrochloric acid was added to washed the organic phase, the aqueous phrase was discarded, the organic phase was then washed again with 150 mL of a 5% sodium hydroxide solution, the organic phase was separated out and concentrated dry, and the resulting oil was purified through neutral alumina column chromatography (petroleum ether:ethyl acetate=3:1) to obtain (S)-3-(3,5-dimethoxyphenyl)cyclohexan-1-one (3.5 g, 15 mmol, colorless oil). Yield: 30%.

MS m/z (ESI): 235 [M+1]$^+$ $^1$H NMS (400 MHz, CDCl$_3$): δ 6.39 (d, J=2.2 Hz, 2H), 6.36 (t, J=2.2 Hz, 1H), 3.81 (s, 6H), 3.01-2.91 (m, 1H), 2.64-2.32 (m, 4H), 2.17-2.07 (m, 2H), 1.87-1.78 (m, 2H).

Step 2

(S)-5-(3,5-dimethoxyphenyl)-2-(2-nitrobenzoyl) cyclohexanone (S)-3-(3,5-dimethoxyphenyl)cyclohexanone (4.0 g, 15 mmol) and tetrahydrofuran (100 ml) were mixed, and cooled to −78° C. under the protection of nitrogen gas. Lithium diisopropylamide (8.3 mL, 17 mmol) was slowly added therein dropwise, and the mixture was warmed up to −40° C. and stirred for 2h. O-nitrobenzoyl chloride (3.5 g, 18 mmol) was slowly added therein, and the mixture was raised to room temperature and stirred for 3 h. Aftertreatment: the mixture was quenched with a saturated ammonium chloride aqueous solution, and the organic phase was desolventized under reduced pressure to obtain (S)-5-(3,5-dimethoxyphenyl)-2-(2-nitrobenzoyl)cyclohexanone (7.4 g, light yellow oil), which was directly used in the next step without further purification.

MS m/z (ESI): 384 [M+1]$^+$

Step 3

(S)-6-(3,5-dimethoxyphenyl)-3-(2-nitrophenyl)-4,5,6,7-tetrahydro-1H-indazole A (S)-5-(3,5-dimethoxyphenyl)-2-(2-nitrobenzoyl)cyclohexanone crude product (7.0 g), hydrazine hydrate (10 mL, 80%), acetic acid (10 mL) and ethanol (100 mL) were mixed, warmed up to 60° C., and stirred for 3 h. Aftertreatment: desolvation was performed under reduced pressure, and the residual was purified through silica gel column chromatography (petroleum ether:ethyl acetate=3:1) to obtain (S)-6-(3,5-dimethoxyphenyl)-3-(2-nitrophenyl)-4,5,6,7-tetrahydro-1H-indazole (2.5 g, yellow solid). Two-step yield: 44%.

MS m/z (ESI): 380 [M+1]$^+$ $^1$H NMS (400 MHz, CDCl$_3$): δ 7.73-7.71 (m, 1H), 7.60-7.54 (m, 2H), 7.36-7.34 (m, 1H), 6.41-6.34 (m, 3H), 3.83 (s, 6H), 2.97-2.82 (m, 1H), 2.69-2.60 (m, 1H), 2.52-2.40 (m, 3H), 2.03 (s, 1H), 1.84-1.78 (m, 1H).

Step 4

(S)-6-(2,6-dichloro-3,5-dimethoxyphenyl)-3-(2-nitrophenyl)-4,5,6,7-tetrahydro-1H-indazole (S)-6-(3,5-dimethoxyphenyl)-3-(2-nitrophenyl)-4,5,6,7-tetrahydro-1H-indazole (2.5 g, 6.5 mmol) was dissolved in 50 mL of acetonitrile. The mixture was cooled to −45° C., and then sulfonyl chloride (2.6 g, 20 mmol) was added dropwise. After the dropwise addition, reaction was performed for 3 h at −45° C., and 5 mL of methanol was added to quench the reaction. Aftertreatment: the mixture was naturally raised to room temperature and then concentrated to remove the solvent, 50 mL of water and 100 mL of ethyl acetate were added therein, the liquids were separated, the organic phase was desolventized under reduced pressure, and passed through a silica gel chromatographic column with a petroleum ether/ethyl acetate (1:1) system to obtain (S)-6-(2,6-dichloro-3,5-dimethoxyphenyl)-3-(2-nitrophenyl)-4,5,6,7-tetrahydro-1H-indazole (1.8 g, 4.0 mmol, off-white solid). Yield: 61%.

MS m/z (ESI): 449 [M+1]$^+$ $^1$H NMS (400 MHz, CDCl$_3$): δ 7.86-7.80 (m, 1H), 7.62-7.60 (m, 2H), 7.46-7.41 (m, 1H), 6.55 (s, 1H), 4.12-4.10 (m, 1H), 3.96 (d, J=1.2 Hz, 6H), 3.52-3.45 (m, 1H), 2.82-2.64 (m, 2H), 2.61-2.51 (m, 2H), 1.87-1.83 (m, 1H).

Step 5

(S)-2-(6-(2,6-dichloro-3,5-dimethoxyphenyl)-4,5,6,7-tetrahydro-1H-indazol-3-yl)aniline (S)-6-(2,6-dichloro-3,5-dimethoxyphenyl)-3-(2-nitrophenyl)-4,5,6,7-tetrahydro-1H-indazole (1.5 g, 3.3 mmol) was dissolved in 50 mL of ethyl acetate, Pd/C (50 mg) was added therein, and the mixture was stirred for 10 h under a hydrogen atmosphere at room temperature. Aftertreatment: palladium carbon was removed by filtration, and the filtrate was concentrated and then passed through a silica gel chromatographic column with pure ethyl acetate to obtain a product (S)-2-(6-(2,6-dichloro-3,5-dimethoxyphenyl)-4,5,6,7-tetrahydro-1H-indazol-3-yl)aniline (0.8 g, white solid). Yield: 57%

MS m/z (ESI): 419 [M+1]

$^1$H NMS (400 MHz, CDCl$_3$): δ 7.34-7.32 (m, 1H), 7.28 (s, 1H), 6.80-6.71 (m, 2H), 6.55 (s, 1H), 4.20-4.07 (m, 1H), 3.95 (s, 6H), 3.52-3.45 (m, 1H), 2.82-2.66 (m, 4H), 1.95-1.86 (m, 1H).

Step 6

(S)—N-(2-(6-(2,6-dichloro-3,5-dimethoxyphenyl)-4,5,6,7-tetrahydro-1H-indazol-3-yl)phenyl)acrylamide The compound (S)-2-(6-(2,6-dichloro-3,5-dimethoxyphenyl)-4,5,6,7-tetrahydro-1H-indazol-3-yl)aniline (120 mg, 0.29 mmol) and N,N-diisopropylethylamine (75 mg, 0.58 mmol) were dissolved in anhydrous dichloromethane (10 mL), and the mixture was cooled to −40° C. Acryloyl chloride (26 mg, 0.29 mmol) was slowly added therein, and reaction was performed for 0.5 h at −40° C. Aftertreatment: the reaction was quenched with 1 ml of methanol added, spin-dried to remove the solvent, and subjected to preparative liquid phase separation and lyophilization to obtain the target product (S)—N-(2-(6-(2,6-dichloro-3,5-dimethoxyphenyl)-4,5,6,7-tetrahydro-1H-indazol-3-yl)phenyl)acrylamide (90 mg, white solid). Yield: 65%.

MS m/z (ESI): 473[M+1]$^+$ $^1$H NMS (400 MHz, DMSO): δ 12.96 (s, 1H), 11.48 (s, 1H), 8.49 (d, J=8.1 Hz, 1H), 7.59 (d, J=7.4 Hz, 1H), 7.32 (t, J=7.6 Hz, 1H), 7.17 (t, J=7.4 Hz, 1H), 6.89 (s, 1H), 6.41-6.16 (m, 2H), 5.81 (d, J=9.6 Hz, 1H), 4.03 (br.s, 1H), 3.93 (d, J=3.7 Hz, 6H), 3.50-3.37 (m, 1H), 2.86-2.59 (m, 4H), 1.84 (d, J=11.4 Hz, 1H).

Purity of the alkaline liquid phase: 99.59% (214 nm), 99.70% (254 nm).

ee: 95%

Embodiment 095

N-(2-(6-(2,6-dichloro-3,5-dimethoxyphenyl)-4,5,6,7-tetrahydro-1H-pyrazolo[3,4-c]pyridin-3-yl)phenyl)acrylamide

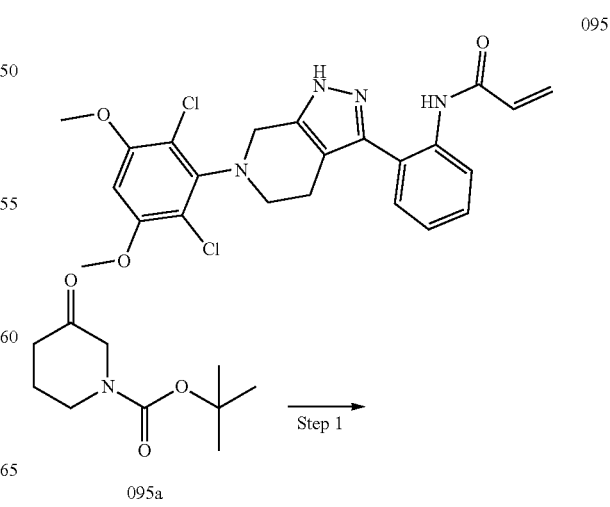

095a

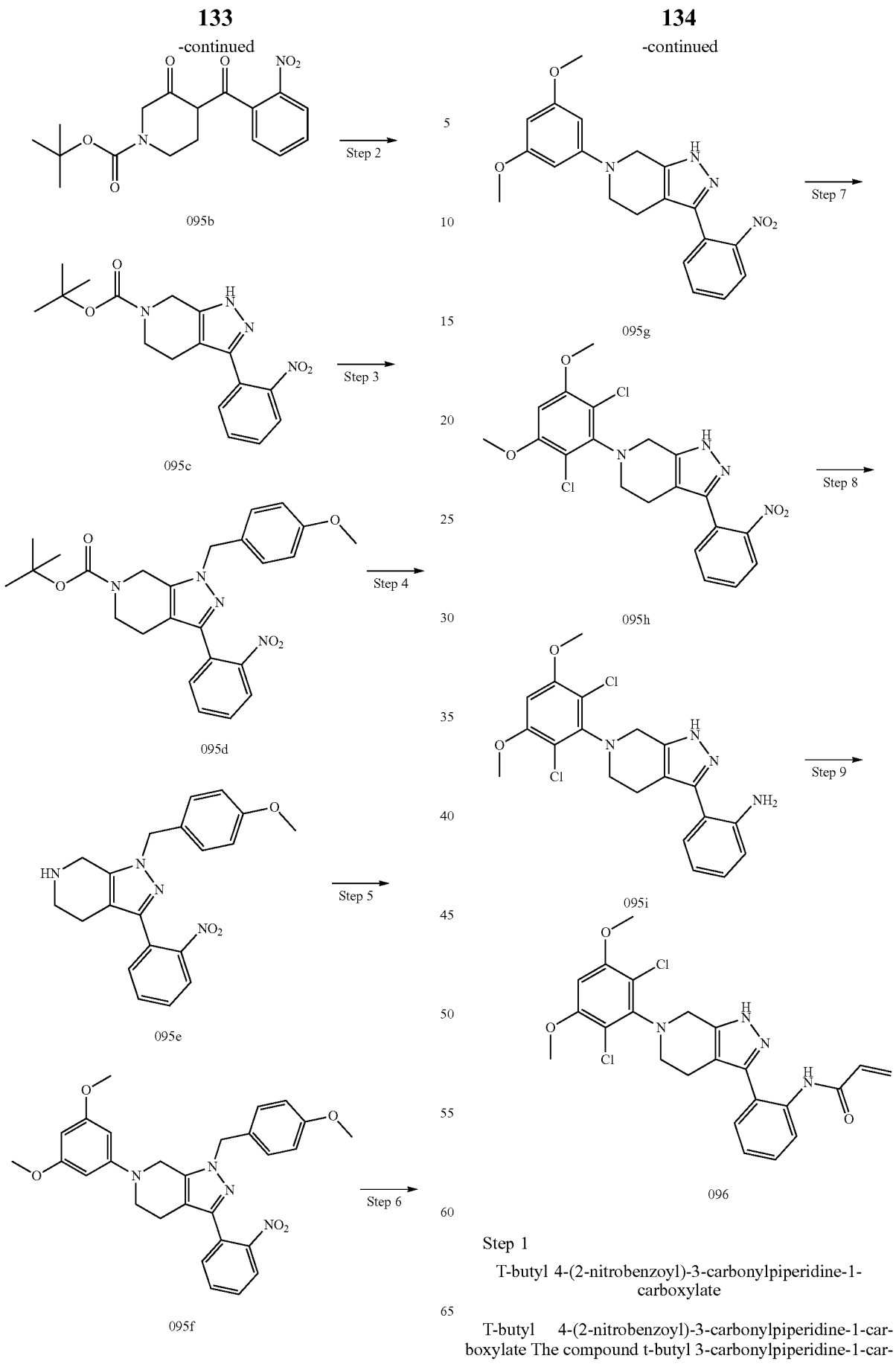

boxylate 095a (20 g, 100.5 mmol, 1 eq) was dissolved in 400 mL of tetrahydrofuran. With the temperature controlled at −78° C., lithium diisopropylamide (60.3 ml, 120.6 mmol, 1.2 eq) was added therein. After the dropwise addition, the mixture was warmed up to −40° C. and reacted for 1 h. Subsequently, 2-nitrobenzoyl chloride (18.6 g, 100.5 mmol, 1 eq) was added into the system at −40° C., and the system was raised to room temperature and reacted for 3 h. Aftertreatment: a saturated ammonium chloride aqueous solution (400 ml) was added therein, the mixture was extracted 3 times with ethyl acetate (200 ml), and the organic phase was desolventized under reduced pressure to obtain the target crude product t-butyl 4-(2-nitrobenzoyl)-3-carbonylpiperidine-1-carboxylate 095b (42 g, yellow oil). Yield: 90%.
Step 2

T-butyl 3-(2-nitrophenyl)-1,4,5,7-tetrahydro-6H-pyrazolo[3,4-c]pyridine-6-carboxylate The compound t-butyl 4-(2-nitrobenzoyl)-3-carbonylpiperidine-1-carboxylate 095b (40 g, 115 mmol, 1 eq), and hydrazine hydrate (14.4 g, 287.5 mmol, 2.5 eq) were dissolved into ethanol/acetic acid 10:1 (200 mL), and reacted for 3 h at 65° C. Aftertreatment: desolvation was performed under reduced pressure, and the residual was purified through silica gel column chromatography (petroleum ether: ethyl acetate=2:1) to obtain the target product t-butyl 3-(2-nitrophenyl)-1,4,5,7-tetrahydro-6H-pyrazolo[3,4-c]pyridine-6-carboxylate 095c (15.3 g, yellow solid). Yield: 39%.
MS m/z (ESI): 345[M+1]$^+$
Step 3

T-butyl 1-(4-methoxybenzyl)-3-(2-nitrophenyl)-1,4,5,7-tetrahydro-6H-pyrazolo[3,4-c]pyridine-6-carboxylate The compound t-butyl 3-(2-nitrophenyl)-1,4,5,7-tetrahydro-6H-pyrazolo[3,4-c]pyridine-6-carboxylate 095c (4 g, 11.6 mmol, 1 eq) was dissolved in DMF (120 mL). At a condition of 0° C., sodium hydride (696 mg, 17.4 mmol, 1.5 eq) was slowly added dropwise, and stirred for 0.5 h. P-methoxybenzyl chloride (2.7 g, 17.4 mmol, 1.5 eq) was added therein and further stirred for 3 h. Aftertreatment: the reaction was quenched with 100 mL of water and extracted with ethyl acetate, the organic phase was desolventized under reduced pressure, and the residual was purified through silica gel column chromatography (petroleum ether: ethyl acetate=3:1) to obtain the target product t-butyl 1-(4-methoxybenzyl)-3-(2-nitrophenyl)-1,4,5,7-tetrahydro-6H-pyrazolo[3,4-c]pyridine-6-carboxylate 095d (7 g, brown solid). Yield: 90%.
MS m/z (ESI): 445 [M+1]$^+$
Step 4

1-(4-methoxybenzyl)-3-(2-nitrophenyl)-4,5,6,7-tetrahydro-1H-pyrazolo[3,4-c]pyridine The compound t-butyl 1-(4-methoxybenzyl)-3-(2-nitrophenyl)-1,4,5,7-tetrahydro-6H-pyrazolo[3,4-c]pyridine-6-carboxylate 095d (7 g, 15.7 mmol, 1 eq) was added into dichloromethane (150 ml). Subsequently, a trifluoroacetic acid solution (50 ml) was added therein at 0-10° C. and stirred for 1 h at that temperature. Aftertreatment: desolvation was performed under reduced pressure, and the residual was purified through silica gel column chromatography (dichloromethane:methanol=10:1) to obtain the target compound 1-(4-methoxybenzyl)-3-(2-nitrophenyl)-4,5,6,7-tetrahydro-1H-pyrazolo[3,4-c]pyridine 095e (3.2 g, brown solid). Yield: 59%.
MS m/z (ESI): 345 [M+1]$^+$
Step 5

6-(3,5-dimethoxyphenyl)-1-(4-methoxybenzyl)-3-(2-nitrophenyl)-4,5,6,7-tetrahydro-1H-pyrazolo[3,4-c]pyridine The compound 1-(4-methoxybenzyl)-3-(2-nitrophenyl)-4,5,6,7-tetrahydro-1H-pyrazolo[3,4-c]pyridine 095e (3 g, 8.7 mmol, 1 eq) was added into toluene (100 ml). 1-bromo-3,5-dimethoxybenzene (2.8 g, 13.05 mmol, 1.5 eq), tris (dibenzylidene acetone)dipalladium (1.6 g, 1.74 mmol, 0.2 eq), binaphthylene diphenylphosphine (2.16 g, 3.48 mmol, 0.4 eq), and sodium tert-butoxide (3.46 g, 36.1 mmol, 3 eq) were added therein, and reaction was performed for 6 h under the protection of nitrogen gas. Aftertreatment: desolvation was performed under reduced pressure, and the residual was purified through silica gel column chromatography (dichloromethane:methanol=10:1) to obtain the target compound 6-(3,5-dimethoxyphenyl)-1-(4-methoxybenzyl)-3-(2-nitrophenyl)-4,5,6,7-tetrahydro-1H-pyrazolo[3,4-c]pyridine 095f (1.38 mg, yellow solid). Yield: 31%.
MS m/z (ESI): 501 [M+1]$^+$
Step 6

6-(3,5-dimethoxyphenyl)-3-(2-nitrophenyl)-4,5,6,7-tetrahydro-1H-pyrazolo[3,4-c]pyridine The compound 6-(3,5-dimethoxyphenyl)-1-(4-methoxybenzyl)-3-(2-nitrophenyl)-4,5,6,7-tetrahydro-1H-pyrazolo[3,4-c]pyridine 095f (1.3 g, 2.6 mmol, 1 eq) was dissolved into trifluoroacetic acid (50 ml). Subsequently, the mixture was warmed up 80° C. and reacted for 3 h under reflux. Aftertreatment: desolvation was performed under reduced pressure, and the residual was purified through silica gel column chromatography (dichloromethane:methanol=10:1) to obtain the target compound 6-(3,5-dimethoxyphenyl)-3-(2-nitrophenyl)-4,5,6,7-tetrahydro-1H-pyrazolo[3,4-c]pyridine 095g (400 mg, brown solid). Yield: 40%.
MS m/z (ESI): 401 [M+1]$^+$
Step 7

6-(2,6-dichloro-3,5-dimethoxyphenyl)-3-(2-nitrophenyl)-4,5,6,7-tetrahydro-1H-pyrazolo[3,4-c]pyridine The compound 6-(3,5-dimethoxyphenyl)-3-(2-nitrophenyl)-4,5,6,7-tetrahydro-1H-pyrazolo[3,4-c]pyridine 095g (250 mg, 0.66 mmol, 1 eq) was added into acetonitrile (20 ml). Subsequently, sulfonyl chloride (240.6 mg, 1.78 mmol, 2.7 eq) was added therein at −40° C. and stirred for 1 h at that temperature. Aftertreatment: the mixture was quenched with 30 ml of water added and extracted with 50 ml of ethyl acetate, the organic phase was desolventized under reduced pressure, and the residual was purified through silica gel column chromatography (petroleum ether:ethyl acetate=1:1) to obtain the target compound 6-(2,6-dichloro-3,5-dimethoxyphenyl)-3-(2-nitrophenyl)-4,5,6,7-tetrahydro-1H-pyrazolo[3,4-c]pyridine 095h (150 mg, light yellow solid). Yield: 50%.
Syntheses in Step 8 and Step 9 were performed with reference to the steps in example 289. Finally, the target product N-(2-(6-(2,6-dichloro-3,5-dimethoxyphenyl)-4,5,6,7-tetrahydro-1H-pyrazolo[3,4-c]pyridine-3-yl)phenyl)acrylamide was obtained.

MS m/z (ESI): 474 [M+1]$^+$ $^1$H NMR (400 MHz, DMSO): δ 12.80 (s, 1H), 10.58 (s, 1H), 8.29 (s, 1H), 6.99 (s, 1H), 6.86 (s, 1H), 6.54 (s, 2H), 6.18 (s, 3H), 5.80 (s, 1H), 3.74 (s, 6H), 3.45 (s, 2H), 2.84 (s, 2H), 1.98 (s, 2H).

Embodiment 281

N-(5-(6-(2,6-difluoro-3,5-dimethoxyphenyl)-4,5,6,7-tetrahydro-1H-indazol-3-yl)-1-methyl-1H-pyrazol-4-yl)acrylamide

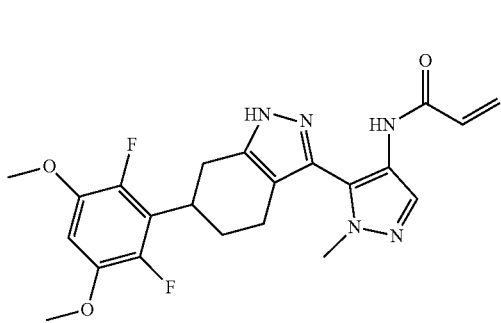

281

6-(3,5-dimethoxyphenyl)-3-(1-methyl-4-nitro-1H-pyrazol-5-yl)-4,5,6,7-tetrahydro-1H-indazole (2 g, 5.2 mmol) and acetonitrile (50 ml) were mixed, select F (3.5 g, 10 mmol) was added therein at 0° C., and the mixture was slowly warmed up to room temperature and stirred overnight. Aftertreatment: desolvation was performed under reduced pressure, and the residual was extracted with dichloromethane (100 mL) and water (100 mL) added, the organic phase was desolventized under reduced pressure, and the residual was purified through silica gel column chromatography (petroleum ether:ethyl acetate=5:4) to obtain 6-(2,6-difluoro-3,5-dimethoxyphenyl)-3-(1-methyl-4-nitro-1H-pyrazol-5-yl)-4,5,6,7-tetrahydro-1H-indazole (800 mg, 1.9 mmol, yellow solid).

Yield: 19%.

Example 281 was synthesized with reference to the operation steps of example 093. A final product N-(5-(6-(2,6-difluoro-3,5-dimethoxyphenyl)-4,5,6,7-tetrahydro-1H-indazol-3-yl)-1-methyl-1H-pyrazol-4-yl)acrylamide was obtained. P1 and P2 were then obtained through chiral column resolution.

Conditions for chiral resolution: device: SFC, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

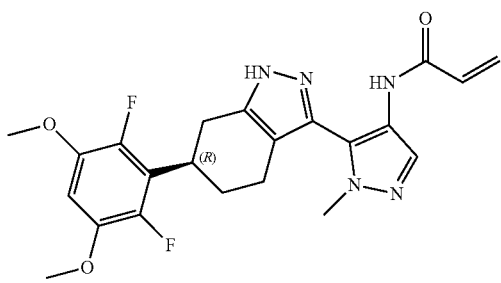

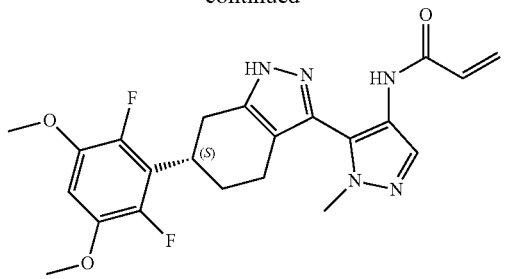

MS m/z (ESI): 443.8[M+1]$^+$

P1: $^1$HNMR (400 MHz, DMSO): δ 12.92 (s, 1H), 9.42 (s, 1H), 7.84 (s, 1H), 6.93 (t, J=8.3 Hz, 1H), 6.53 (dd, J=17.0, 10.2 Hz, 1H), 6.19 (dd, J=17.0, 2.1 Hz, 1H), 5.66 (dd, J=10.2, 2.1 Hz, 1H), 3.86 (s, 6H), 3.76 (s, 3H), 3.43-3.36 (m, 1H), 2.98-2.92 (m, 2H), 2.47-2.38 (m, 1H), 2.13-2.05 (m, 1H), 1.90 (d, J=12.4 Hz, 1H).

e.e.99.0%

P2: $^1$HNMR (400 MHz, DMSO): δ 12.92 (s, 1H), 9.42 (s, 1H), 7.84 (s, 1H), 6.93 (t, J=8.3 Hz, 1H), 6.53 (dd, J=17.0, 10.2 Hz, 1H), 6.19 (dd, J=17.0, 2.1 Hz, 1H), 5.66 (dd, J=10.2, 2.1 Hz, 1H), 3.86 (s, 6H), 3.76 (s, 3H), 3.43-3.36 (m, 1H), 2.98-2.92 (m, 2H), 2.47-2.38 (m, 1H), 2.13-2.05 (m, 1H), 1.90 (d, J=12.4 Hz, 1H).

e.e.99.8%

Embodiment 283

N-(2-(6-(2,6-dichloro-3,5-dimethoxyphenyl)-4,5,6,7-tetrahydro-1H-indazol-3-yl)-4-(4-methylpiperazin-1-yl)phenyl)acrylamide

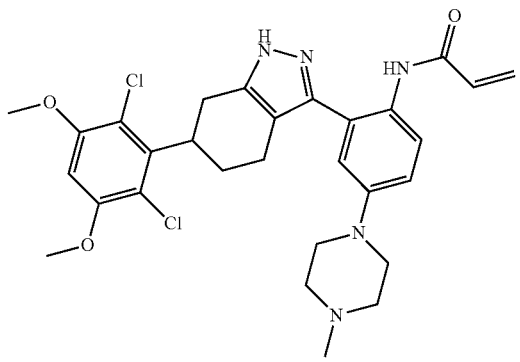

283

Example 283 was synthesized with reference to the steps in example 137, except that in Step 5, N—N'dimethyl-N-methylethylene diamine was replaced with 1-methyl piperazine. Finally, the target product N-(2-(6-(2,6-dichloro-3,5-dimethoxyphenyl)-4,5,6,7-tetrahydro-1H-indazol-3-yl)-4-(4-methylpiperazin-1-yl)phenyl)acrylamide was obtained.

Separation conditions for the final product (racemate): device: mass spectrogram guided prep-HPLC; chromatographic column: -Gemini-C18 150×21.2 mm, 5 µm, mobile phase: ACN-H20 (0.05% NH3), gradient: 60-80.

Conditions for chiral resolution: SFC device, chromatographic column: chiralpak-AS, mobile phase: CO2-ETOH (DEA). The one with a short holding time on the SFC machine was named as P1, and the one with a long holding time was named as P2. One of P1 and P2 was the R-isomer, and the other was the S-isomer.

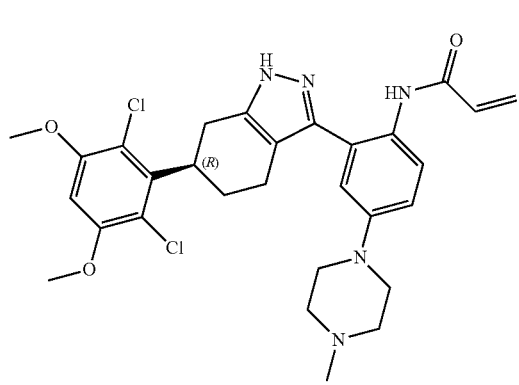

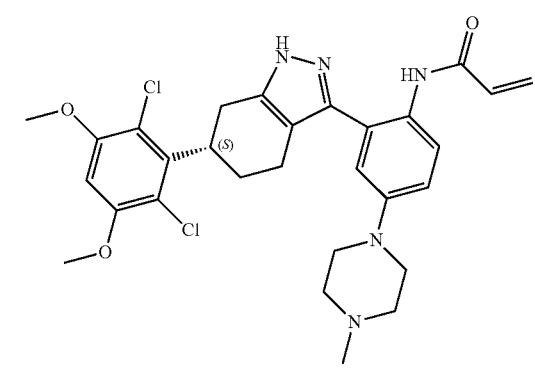

P1: MS m/z (ESI): 569.9[M+1]

ee: 96.995%

$^1$H NMR (400 MHz, MeOD): δ 8.01 (d, J=8.4 Hz, 1H), 7.04 (s, 1H), 6.94 (d, J=8.4 Hz, 1H), 6.67 (s, 1H), 6.30-6.19 (m, 2H), 5.67 (d, J=9.3 Hz, 1H), 4.53 (s, 2H), 4.07 (s, 1H), 3.83 (d, J=3.4 Hz, 6H), 3.25 (s, 5H), 2.95 (s, 4H), 2.65 (dd, J=21.0, 14.8 Hz, 3H), 2.57 (s, 3H).

P2: MS m/z (ESI): 569.8[M+1]

ee: 97.5503%

$^1$H NMR (400 MHz, MeOD): δ 8.00 (d, J=7.9 Hz, 1H), 7.03 (s, 1H), 6.94 (d, J=9.1 Hz, 1H), 6.67 (s, 1H), 6.24 (d, J=9.4 Hz, 2H), 5.66 (d, J=9.1 Hz, 1H), 4.52 (s, 2H), 4.07 (s, 1H), 3.83 (d, J=3.6 Hz, 6H), 3.25 (s, 5H), 2.92 (d, J=8.9 Hz, 4H), 2.68 (dd, J=15.9, 6.1 Hz, 2H), 2.60 (s, 1H), 2.53 (s, 3H).

Embodiment 284

N-(2-(6-(2,6-dichloro-3,5-dimethoxyphenyl)-4,5,6,7-tetrahydro-1H-indazol-3-yl)-5-(dimethylamino)phenyl)acrylamide

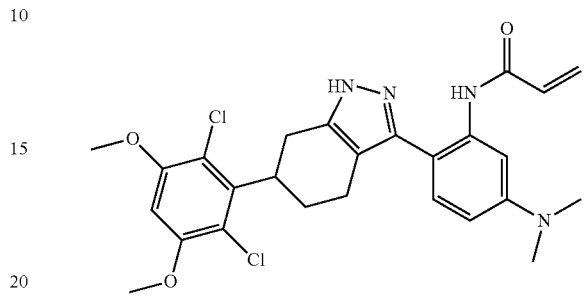

Example 284 was synthesized with reference to example 133, except that in Step 5, N—N'dimethyl-N-methylethylene diamine was replaced with dimethylamine hydrochloride.

Conditions for chiral resolution: SFC device, chromatographic column: chiralpak-IC, mobile phase: CO2-ETOH (DEA). The one with a short holding time on the SFC machine was named as P1, and the one with a long holding time was named as P2. One of P1 and P2 was the R-isomer, and the other was the S-isomer.

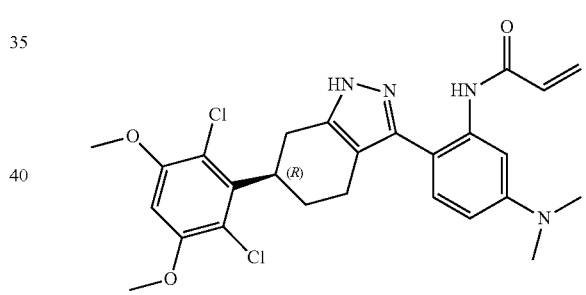

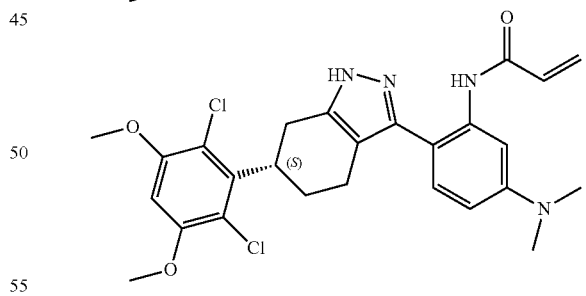

MS m/z (ESI): 516.4 [M+1]

P1: $^1$H NMR (400 MHz, DMSO): δ 12.73 (s, 1H), 11.67 (s, 1H), 8.08 (s, 1H), 7.40 (s, 1H), 7.23-7.15 (m, 1H), 6.89 (s, 1H), 6.54 (d, J=7.4 Hz, 1H), 6.26 (s, 1H), 5.80 (s, 1H), 3.93 (d, J=3.7 Hz, 6H), 2.94 (s, 6H), 2.73 (s, 3H), 2.00 (d, J=7.5 Hz, 2H), 1.82 (s, 2H).

P2: $^1$H NMR (400 MHz, DMSO): δ 12.74 (s, 1H), 11.67 (s, 1H), 8.09 (s, 1H), 7.41 (d, J=8.5 Hz, 1H), 7.23-7.17 (m, 1H), 6.89 (s, 1H), 6.54 (d, J=8.1 Hz, 1H), 6.26 (s, 1H), 5.81 (s, 1H), 3.93 (d, J=3.7 Hz, 6H), 2.94 (s, 6H), 2.73 (s, 3H), 2.00 (dd, J=14.4, 6.8 Hz, 2H), 1.82 (s, 2H).

Embodiment 285

N-(2-(6-(2,6-dichloro-3,5-dimethoxyphenyl)-4,5,6,7-tetrahydro-1H-indazol-3-yl)-4-(dimethylamino)phenyl)acrylamide

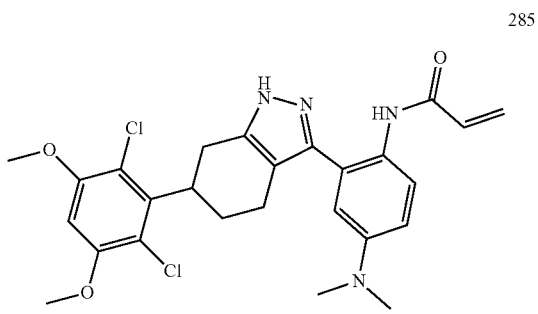 [SMILES: C=CC(=O)Nc1ccc(N(C)C)cc1-c1n[nH]c2c1CCC(c1c(Cl)c(OC)cc(OC)c1Cl)C2]

Example 285 was synthesized with reference to the operation steps of example 137, except that in Step 5, N—N'dimethyl-N-methylethylene diamine was replaced with dimethylamine hydrochloride. P1 and P2 were then obtained by chiral column resolution.

Conditions for chiral resolution: device: SFC, chromatographic column: chiralpak-IC, mobile phase: HEX-EtOH (DEA).

The one with a short holding time on the SFC machine was named as P1, and the one with a long holding time was named as P2. One of P1 and P2 was the R-isomer, and the other was the S-isomer.

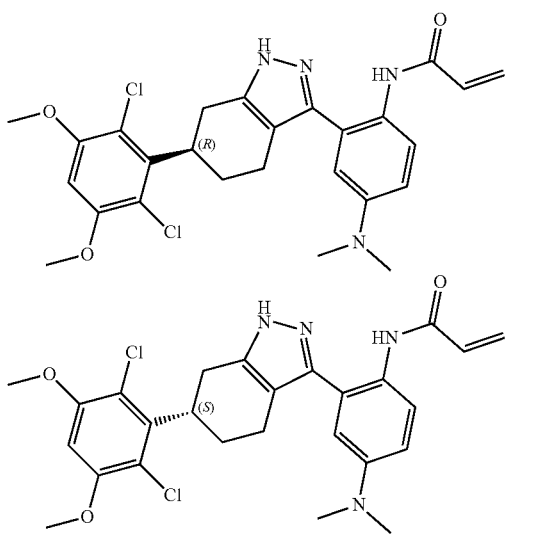

MS m/z (ESI): 514.7 [M+1]

P1: $^1$H NMR (400 MHz, DMSO): δ 12.90 (s, 1H), 10.96 (s, 1H), 8.22 (s, 1H), 6.88 (s, 1H), 6.83 (s, 1H), 6.74 (dd, J=9.1, 2.8 Hz, 1H), 6.41-6.25 (m, 1H), 6.21-6.16 (m, 1H), 5.71 (dd, J=10.0, 1.6 Hz, 1H), 3.93 (d, J=3.8 Hz, 6H), 2.91 (s, 6H), 2.84-2.58 (m, 5H), 2.51 (q, J=2 Hz, 2H).

P2: $^1$H NMR (400 MHz, DMSO): δ 12.90 (s, 1H), 10.96 (s, 1H), 8.22 (s, 1H), 6.88 (s, 1H), 6.83 (s, 1H), 6.74 (dd, J=9.1, 2.8 Hz, 1H), 6.41-6.25 (m, 1H), 6.21-6.16 (m, 1H), 5.71 (dd, J=10.0, 1.6 Hz, 1H), 3.93 (d, J=3.8 Hz, 6H), 2.91 (s, 6H), 2.84-2.58 (m, 5H), 2.51 (q, J=2 Hz, 2H)

ee: 95.9%

Embodiment 286

N-(2-(6-(2,6-dichloro-3,5-dimethoxyphenyl)-4,5,6,7-tetrahydro-1H-indazole-3-yl)-4-methylphenyl)acrylamide

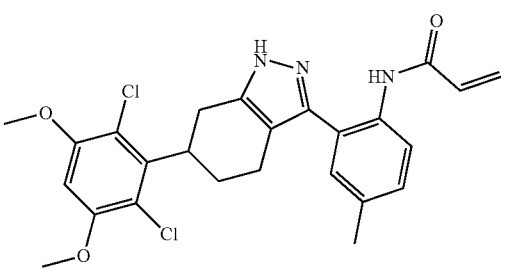

Example 286 was synthesized with reference to example 289, except that in Step 1, 4-chloro-2-nitrobenzoic acid was replaced with 5-methyl-2-nitrobenzoic acid. Finally, the target product N-(2-(6-(2,6-dichloro-3,5-dimethoxyphenyl)-4,5,6,7-tetrahydro-1H-indazol-3-yl)-4-methylphenyl)acrylamide was obtained.

MS m/z (ESI): 486.1 [M+1]$^+$ $^1$H NMR (400 MHz, CDCl$_3$): δ 10.86 (s, 1H), 8.52 (d, J=8.3 Hz, 1H), 7.31 (s, 1H), 7.15 (d, J=8.4 Hz, 1H), 6.54 (s, 1H), 6.32 (m, 2H), 5.69 (dd, J=10.0, 1.4 Hz, 1H), 4.20-4.14 (m, 1H), 3.89-3.56 (m, 7H), 3.66-3.54 (m, 1H), 2.87-2.72 (m, 4H), 2.35 (s, 3H).

Embodiment 287

N-(4-chloro-2-(6-(2,6-dichloro-3,5-dimethoxyphenyl)-4,5,6,7-tetrahydro-1H-indazol-3-yl)phenyl)acrylamide

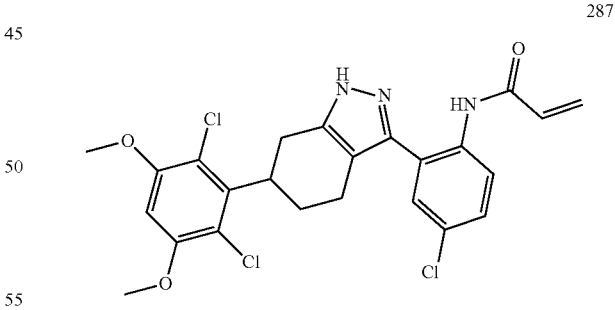

Example 287 was synthesized with reference to example 289, except that in Step 1, 4-chloro-2-nitrobenzoic acid was replaced with 5-chloro-2-nitrobenzoic acid. Finally, the target product N-(4-chloro-2-(6-(2,6-dichloro-3,5-dimethoxyphenyl)-4,5,6,7-tetrahydro-1H-indazol-3-yl)phenyl)acrylamide was obtained.

Two isomers P1 (27 mg) and P2 (25 mg) were obtained through chiral resolution.

Conditions for chiral resolution: device: SFC, chromatographic column: chiralpak-OD, mobile phase: CO2-ETOH (DEA).

The one with a short holding time on the SFC machine was named as P1, and the one with a long holding time was named as P2. One of P1 and P2 was the R-isomer, and the other was the S-isomer.

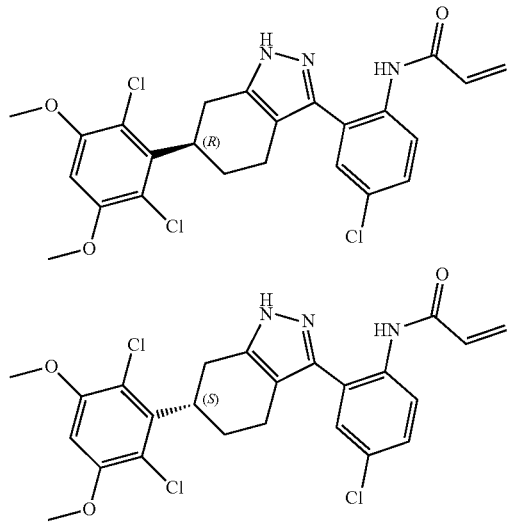

P1: ¹H NMR (400 MHz, CDCl₃): δ 11.26 (s, 1H), 8.68 (d, J=8.9 Hz, 1H), 7.50 (d, J=2.5 Hz, 1H), 7.32-7.24 (m, 2H), 6.54 (s, 1H), 6.37-6.22 (m, 2H), 5.73-5.70 (m, 1H), 4.26-4.10 (m, 1H), 3.94 (s, 3H), 3.93 (s, 3H), 3.63-3.56 (m, 1H), 2.87-2.76 (m, 4H), 1.98-1.95 (m, 1H).

P2: ¹H NMR (400 MHz, CDCl₃): δ 11.29 (s, 1H), 8.67 (d, J=8.9 Hz, 1H), 7.50 (d, J=2.5 Hz, 1H), 7.29-7.24 (m, 1H), 6.54 (s, 1H), 6.37-6.21 (m, 2H), 5.73-5.70 (m, 1H), 4.22-4.12 (m, 1H), 3.94 (s, 3H), 3.93 (s, 3H), 3.62-3.55 (m, 1H), 2.91-2.72 (m, 4H), 2.01-1.91 (m, 1H).

ee: 99.1%

Embodiment 288

N-(2-(6-(2,6-dichloro-3,5-dimethoxyphenyl)-4,5,6,7-tetrahydro-1H-indazol-3-yl)-5-methylphenyl)acrylamide

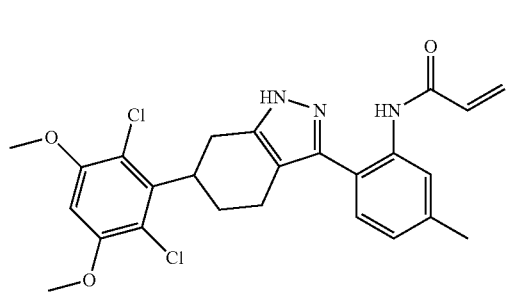

Example 288 was synthesized with reference to example 289, except that in Step 1, 4-chloro-2-nitrobenzoic acid was replaced with 4-methyl-2-nitrobenzoic acid. Finally, the target product N-(2-(6-(2,6-dichloro-3,5-dimethoxyphenyl)-4,5,6,7-tetrahydro-1H-indazol-3-yl)-5-methylphenyl)acrylamide was obtained.

Conditions for chiral resolution: Chiral prepHPLC device, chromatographic column: chiralpak-IC, mobile phase: CO2-ETOH (DEA). The one with a short holding time on the machine was named as P1, and the one with a long holding time was named as P2. One of P1 and P2 was the R-isomer, and the other was the S-isomer.

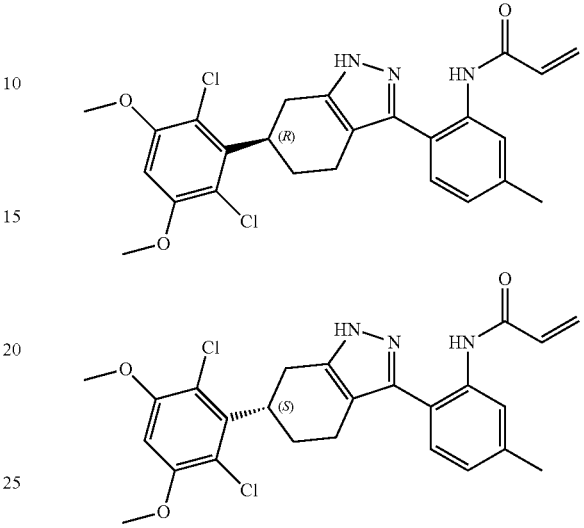

MS m/z (ESI): 487.4 [M+1]⁺

P1: ¹H NMR (400 MHz, DMSO): δ 12.91 (s, 1H), 11.48 (s, 1H), 8.35 (s, 1H), 7.48 (d, J=7.8 Hz, 1H), 6.99 (d, J=8.2 Hz, 1H), 6.89 (s, 1H), 6.34-6.22 (m, 2H), 5.81 (d, J=9.4 Hz, 1H), 4.02 (s, 1H), 3.93 (d, J=3.7 Hz, 6H), 3.53-3.35 (m, 2H), 2.74 (t, J=17.6 Hz, 3H), 2.34 (s, 3H), 1.84 (d, J=10.8 Hz, 1H).

P2: ¹H NMR (400 MHz, DMSO): δ 12.91 (s, 1H), 11.48 (s, 1H), 8.35 (s, 1H), 7.48 (d, J=8.0 Hz, 1H), 7.00 (d, J=7.6 Hz, 1H), 6.89 (s, 1H), 6.34-6.22 (m, 2H), 5.81 (d, J=9.2 Hz, 1H), 4.02 (s, 1H), 3.93 (d, J=3.7 Hz, 6H), 3.47-3.36 (m, 2H), 2.76 (d, J=15.3 Hz, 3H), 2.34 (s, 3H), 1.84 (d, J=11.5 Hz, 1H).

Embodiment 289

N-(5-chloro-2-(6-(2,6-dichloro-3,5-dimethoxyphenyl)-4,5,6,7-tetrahydro-1H-indazol-3-yl)phenyl)acrylamide

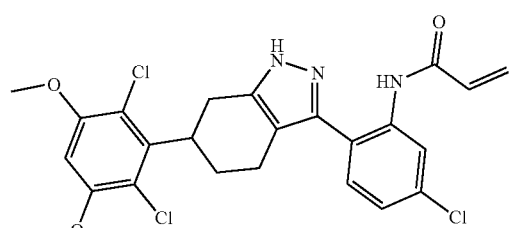

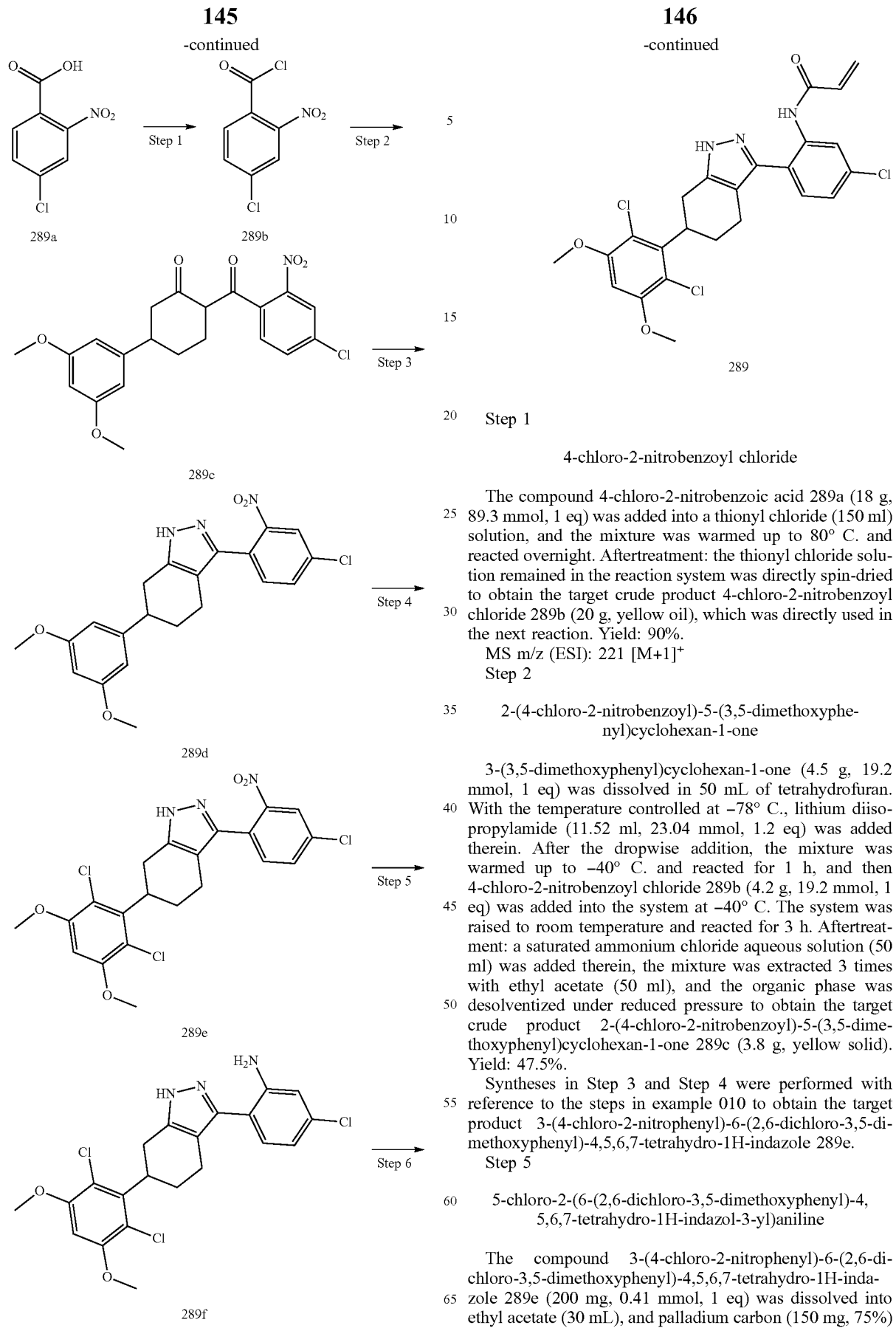

Step 1

4-chloro-2-nitrobenzoyl chloride

The compound 4-chloro-2-nitrobenzoic acid 289a (18 g, 89.3 mmol, 1 eq) was added into a thionyl chloride (150 ml) solution, and the mixture was warmed up to 80° C. and reacted overnight. Aftertreatment: the thionyl chloride solution remained in the reaction system was directly spin-dried to obtain the target crude product 4-chloro-2-nitrobenzoyl chloride 289b (20 g, yellow oil), which was directly used in the next reaction. Yield: 90%.

MS m/z (ESI): 221 [M+1]$^+$

Step 2

2-(4-chloro-2-nitrobenzoyl)-5-(3,5-dimethoxyphenyl)cyclohexan-1-one 3-(3,5-dimethoxyphenyl)cyclohexan-1-one (4.5 g, 19.2 mmol, 1 eq) was dissolved in 50 mL of tetrahydrofuran. With the temperature controlled at −78° C., lithium diisopropylamide (11.52 ml, 23.04 mmol, 1.2 eq) was added therein. After the dropwise addition, the mixture was warmed up to −40° C. and reacted for 1 h, and then 4-chloro-2-nitrobenzoyl chloride 289b (4.2 g, 19.2 mmol, 1 eq) was added into the system at −40° C. The system was raised to room temperature and reacted for 3 h. Aftertreatment: a saturated ammonium chloride aqueous solution (50 ml) was added therein, the mixture was extracted 3 times with ethyl acetate (50 ml), and the organic phase was desolventized under reduced pressure to obtain the target crude product 2-(4-chloro-2-nitrobenzoyl)-5-(3,5-dimethoxyphenyl)cyclohexan-1-one 289c (3.8 g, yellow solid). Yield: 47.5%.

Syntheses in Step 3 and Step 4 were performed with reference to the steps in example 010 to obtain the target product 3-(4-chloro-2-nitrophenyl)-6-(2,6-dichloro-3,5-dimethoxyphenyl)-4,5,6,7-tetrahydro-1H-indazole 289e.

Step 5

5-chloro-2-(6-(2,6-dichloro-3,5-dimethoxyphenyl)-4,5,6,7-tetrahydro-1H-indazol-3-yl)aniline The compound 3-(4-chloro-2-nitrophenyl)-6-(2,6-dichloro-3,5-dimethoxyphenyl)-4,5,6,7-tetrahydro-1H-indazole 289 (200 mg, 0.41 mmol, 1 eq) was dissolved into ethyl acetate (30 mL), and palladium carbon (150 mg, 75%) was added therein. Hydrogen gas was fed-in and reaction was performed for 3 h at room temperature. Aftertreatment: palladium carbon was removed by suction filtration, and the solution was washed 3 times with ethyl acetate and spin-dried to obtain the target product 5-chloro-2-(6-(2,6-dichloro-3,5-dimethoxyphenyl)-4,5,6,7-tetrahydro-1H-indazol-3-yl)aniline 289f (100 mg, yellow solid). Yield: 54%.

MS m/z (ESI): 453.8 [M+1]$^+$

Step 6

N-(5-chloro-2-(6-(2,6-dichloro-3,5-dimethoxyphenyl)-4,5,6,7-tetrahydro-1H-indazolo-3-yl)phenyl)acrylamide The compound 5-chloro-2-(6-(2,6-dichloro-3,5-dimethoxyphenyl)-4,5,6,7-tetrahydro-1H-indazol-3-yl)aniline 289f (100 mg, 0.22 mmol, 1 eq) and N,N-diisopropyl ethylamine (85 mg, 0.66 mmol, 3 eq) were dissolved into anhydrous dichloromethane (30 mL), and the mixture was cooled to −40° C. A solution of acryloyl chloride (18 mg, 0.198 mmol, 0.9 eq) in dichloromethane was slowly added therein, and reaction was performed for 0.5 h. Aftertreatment: the mixture was spin-dried to remove the solvent, and subjected to preparative liquid phase separation and lyophilization to obtain the target product N-(5-chloro-2-(6-(2,6-dichloro-3,5-dimethoxyphenyl)-4,5,6,7-tetrahydro-1H-indazol-3-yl)phenyl)acrylamide (5.8 mg, white solid). Yield: 14%.

Conditions for chiral resolution: Chiral prepHPLC device, chromatographic column: chiralpak-IC, mobile phase: CO2-ETOH (DEA). The one with a short holding time on the machine was named as P1, and the one with a long holding time was named as P2. One of P1 and P2 was the R-isomer, and the other was the S-isomer.

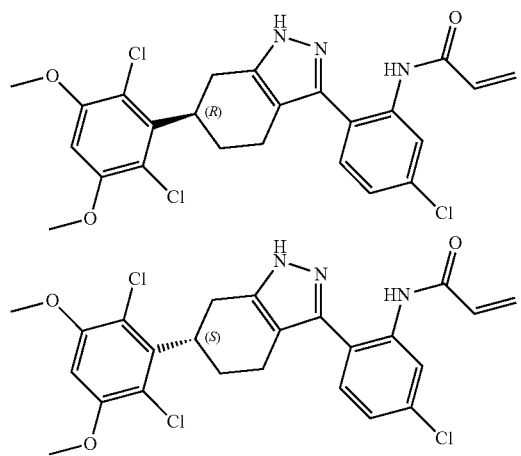

MS m/z (ESI): 507 [M+1]$^+$

P1: $^1$H NMR (400 MHz, DMSO): δ 13.06 (s, 1H), 11.69 (s, 1H), 8.62 (s, 1H), 7.62 (d, J=8.1 Hz, 1H), 7.24 (d, J=5.3 Hz, 1H), 7.23 (s, 1H), 6.90 (s, 1H), 6.34-6.25 (m, 2H), 5.87 (d, J=11.0 Hz, 1H), 4.03 (s, 1H), 3.93 (d, J=3.6 Hz, 6H), 3.49-3.39 (m, 1H), 2.78 (d, J=15.8 Hz, 3H), 2.65 (d, J=12.6 Hz, 1H), 1.85 (d, J=10.8 Hz, 1H).

P2: $^1$H NMR (400 MHz, DMSO): δ 13.07 (s, 1H), 11.69 (s, 1H), 8.62 (s, 1H), 7.62 (d, J=8.4 Hz, 1H), 7.24 (d, J=8.2 Hz, 1H), 6.89 (s, 1H), 6.31 (t, J=5.9 Hz, 2H), 5.88 (s, 1H), 4.07-3.98 (m, 1H), 3.93 (d, J=3.6 Hz, 6H), 3.48-3.39 (m, 1H), 2.78 (d, J=15.4 Hz, 4H), 1.85 (d, J=11.6 Hz, 1H).

Embodiment 291

N-(2-(6-(2,6-dichloro-3,5-dimethoxyphenyl)-4,5,6,7-tetrahydro-1H-indazol-3-yl)-5-fluorophenyl)acrylamide

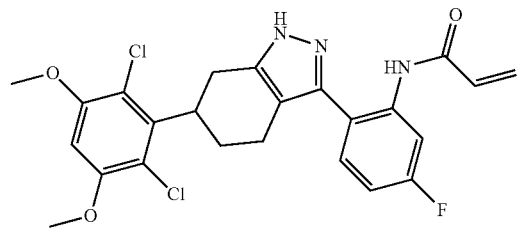

Example 291 was synthesized with reference to the steps in example 289, except that in Step 1, 4-chloro-2-nitrobenzoic acid was replaced with 4-fluoro-2-nitrobenzoic acid. Finally, the target product N-(2-(6-(2,6-dichloro-3,5-dimethoxyphenyl)-4,5,6,7-tetrahydro-1H-indazol-3-yl)-5-fluorophenyl)acrylamide was obtained.

Conditions for chiral resolution: device: Chiral prepHPLC, chromatographic column: chiralpak-AD, mobile phase: HEX-ETOH (DEA). The one with a short holding time on the SFC machine was named as P1, and the one with a long holding time was named as P2. One of P1 and P2 was the R-isomer, and the other was the S-isomer.

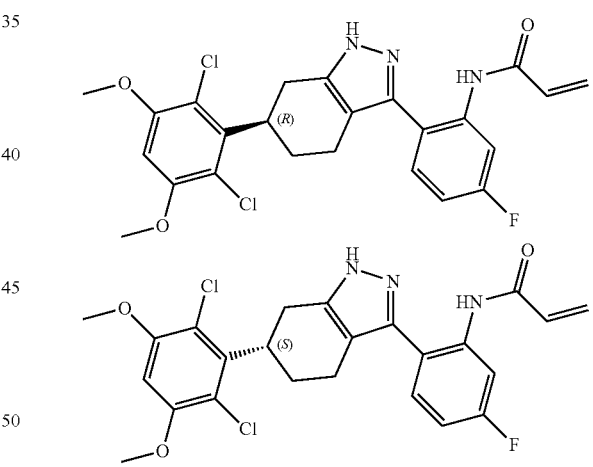

P1: MS m/z (ESI): 489.8[M+1]$^+$
ee: 100%
$^1$H NMR (400 MHz, DMSO): δ 13.01 (s, 1H), 11.74 (s, 1H), 8.39 (d, J=13.0 Hz, 1H), 7.63 (s, 1H), 7.02 (s, 1H), 6.89 (s, 1H), 6.30 (d, J=2.6 Hz, 2H), 5.87 (d, J=7.7 Hz, 1H), 4.02 (s, 1H), 3.93 (d, J=3.6 Hz, 6H), 3.47-3.39 (m, 1H), 2.82-2.61 (m, 4H), 1.83 (s, 1H).

P2: MS m/z (ESI): 489.9 [M+1]$^+$
ee: 100%
$^1$H NMR (400 MHz, MCOD) δ 8.33 (s, 1H), 7.60 (s, 1H), 6.94 (s, 1H), 6.77 (s, 1H), 6.36 (d, J=4.8 Hz, 2H), 5.87-5.78 (m, 1H), 4.16 (s, 1H), 3.93 (d, J=3.7 Hz, 6H), 3.56 (dd, J=15.8, 12.2 Hz, 1H), 2.78 (dd, J=15.9, 5.5 Hz, 4H), 1.88 (s, 1H).

Embodiment 292

N-(2-(6-(2,6-dichloro-3,5-dimethoxyphenyl)-4,5,6,7-tetrahydro-1H-indazol-3-yl)-4-fluorophenyl)acrylamide

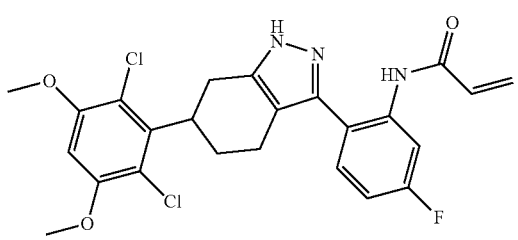

291

Example 292 was synthesized with reference to the operation steps in example 291, except that in Step 1, 4-fluoro-2-nitrobenzoic acid was replaced with 5-fluoro-2-nitrobenzoic acid. Finally, the target product N-(2-(6-(2,6-dichloro-3,5-dimethoxyphenyl)-4,5,6,7-tetrahydro-1H-indazol-3-yl)-4-fluorophenyl)acrylamide 292 was obtained. P1 and P2 were then obtained through chiral column resolution.

Conditions for chiral resolution: device: SFC, chromatographic column: chiralpak-IC, mobile phase: HEX-EtOH (DEA). The one with a short holding time on the SFC machine was named as P1, and the one with a long holding time was named as P2. One of P1 and P2 was the R-isomer, and the other was the S-isomer.

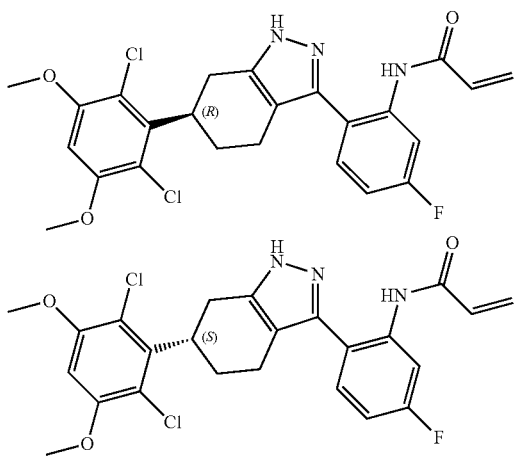

MS m/z (ESI): 490 [M+1]$^+$

P1: $^1$H NMR (400 MHz, MeOD): δ 8.83 (s, 1H), 7.68 (d, J=9.7 Hz, 1H), 7.44 (t, J=7.6 Hz, 1H), 7.14 (s, 1H), 6.75-6.61 (m, 2H), 6.13 (dd, J=7.6, 2.8 Hz, 1H), 4.47 (s, 1H), 4.27 (d, J=3.7 Hz, 6H), 3.95-3.81 (m, 1H), 3.13 (s, 4H), 2.23 (d, J=9.2 Hz, 1H).

P2: $^1$H NMR (400 MHz, MeOD): δ 8.83 (s, 1H), 7.68 (d, J=9.7 Hz, 1H), 7.44 (t, J=7.6 Hz, 1H), 7.14 (s, 1H), 6.75-6.61 (m, 2H), 6.13 (dd, J=7.6, 2.8 Hz, 1H), 4.47 (s, 1H), 4.27 (d, J=3.7 Hz, 6H), 3.95-3.81 (m, 1H), 3.13 (s, 4H), 2.23 (d, J=9.2 Hz, 1H).

Embodiment 293

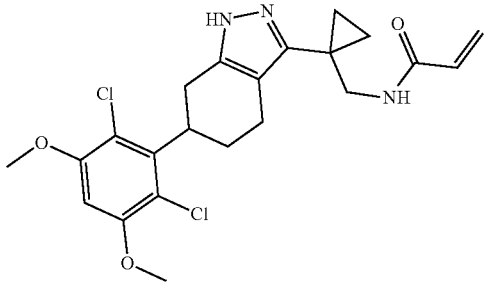

293

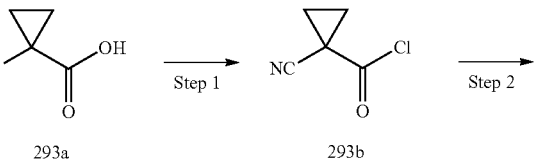

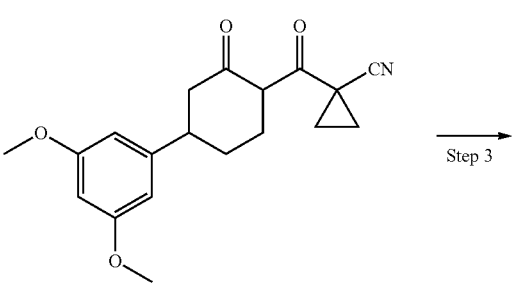

293c

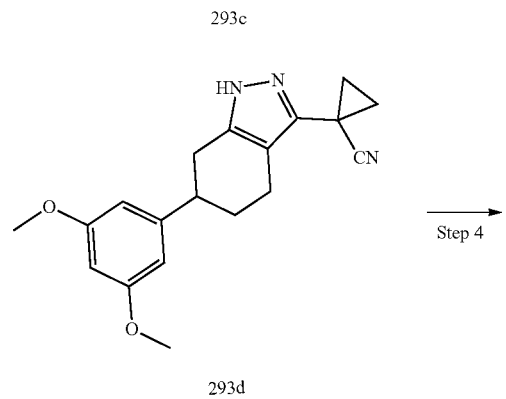

293d

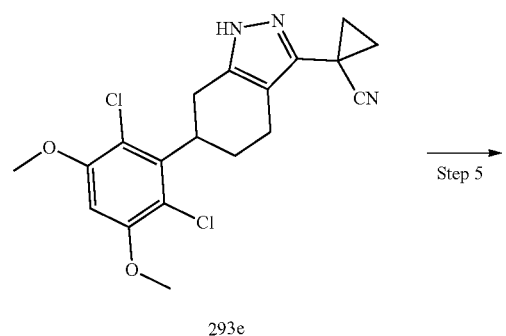

293e

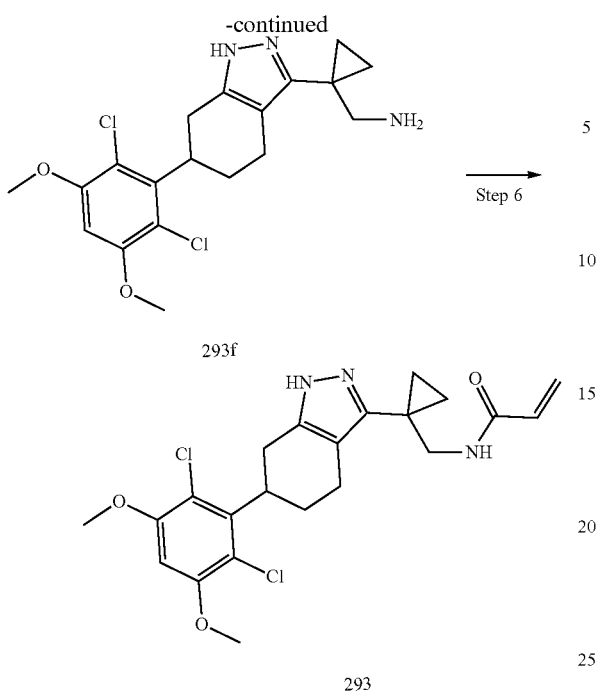

Step 1

1-cyanocyclopropane-1-formyl chloride

The compound 293a (2 g, 18 mmol, 1 eq) was dissolved in thionyl chloride (10 ml) solution. The oil bath was heated to 80° C. The mixture was stirred for 2 h and cooled to room temperature. Aftertreatment: the system was concentrated under reduced pressure to obtain a crude product. 1-cyanocyclopropane-1-formyl chloride 293b (1.9 g, yellow oil). Yield: 83%.

Step 2

1-(4-(3,5-dimethoxyphenyl)-2-carbonylcyclohexane-1-carbonyl)cyclopropane-1-formonitrile The compound 3-(3,5-dimethoxyphenyl)cyclohexan-1-one (3.4 g, 14 mmol, 1 eq) was dissolved in 50 mL of tetrahydrofuran. With the temperature controlled at −78° C., lithium diisopropylamide (8.4 ml, 16.8 mmol, 1.2 eq) was added therein. After the dropwise addition, the mixture was warmed up to −40° C. and reacted for 1 h, and then 1-cyanocyclopropane-1-formyl chloride 293b (1.8 g, 14 mmol, 1 eq) was added into the system at −40° C. The system was raised to room temperature and reacted for 3 h. Aftertreatment: a saturated ammonium chloride aqueous solution (30 ml) was added therein, the mixture was extracted 3 times with ethyl acetate (100 ml), and the organic phase was desolventized under reduced pressure to obtain the target crude product 1-(4-(3,5-dimethoxyphenyl)-2-carbonylcyclohexane-1-carbonyl)cyclopropane-1-formonitrile 293c (2.6 g, yellow oil). Yield: 55%.

Step 3

1-(6-(3,5-dimethoxyphenyl)-4,5,6,7-tetrahydro-1H-indazol-3-yl)cyclopropane-1-formonitrile The compound 1-(4-(3,5-dimethoxyphenyl)-2-carbonylcyclohexane-1-carbonyl)cyclopropane-1-formonitrile 293c (2.6 g, 8 mmol, 1 eq), and hydrazine hydrate (1 g, 20 mmol, 2.5 eq) were dissolved into ethanol/acetic acid 10:1 (20 mL), and reacted for 3 h at 65° C. Aftertreatment: desolvation was performed under reduced pressure, and the residual was purified through silica gel column chromatography (petroleum ether:ethyl acetate=2:1) to obtain the target product 1-(6-(3,5-dimethoxyphenyl)-4,5,6,7-tetrahydro-1H-indazol-3-yl)cyclopropane-1-formonitrile 293d (1.1 g, yellow solid). Yield: 43%.

MS m/z (ESI): 324.2 [M+1]$^+$

Step 4

1-(6-(2,6-dichloro-3,5-dimethoxyphenyl)-4,5,6,7-tetrahydro-1H-indazol-3-yl)cyclopropane-1-formonitrile The compound 1-(6-(3,5-dimethoxyphenyl)-4,5,6,7-tetrahydro-1H-indazol-3-yl)cyclopropane-1-formonitrile 293d (1.0 g, 3 mmol, 1 eq) was dissolved in ACN and stirred at −40° C., and sulfuric oxychloride was added dropwise. The mixture was further stirred for 3 h at −40° C. After the mixture was finished, it was raised to room temperature. Aftertreatment: desolvation was performed under reduced pressure, and the residual was purified through silica gel column chromatography (petroleum ether:ethyl acetate=2:1) to obtain the target product 1-(6-(2,6-dichloro-3,5-dimethoxyphenyl)-4,5,6,7-tetrahydro-1H-indazol-3-yl)cyclopropane-1-formonitrile 293e (0.4 g, yellow solid). Yield: 33%.

MS m/z (ESI): 392.2 [M+1]$^+$

Step 5

(1-(6-(2,6-dichloro-3,5-dimethoxyphenyl)-4,5,6,7-tetrahydro-1H-indazol-3-yl)cyclopropyl)methylamine The compound 1-(6-(2,6-dichloro-3,5-dimethoxyphenyl)-4,5,6,7-tetrahydro-1H-indazol-3-yl)cyclopropane-1-formonitrile 293e (0.4 g, 1 mmol, 1 eq) and BH3 (2 ml, 2 mmol, 2 eq) were dissolved in THF, and the mixture was stirred for 3 h at 60° C. after the tube was sealed. Then methanol was added therein. The mixture was further stirred for 3 h at 60° C. and the reaction was finished. Aftertreatment: desolvation was performed under reduced pressure, and the residual was purified through silica gel column chromatography (petroleum ether:ethyl acetate=2:1) to obtain the target product (1-(6-(2,6-dichloro-3,5-dimethoxyphenyl)-4,5,6,7-tetrahydro-1H-indazol-3-yl)cyclopropyl) methylamine 293f (120 mg, yellow solid). Yield: 30%.

MS m/z (ESI): 396.1 [M+1]$^+$

Step 6

N-((1-(6-(2,6-dichloro-3,5-dimethoxyphenyl)-4,5,6,7-tetrahydro-1H-indazol-3-yl)cyclopropyl)methyl)acrylamide The compound (1-(6-(2,6-dichloro-3,5-dimethoxyphenyl)-4,5,6,7-tetrahydro-1H-indazol-3-yl)cyclopropyl)methylamine 293f (120 mg, 0.3 mmol, 1 eq) and DIEA (116 mg, 0.9 mmol, 3 eq) were dissolved in DCM, and stirred at −40° C. Then acryloyl chloride (28 mg, 0.3 mmol, 1 eq) was added dropwise, and the mixture was stirred for 0.5 h at −40° C. and the reaction was finished. Aftertreatment: sending for preparation. Target product: N-((1-(6-(2,6-dichloro-3,5-dimethoxyphenyl)-4,5,6,7-tetrahydro-1H-indazol-3-yl)cyclopropyl)methyl)acrylamide. Separation conditions for the final product (racemate): device: mass spectrogram guided prep-HPLC; chromatographic column: -Gemini-C18 150× 21.2 mm, 5 μm, mobile phase: ACN-H20 (0.05% NH3), gradient: 60-80.

Conditions for chiral resolution: device: SFC, chromatographic column: chiralpak-AS, mobile phase: CO2-ETOH (DEA). The one with a short holding time on the SFC machine was named as P1, and the one with a long holding time was named as P2. One of P1 and P2 was the R-isomer, and the other was the S-isomer.

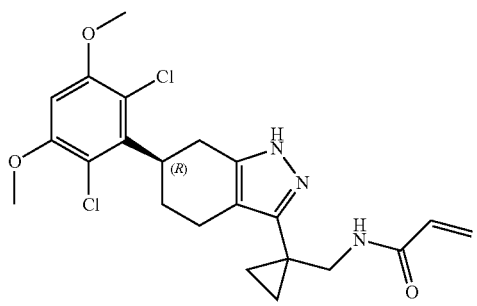

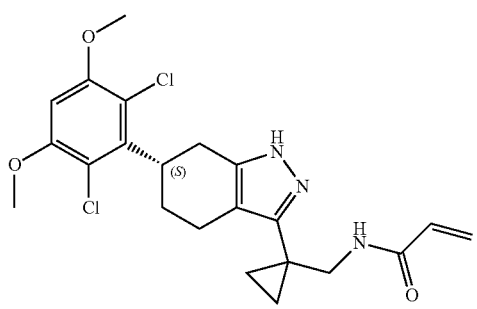

P1: ¹H NMR (400 MHz, DMSO): δ 12.23-12.18 (m, 1H), 8.12-8.02 (m, 2H), 6.86 (s, 1H), 6.30-6.23 (m, 1H), 6.06 (dd, J=17.0, 2.1 Hz, 1H), 5.56 (d, J=11.9 Hz, 1H), 3.92 (d, J=2.2 Hz, 7H), 3.31 (s, 2H), 2.68 (s, 1H), 2.58 (s, 1H), 1.75-1.70 (m, 1H), 1.24 (s, 1H), 0.91-0.65 (m, 6H).

P2: ¹H NMR (400 MHz, DMSO): δ 12.23-12.18 (m, 1H), 8.12-8.02 (m, 2H), 6.86 (s, 1H), 6.30-6.23 (m, 1H), 6.06 (dd, J=17.0, 2.1 Hz, 1H), 5.56 (d, J=11.9 Hz, 1H), 3.92 (d, J=2.2 Hz, 7H), 3.31 (s, 2H), 2.68 (s, 1H), 2.58 (s, 1H), 1.75-1.70 (m, 1H), 1.24 (s, 1H), 0.91-0.65 (m, 6H).

MS m/z (ESI): 450.1 [M+1]⁺

Embodiment 295

N-(2-(6-(2,6-dichloro-3,5-dimethoxyphenyl)-4,5,6,7-tetrahydro-1H-indazol-3-yl)-4-morpholinophenyl) acrylamide

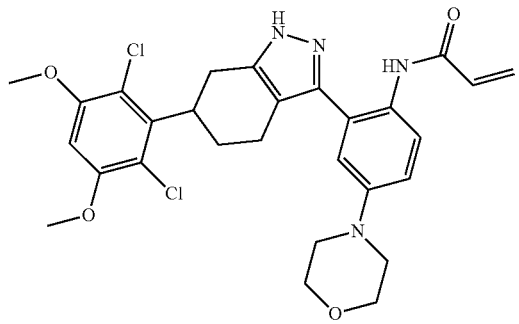

Example 295 was synthesized with reference to the steps in example 137, except that in Step 5, N1,N1,N2-trimethylethane-1,2-diamine was replaced with morpholine. Finally, the target product N-(2-(6-(2,6-dichloro-3,5-dimethoxyphenyl)-4,5,6,7-tetrahydro-1H-indazol-3-yl)-4-morpholinophenyl)acrylamide was obtained.

Conditions for chiral resolution: device: Chiral prep-HPLC, chromatographic column: chiralpak-AD, mobile phase: HEX-ETOH (DEA). The one with a short holding time on the SFC machine was named as P1, and the one with a long holding time was named as P2. One of P1 and P2 was the R-isomer, and the other was the S-isomer.

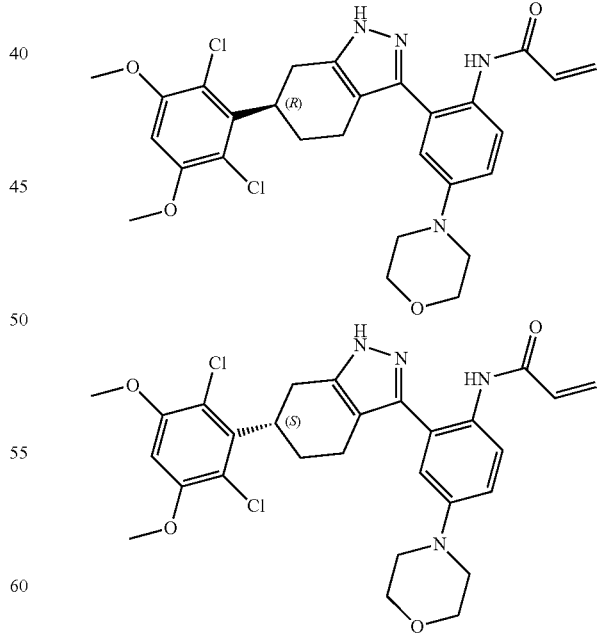

P1: MS m/z (ESI): 557.0[M+1]⁺
ee: 100% (214 nm); 100% (254 nm)
¹H NMR (400 MHz, DMSO): δ 12.93 (s, 1H), 11.08 (s, 1H), 8.30 (s, 1H), 7.04 (s, 1H), 6.95 (d, J=8.3 Hz, 1H), 6.89

(s, 1H), 6.30 (s, 1H), 6.22 (s, 1H), 5.76 (s, 1H), 4.03 (s, 1H), 3.93 (d, J=3.7 Hz, 6H), 3.76 (t, J=4.4 Hz, 4H), 3.12 (d, J=3.5 Hz, 4H), 2.94-2.53 (m, 5H), 1.80 (s, 1H).

P2: MS m/z (ESI): 557.0[M+1]

ee: 98.128% (214 nm); 98.596% (254 nm)

$^1$H NMR (400 MHz, DMSO): δ 12.93 (s, 1H), 11.09 (s, 1H), 8.33 (s, 1H), 7.01 (d, J=41.8 Hz, 2H), 6.89 (s, 1H), 6.28 (s, 1H), 6.22 (s, 1H), 5.75 (d, J=9.5 Hz, 1H), 4.04 (s, 1H), 3.93 (d, J=3.2 Hz, 6H), 3.75 (s, 4H), 3.12 (s, 4H), 2.76 (d, J=20.8 Hz, 5H), 1.82 (s, 1H).

Embodiment 296

N-(2-(6-(2,6-dichloro-3,5-dimethoxyphenyl)-4,5-dihydro-1H-indazol-3-yl)-5-fluorophenyl)acrylamide

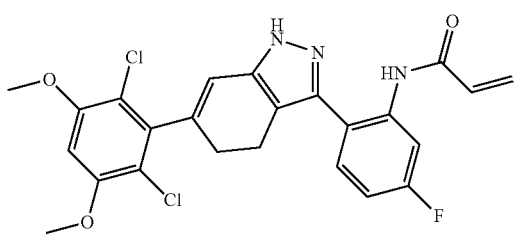

296

In the process of synthesis of 291, a by-product N-(2-(6-(2,6-dichloro-3,5-dimethoxyphenyl)-4,5-dihydro-1H-indazol-3-yl)-5-fluorophenyl)acrylamide was obtained by separation.

MS m/z (ESI): 487.8 [M+1]$^+$

HPLC: 91.273% (214 nm); 94.245% (254 nm)

$^1$H NMR (400 MHz, DMSO): δ 13.26 (s, 1H), 12.80 (s, 1H), 11.44 (s, 1H), 9.71 (s, 1H), 8.33 (s, 1H), 7.55 (s, 2H), 7.07 (s, 1H), 6.92 (s, 1H), 6.40 (s, 2H), 6.28 (d, J=16.9 Hz, 1H), 5.84 (s, 1H), 3.94 (s, 6H), 2.95 (s, 1H), 2.44-2.27 (m, 1H).

Embodiment 297

N-(2-(6-(2,6-dichloro-3,5-dimethoxyphenyl)-4,5-dihydro-1H-indazol-3-yl)-4-fluorophenyl)acrylamide

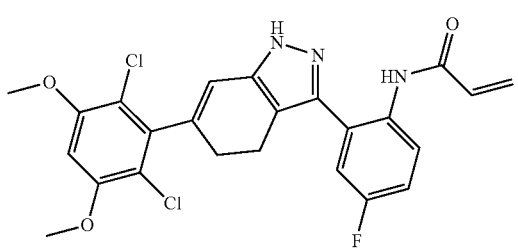

297

In the process of synthesis of 292, a by-product N-(2-(6-(2,6-dichloro-3,5-dimethoxyphenyl)-4,5-dihydro-1H-indazol-3-yl)-4-fluorophenyl)acrylamide was obtained by separation.

MS m/z (ESI): 488.0 [M+1]+

$^1$H NMR (400 MHz, MeOD): δ 8.36 (s, 1H), 7.76 (s, 1H), 7.28 (s, 1H), 7.13 (s, 1H), 6.81 (s, 1H), 6.38 (s, 3H), 5.80 (d, J=8.4 Hz, 1H), 3.96 (s, 6H), 3.00 (d, J=9.7 Hz, 1H), 2.62 (s, 1H).

Embodiment 298

N-(2-(6-(2,6-dichloro-3,5-dimethoxyphenyl)-4,5-dihydro-1H-indazol-3-yl)-5-methylphenyl)acrylamide

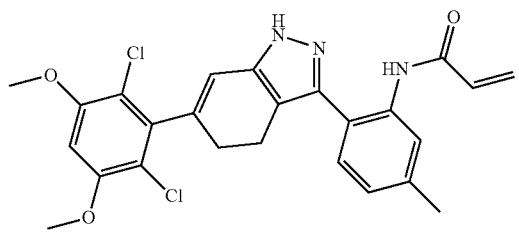

298

In the process of synthesis of 288, a by-product N-(2-(6-(2,6-dichloro-3,5-dimethoxyphenyl)-4,5-dihydro-1H-indazol-3-yl)-5-methylphenyl)acrylamide was obtained by separation.

MS m/z (ESI): 485.4 [M+1]$^+$ $^1$H NMR (300 MHz, DMSO) δ 12.83 (s, 2H), 11.08 (s, 1H), 8.28 (s, 1H), 7.42 (d, J=35.7 Hz, 2H), 7.18-6.81 (m, 4H), 6.34 (s, 4H), 6.18 (d, J=16.7 Hz, 2H), 5.70 (d, J=8.6 Hz, 2H), 3.92 (s, 12H), 2.47 (s, 8H), 2.34 (s, 6H).

Embodiment 299

N-(2-(6-(2,6-dichloro-3,5-dimethoxyphenyl)-4,5-dihydro-1H-indazol-3-yl)-4-(dimethylamino)phenyl)acrylamide

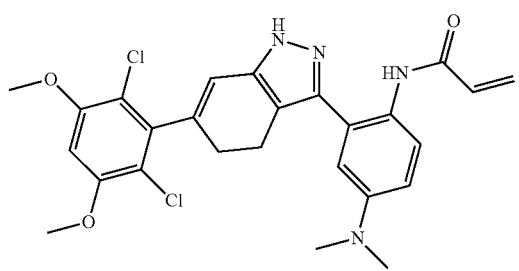

299

In the process of synthesis of 285, a by-product N-(2-(6-(2,6-dichloro-3,5-dimethoxyphenyl)-4,5-dihydro-1H-indazol-3-yl)-4-(dimethylamino)phenyl)acrylamide was obtained by separation.

MS m/z (ESI): 512.7 [M+1]+

$^1$H NMR (400 MHz, DMSO): δ 12.90 (s, 1H), 10.96 (s, 1H), 8.22 (s, 1H), 6.88 (s, 1H), 6.83 (s, 1H), 6.74 (dd, J=9.1, 2.8 Hz, 1H), 6.41-6.25 (m, 1H), 6.18 (dd, J=17.0, 1.7 Hz,

1H), 5.75-5.69 (m, 1H), 3.93 (d, J=3.8 Hz, 6H), 2.91 (s, 6H), 2.84-2.58 (m, 5H), 2.51 (dt, J=3.5, 1.7 Hz, 2H).

Embodiment 300

N-(2-(6-(2,6-dichloro-3,5-di methoxyphenyl)-4,5-dihydro-1H-indazol-3-yl)-4-morpholinophenyl)acrylamide

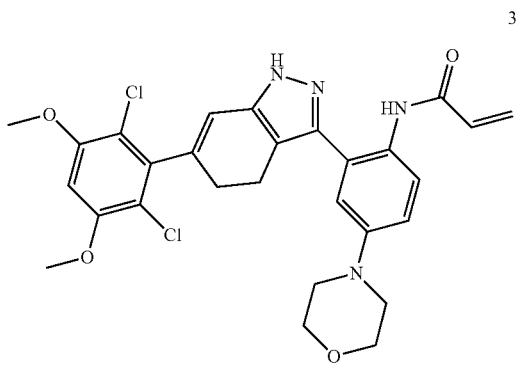

In the process of synthesis of 295, a by-product N-(2-(6-(2,6-dichloro-3,5-dimethoxyphenyl)-4,5-dihydro-1H-indazol-3-yl)-4-morpholinophenyl)acrylamide was obtained by separation.

MS m/z (ESI): 555.0 [M+1]$^+$

HPLC: 82.029% (214 nm); 82.027% (254 nm)

$^1$H NMR (400 MHz, DMSO): δ 12.95 (s, 1H), 7.95-7.68 (m, 1H), 7.00 (d, J=8.5 Hz, 2H), 6.91 (t, J=12.6 Hz, 2H), 6.40 (d, J=24.2 Hz, 2H), 6.19 (d, J=17.0 Hz, 1H), 5.70 (d, J=9.8 Hz, 1H), 3.94 (s, 6H), 3.75 (s, 4H), 3.14 (s, 4H), 2.71 (d, J=24.4 Hz, 2H), 2.41 (s, 2H).

Embodiment 301

N-(2-(6-(2,6-difluoro-3,5-dimethoxyphenyl)-4,5,6,7-tetrahydro-1H-indazol-3-yl)-4-(4-methylpiperazin-1-yl)phenyl)acrylamide

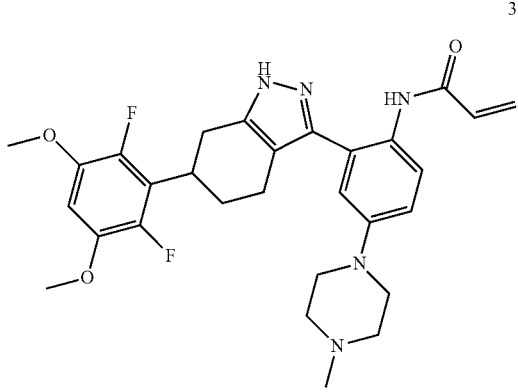

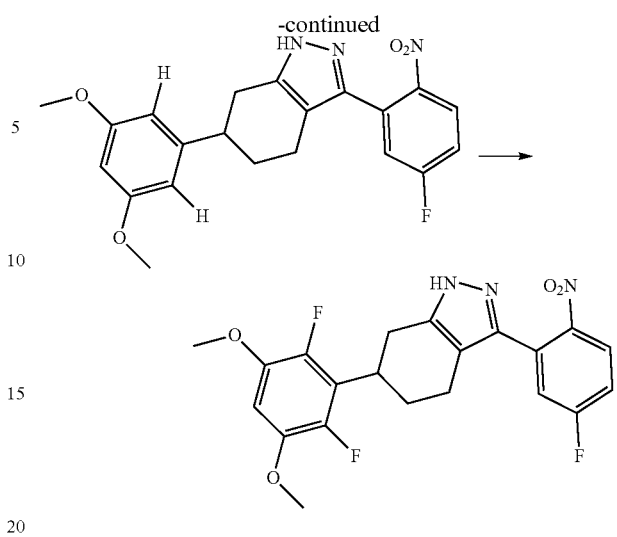

6-(2,6 difluoro-3,5-dimethoxyphenyl)-3-(5-fluoro-2-nitrophenyl)-4,5,6,7-tetrahydro-1H-indazole 6-(3,5-dimethoxyphenyl)-3-(5-fluoro-2-nitrophenyl)-4,5,6,7-tetrahydro-1H-indazole (3.33 g, 8.13 mmol) and acetonitrile (100 ml) were mixed, select F (5.93 g, 16.26 mmol) was added therein at 0° C., and the mixture was slowly warmed up to room temperature and stirred for 2 h. Aftertreatment: desolvation was performed under reduced pressure, and the residual was extracted with dichloromethane (100 mL) and water (100 mL) added, the organic phase was desolventized under reduced pressure, and the residual was purified through silica gel column chromatography (petroleum ether: ethyl acetate=5:1) to obtain 6-(2,6-difluoro-3,5-dimethoxyphenyl)-3-(5-fluoro-2-nitrophenyl)-4,5,6,7-tetrahydro-1H-indazole (700 mg, 1.61 mmol, yellow solid). Yield: 19%.

Example 301 was synthesized with reference to the operation steps of example 283, except that in Step 4, 6-(2,6-dichloro-3,5-dimethoxyphenyl)-3-(5-fluoro-2-nitrophenyl)-4,5,6,7-tetrahydro-1H-indazole was replaced with 6-(2,6-difluoro-3,5-dimethoxyphenyl)-3-(5-fluoro-2-nitrophenyl)-4,5,6,7-tetrahydro-1H-indazole. Finally, the target product N-(2-(6-(2,6-difluoro-3,5-dimethoxyphenyl)-4,5,6,7-tetrahydro-1H-indazol-3-yl)-4-(4-piperazin-1-yl)phenyl)acrylamide 301 was obtained. P1 and P2 were then obtained through chiral column resolution. Conditions for chiral resolution: SFC device, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

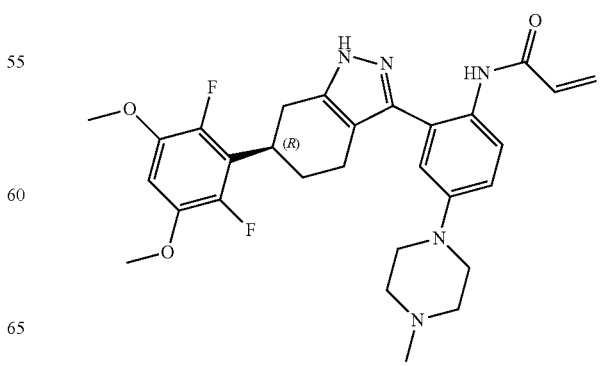

159

-continued

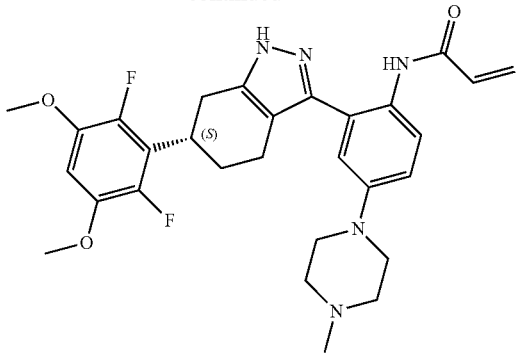

P1: MS m/z (ESI): 538.1 [M+1]+
ee: 100%
$^1$HNMR (400 MHz, DMSO): δ 12.91 (s, 1H), 11.08 (s, 1H), 8.29 (s, 1H), 7.02 (s, 1H), 6.94 (d, J=8.3 Hz, 2H), 6.30 (s, 1H), 6.19 (d, J=17.0 Hz, 1H), 5.73 (d, J=10.1 Hz, 1H), 3.86 (s, 6H), 3.37 (s, 2H), 3.14 (s, 4H), 2.92 (s, 2H), 2.67 (s, 1H), 2.46 (s, 4H), 2.22 (s, 3H), 1.99 (s, 2H).

P2: MS m/z (ESI): 538.2[M+1]+
ee: 97.8%
$^1$H NMR (400 MHz, DMSO): δ 12.90 (s, 1H), 11.08 (s, 1H), 8.29 (s, 1H), 7.02 (s, 1H), 6.93 (t, J=8.0 Hz, 2H), 6.30 (s, 1H), 6.19 (d, J=16.9 Hz, 1H), 5.73 (d, J=10.1 Hz, 1H), 3.86 (s, 6H), 3.37 (s, 2H), 3.14 (s, 4H), 2.94 (d, J=9.5 Hz, 2H), 2.68 (s, 1H), 2.46 (s, 4H), 2.22 (s, 3H), 2.08 (s, 1H), 1.99 (s, 1H).

Embodiment 302

N-(5-(6-(2-fluoro-3,5-dimethoxyphenyl)-4,5,6,7-tetrahydro-1H-indazol-3-yl)-1-methyl-1H-pyrazol-4-yl)acrylamide

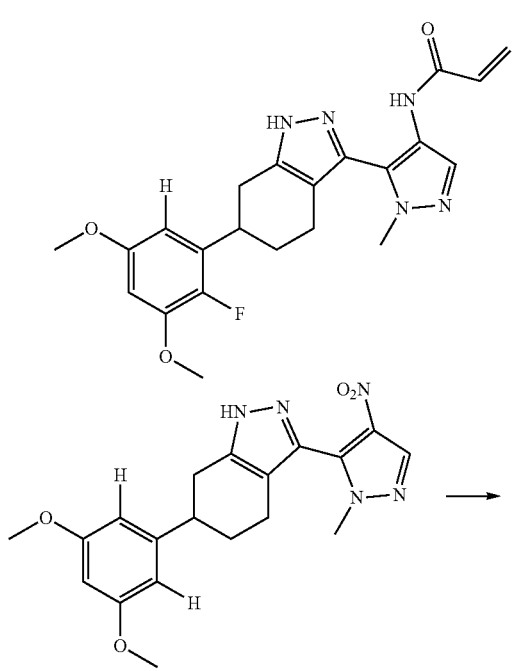

160

-continued

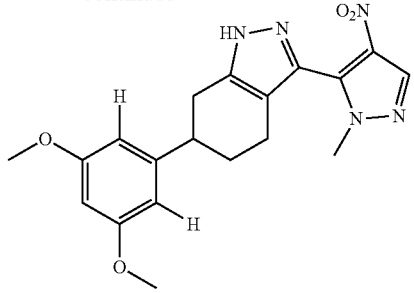

6-(2-fluoro-3,5-dimethoxyphenyl)-3-(1-methyl-4-nitro-1H-pyrazol-5-yl)-4,5,6,7-tetrahydro-1H-indazole 6-(3,5-dimethoxyphenyl)-3-(1-methyl-4-nitro-1H-pyrazol-5-yl)-4,5,6,7-tetrahydro-1H-indazole (1.7 g, 4.4 mmol) and acetonitrile (50 ml) were mixed, select F (1.7 g, 4.4 mmol) was added therein at 0° C., and the mixture was slowly warmed up to room temperature and stirred for 2 h. Aftertreatment: desolvation was performed under reduced pressure, and the residual was extracted with dichloromethane (50 mL) and water (50 mL) added, the organic phase was desolventized under reduced pressure, and the residual was purified through silica gel column chromatography (petroleum ether:ethyl acetate=5:4) to obtain 6-(2-fluoro-3,5-dimethoxyphenyl)-3-(1-methyl-4-nitro-1H-pyrazol-5-yl)-4,5,6,7-tetrahydro-1H-indazole (800 mg, 1.9 mmol, yellow solid). Yield: 47%.

Example 302 was synthesized with reference to the operation steps of example 140, except that in Step 4, 6-(2,6-dichloro-3,5-dimethoxyphenyl)-3-(1-methyl-4-nitro-1H-pyrazol-5-yl)-4,5,6,7-tetrahydro-1H-indazole was replaced with 6-(2-fluoro-3,5-dimethoxyphenyl)-3-(1-methyl-4-nitro-1H-pyrazol-5-yl)-4,5,6,7-tetrahydro-1H-indazole.

Finally, the target product N-(5-(6-(2-fluoro-3,5-dimethoxyphenyl)-4,5,6,7-tetrahydro-1H-indazol-3-yl)-1-methyl-1H-pyrazol-4-yl)acrylamide 302 was obtained. P1 and P2 were then obtained through chiral column resolution. Conditions for chiral resolution: SFC device, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

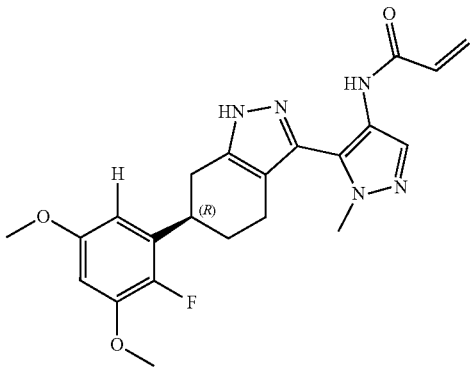

-continued

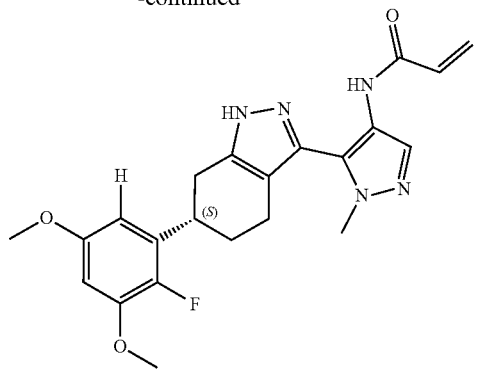

MS m/z (ESI): 426.0[M+1]⁺

P1: ¹H NMR (400 MHz, DMSO) δ 12.91 (s, 1H), 9.41 (s, 1H), 7.81 (s, 1H), 6.61 (dd, J=7.0, 2.8 Hz, 1H), 6.56-6.46 (m, 1H), 6.18 (dd, J=17.0, 2.0 Hz, 1H), 5.70-5.62 (m, 1H), 3.83 (s, 3H), 3.77 (s, 3H), 3.75 (s, 3H), 3.32-3.20 (m, 1H), 2.96-2.72 (m, 1H), 2.48-2.30 (m, 1H), 1.89 (s, 1H).

P2: ¹H NMR (400 MHz, DMSO) δ 12.91 (s, 1H), 9.41 (s, 1H), 7.81 (s, 1H), 6.61 (dd, J=7.0, 2.8 Hz, 1H), 6.56-6.46 (m, 1H), 6.19 (dd, J=17.0, 2.0 Hz, 1H), 5.66 (dd, J=10.2, 1.8 Hz, 1H), 3.83 (s, 3H), 3.77 (s, 3H), 3.75 (s, 3H), 3.25 (d, J=9.5 Hz, 1H), 2.90 (dd, J=15.7, 5.2 Hz, 1H), 2.85-2.70 (m, 1H), 2.49-2.30 (m, 1H), 1.89 (s, 1H).

e.e. 99.6%

Embodiment 303

N-(5-(6-(2-chloro-6-fluoro-3,5-dimethoxyphenyl)-4,5,6,7-tetrahydro-1H-indazol-3-yl)-1-methyl-1H-pyrazol-4-yl)acrylamide

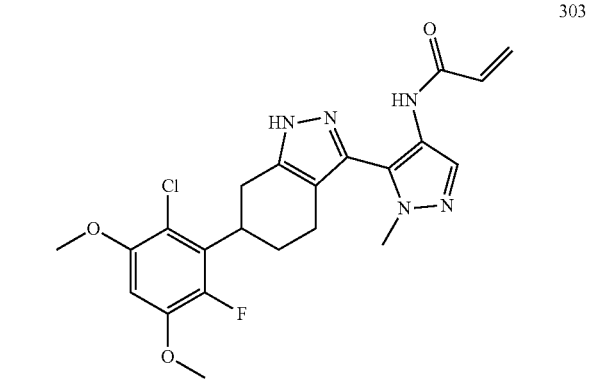

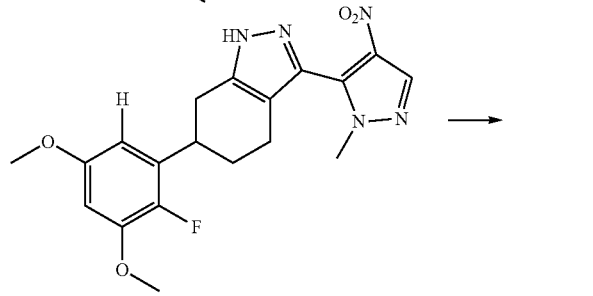

-continued

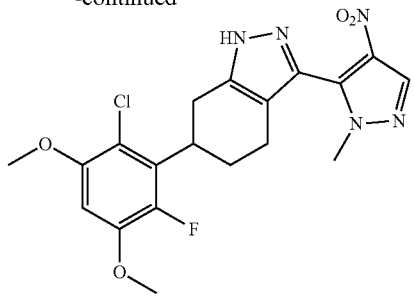

6-(2-chloro-6-fluoro-3,5-dimethoxyphenyl)-3-(1-methyl-4-nitro-1H-pyrazol-5-yl)-4,5,6,7-tetrahydro-1H-indazole 6-(2-fluoro-3,5-dimethoxyphenyl)-3-(1-methyl-4-nitro-1H-pyrazol-5-yl)-4,5,6,6,7-tetrahydro-1H-indazole (556 mg, 1.38 mmol), N-chlorosuccinimide (184 mg, 1.38 mmol) and acetic acid (20 mL) were mixed, warmed up 80° C. and reacted for 3 h. Aftertreatment: dichloromethane and water were added and layered, the organic phase was desolventized under reduced pressure and passed through a silica gel chromatographic column with a petroleum ether/ethyl acetate (1:1) system to obtain a yellow solid product 6-(2-chloro-6-fluoro-3,5-dimethoxyphenyl)-3-(1-methyl-4-nitro-1H-pyrazol-5-yl)-4,5,6,7-tetrahydro-1H-indazole (230 mg, 38%).

Example 303 was synthesized with reference to the operation steps of example 302, except that in Step 5, 6-(2-fluoro-3,5-dimethoxyphenyl)-3-(1-methyl-4-nitro-1H-pyrazol-5-yl)-4,5,6,7-tetrahydro-1H-indazole was replaced with 6-(2-chloro-6-fluoro-3,5-dimethoxyphenyl)-3-(1-methyl-4-nitro-1H-pyrazol-5-yl)-4,5,6,7-tetrahydro-1H-indazole. Finally, the target product N-(5-(6-(2-chloro-6-fluoro-3,5-dimethoxyphenyl)-4,5,6,7-tetrahydro-1H-indazole-3-yl)-1-methyl-1H-pyrazol-4-yl)acrylamide 303 was obtained. P1 and P2 were then obtained through chiral column resolution. Conditions for chiral resolution: device: SFC, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

MS m/z (ESI): 460.0 [M+1]⁺

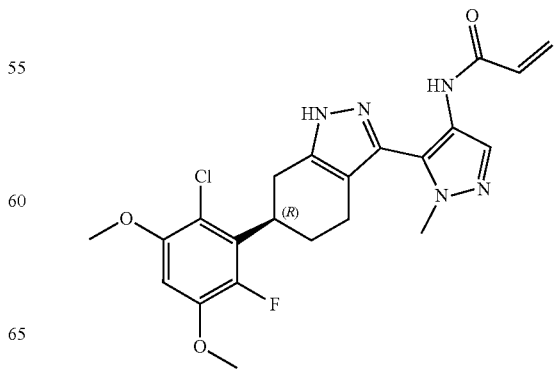

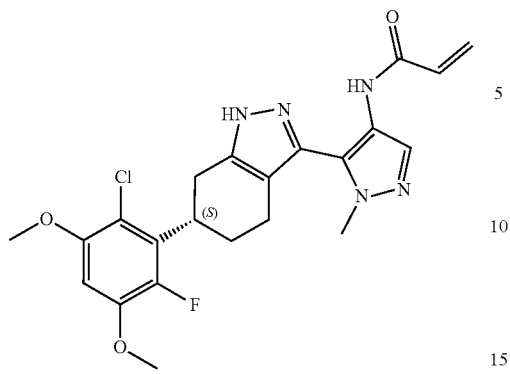

P1: NMR (400 MHz, DMSO): δ 12.95 (s, 1H), 9.48 (s, 1H), 7.85 (s, 1H), 6.91 (d, J=7.8 Hz, 2H), 6.53 (dd, J=17.0, 10.2 Hz, 1H), 6.19 (dd, J=17.0, 2.1 Hz, 1H), 5.66 (dd, J=10.2, 2.1 Hz, 1H), 3.90 (s, 3H), 3.89 (s, 3H), 3.76 (s, 3H), 3.65 (dd, J=16.9, 11.1 Hz, 2H), 2.86 (dd, J=15.6, 5.2 Hz, 1H), 2.58 (dq, J=7.8, 5.5 Hz, 1H), 2.49-2.35 (m, 2H), 2.21 (s, 1H).

P2: $^1$H NMR (400 MHz, DMSO): δ 12.94 (s, 1H), 9.47 (s, 1H), 7.85 (s, 1H), 6.91 (d, J=7.8 Hz, 2H), 6.52 (dd, J=17.0, 10.2 Hz, 1H), 6.19 (dd, J=17.0, 2.1 Hz, 1H), 5.66 (dd, J=10.2, 2.1 Hz, 1H), 3.90 (s, 3H), 3.89 (s, 3H), 3.76 (s, 3H), 3.71-3.58 (m, 2H), 2.86 (dd, J=15.7, 5.3 Hz, 1H), 2.38-2.46 (m, 2H), 2.21 (s, 1H), 1.87 (d, J=11.9 Hz, 1H).

Embodiment 304

N-(2-(6-(2,6-dichloro-3,5-dimethoxyphenyl)-4,5-dihydro-1H-indazol-3-yl)-5-(dimethylamino)phenyl)acrylamide

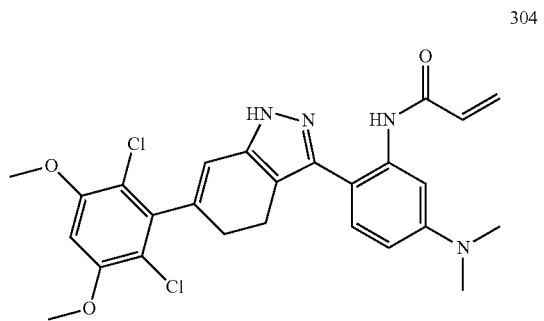 [SMILES: C=CC(=O)Nc1cc(N(C)C)ccc1-c1n[nH]c2c1CCC(c1c(Cl)c(OC)cc(OC)c1Cl)=C2]

In the process of synthesis of 284, a by-product N-(2-(6-(2,6-dichloro-3,5-dimethoxyphenyl)-4,5-dihydro-1H-indazol-3-yl)-5-(dimethylamino)phenyl)acrylamide was obtained by separation.

MS m/z (ESI): 514.4 [M+1]$^+$ $^1$H NMR (400 MHz, DMSO): δ 12.75 (d, J=187.3 Hz, 1H), 11.36 (s, 1H), 9.41 (s, 1H), 8.07 (s, 1H), 7.27 (s, 3H), 6.91 (s, 2H), 6.60 (s, 3H), 6.39-6.03 (m, 6H), 5.75 (s, 2H), 3.94 (s, 12H), 2.95 (s, 12H), 2.52 (s, 4H), 2.34 (s, 4H).

Embodiment 310

N-(5-(6-(3,5-dimethoxyphenyl)-4,5,6,7-tetrahydro-1H-indazol-3-yl)-1-methyl-1H-pyrazol-4-yl)acrylamide

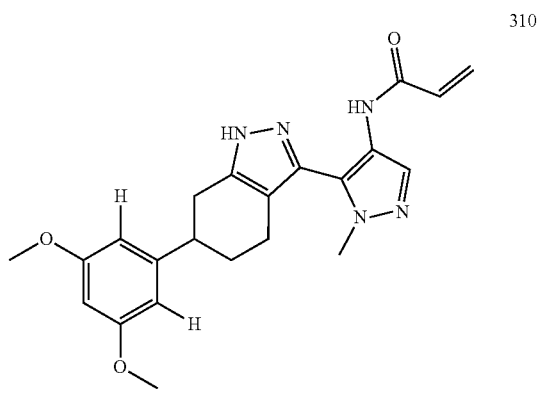 [SMILES: C=CC(=O)Nc1cnn(C)c1-c1n[nH]c2c1CCC(c1cc(OC)cc(OC)c1)C2]

Example 310 was synthesized with reference to the operation steps of example 140, except that in Step 4, 6-(2,6-dichloro-3,5-dimethoxyphenyl)-3-(1-methyl-4-nitro-1H-pyrazol-5-yl)-4,5,6,7-tetrahydro-1H-indazole was replaced with 6-(3,5-dimethoxyphenyl)-3-(1-methyl-4-nitro-1H-pyrazol-5-yl)-4,5,6,7-tetrahydro-1H-indazole. Finally, the target product N-(5-(6-(3,5-dimethoxyphenyl)-4,5,6,7-tetrahydro-1H-indazol-3-yl)-1-methyl-1H-pyrazol-4-yl)acrylamide 310 was obtained.

Conditions for chiral resolution: SFC device, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

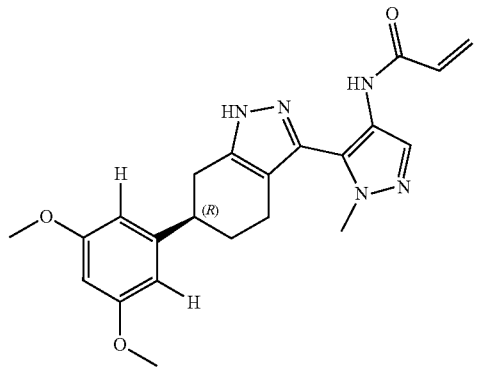

-continued

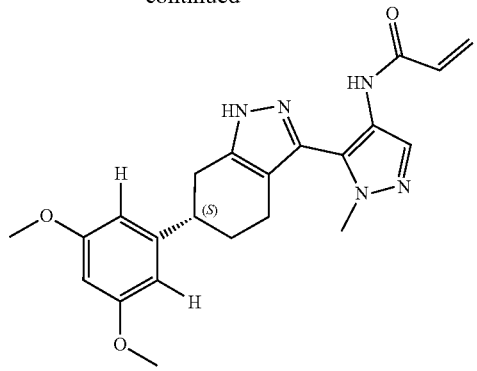

MS m/z (ESI): 407.8 [M+1]+

P1: ¹H NMR (400 MHz, DMSO): δ 12.89 (s, 1H), 9.43 (s, 1H), 7.80 (s, 1H), 6.57-6.46 (m, 3H), 6.37 (t, J=2.2 Hz, 1H), 6.19 (dd, J=17.0, 2.1 Hz, 1H), 5.66 (dd, J=10.2, 2.0 Hz, 1H), 3.77 (s, 3H), 3.74 (s, 6H), 3.00-2.86 (m, 2H), 2.75 (t, J=14.3 Hz, 1H), 2.49-2.41 (m, 1H), 2.36 (d, J=16.9 Hz, 1H), 1.97-1.75 (m, 2H).

P2: ¹H NMR (400 MHz, DMSO): δ 12.89 (s, 1H), 9.43 (s, 1H), 7.80 (s, 1H), 6.57-6.45 (m, 3H), 6.37 (t, J=2.2 Hz, 1H), 6.18 (dd, J=17.0, 2.0 Hz, 1H), 5.66 (dd, J=10.2, 1.9 Hz, 1H), 3.77 (s, 3H), 3.74 (s, 6H), 2.92 (d, J=11.9 Hz, 2H), 2.75 (t, J=14.1 Hz, 1H), 2.49-2.41 (m, 1H), 2.36 (d, J=14.9 Hz, 1H), 2.01-1.77 (m, 2H).

ee: 100%

Embodiment 311

N-(5-(6-(2-chloro-3,5-dimethoxyphenyl)-4,5,6,7-tetrahydro-1H-indazol-3-yl)-1-methyl-1H-pyrazol-4-yl)acrylamide

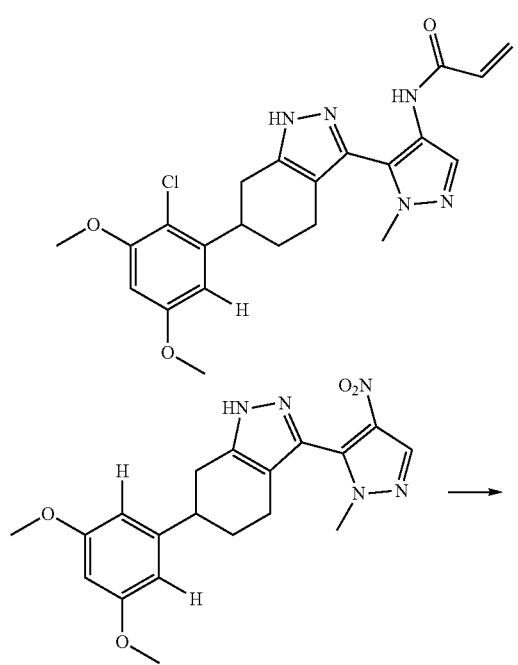

-continued

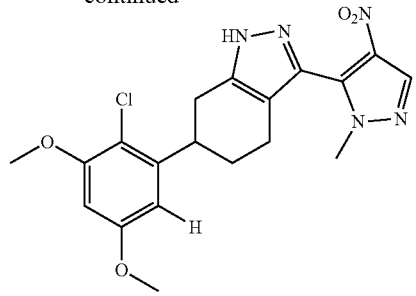

6-(3,5-dimethoxyphenyl)-3-(1-methyl-4-nitro-1H-pyrazol-5-yl)-4,5,6,7-tetrahydro-1H-indazole (250 mg, 0.6 mmol), N-chlorosuccinimide (85 mg, 0.6 mmol) and acetic acid (10 mL) were mixed, warmed up 80° C. and reacted for 3 h. Aftertreatment: dichloromethane and water were added and layered, the organic phase was desolventized under reduced pressure and passed through a silica gel chromatographic column with a petroleum ether/ethyl acetate (1:1) system to obtain a yellow solid product 6-(2-chloro-3,5-dimethoxyphenyl)-3-(1-methyl-4-nitro-1H-pyrazol-5-yl)-4,5,6,7-tetrahydro-1H-indazole (150 mg, 55%).

Example 311 was synthesized with reference to the operation steps of example 302, except that in Step 5, 6-(2-fluoro-3,5-dimethoxyphenyl)-3-(1-methyl-4-nitro-1H-pyrazol-5-yl)-4,5,6,7-tetrahydro-1H-indazole was replaced with 6-(2-chloro-3,5-dimethoxyphenyl)-3-(1-methyl-4-nitro-1H-pyrazol-5-yl)-4,5,6,7-tetrahydro-1H-indazole. Finally, the target product N-(5-(6-(2-chloro-3,5-dimethoxyphenyl)-4,5,6,7-tetrahydro-1H-indazol-3-yl)-1-methyl-1H-pyrazol-4-yl)acrylamide 311 was obtained.

Conditions for chiral resolution: SFC device, chromatographic column: chiralpak-AD, mobile phase: CO2-IPA (DEA). The one with a short holding time on the SFC machine was named as P1, and the one with a long holding time was named as P2. One of P1 and P2 was the R-isomer, and the other was the S-isomer.

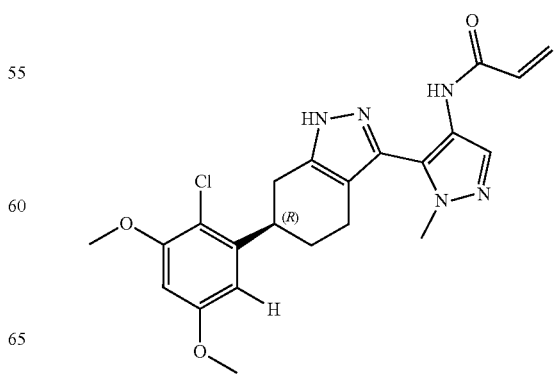

-continued

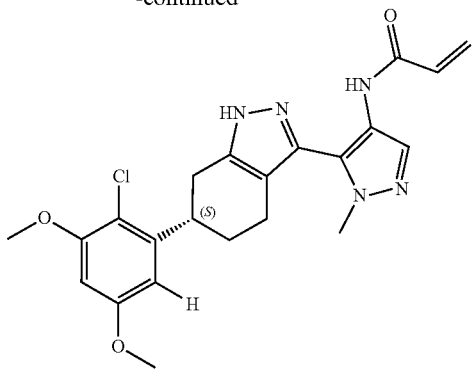

MS m/z (ESI): 442.0[M+1]$^+$

P1: $^1$H NMR (400 MHz, DMSO): δ 12.96 (s, 1H), 9.49 (s, 1H), 7.83 (s, 1H), 6.62 (d, J=2.9 Hz, 2H), 6.52 (dd, J=17.0, 10.2 Hz, 1H), 6.19 (d, J=17.0 Hz, 1H), 5.66 (d, J=10.2 Hz, 1H), 3.86 (s, 3H), 3.79 (s, 3H), 3.76 (s, 3H), 3.46 (s, 2H), 2.94 (dd, J=15.7, 5.1 Hz, 1H), 2.75-2.66 (m, 1H), 2.38 (d, J=14.5 Hz, 1H), 1.90 (s, 1H).

P2: $^1$H NMR (400 MHz, DMSO): δ 12.99 (s, 1H), 9.49 (s, 1H), 7.83 (s, 1H), 6.62 (d, J=3.0 Hz, 2H), 6.52 (dd, J=17.0, 10.2 Hz, 1H), 6.19 (d, J=17.0 Hz, 1H), 5.66 (d, J=10.1 Hz, 1H), 3.86 (s, 3H), 3.79 (s, 3H), 3.76 (s, 3H), 3.53-3.42 (m, 2H), 2.94 (dd, J=15.5, 4.7 Hz, 1H), 2.76-2.65 (m, 1H), 2.39 (d, J=14.9 Hz, 1H), 1.90 (s, 1H).

FGFR4 Activity Inhibition Test

The influence of the compound of the present invention on the activity of the tyrosine kinase FGFR4 was evaluated by an in vitro kinase assay experiment.

The experimental method is summarized as follows:

A HTRF® KinEASE™-TK 20000 tests kinase assay kit from CISBIO Corp. was used. The kit provided a biotin-labeled substrate, an EU-labeled phosphorylation site-specific antibody, and XL665-labeled avidin and a related buffer. FGFR4 phosphorylated the substrate, Eu-Ab identified the phosphorylated substrate, and XL665-SA binded to the biotin on the substrate, making Eu get closer to XL665, thus generating the HTRF signal. Changes in the activity of kinase was detected by reading the intensity of the HTRF signal. In the kinase assay experiment, there were mainly two steps of reaction: kinase reaction and assay reaction, respectively. In the kinase reaction, the kinase consumed ATP to phosphorylate the substrate, and at the same time produced a substrate containing a phosphate group. In the assay reaction, an assay reagent was added to terminate the kinase reaction. At the same time, the specific antibody and the XL665-labeled avidin in the assay reagent were binded to the phosphate group on the substrate and biotin respectively to generate HTRF signals. The signal intensity was directly proportional to the phosphorylation level of the substrate, and thereby the activity of the kinase FGFR4 could be quantitatively assayed.

During the assay, the binding and incubation of the compound with the enzyme was carried out at room temperature for 60 min. The kinase reaction was carried out at a constant temperature of 37° C. for 40 min. A Corning 3674 black 384-well assay plate was used. The kinase human FGFR4 protein (460-802 amino acids) was commercially available from CAMA Company (Art. No. 08-136). The kinase substrates were TK (commercially available from Cisbio) and ATP (Sigma). The optical signals were read by a microplate reader TECAN Spark 10M plate reader (TECAN). The kinase reaction buffer comprised 1× Enzymatic buffer (CISBIO) 5 mM MgCl$_2$ (Sigma) and 1 mM DTT (Sigma). The kinase FGFR4 was formulated with a buffer into a kinase reaction solution at a concentration of 0.25 μg/ml. The substrate reaction solution comprised 0.75 μM substrate and 500 μm ATP.

IC$_{50}$ of the compound was calculated from 10 concentration points by the following formula. First, the compound was dissolved and diluted with 100% DMSO into a 96-well plate at 3 concentrations: 4 mM, 40 μM, and 0.4 μM. 8 μl of the compound was transferred to a 384 LDV Echo Source plate, and the compound was transferred to an Assay plate with Echo550 to obtain 10 concentration points. Each concentration point was provided with two copy holes (starting point 10 μM, 3-fold dilution). First, 6 μL of the kinase solution was added into the 384-well assay plate, mixed uniformly and then incubated at room temperature for 60 min. Then 4 μL of the substrate reaction solution was added, and the total reaction volume was 10 μL. The reaction mixture was reacted at a constant temperature of 37° C. for 40 min. Subsequently, 10 μL of the kinase assay reagent was added and the reaction was terminated. Then the numerical values were read on the TECAN plate reader.

The inhibition percentage was calculated based on the following formula:

% inhibition=[1−(RLU$_{compound}$−RLU$_{min}$)/(RLU$_{max}$−RLU$_{min}$)]×100 wherein RLU$_{compound}$ is the luminescence reading at the given compound concentration, RLU$_{min}$ is the luminescence reading without the addition of kinase, and RLU$_{max}$ is the luminescence reading without the addition of the compound. IC$_{50}$ of the compound was calculated by the XLfit program in Excel.

| Compound number | IC50 (nM) |
|---|---|
| 015 | 80 |
| 093 | 29.22 |
| 096 | 348.25 |
| 98 | 7251.51 |
| 103 | 101.1 |
| 107 | 340.21 |
| 111 | 76.94 |
| 113 | 1881.25 |
| 114 | 158.48 |
| 133 | 4.56 |
| 137 | 27.82 |
| 140 | 24.62 |
| 015-P1 | 949.56 |
| 015-P2 | 55.51 |
| 281 | P1 = 5.73 |
|  | P2 = 2.96 |
| 283 | P1 = 190.00 |
|  | P2 = 45.00 |
| 284 | P1 = 628.39 |
|  | P2 = 165.59 |
| 285 | P1 = 2616.21 |
|  | P2 = 479.39 |
| 286 | 3669.50 |
| 287 | P1 = 157.54 |
|  | P2 = 91.08 |
| 288 | P1 = 158.39 |
|  | P2 = 922.6 |
| 289 | P1 = 108.77 |
|  | P2 = 210.06 |
| 291 | P1 = 557.00 |
|  | P2 = 132.00 |
| 292 | P1 = 813.35 |
|  | P2 = 135.07 |
| 293 | P1 = 1899.07 |
|  | P2 = 7400.39 |

-continued

| Compound number | IC50 (nM) |
|---|---|
| 295 | P1 = 1663.88 |
| | P2 = 409.45 |
| 296 | 118.00 |
| 297 | 236.25 |
| 298 | 158.95 |
| 299 | 1544.61 |
| 300 | 504.42 |
| 301 | P1 = 3.4 |
| | P2 = 11.8 |
| 302 | P1 = 85.5 |
| | P2 = 35.4 |
| 303 | P1 = 6.0 |
| | P2 = 5.5 |
| 304 | 174.00 |
| 310 | P1 = 445.9 |
| | P2 = 170.6 |
| 311 | P1 = 202.8 |
| | P2 = 129.3 |

Conclusion: the compound of the present invention has an evident inhibition effect on the activity of tyrosine kinase FGFR4.

The above content is the further detailed description of the present invention in combination with the particular preferred embodiments, and it should not be regarded that the particular implementation of the present invention is limited to these descriptions. Those of ordinary skill in the art to which the present invention belongs can also make some simple deduction or replacement without departing from the concept of the present invention, which shall all be deemed to belong to the protection scope of the present invention.

The invention claimed is:

1. A compound as shown in the general formula (I) or a pharmaceutically acceptable salt, tautomer, racemate, enantiomer, diastereomer hydrate or solvate thereof,

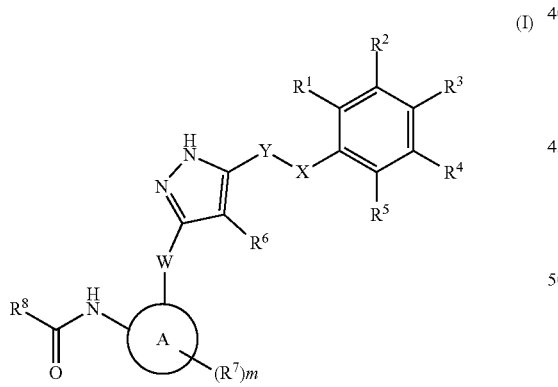

(I)

wherein
ring A is not present or is selected from the group consisting of 6-14 membered arylene, 5-10 membered heteroarylene, $C_3$-$C_8$ cycloalkylene and 3-10 membered heterocyclylene;
$R^1$, $R^2$, $R^3$, $R^4$ and $R^5$ are each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$, —$NR^{11}R^{12}$, —$C(O)R^{13}$, —$C(O)OR^{13}$, —$C(O)NR^{11}R^{12}$, —$NR^{11}C(O)R^{13}$, —$NR^{11}C(O)OR^{13}$, —$NR^{11}C(O)NR^{11}R^{12}$, —$OC(O)R^{13}$, —$OC(O)OR^{13}$, —$OC(O)NR^{11}R^{12}$, —$S(O)_pR^{13}$, —$S(O)_pOR^{13}$, —$S(O)_pNR^{11}R^{12}$, —$OS(O)_pR^{13}$ and —$NR^{11}S(O)_pR^{13}$;
$R^6$ is each independently selected from the group consisting of H and —$CH_2CH_2$—, and when $R^6$ is —$CH_2CH_2$—, the other end thereof is connected to X, and optionally one methylene group of —$CH_2CH_2$— is replaced with —O— or —NH—;
$R^7$ is each independently selected from the group consisting of H, halogen, cyano, $NO_2$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, —$OR^{13}$ or —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl, which is optionally substituted by $C_1$-$C_6$ alkyl or $C_1$-$C_6$ haloalkyl;
$R^8$ is selected from the group consisting of optionally substituted $C_2$-$C_6$ alkenyl and $C_2$-$C_6$ alkynyl;
$R^{11}$, $R^{12}$ and $R^{13}$ are each independently selected from the group consisting of H, $C_1$-$C_6$ alkyl, $C_1$-$C_6$ heteroalkyl, $C_3$-$C_8$ cycloalkyl, 3-10 membered heterocyclyl, 5-10 membered heteroaryl and 6-14 membered aryl;
X is selected from the group consisting of —O—, —NH— and —$CH_2$—; and Y is selected from the group consisting of —O—, —NH— and —$CH_2$—; provided that at least one of X and Y is $CH_2$;
W is selected from the group consisting of a chemical bond, —NH— and —$CH_2$—;
m is 0, 1, 2, 3 or 4; and
p is 1 or 2.

2. A compound as shown in the general formula (I) or a pharmaceutically acceptable salt, tautomer, racemate, enantiomer, diastereomer hydrate or solvate thereof according to claim 1, which is a compound as shown in the general formula (II):

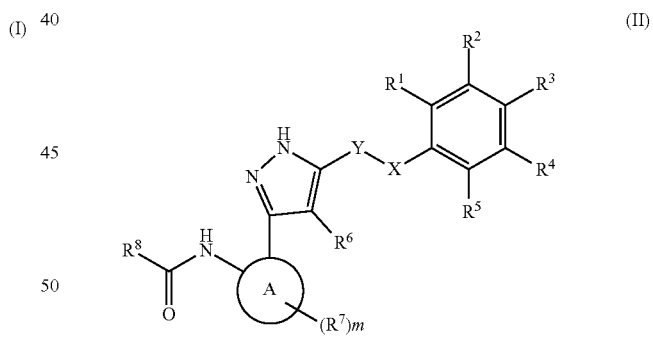

(II)

wherein
ring A is selected from the group consisting of 6-10 membered arylene, 5-6 membered heteroarylene or $C_3$-$C_8$ cycloalkylene;
$R^1$, $R^2$, $R^3$, $R^4$ and $R^5$ are each independently selected from the group consisting of H, halogen, $C_1$-$C_6$ alkyl, $C_1$-$C_6$ haloalkyl, $C_1$-$C_6$ alkoxy or $C_1$-$C_6$ haloalkoxy;
$R^6$ is each independently selected from the group consisting of H and —$CH_2CH_2$—, and when $R^6$ is —$CH_2CH_2$—, the other end thereof is connected to X;
$R^7$ is each independently selected from the group consisting of H, $C_1$-$C_6$ alkyl, $C_1$-$C_6$ haloalkyl and —$NR^aR^b$, wherein $R^a$ and $R^b$ are each independently selected from the group consisting of H and $C_1$-$C_6$ alkyl optionally substituted by —NR$^c$R$^d$; and R$^c$ and R$^d$ are each independently selected from the group consisting of H and C$_1$-C$_6$ alkyl;

R$^8$ is selected from the group consisting of optionally substituted C$_2$-C$_6$ alkenyl and C$_2$-C$_6$ alkynyl; and X is selected from the group consisting of —O—, —NH— and —CH$_2$—; and Y is selected from the group consisting of —O—, —NH— and —CH$_2$—; provided that at least one of X and Y is CH$_2$; m is 0, 1, 2, 3 or 4.

3. A compound as shown in the general formula (I) or a pharmaceutically acceptable salt, tautomer, racemate, enantiomer, diastereomer hydrate or solvate thereof according to claim 1, which is a compound as shown in the general formula (III):

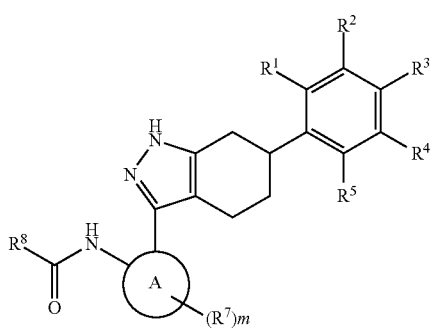

(III)

wherein ring A is 6-10 membered arylene, 5-6 membered heteroarylene or C$_3$-C$_8$ cycloalkylene;

R$^1$, R$^2$, R$^3$, R$^4$ and R$^5$ are each independently selected from the group consisting of H, halogen, C$_1$-C$_6$ alkyl, C$_1$-C$_6$ haloalkyl, C$_1$-C$_6$ alkoxy or C$_1$-C$_6$ haloalkoxy;

R$^7$ is each independently selected from the group consisting of H, halogen, C$_1$-C$_6$ alkyl, C$_1$-C$_6$ haloalkyl and —NR$^a$R$^b$, wherein R$^a$ and R$^b$ are each independently selected from the group consisting of H and C$_1$-C$_6$ alkyl optionally substituted by —NR$^c$R$^d$; R$^c$ and R$^d$ are each independently selected from the group consisting of H and C$_1$-C$_6$ alkyl; or R$^a$ and R$^b$ together with the N atom connected thereto form 3-10 membered heterocyclyl, which is optionally substituted by C$_1$-C$_6$ alkyl or C$_1$-C$_6$ haloalkyl;

R$^8$ is selected from the group consisting of optionally substituted C$_2$-C$_6$ alkenyl and C$_2$-C$_6$ alkynyl; and m is 0, 1, 2, 3 or 4.

4. A compound as shown in the general formula (I) or a pharmaceutically acceptable salt, tautomer, racemate, enantiomer, diastereomer hydrate or solvate thereof according to claim 1, which is a compound as shown in the general formula (IV):

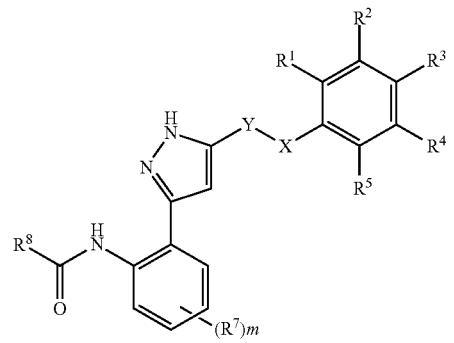

(IV)

wherein

R$^1$, R$^2$, R$^3$, R$^4$ and R$^5$ are each independently selected from the group consisting of H, halogen, C$_1$-C$_6$ alkyl, C$_1$-C$_6$ haloalkyl, C$_1$-C$_6$ alkoxy or C$_1$-C$_6$ haloalkoxy;

R$^7$ is each independently selected from the group consisting of H, C$_1$-C$_6$ alkyl or C$_1$-C$_6$ haloalkyl;

R$^8$ is selected from the group consisting of C$_2$-C$_6$ alkenyl and C$_2$-C$_6$ alkynyl;

X is —NH—, and Y is —CH$_2$—; or

X is —CH$_2$—, and Y is —NH—; and m is 0, 1, 2, 3 or 4.

5. A compound as shown in the general formula (I) or a pharmaceutically acceptable salt, tautomer, racemate, enantiomer, diastereomer hydrate or solvate thereof according to claim 1, which is a compound as shown in the general formula (V):

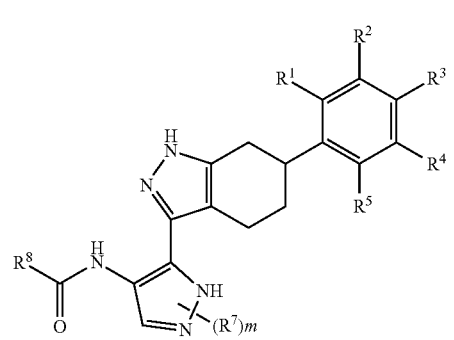

(V)

wherein

R$^1$, R$^2$, R$^3$, R$^4$ and R$^5$ are each independently selected from the group consisting of H, halogen, C$_1$-C$_6$ alkyl, C$_1$-C$_6$ haloalkyl, C$_1$-C$_6$ alkoxy or C$_1$-C$_6$ haloalkoxy;

R$^7$ is each independently selected from the group consisting of H, C$_1$-C$_6$ alkyl or C$_1$-C$_6$ haloalkyl;

R$^8$ is selected from the group consisting of C$_2$-C$_6$ alkenyl and C$_2$-C$_6$ alkynyl; and m is 0, 1 or 2.

6. A compound as shown in the general formula (I) or a pharmaceutically acceptable salt, tautomer, racemate, enantiomer, hydrate or solvate thereof according to claim 1, which is a compound as shown in the general formula (VI):

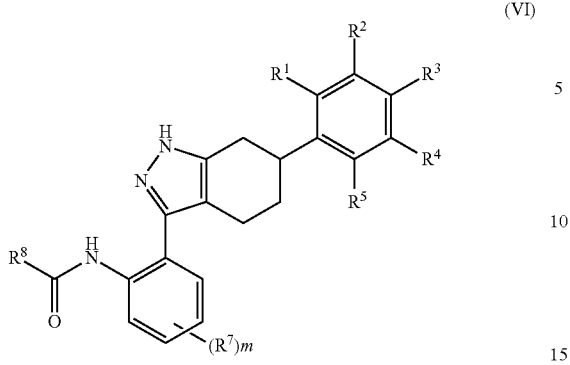

(VI)

wherein
- $R^1$, $R^2$, $R^3$, $R^4$ and $R^5$ are each independently selected from the group consisting of H, halogen, $C_1$-$C_6$ alkyl, $C_1$-$C_6$ haloalkyl, $C_1$-$C_6$ alkoxy or $C_1$-$C_6$ haloalkoxy;
- $R^7$ is each independently selected from the group consisting of H, halogen, $C_1$-$C_6$ alkyl, $C_1$-$C_6$ haloalkyl, $C_1$-$C_6$ alkoxy, $C_1$-$C_6$ haloalkoxy or —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 heterocyclyl, which is optionally substituted by $C_1$-$C_6$ alkyl or $C_1$-$C_6$ haloalkyl;
- $R^8$ is selected from the group consisting of optionally substituted $C_2$-$C_6$ alkenyl and $C_2$-$C_6$ alkynyl; and
- m is 0, 1, 2, 3 or 4.

7. A compound as shown in the general formula (I) or a pharmaceutically acceptable salt, tautomer, racemate, enantiomer, hydrate or solvate thereof according to claim 1, which is a compound as shown in the general formula (VII):

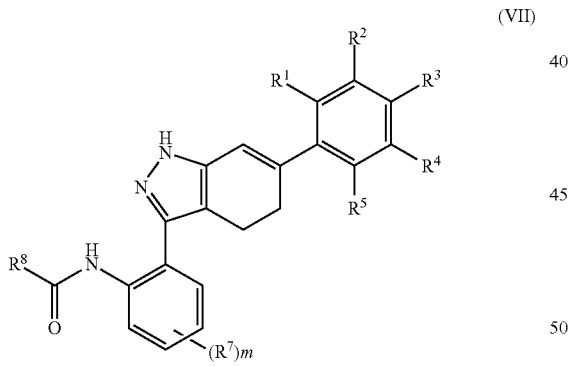

(VII)

wherein
- $R^1$ and $R^5$ are each independently halogen;
- $R^2$ and $R^4$ are each independently $C_1$-$C_6$ alkoxy;
- $R^3$ is H;
- $R^7$ is each independently selected from the group consisting of halogen, $C_1$-$C_6$ alkyl, $C_1$-$C_6$ haloalkyl and —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl, which is optionally substituted by $C_1$-$C_6$ alkyl or $C_1$-$C_6$ haloalkyl;
- $R^8$ is optionally substituted $C_2$-$C_6$ alkenyl; and
- m is 0, 1, 2, 3 or 4.

8. A compound or a pharmaceutically acceptable salt, tautomer, racemate, enantiomer, hydrate or solvate thereof, wherein the compound is selected from the group consisting of:

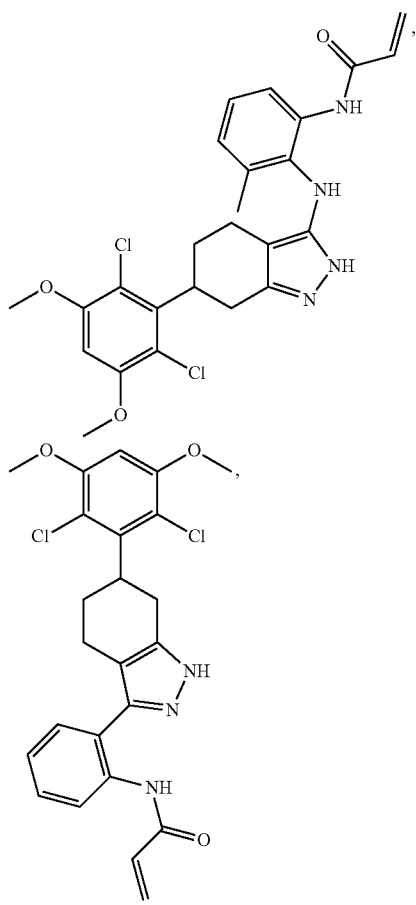

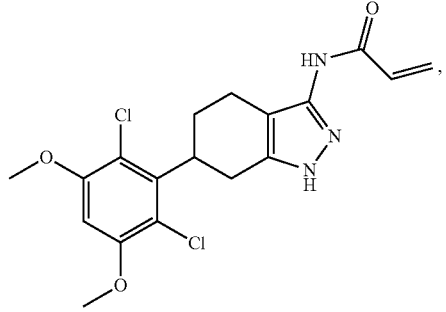

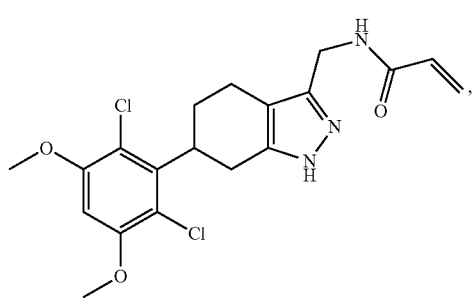

175
-continued
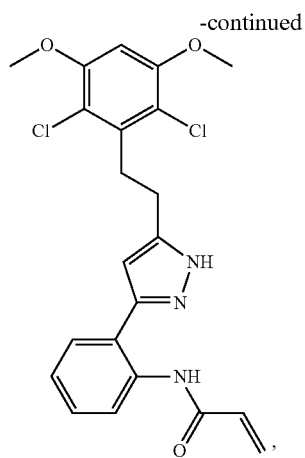
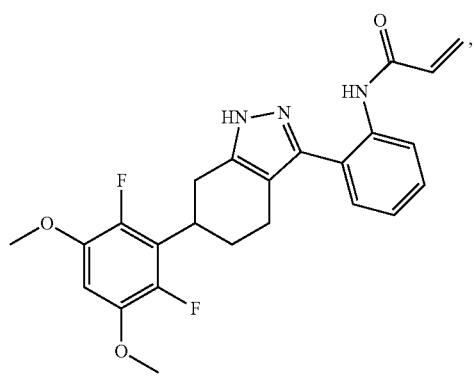
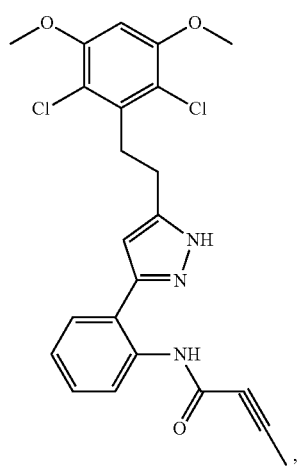
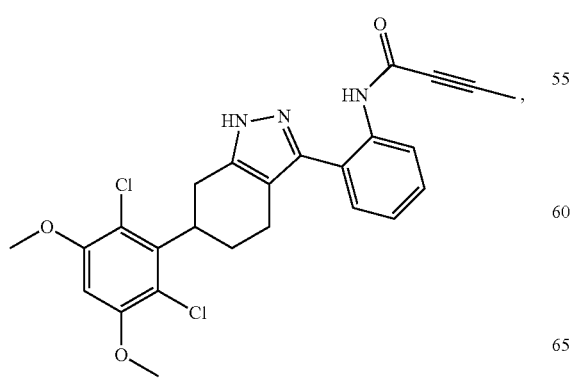
176
-continued
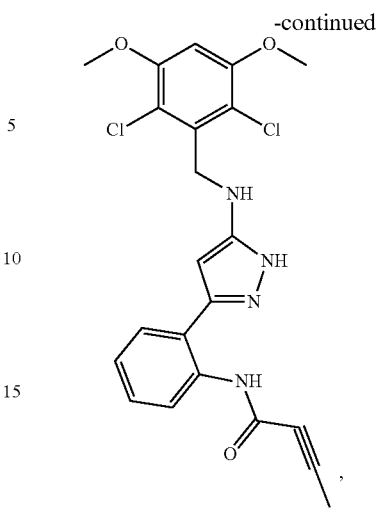
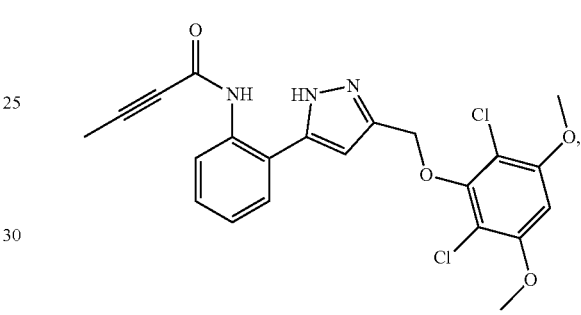
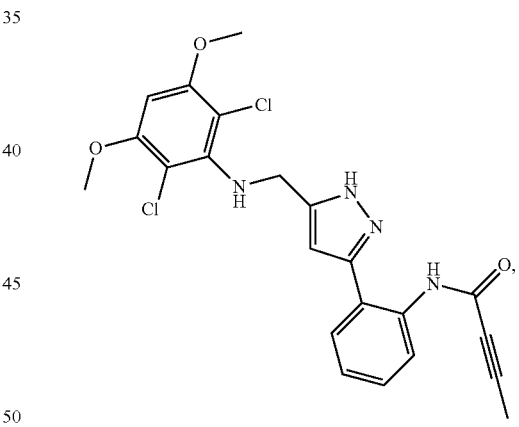
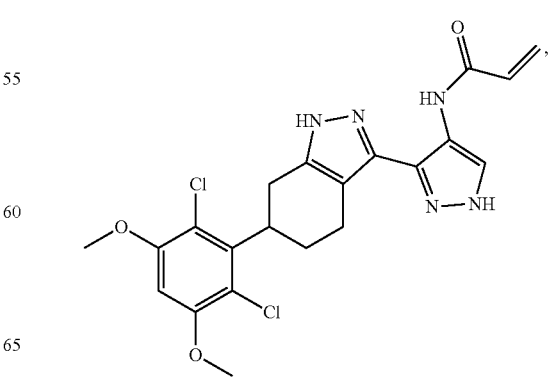

177
-continued
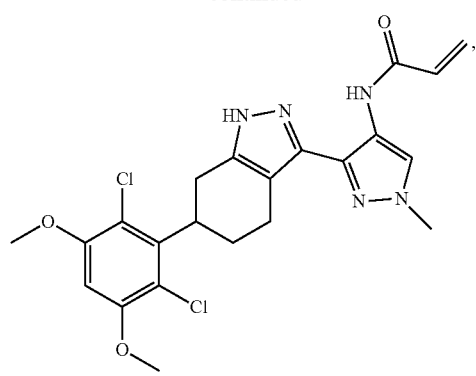
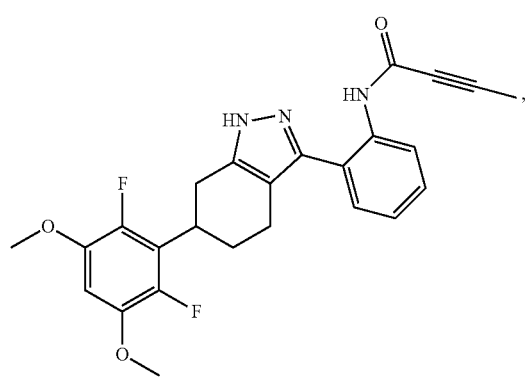
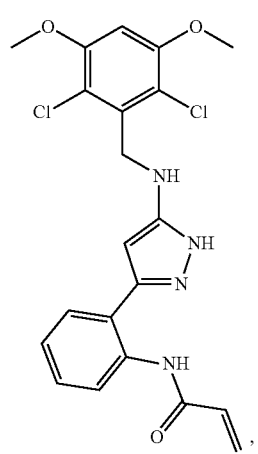
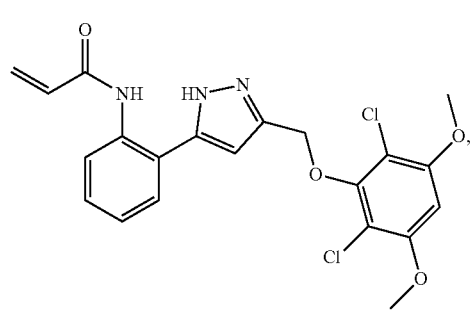
178
-continued
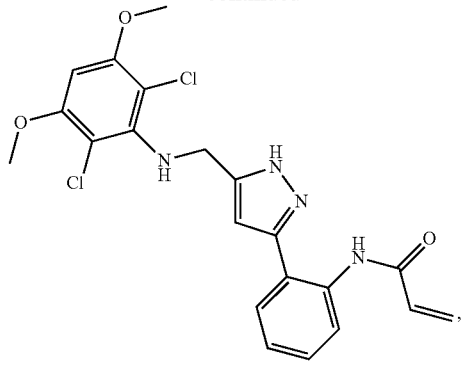
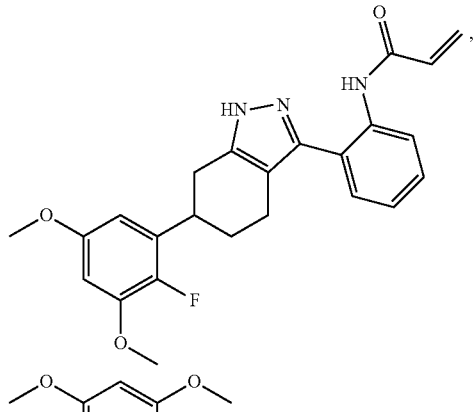
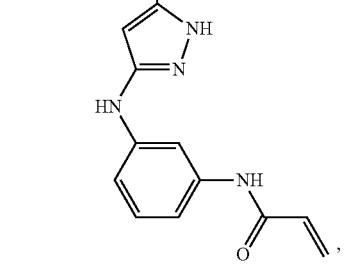

179
-continued
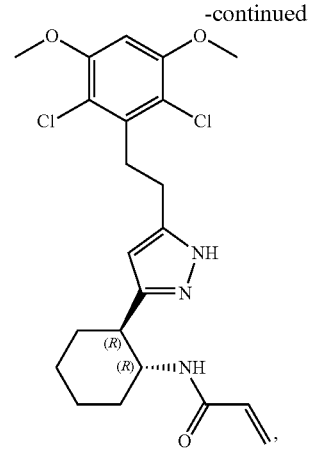
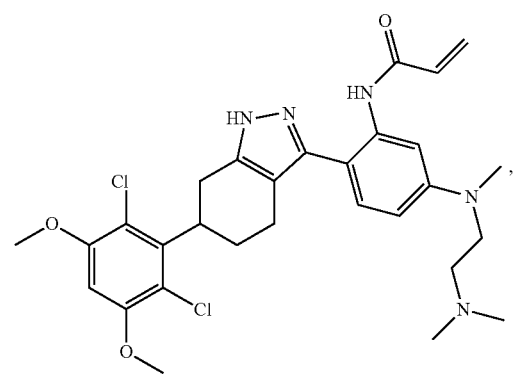
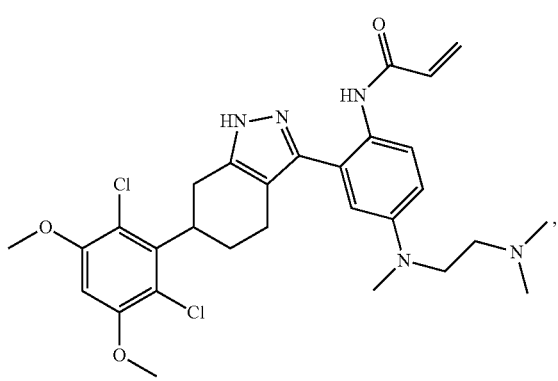
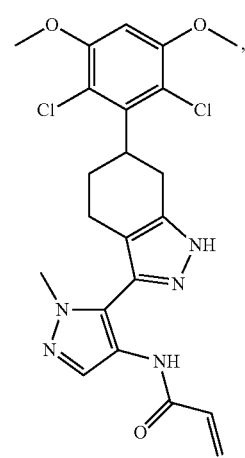
180
-continued
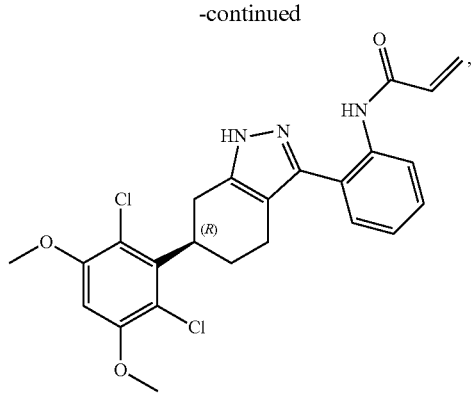
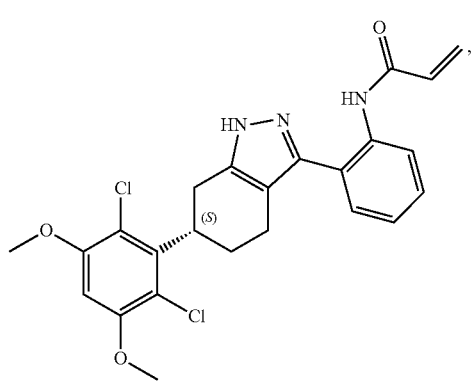
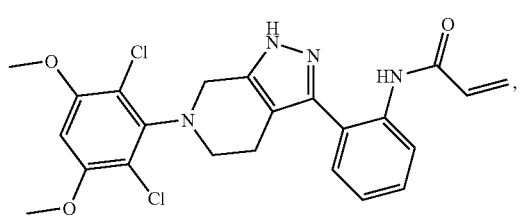
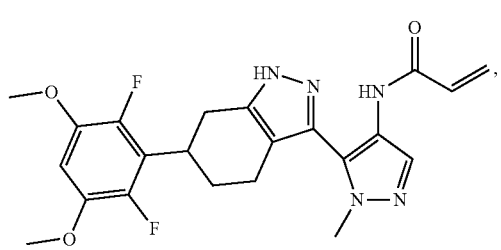
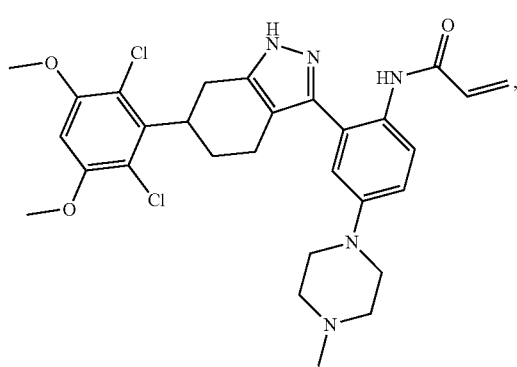

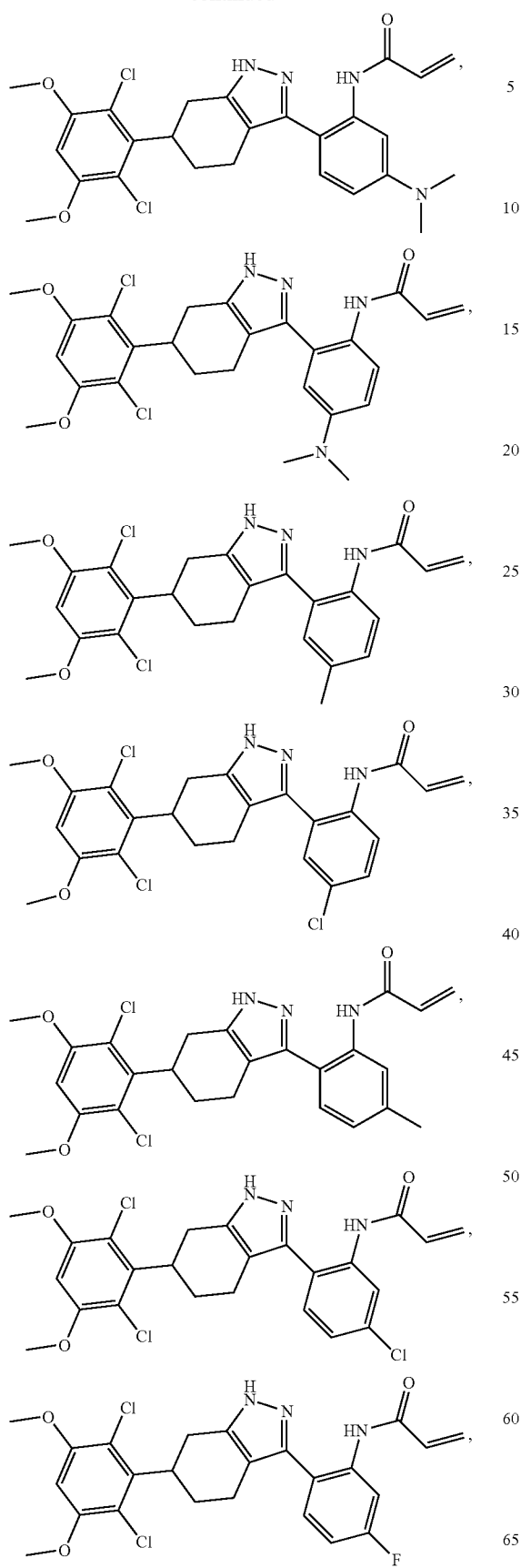
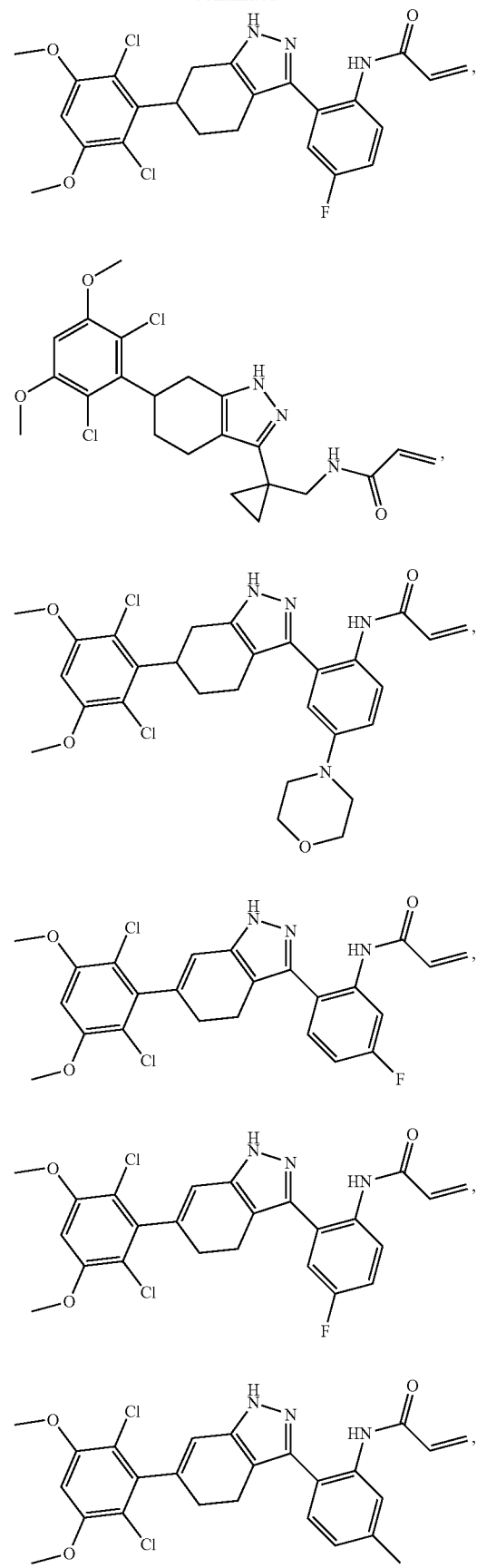

183
-continued
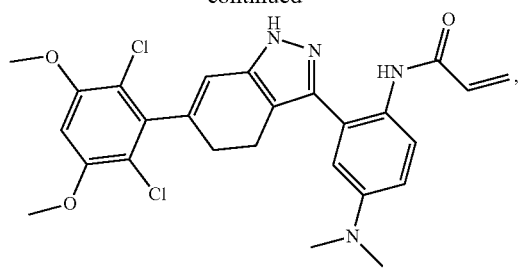
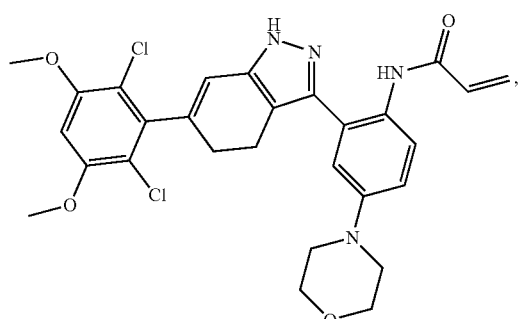
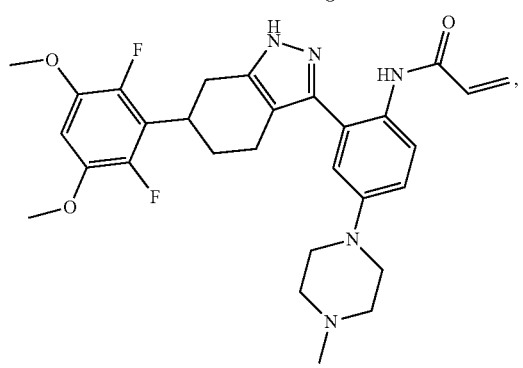
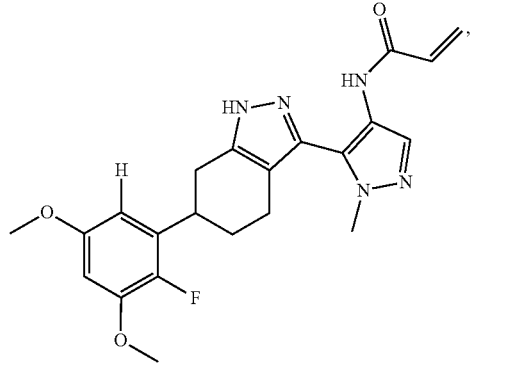
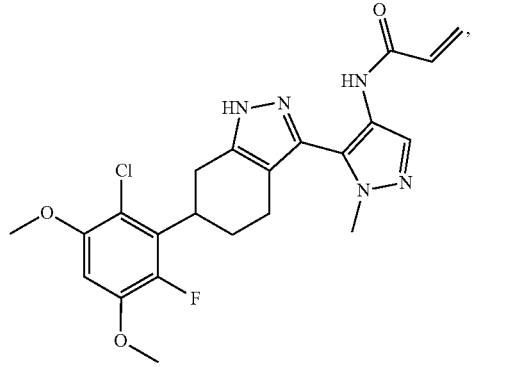
184
-continued
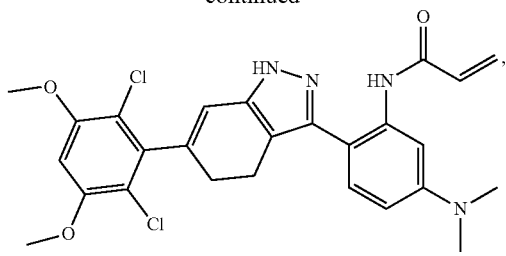
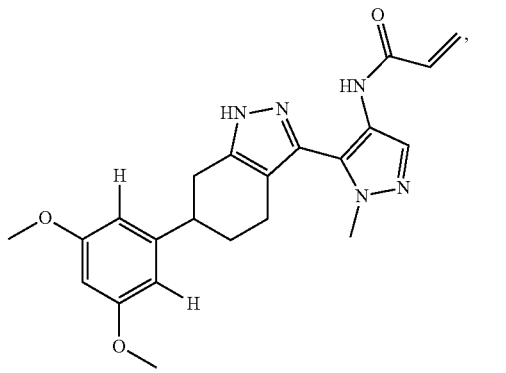
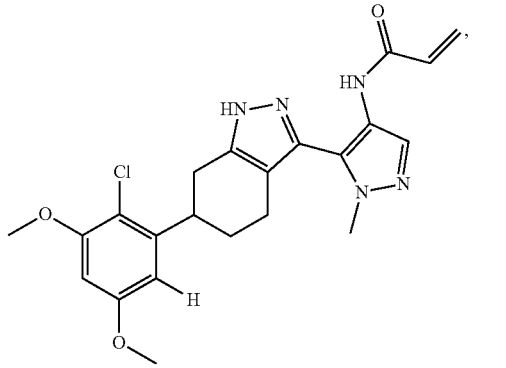
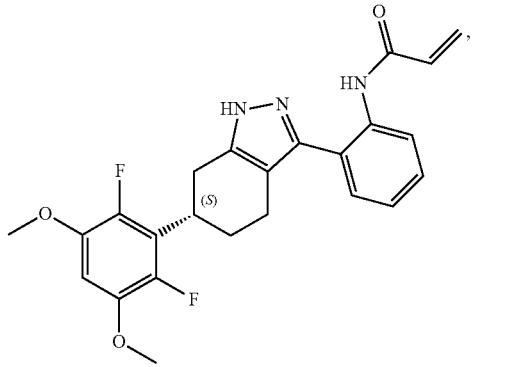
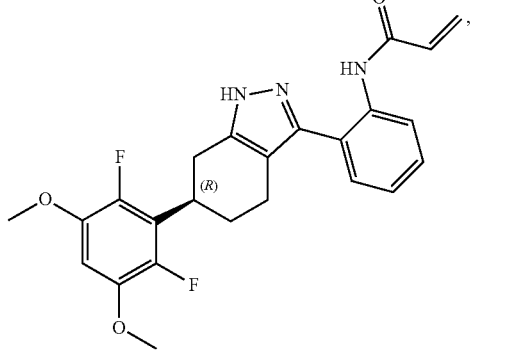

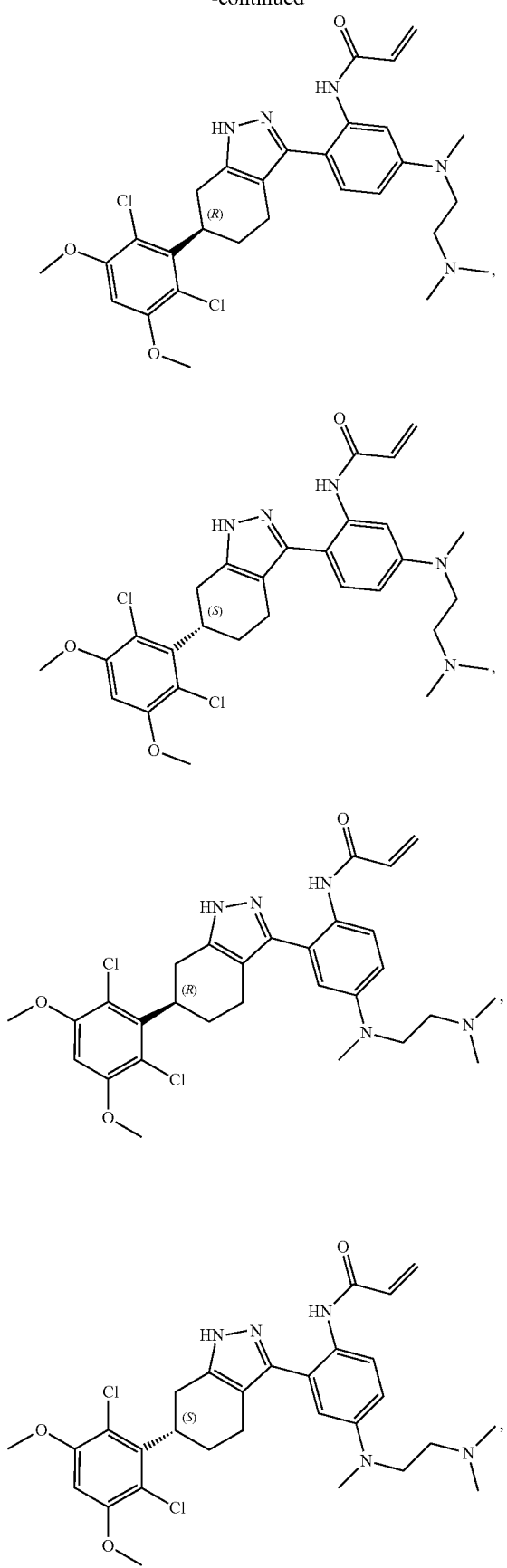
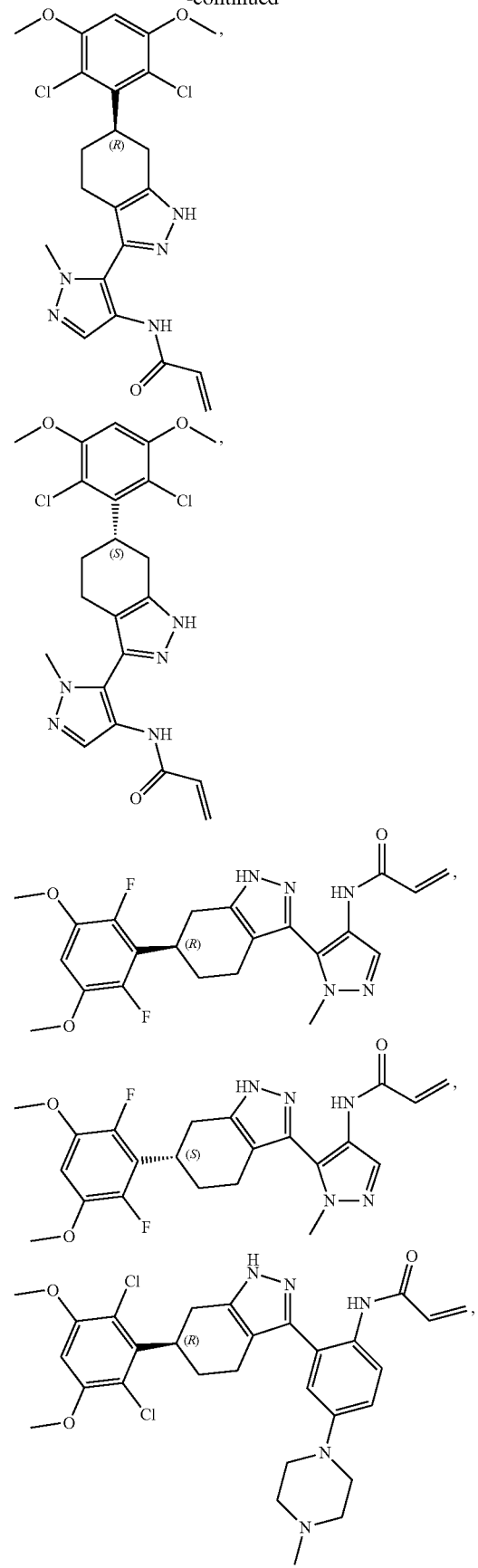

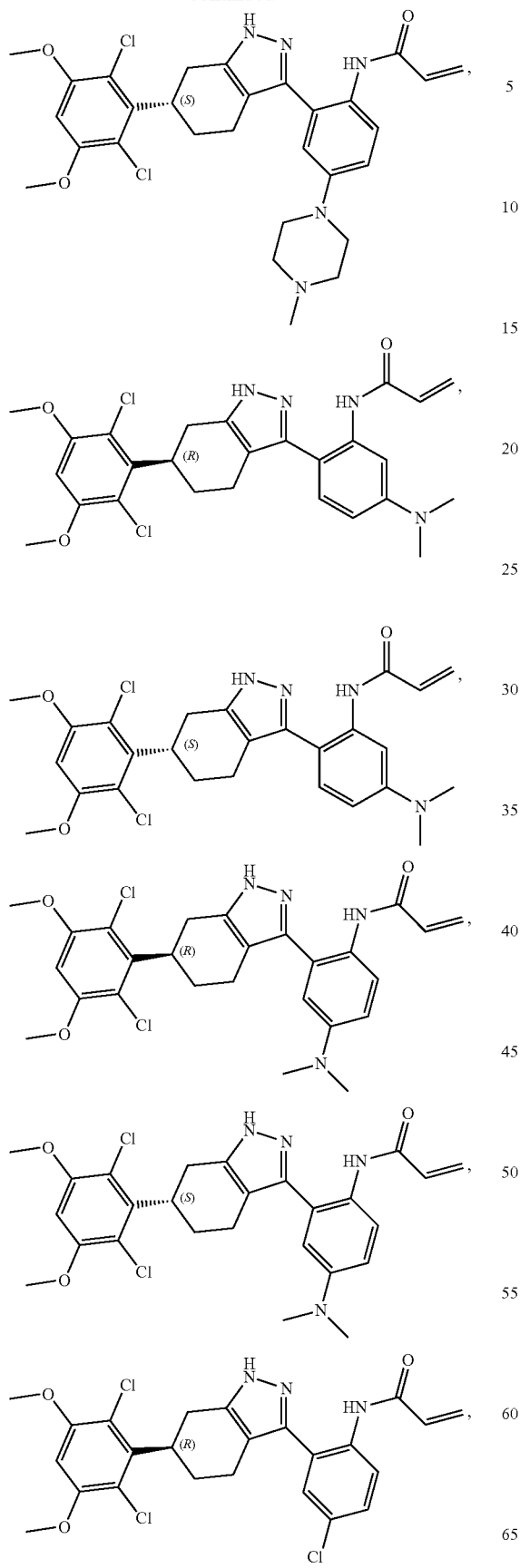
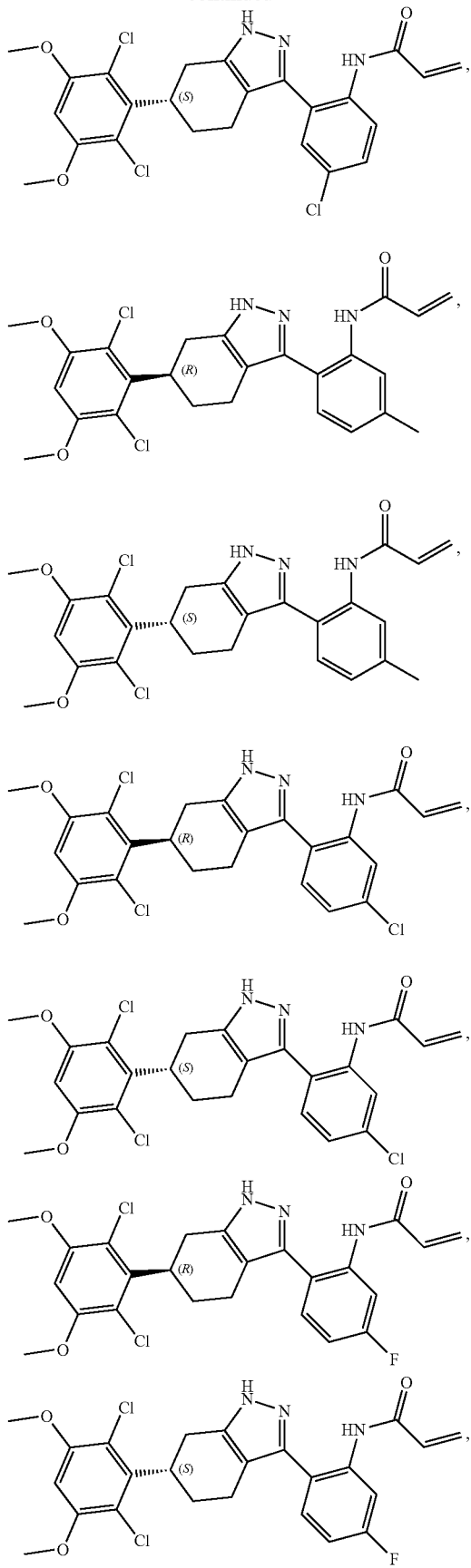

189
-continued
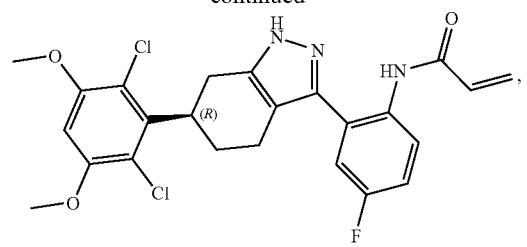
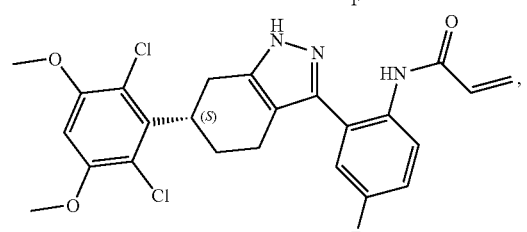
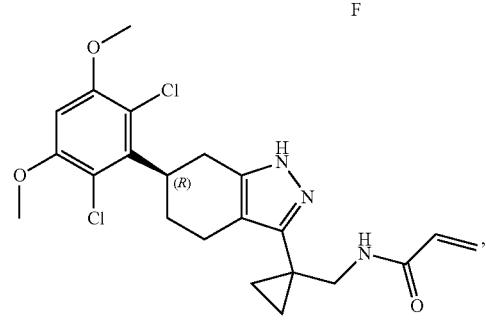
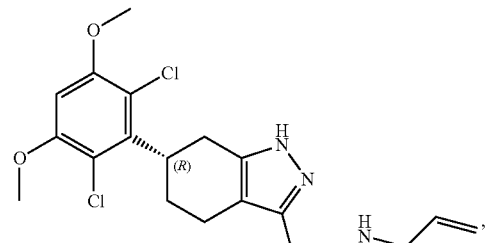
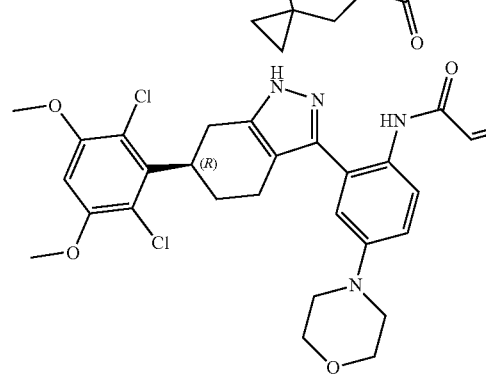
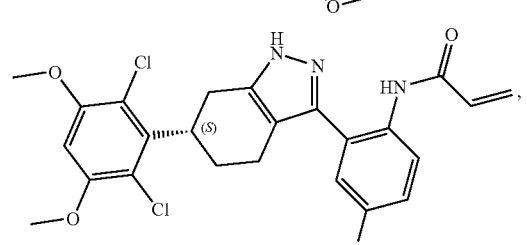
190
-continued
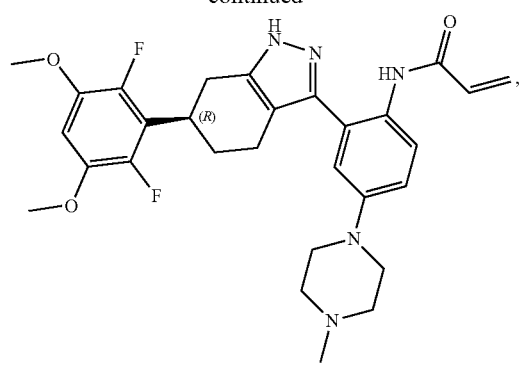
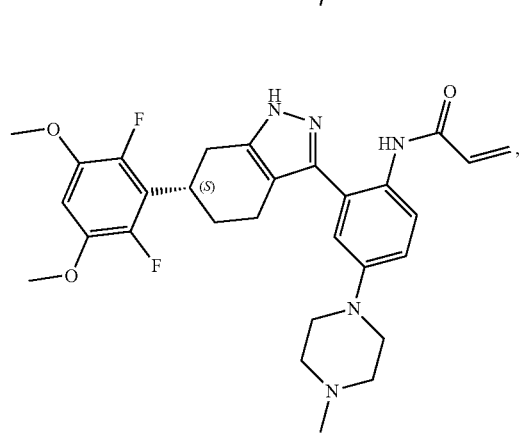
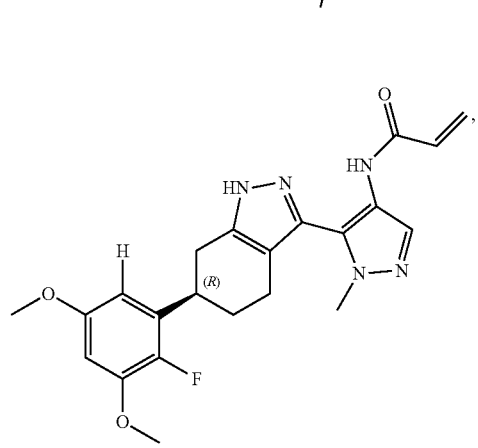
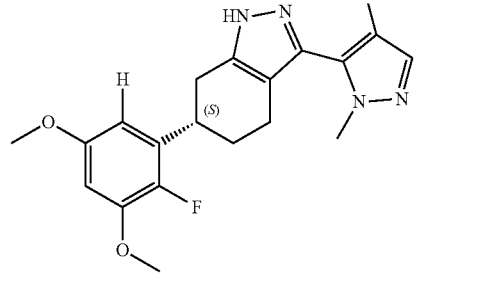

191
-continued

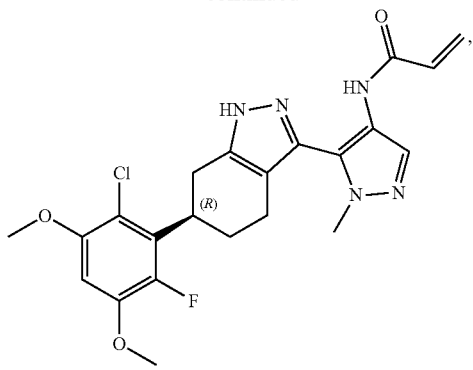

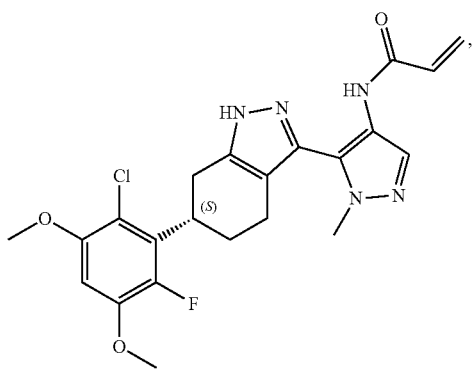

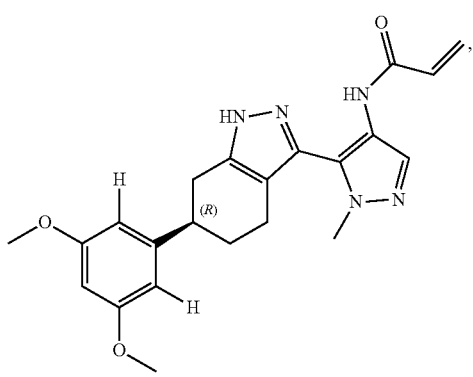

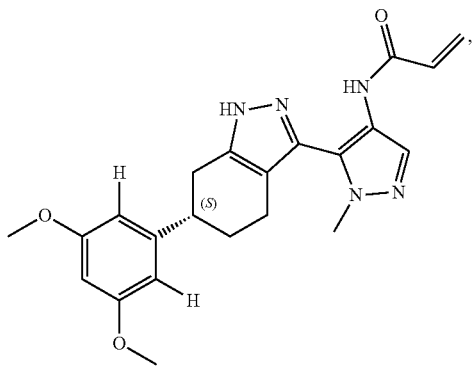

192
-continued

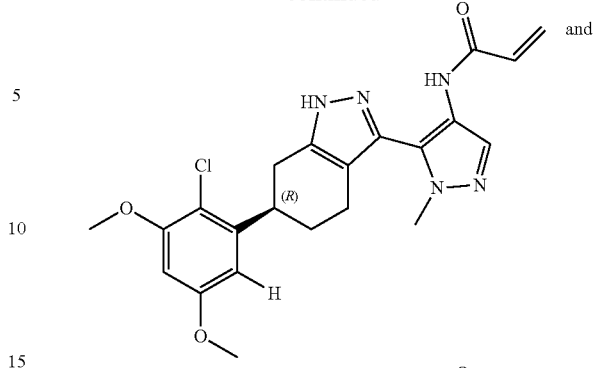

and

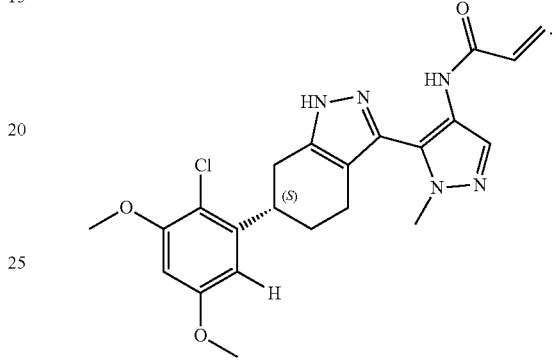

9. A pharmaceutical composition containing the compound or a pharmaceutically acceptable salt, tautomer, racemate, enantiomer, hydrate or solvate thereof according to claim 1, and a pharmaceutically acceptable excipient.

10. A method for treating FGFR4 tyrosine kinase-mediated diseases in a subject, comprising administering to the subject the compound or a pharmaceutically acceptable salt, tautomer, racemate, enantiomer, hydrate or solvate thereof according to claim 1, wherein the disease is selected from the group consisting of gastric cancer, thyroid cancer, prostate cancer, breast cancer, sarcoma, skin cancer, liver cancer, pancreatic cancer, lung cancer, kidney cancer, colorectal cancer, and ovarian cancer.

11. The method according to claim 10, wherein the sarcoma is rhabdomyosarcoma, the skin cancer is melanoma, the liver cancer is hepatocellular carcinoma or cholangiocarcinoma, the pancreatic cancer is pancreatic intraepithelial neoplasia or pancreatic ductal adenocarcinoma, the lung cancer is non-small-cell lung cancer or pulmonary adenocarcinoma, or the kidney cancer is renal cell carcinoma.

12. The compound or a pharmaceutically acceptable salt, tautomer, racemate, enantiomer, diastereomer, hydrate or solvate thereof according to claim 3, wherein
ring A is phenylene or 5-6 membered heteroarylene;
$R^1$ and $R^5$ are each independently H or halogen;
$R^2$ and $R^4$ are each independently $C_1$-$C_6$ alkoxy;
$R^3$ is H;
$R^7$ is each independently selected from the group consisting of H, halogen, $C_1$-$C_6$ alkyl, $C_1$-$C_6$ haloalkyl and —$NR^aR^b$, wherein $R^a$ and $R^b$ are each independently selected from the group consisting of H and $C_1$-$C_6$ alkyl optionally substituted by —$NR^cR^d$; $R^c$ and $R^d$ are each independently selected from the group consisting of H and $C_1$-$C_6$ alkyl; or $R^a$ and $R^b$ together with the N atom connected thereto form 3-10 membered heterocyclyl, which is optionally substituted by $C_1$-$C_6$ alkyl or $C_1$-$C_6$ haloalkyl;

$R^8$ is selected from the group consisting of optionally substituted $C_2$-$C_6$ alkenyl and $C_2$-$C_6$ alkynyl; and m is 0, 1, 2, 3 or 4.

13. The compound or a pharmaceutically acceptable salt, tautomer, racemate, enantiomer, diastereomer, hydrate or solvate thereof according to claim 5, wherein ring A is phenylene or 5-6 membered heteroarylene;

$R^1$ and $R^5$ are each independently Cl or F;

$R^2$ and $R^4$ are each independently —$OCH_3$;

$R^3$ is H;

$R^7$ is H and $C_1$-$C_6$ alkyl;

$R^8$ is vinyl; and m 1.

14. The compound or a pharmaceutically acceptable salt, tautomer, racemate, enantiomer, diastereomer, hydrate or solvate thereof according to claim 1, wherein ring A is phenylene or pyrazolylene.

15. The compound or a pharmaceutically acceptable salt, tautomer, racemate, enantiomer, diastereomer, hydrate or solvate thereof according to claim 1, wherein $R^1$ and $R^5$ are each independently halogen.

16. The compound or a pharmaceutically acceptable salt, tautomer, racemate, enantiomer, diastereomer, hydrate or solvate thereof according to claim 1, wherein $R^2$ and $R^4$ are each independently $C_1$-$C_6$ alkoxy.

17. The compound or a pharmaceutically acceptable salt, tautomer, racemate, enantiomer, diastereomer, hydrate or solvate thereof according to claim 1, wherein $R^7$ is each independently selected from the group consisting of H, halogen, $C_1$-$C_6$ alkyl, $C_1$-$C_6$ haloalkyl and —$NR^aR^b$, wherein $R^a$ and $R^b$ together with the N atom connected thereto form 6 membered heterocyclyl, which is optionally substituted by $C_1$-$C_6$ alkyl or $C_1$-$C_6$ haloalkyl.

18. The compound or a pharmaceutically acceptable salt, tautomer, racemate, enantiomer, diastereomer, hydrate or solvate thereof according to claim 1, wherein $R^7$ is each independently selected from the group consisting of H, halogen, methyl, —$N(CH_3)CH_2CH_2N(CH_3)_2$, —$N(CH_3)_2$, 4-methyl-piperazinyl and morpholinyl.

19. The compound or a pharmaceutically acceptable salt, tautomer, racemate, enantiomer, diastereomer, hydrate or solvate thereof according to claim 1, wherein $R^8$ is vinyl or propynyl.

20. The compound or a pharmaceutically acceptable salt, tautomer, racemate, enantiomer, diastereomer, hydrate or solvate thereof according to claim 1, wherein X is —$CH_2$—; and Y is selected from the group consisting of —O—, —NH— and —$CH_2$—.

21. The compound or a pharmaceutically acceptable salt, tautomer, racemate, enantiomer, diastereomer, hydrate or solvate thereof according to claim 1, wherein W is selected from the group consisting of a chemical bond and —$CH_2$—.

22. The compound or a pharmaceutically acceptable salt, tautomer, racemate, enantiomer, diastereomer, hydrate or solvate thereof according to claim 1, wherein m is 0 or 1.

\* \* \* \* \*

UNITED STATES PATENT AND TRADEMARK OFFICE
CERTIFICATE OF CORRECTION

PATENT NO. : 11,279,697 B2
APPLICATION NO. : 16/644919
DATED : March 22, 2022
INVENTOR(S) : Shao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 29 days.

Signed and Sealed this
Twenty-ninth Day of November, 2022

Katherine Kelly Vidal
*Director of the United States Patent and Trademark Office*